US006316603B1

(12) United States Patent
McTigue et al.

(10) Patent No.: US 6,316,603 B1
(45) Date of Patent: Nov. 13, 2001

(54) MODIFICATIONS OF THE VEGF RECEPTOR-2 PROTEIN AND METHODS OF USE

(75) Inventors: Michele A. McTigue, Encinitas; Chris Pinko; Camran V. Parast, both of San Diego; Michael R. Gehring, Ramona; Chen-Chen Kan, Del Mare; Krzysztof Appelt, Poway; John A. Wickersham, Escondido; Richard E. Showalter, Lakeside; Anna M. Tempcyzk-Russell, San Diego; Barbara Mroczkowski, Encinitas; Jesus E. Villafranca, San Diego, all of CA (US)

(73) Assignee: Agouron Pharmaceuticals, Inc., La Jolla, CA (US)

( * ) Notice: Subject to any disclaimer, the term of this patent is extended or adjusted under 35 U.S.C. 154(b) by 0 days.

(21) Appl. No.: 09/390,326

(22) Filed: Sep. 7, 1999

Related U.S. Application Data

(60) Provisional application No. 60/099,503, filed on Sep. 8, 1998.

(51) Int. Cl.$^7$ .............................. C07K 1/00; C07K 14/00; C12N 9/00
(52) U.S. Cl. ........................... 530/402; 435/183; 530/350
(58) Field of Search ................... 514/44, 23.1; 435/69.1, 435/69.7; 536/23.1

(56) References Cited

U.S. PATENT DOCUMENTS

| 4,966,849 | 10/1990 | Valee et al. . |
| 5,217,999 | 6/1993 | Levitzki et al. . |
| 5,302,606 | 4/1994 | Spada et al. . |
| 5,330,992 | 7/1994 | Eissenstat et al. . |
| 6,037,329 | * 3/2000 | Baird et al. ........................... 514/44 |

FOREIGN PATENT DOCUMENTS

| WO94/03427 | 2/1991 | (WO) . |
| WO91/15495 | 10/1991 | (WO) . |
| WO92/20642 | 11/1992 | (WO) . |
| WO92/21660 | 12/1992 | (WO) . |
| WO94/10202 | 5/1994 | (WO) . |
| WO 98/49300 | 11/1998 | (WO) . |

OTHER PUBLICATIONS

Heidaran et al., "Deletion or substitution within the alpha platelet–derived growth factor receptor kinase insert domain," Mol. Cel. Biol., 1991, vol. 11, No. 1, pp. 134–142.*

McTigue et al., "Crystal structure of the kinase domain of human vascular endothelial growth factor receptor 2: A key enzyme in angiogensis," Structure, 1999, vol. 7, No. 3, pp. 319–330.*

Terman et al., "Identification of KDR tyrosine kinase as a receptor for vascular endothelial cell growth factor." Biochemical and Biophysical Research Communications, vol. 187, No. 3, pp. 1579–1586.*

McTigue, et al., "Crystal structure of the kinase domain of human vascular endothelial growth factor receptor 2: a key enzyme in angiogenesis," Structure 1999;7:319–330.

Al–Obeidi, et al., "Protein Tyrosine Kinases: Structure, Substrate Specificity, and Drug Discovery," Biopolymers (Peptide Science), vol. 47, 197–223 (1998).

Wei, et al., "Expression, Characterization, and Crystallization of the Catalytic Core of the Human Insulin Receptor Protein–tyrosine Kinase Domain," J. Biol. Chem. 1995; 270(14):8122–8130.

SCOPES, "Protein Purification: Principles and Practice," Second Ed., 1987, pp. 297–301.

Mohammadi, et al., "Structures of the Tyrosine Kinase Domain of Fibroblast Growth Factor Receptor in Complex with Inhibitors," Science 1997; 276: 955–960.

McDonald, et al., "The first structure of a receptor tyrosine kinase domain: a further step in understanding the molecular basis of insulin action," Structure 1995; 3:1–6.

Hubbard, et al., "Crystal structure of the tyrosine kinase domain of the human insulin receptor," Nature 1994; 372:746–754.

Singh, et al., "Structure–Based Design of a Potent, Selective, and Irreversible Inhibitor of the Catalytic Domain of the erbB Receptor Subfamily of Protein Tyrosine Kinases," J. Med. Chem. 1997; 40: 1130–1135.

Adamis et al., Arch. Ophthalmol., 114:66–71 (1996).

Agouron Pharmaceuticals, Inc. "Agouron Solves Structure of Key Target for Drugs to Block Angiogenesis: Human VEGF Receptor 2 Kinase", Mar. 4, 1999.

Bazenet et al., Mol. Cell. Biol., 16:6926–6936 (1996).

Borgström et al, Cancer Res., 56:4032–4039 (1996).

Bourne, H.R., et al., Basic& Clinical Pharmacology , 3$^{rd}$ Edition (Katzung et al., eds), Chapter 3, pp. 9–22 (1987).

Choudhury et al., FEBS Letters, 282(2):351–354 (May, 1991).

(List continued on next page.)

Primary Examiner—John S. Brusca
Assistant Examiner—Young Kim

(57) ABSTRACT

A 2.4 Å crystal structure of a protein construct containing the catalytic kinase domain of vascular endothelial growth factor receptor 2 (VEGFR2/KDR), a key enzyme in angiogenesis, has been determined in an unliganded, phosphorylated state. This protein construct, contains a modified catalytic linker and has comparable in vitro kinase activity to constructs containing the entire KID. The resulting construct retains comparable in vitro kinase activity to that of the wild-type KID, and more importantly, allows complete crystallization of the protein such that it may be characterized by X-ray crystallography. The present invention further discloses the use of x-ray crystallographic data for identification and construction of possible therapeutic compounds in the treatment of various disease conditions.

10 Claims, 67 Drawing Sheets

OTHER PUBLICATIONS

Dvorak et al., *Am. J. Path.*, 146:1029–1039 (1995).
De Vries et al., *Science*, 255:989–991 (1992).
Dougher–Vermazen et al., *Biochem. Biophys. Res. Comm.*, 205:728–738 (1994).
Ferrara & Henzel, *Biochem. Biphys. Res. Comm*, 161:851–858 (1989)—Abstract only.
Ferrara N. and Davis–Smyth, *Endocrine Rev.*, 18: 4–25 (1997).
Folkham, *J. Natl., Cancer Inst.*, 82:4–6 (1991).
Folkman et al., *J. Biol. Chem.*, 267:10931–10934 (1992).
Heidaran et al., *Mol. Cell. Biol.*, 11: 134–142 (1991).
Hori et al., *Cancer Res.*, 51:6180–9184 (1991).
Houck, et al., *J. Biol. Chem.*, 267:26031–26037 (1992).
Hubbard, *EMBO J.*, 16:5572–5581 (FGFRI) (1997).
Hubbard, et al., *Nature*, 372:746–754 (1994).
Jellinek, et al., *Biochemistry*, 3:10450–56 (1994).
Johnson et al., *Cell*, 85:149–158 (1996).
kazlauskas et al., *Mol. Cell Biol.*, 12:2534–2544 (1992).
Kim et al., *Nature*, 362:841–843 (1993).
Kinsella, et al., *Exp. Cell Res.*, 199:56–62 (1992).
Klagsburn & Soker, *Current Biology*, 3:699–702 (1993).
Knighton et al., *Science*, 253:407–413 (1991).
Kumar and Fidler, *In Vivo*, 18:24–34 (1998)—Abstract only.
Lev et al., *Proc. Natl. Acad. Sci. USA*, 89:678–682 (1992).
Matsui, T., et al., *Science*, 243:800–804 (1989).
McLeskey et al., *Cancer Res.*, 53:2168–2177 (1993).
McRee et al., *J. Struct. Biol.*, 125 (2–3):156–165 (1999)—Abstract only.
Mohammadi et al., *Cell*, 86:577–87 (1996).
Mohammadi et al., *Science*, 276:955–960 (1997).
Parast et al., *Biochemistry*, 37(47):16788–16801 (Nov. 5, 1998).
Pepper, M.S., *Vasc. Med.*, 1:259–266 (1996)—Abstract Only.
Reedjik, et al., *EMBO J.*, 11:1365–1372 (1992).
Risau, W., *FASEB J.*, 9:926–933 (1995).
Schuchter, et al., *Cancer Res.*, 51:682–687 (1991).
Seetharm, et al., *Oncogene*, 10:135–147 (1995).
Severinsson et al., *Mol. Cell. Biol.*, 10:801–809 (1990).
Shalaby et al., *Nature*, 376:576–579 (1995).
Shibuya, et al., *Oncogene*, 5:519–524 (1990).
Szekanecz, et al., *J. Investig. Med.*, 46:27–41 (1998).
Takano, et al., *Mol. Bio. Cell*, 4:358A, (1993).
Taylor, et al., *EMBO Journal*, 8(7):2029–2037 (1989).
Terman et al., *Biochem Biophys. Res. Commun.*, 187:1579–8 (1992).
Thomas & Kendall, *Proc. Natl. Acad. Sci.*, 90:10705–09, (1994).
Tolentino and Adamis, *Int. Ophthalmol. Clin*, 38:77–94, (1988).
Vaisman et al., *J. Biol. Chem.*, 265: 19461–19566, (1990).
Waltenberger et al., *J. Biol. Chem.*, 269:26988–26995, (1994).
Wei et al., *J. Biol. Chem.*, 270:8122–8130, (1995).
Weidner, et al., *New Engl. J. Med.*, 324:1–5, (1991).
Yamaguchi and Hendrickson, *Nature*, 384:484–489 (1996).
Yu et al., *Mol. Cell. Biol.*, 11:3780–3785 (1991).

* cited by examiner

FIG. 1a

```
                        αB                                       nucleotide-binding
                                                                       loop
                                                                 β1                    β2
VEGF-R2  806  MDPDELPLDEHCERLPYDASKWEFPRDRLKLGKPLGRGAFGQVEADAFGIDKTATCR--    863
FGFR1    456  ---MLAGVSEY--ELP-EDPRWELPRDRLVGKPLGEGCFGQVLAEAIGLDKDKPNRVT     509
IRK      978  VFPCSVYVPDEWEVSREKITLLRELGQGSFGMVEGNARDIIKGEAE--T              1025
VEGF-R1  799  MDPDEVPLDEQCERLPYDASKWEFARERLKLGKSLGRGAFGKVQASAFGIKKSPTCR--    856
PDGFRα   576  DPMQLPYD-SRWEFPRDGLVLGRVLGSGAFGKVEGTAYGLSRSQPVM--              622

β3                                      αC                        β4                       β5
VEGF-R2  864  TVAVKMLKEGATHSEHRALMSELKILIHIGHHLNVVNLLGACTKPGGPLMVIVEFCKFGN   923
FGFR1    510  KVAVKMLKSDATEKDLSDLISEMEMMKMIGKHKNIINLLGACT-QDGPLYVIVEYASKGN   568
IRK      1026 RVAVKTVNESASLRERIEFLNEASVMKGFTCH-HVVRLLGVVSK-GQPTLVVMELMAHGD   1083
VEGF-R1  857  TVAVKMLKEGATASEYKALMTELKILTHIGHHLNVVNLLGACTKQGGPLMVIVEYCKYGN   916
PDGFRα   623  KVAVKMLKPTARSSEKQALMSELKIMTHLGPHLNIVNLLGACTK-SGPIYIITEYCFYGD   681

αD                                          kinase insert domain
VEGF-R2  924  LSTYLRSKRNEFVPYKTKGARFRQGKDYVG---------------------            953
FGFR1    569  LREYLQARRPPGLEYCYN-----------------------------                586
IRK      1084 LKSYLRSLRPEA----------------------------------                 1095
VEGF-R1  917  LSNYLKSKRDLFFLNKDAALHMEPKKEKME-------------------              946
PDGFRα   682  LVNYLHKNRDSFLSHHPEKPKKELDIFGLNPADESTRSYVILSFENNGDYMDMKQADTTQ   741

αE
VEGF-R2  954  ---AIPVDLKRRLDSITSSQSSASSGFVEEKSLSDVEEEEAPEDLYKDFLTLEHLICYSF   1010
FGFR1    587  ---------------------------PSHNPEEQLSSKDLVSCAY                605
IRK      1096 ---------------------------ENNPGRPPPTLQEMQMAA                 1114
VEGF-R1  947  -----------------------VEEEDSDGFYKEPITMEDLISYSF                1004
PDGFRα   742  YVPMLERKEVSKYSDIQRSLYDRPASYKK-KSMLDSEVKNLLSDDNSEGLTLLDLLSFTY   800
```

FIG. 1b

```
                 catalytic loop      β7          β8         activation loop
VEGF-R2  1011  QVAKGMEFDLASRKCIHRDLAARNILLSEKNVVKICDFGLARDIYKDPDYVRKGDARLPLK   1070
FGFR1     606  QVARGMEYSLASKKCIHRDLAARNVLVTEDNVMKIADFGLARDIHHIDYYKKTTNGRLPVK    665
IRK      1115  EIADGMEY-LNAKKFVHRDLAARNCMVAHDFTVKIGDFGMTRDIYETDYYRKGGKGLLPVR   1174
VEGF-R1  1005  QVARGMEFDLSSRKCIHRDLAARNILLSENNVVKIDDFGLARDIYKNPDYVRKGDTRLPLK   1064
PDGFRα    801  QVARGMEF-LASKKCIHRDLAARNVLLAGKIVKIDDFGLARDIMHDSNYVSKGSTFLPVK    860

αEF                  αF                        αG
VEGF-R2  1071  WMAPETIFDRVYTIQSDVWSFGVLLWEIFSLGASPYPGVKIDEEFCRRLKEGTRMRRAPDY   923
FGFR1     666  WMAPEALFDRIYTHQSDVWSFGVLLWEIFTLGGSPYPGVPVEELF-KLLKEGHRMDRKPSN   568
IRK      1175  WMAPESLKDGVFTTSSDMWSFGVV WEITSLAEQPYQGLSNEQVL-KFVMDGGYLDLQPDN  1083
VEGF-R1  1065  WMAPESIFDKIYSTKSDVWSYGVLLWEIFSLGGSPYPGVQMDEDFCSRLREGMRMRRAPEY   916
PDGFRα    861  WMAPESIFDNLYTTLSDVWSYGILLWEIFSLGGTPYPGMMVDSTFYNKIKSGYRMAFKPDH   681

αH                                    αI
VEGF-R2  1131  TTPEMYQTMLDCWHGEPSQRPTFSELVEHLGNLLQANAQQD                       1171
FGFR1     725  CTNELYMMMRDCWHAVPSQRPTFKQLVEDLDRIVALTSNQE                        765
IRK      1234  CPERVTDLMRMCWQFNPNMRPTFLEIVNLLKDDLHPSFPEV                       1274
VEGF-R1  1125  STPEIYQIMLDCWHRDPKERPRFAELVEKLGDLLQANVQQD                       1165
PDGFRα    921  ATSEVYEIMVKCWNSEPEKRPSFYHLSEIVENLLPGQYKKS                        961
```

VEGFR2D50P

FGFR1

IRKP

FIG. 7(1)

| ATOM | 1  | CB  | LEU | 820 | 49.908 | 45.905 | 17.938 | 1.00 | 48.95 |
|------|----|-----|-----|-----|--------|--------|--------|------|-------|
| ATOM | 2  | CG  | LEU | 820 | 50.568 | 45.069 | 16.833 | 1.00 | 43.57 |
| ATOM | 3  | CD1 | LEU | 820 | 50.004 | 45.358 | 15.456 | 1.00 | 43.59 |
| ATOM | 4  | CD2 | LEU | 820 | 52.066 | 45.345 | 16.886 | 1.00 | 47.45 |
| ATOM | 5  | C   | LEU | 820 | 49.216 | 48.321 | 17.530 | 1.00 | 48.14 |
| ATOM | 6  | O   | LEU | 820 | 48.196 | 48.587 | 18.187 | 1.00 | 52.58 |
| ATOM | 9  | N   | LEU | 820 | 50.481 | 47.725 | 19.581 | 1.00 | 53.68 |
| ATOM | 11 | CA  | LEU | 820 | 50.302 | 47.387 | 18.117 | 1.00 | 50.63 |
| ATOM | 12 | N   | PRO | 821 | 49.435 | 48.842 | 16.306 | 1.00 | 41.32 |
| ATOM | 13 | CD  | PRO | 821 | 50.680 | 48.870 | 15.520 | 1.00 | 45.54 |
| ATOM | 14 | CA  | PRO | 821 | 48.465 | 49.733 | 15.700 | 1.00 | 31.06 |
| ATOM | 15 | CB  | PRO | 821 | 49.067 | 49.985 | 14.352 | 1.00 | 28.89 |
| ATOM | 16 | CG  | PRO | 821 | 50.509 | 50.148 | 14.734 | 1.00 | 43.44 |
| ATOM | 17 | C   | PRO | 821 | 47.123 | 49.165 | 15.569 | 1.00 | 26.14 |
| ATOM | 18 | O   | PRO | 821 | 46.948 | 47.970 | 15.374 | 1.00 | 26.03 |
| ATOM | 19 | N   | TYR | 822 | 46.154 | 50.024 | 15.776 | 1.00 | 16.25 |
| ATOM | 21 | CA  | TYR | 822 | 44.799 | 49.643 | 15.582 | 1.00 | 18.88 |
| ATOM | 22 | CB  | TYR | 822 | 44.061 | 49.519 | 16.916 | 1.00 | 17.42 |
| ATOM | 23 | CG  | TYR | 822 | 42.584 | 49.316 | 16.728 | 1.00 | 18.46 |
| ATOM | 24 | CD1 | TYR | 822 | 41.674 | 50.341 | 17.047 | 1.00 | 21.12 |
| ATOM | 25 | CE1 | TYR | 822 | 40.314 | 50.206 | 16.812 | 1.00 | 13.80 |
| ATOM | 26 | CD2 | TYR | 822 | 42.086 | 48.144 | 16.175 | 1.00 | 12.24 |
| ATOM | 27 | CE2 | TYR | 822 | 40.714 | 47.997 | 15.951 | 1.00 | 13.44 |
| ATOM | 28 | CZ  | TYR | 822 | 39.838 | 49.028 | 16.268 | 1.00 | 14.38 |
| ATOM | 29 | OH  | TYR | 822 | 38.480 | 48.887 | 16.073 | 1.00 | 19.73 |
| ATOM | 31 | C   | TYR | 822 | 44.253 | 50.760 | 14.705 | 1.00 | 16.93 |
| ATOM | 32 | O   | TYR | 822 | 44.172 | 51.904 | 15.112 | 1.00 | 20.70 |
| ATOM | 33 | N   | ASP | 823 | 44.054 | 50.456 | 13.439 | 1.00 | 15.20 |
| ATOM | 35 | CA  | ASP | 823 | 43.509 | 51.418 | 12.506 | 1.00 | 13.55 |
| ATOM | 36 | CB  | ASP | 823 | 43.856 | 50.945 | 11.091 | 1.00 | 11.37 |
| ATOM | 37 | CG  | ASP | 823 | 43.456 | 51.933 | 10.016 | 1.00 | 16.45 |
| ATOM | 38 | OD1 | ASP | 823 | 42.546 | 52.754 | 10.258 | 1.00 | 21.86 |
| ATOM | 39 | OD2 | ASP | 823 | 44.022 | 51.854 | 8.904  | 1.00 | 12.33 |
| ATOM | 40 | C   | ASP | 823 | 41.983 | 51.489 | 12.738 | 1.00 | 14.14 |
| ATOM | 41 | O   | ASP | 823 | 41.224 | 50.722 | 12.172 | 1.00 | 19.73 |
| ATOM | 42 | N   | ALA | 824 | 41.539 | 52.415 | 13.572 | 1.00 | 11.88 |
| ATOM | 44 | CA  | ALA | 824 | 40.126 | 52.554 | 13.876 | 1.00 | 14.80 |
| ATOM | 45 | CB  | ALA | 824 | 39.928 | 53.610 | 14.973 | 1.00 | 12.02 |
| ATOM | 46 | C   | ALA | 824 | 39.259 | 52.893 | 12.658 | 1.00 | 19.09 |
| ATOM | 47 | O   | ALA | 824 | 38.062 | 52.610 | 12.641 | 1.00 | 23.54 |

FIG. 7(2)

| | | | | | | | | |
|---|---|---|---|---|---|---|---|---|
| ATOM | 48 | N | SER | 825 | 39.857 | 53.496 | 11.635 | 1.00 18.25 |
| ATOM | 50 | CA | SER | 825 | 39.118 | 53.867 | 10.450 | 1.00 12.65 |
| ATOM | 51 | CB | SER | 825 | 40.023 | 54.678 | 9.543 | 1.00 11.88 |
| ATOM | 52 | OG | SER | 825 | 39.315 | 55.003 | 8.370 | 1.00 20.94 |
| ATOM | 54 | C | SER | 825 | 38.669 | 52.594 | 9.746 | 1.00 12.30 |
| ATOM | 55 | O | SER | 825 | 37.543 | 52.461 | 9.317 | 1.00 14.94 |
| ATOM | 56 | N | LYS | 826 | 39.557 | 51.633 | 9.642 | 1.00 14.98 |
| ATOM | 58 | CA | LYS | 826 | 39.188 | 50.396 | 8.988 | 1.00 22.45 |
| ATOM | 59 | CB | LYS | 826 | 40.445 | 49.660 | 8.483 | 1.00 16.46 |
| ATOM | 60 | CG | LYS | 826 | 40.091 | 48.370 | 7.820 | 1.00 23.00 |
| ATOM | 61 | CD | LYS | 826 | 40.962 | 48.071 | 6.657 | 1.00 26.19 |
| ATOM | 62 | CE | LYS | 826 | 42.391 | 48.041 | 7.092 | 1.00 35.70 |
| ATOM | 63 | NZ | LYS | 826 | 43.272 | 48.003 | 5.891 | 1.00 40.17 |
| ATOM | 67 | C | LYS | 826 | 38.324 | 49.437 | 9.839 | 1.00 21.47 |
| ATOM | 68 | O | LYS | 826 | 37.363 | 48.850 | 9.336 | 1.00 22.56 |
| ATOM | 69 | N | TRP | 827 | 38.589 | 49.376 | 11.144 | 1.00 20.96 |
| ATOM | 71 | CA | TRP | 827 | 37.917 | 48.406 | 11.996 | 1.00 16.87 |
| ATOM | 72 | CB | TRP | 827 | 38.974 | 47.620 | 12.785 | 1.00 18.53 |
| ATOM | 73 | CG | TRP | 827 | 39.942 | 46.898 | 11.910 | 1.00 12.95 |
| ATOM | 74 | CD2 | TRP | 827 | 39.643 | 45.810 | 11.029 | 1.00 9.73 |
| ATOM | 75 | CE2 | TRP | 827 | 40.795 | 45.562 | 10.274 | 1.00 9.36 |
| ATOM | 76 | CE3 | TRP | 827 | 38.505 | 45.038 | 10.801 | 1.00 11.54 |
| ATOM | 77 | CD1 | TRP | 827 | 41.233 | 47.231 | 11.684 | 1.00 12.87 |
| ATOM | 78 | NE1 | TRP | 827 | 41.753 | 46.440 | 10.689 | 1.00 10.49 |
| ATOM | 80 | CZ2 | TRP | 827 | 40.848 | 44.565 | 9.299 | 1.00 12.36 |
| ATOM | 81 | CZ3 | TRP | 827 | 38.556 | 44.053 | 9.826 | 1.00 10.55 |
| ATOM | 82 | CH2 | TRP | 827 | 39.718 | 43.830 | 9.087 | 1.00 11.88 |
| ATOM | 83 | C | TRP | 827 | 36.830 | 48.795 | 12.953 | 1.00 17.75 |
| ATOM | 84 | O | TRP | 827 | 35.985 | 47.951 | 13.271 | 1.00 15.08 |
| ATOM | 85 | N | GLU | 828 | 36.855 | 50.043 | 13.416 | 1.00 16.92 |
| ATOM | 87 | CA | GLU | 828 | 35.908 | 50.518 | 14.413 | 1.00 19.52 |
| ATOM | 88 | CB | GLU | 828 | 36.289 | 51.920 | 14.885 | 1.00 17.10 |
| ATOM | 89 | CG | GLU | 828 | 35.581 | 52.363 | 16.148 | 1.00 12.70 |
| ATOM | 90 | CD | GLU | 828 | 36.106 | 51.707 | 17.400 | 1.00 21.57 |
| ATOM | 91 | OE1 | GLU | 828 | 37.219 | 51.118 | 17.386 | 1.00 21.15 |
| ATOM | 92 | OE2 | GLU | 828 | 35.402 | 51.819 | 18.426 | 1.00 22.43 |
| ATOM | 93 | C | GLU | 828 | 34.494 | 50.510 | 13.910 | 1.00 20.94 |
| ATOM | 94 | O | GLU | 828 | 34.245 | 51.024 | 12.818 | 1.00 26.92 |
| ATOM | 95 | N | PHE | 829 | 33.569 | 49.990 | 14.734 | 1.00 21.12 |
| ATOM | 97 | CA | PHE | 829 | 32.138 | 49.880 | 14.391 | 1.00 17.93 |
| ATOM | 98 | CB | PHE | 829 | 31.791 | 48.400 | 14.160 | 1.00 16.42 |
| ATOM | 99 | CG | PHE | 829 | 30.384 | 48.164 | 13.669 | 1.00 20.17 |

FIG. 7(3)

| | | | | | | | |
|---|---|---|---|---|---|---|---|
| ATOM | 100 | CD1 | PHE | 829 | 30.020 | 48.484 | 12.363 1.00 21.31 |
| ATOM | 101 | CD2 | PHE | 829 | 29.415 | 47.612 | 14.516 1.00 23.04 |
| ATOM | 102 | CE1 | PHE | 829 | 28.712 | 48.254 | 11.921 1.00 18.76 |
| ATOM | 103 | CE2 | PHE | 829 | 28.093 | 47.375 | 14.071 1.00 15.20 |
| ATOM | 104 | CZ | PHE | 829 | 27.750 | 47.692 | 12.792 1.00 17.17 |
| ATOM | 105 | C | PHE | 829 | 31.310 | 50.495 | 15.533 1.00 14.65 |
| ATOM | 106 | O | PHE | 829 | 31.574 | 50.211 | 16.686 1.00 16.15 |
| ATOM | 107 | N | PRO | 830 | 30.270 | 51.298 | 15.224 1.00 13.29 |
| ATOM | 108 | CD | PRO | 830 | 29.707 | 51.633 | 13.901 1.00 11.63 |
| ATOM | 109 | CA | PRO | 830 | 29.481 | 51.918 | 16.292 1.00 14.76 |
| ATOM | 110 | CB | PRO | 830 | 28.636 | 52.948 | 15.565 1.00 13.82 |
| ATOM | 111 | CG | PRO | 830 | 28.414 | 52.364 | 14.252 1.00 14.42 |
| ATOM | 112 | C | PRO | 830 | 28.629 | 51.005 | 17.098 1.00 19.79 |
| ATOM | 113 | O | PRO | 830 | 27.750 | 50.339 | 16.562 1.00 26.60 |
| ATOM | 114 | N | ARG | 831 | 28.830 | 51.060 | 18.410 1.00 18.39 |
| ATOM | 116 | CA | ARG | 831 | 28.085 | 50.246 | 19.335 1.00 14.56 |
| ATOM | 117 | CB | ARG | 831 | 28.469 | 50.580 | 20.743 1.00 11.53 |
| ATOM | 118 | CG | ARG | 831 | 29.808 | 50.050 | 21.092 1.00 12.65 |
| ATOM | 119 | CD | ARG | 831 | 30.117 | 50.265 | 22.554 1.00 12.46 |
| ATOM | 120 | NE | ARG | 831 | 31.261 | 51.148 | 22.584 1.00 20.55 |
| ATOM | 122 | CZ | ARG | 831 | 32.469 | 50.756 | 22.885 1.00 12.04 |
| ATOM | 123 | NH1 | ARG | 831 | 32.688 | 49.518 | 23.234 1.00 23.80 |
| ATOM | 126 | NH2 | ARG | 831 | 33.467 | 51.501 | 22.526 1.00 23.84 |
| ATOM | 129 | C | ARG | 831 | 26.625 | 50.415 | 19.174 1.00 18.55 |
| ATOM | 130 | O | ARG | 831 | 25.852 | 49.561 | 19.607 1.00 25.61 |
| ATOM | 131 | N | ASP | 832 | 26.221 | 51.517 | 18.552 1.00 25.32 |
| ATOM | 133 | CA | ASP | 832 | 24.794 | 51.734 | 18.354 1.00 29.47 |
| ATOM | 134 | CB | ASP | 832 | 24.393 | 53.230 | 18.408 1.00 34.15 |
| ATOM | 135 | CG | ASP | 832 | 24.817 | 54.036 | 17.174 1.00 33.50 |
| ATOM | 136 | OD1 | ASP | 832 | 25.519 | 53.528 | 16.280 1.00 34.09 |
| ATOM | 137 | OD2 | ASP | 832 | 24.422 | 55.216 | 17.110 1.00 41.48 |
| ATOM | 138 | C | ASP | 832 | 24.230 | 51.000 | 17.139 1.00 27.13 |
| ATOM | 139 | O | ASP | 832 | 23.023 | 50.905 | 16.991 1.00 28.08 |
| ATOM | 140 | N | ARG | 833 | 25.104 | 50.466 | 16.290 1.00 24.18 |
| ATOM | 142 | CA | ARG | 833 | 24.684 | 49.695 | 15.134 1.00 19.93 |
| ATOM | 143 | CB | ARG | 833 | 25.661 | 49.902 | 14.011 1.00 25.94 |
| ATOM | 144 | CG | ARG | 833 | 25.313 | 51.073 | 13.158 1.00 38.97 |
| ATOM | 145 | CD | ARG | 833 | 25.929 | 50.901 | 11.766 1.00 53.19 |
| ATOM | 146 | NE | ARG | 833 | 25.525 | 51.930 | 10.807 1.00 63.47 |
| ATOM | 148 | CZ | ARG | 833 | 25.419 | 53.229 | 11.087 1.00 70.42 |
| ATOM | 149 | NH1 | ARG | 833 | 25.040 | 54.080 | 10.139 1.00 74.08 |
| ATOM | 152 | NH2 | ARG | 833 | 25.695 | 53.690 | 12.306 1.00 72.08 |
| ATOM | 155 | C | ARG | 833 | 24.656 | 48.218 | 15.498 1.00 18.62 |

FIG. 7(4)

| | | | | | | | | |
|---|---|---|---|---|---|---|---|---|
| ATOM | 156 | O   | ARG  | 833 | 24.289 | 47.370 | 14.690 | 1.00 18.27 |
| ATOM | 157 | N   | LEU  | 834 | 25.013 | 47.943 | 16.747 | 1.00 18.35 |
| ATOM | 159 | CA  | LEU  | 834 | 25.089 | 46.600 | 17.329 | 1.00 22.59 |
| ATOM | 160 | CB  | LEU  | 834 | 26.488 | 46.398 | 17.946 | 1.00 25.91 |
| ATOM | 161 | CG  | LEU  | 834 | 27.073 | 45.003 | 18.139 | 1.00 24.64 |
| ATOM | 162 | CD1 | LEU  | 834 | 27.185 | 44.327 | 16.805 | 1.00 21.77 |
| ATOM | 163 | CD2 | LEU  | 834 | 28.428 | 45.085 | 18.785 | 1.00 17.43 |
| ATOM | 164 | C   | LEU  | 834 | 23.988 | 46.326 | 18.387 | 1.00 24.77 |
| ATOM | 165 | O   | LEU  | 834 | 23.886 | 46.973 | 19.433 | 1.00 24.03 |
| ATOM | 166 | N   | LYS  | 835 | 23.173 | 45.335 | 18.087 | 1.00 28.94 |
| ATOM | 168 | CA  | LYS  | 835 | 22.072 | 44.942 | 18.940 | 1.00 32.84 |
| ATOM | 169 | CB  | LYS  | 835 | 20.794 | 44.913 | 18.081 | 1.00 31.34 |
| ATOM | 170 | CG  | LYS  | 835 | 19.529 | 44.697 | 18.839 | 1.00 36.63 |
| ATOM | 171 | CD  | LYS  | 835 | 18.359 | 44.407 | 17.940 | 1.00 39.31 |
| ATOM | 172 | CE  | LYS  | 835 | 17.074 | 44.414 | 18.783 | 1.00 48.99 |
| ATOM | 173 | NZ  | LYS  | 835 | 17.074 | 43.448 | 19.950 | 1.00 48.86 |
| ATOM | 177 | C   | LYS  | 835 | 22.431 | 43.532 | 19.420 | 1.00 31.79 |
| ATOM | 178 | O   | LYS  | 835 | 22.408 | 42.609 | 18.616 | 1.00 34.57 |
| ATOM | 179 | N   | LEU  | 836 | 22.854 | 43.395 | 20.680 | 1.00 33.17 |
| ATOM | 181 | CA  | LEU  | 836 | 23.229 | 42.101 | 21.277 | 1.00 34.01 |
| ATOM | 182 | CB  | LEU  | 836 | 23.970 | 42.292 | 22.593 | 1.00 33.96 |
| ATOM | 183 | CG  | LEU  | 836 | 25.400 | 42.796 | 22.462 | 1.00 42.50 |
| ATOM | 184 | CD1 | LEU  | 836 | 26.082 | 42.858 | 23.854 | 1.00 41.15 |
| ATOM | 185 | CD2 | LEU  | 836 | 26.153 | 41.860 | 21.501 | 1.00 40.93 |
| ATOM | 186 | C   | LEU  | 836 | 22.053 | 41.181 | 21.547 | 1.00 33.27 |
| ATOM | 187 | O   | LEU  | 836 | 21.017 | 41.631 | 22.025 | 1.00 31.15 |
| ATOM | 188 | N   | GLY  | 837 | 22.268 | 39.882 | 21.330 | 1.00 36.34 |
| ATOM | 190 | CA  | GLY  | 837 | 21.228 | 38.881 | 21.536 | 1.00 34.95 |
| ATOM | 191 | C   | GLY  | 837 | 21.603 | 37.761 | 22.497 | 1.00 35.64 |
| ATOM | 192 | O   | GLY  | 837 | 22.203 | 37.980 | 23.554 | 1.00 39.23 |
| ATOM | 193 | N   | LYS  | 838 | 21.254 | 36.541 | 22.126 | 1.00 35.31 |
| ATOM | 195 | CA  | LYS  | 838 | 21.531 | 35.375 | 22.962 | 1.00 37.86 |
| ATOM | 196 | CB  | LYS  | 838 | 20.647 | 34.192 | 22.539 | 1.00 41.52 |
| ATOM | 197 | C   | LYS  | 838 | 22.991 | 34.935 | 22.989 | 1.00 35.93 |
| ATOM | 198 | O   | LYS  | 838 | 23.650 | 34.851 | 21.946 | 1.00 34.37 |
| ATOM | 199 | N   | PRO  | 839 | 23.499 | 34.608 | 24.187 | 1.00 33.68 |
| ATOM | 200 | CD  | PRO  | 839 | 22.820 | 34.757 | 25.486 | 1.00 34.48 |
| ATOM | 201 | CA  | PRO  | 839 | 24.880 | 34.158 | 24.363 | 1.00 37.11 |
| ATOM | 202 | CB  | PRO  | 839 | 24.927 | 33.750 | 25.833 | 1.00 37.46 |
| ATOM | 203 | CG  | PRO  | 839 | 23.970 | 34.710 | 26.472 | 1.00 37.04 |
| ATOM | 204 | C   | PRO  | 839 | 25.148 | 32.963 | 23.474 | 1.00 39.09 |
| ATOM | 205 | O   | PRO  | 839 | 24.303 | 32.085 | 23.327 | 1.00 38.13 |
| ATOM | 206 | N   | LEU  | 840 | 26.261 | 33.013 | 22.767 | 1.00 43.08 |

FIG. 7(5)

| | | | | | | | |
|---|---|---|---|---|---|---|---|
| ATOM | 208 | CA | LEU | 840 | 26.646 | 31.915 | 21.917 | 1.00 | 47.73 |
| ATOM | 209 | CB | LEU | 840 | 27.396 | 32.426 | 20.692 | 1.00 | 41.83 |
| ATOM | 210 | CG | LEU | 840 | 26.386 | 32.957 | 19.697 | 1.00 | 39.60 |
| ATOM | 211 | CD1 | LEU | 840 | 27.080 | 33.697 | 18.595 | 1.00 | 42.69 |
| ATOM | 212 | CD2 | LEU | 840 | 25.582 | 31.795 | 19.156 | 1.00 | 38.40 |
| ATOM | 213 | C | LEU | 840 | 27.523 | 30.987 | 22.747 | 1.00 | 54.84 |
| ATOM | 214 | O | LEU | 840 | 27.479 | 29.768 | 22.577 | 1.00 | 59.76 |
| ATOM | 215 | N | GLY | 841 | 28.248 | 31.563 | 23.706 | 1.00 | 60.51 |
| ATOM | 217 | CA | GLY | 841 | 29.140 | 30.781 | 24.547 | 1.00 | 60.96 |
| ATOM | 218 | C | GLY | 841 | 29.660 | 31.544 | 25.750 | 1.00 | 63.95 |
| ATOM | 219 | O | GLY | 841 | 29.497 | 32.764 | 25.857 | 1.00 | 64.35 |
| ATOM | 220 | N | ARG | 842 | 30.279 | 30.809 | 26.668 | 1.00 | 65.26 |
| ATOM | 222 | CA | ARG | 842 | 30.823 | 31.388 | 27.887 | 1.00 | 65.12 |
| ATOM | 223 | CB | ARG | 842 | 30.027 | 30.897 | 29.091 | 1.00 | 61.50 |
| ATOM | 224 | C | ARG | 842 | 32.300 | 30.995 | 28.004 | 1.00 | 64.23 |
| ATOM | 225 | O | ARG | 842 | 32.957 | 30.720 | 26.986 | 1.00 | 68.80 |
| ATOM | 226 | N | GLY | 843 | 32.822 | 31.003 | 29.226 | 1.00 | 60.14 |
| ATOM | 228 | CA | GLY | 843 | 34.206 | 30.639 | 29.453 | 1.00 | 60.53 |
| ATOM | 229 | C | GLY | 843 | 34.676 | 31.165 | 30.789 | 1.00 | 62.56 |
| ATOM | 230 | O | GLY | 843 | 33.902 | 31.764 | 31.535 | 1.00 | 61.31 |
| ATOM | 231 | N | ALA | 844 | 35.925 | 30.888 | 31.140 | 1.00 | 66.30 |
| ATOM | 233 | CA | ALA | 844 | 36.450 | 31.390 | 32.403 | 1.00 | 69.69 |
| ATOM | 234 | CB | ALA | 844 | 37.655 | 30.574 | 32.851 | 1.00 | 68.47 |
| ATOM | 235 | C | ALA | 844 | 36.839 | 32.855 | 32.212 | 1.00 | 73.15 |
| ATOM | 236 | O | ALA | 844 | 36.723 | 33.667 | 33.144 | 1.00 | 75.00 |
| ATOM | 237 | N | PHE | 845 | 37.251 | 33.184 | 30.981 | 1.00 | 76.12 |
| ATOM | 239 | CA | PHE | 845 | 37.699 | 34.538 | 30.618 | 1.00 | 74.99 |
| ATOM | 240 | CB | PHE | 845 | 39.135 | 34.479 | 30.014 | 1.00 | 72.01 |
| ATOM | 241 | C | PHE | 845 | 36.766 | 35.353 | 29.700 | 1.00 | 73.81 |
| ATOM | 242 | O | PHE | 845 | 36.404 | 36.499 | 30.020 | 1.00 | 76.82 |
| ATOM | 243 | N | GLY | 846 | 36.368 | 34.767 | 28.576 | 1.00 | 68.48 |
| ATOM | 245 | CA | GLY | 846 | 35.527 | 35.495 | 27.645 | 1.00 | 61.76 |
| ATOM | 246 | C | GLY | 846 | 34.102 | 35.023 | 27.606 | 1.00 | 57.98 |
| ATOM | 247 | O | GLY | 846 | 33.658 | 34.305 | 28.491 | 1.00 | 59.43 |
| ATOM | 248 | N | GLN | 847 | 33.400 | 35.413 | 26.553 | 1.00 | 55.08 |
| ATOM | 250 | CA | GLN | 847 | 32.006 | 35.050 | 26.354 | 1.00 | 52.26 |
| ATOM | 251 | CB | GLN | 847 | 31.160 | 35.668 | 27.449 | 1.00 | 55.14 |
| ATOM | 252 | CG | GLN | 847 | 29.706 | 35.703 | 27.075 | 1.00 | 61.40 |
| ATOM | 253 | CD | GLN | 847 | 28.951 | 36.735 | 27.844 | 1.00 | 65.75 |
| ATOM | 254 | OE1 | GLN | 847 | 27.772 | 36.543 | 28.150 | 1.00 | 69.74 |
| ATOM | 255 | NE2 | GLN | 847 | 29.614 | 37.852 | 28.166 | 1.00 | 68.83 |
| ATOM | 258 | C | GLN | 847 | 31.508 | 35.573 | 25.001 | 1.00 | 47.29 |
| ATOM | 259 | O | GLN | 847 | 31.637 | 36.764 | 24.713 | 1.00 | 52.89 |

FIG. 7(6)

| ATOM | 260 | N   | VAL | 848 | 30.912 | 34.707 | 24.195 | 1.00 | 38.17 |
|------|-----|-----|-----|-----|--------|--------|--------|------|-------|
| ATOM | 262 | CA  | VAL | 848 | 30.418 | 35.122 | 22.898 | 1.00 | 30.28 |
| ATOM | 263 | CB  | VAL | 848 | 30.792 | 34.137 | 21.833 | 1.00 | 28.01 |
| ATOM | 264 | CG1 | VAL | 848 | 30.542 | 34.744 | 20.442 | 1.00 | 23.32 |
| ATOM | 265 | CG2 | VAL | 848 | 32.239 | 33.759 | 22.016 | 1.00 | 22.18 |
| ATOM | 266 | C   | VAL | 848 | 28.920 | 35.262 | 22.939 | 1.00 | 31.80 |
| ATOM | 267 | O   | VAL | 848 | 28.221 | 34.525 | 23.625 | 1.00 | 32.87 |
| ATOM | 268 | N   | ILE | 849 | 28.410 | 36.196 | 22.166 | 1.00 | 29.87 |
| ATOM | 270 | CA  | ILE | 849 | 26.990 | 36.436 | 22.159 | 1.00 | 25.35 |
| ATOM | 271 | CB  | ILE | 849 | 26.602 | 37.448 | 23.328 | 1.00 | 31.46 |
| ATOM | 272 | CG2 | ILE | 849 | 27.766 | 38.373 | 23.732 | 1.00 | 32.09 |
| ATOM | 273 | CG1 | ILE | 849 | 25.353 | 38.244 | 23.003 | 1.00 | 31.00 |
| ATOM | 274 | CD1 | ILE | 849 | 24.895 | 39.035 | 24.199 | 1.00 | 37.56 |
| ATOM | 275 | C   | ILE | 849 | 26.493 | 36.851 | 20.798 | 1.00 | 23.02 |
| ATOM | 276 | O   | ILE | 849 | 27.167 | 37.540 | 20.070 | 1.00 | 27.56 |
| ATOM | 277 | N   | GLU | 850 | 25.376 | 36.294 | 20.390 | 1.00 | 25.56 |
| ATOM | 279 | CA  | GLU | 850 | 24.802 | 36.626 | 19.107 | 1.00 | 26.63 |
| ATOM | 280 | CB  | GLU | 850 | 23.577 | 35.785 | 18.894 | 1.00 | 27.45 |
| ATOM | 281 | CG  | GLU | 850 | 23.414 | 35.361 | 17.487 | 1.00 | 34.57 |
| ATOM | 282 | CD  | GLU | 850 | 22.155 | 34.590 | 17.293 | 1.00 | 34.46 |
| ATOM | 283 | OE1 | GLU | 850 | 21.602 | 34.655 | 16.184 | 1.00 | 42.38 |
| ATOM | 284 | OE2 | GLU | 850 | 21.710 | 33.924 | 18.248 | 1.00 | 40.93 |
| ATOM | 285 | C   | GLU | 850 | 24.422 | 38.111 | 19.028 | 1.00 | 27.83 |
| ATOM | 286 | O   | GLU | 850 | 24.240 | 38.755 | 20.047 | 1.00 | 25.02 |
| ATOM | 287 | N   | ALA | 851 | 24.291 | 38.640 | 17.814 | 1.00 | 29.11 |
| ATOM | 289 | CA  | ALA | 851 | 23.958 | 40.043 | 17.621 | 1.00 | 27.32 |
| ATOM | 290 | CB  | ALA | 851 | 25.080 | 40.922 | 18.170 | 1.00 | 18.65 |
| ATOM | 291 | C   | ALA | 851 | 23.731 | 40.387 | 16.160 | 1.00 | 26.61 |
| ATOM | 292 | O   | ALA | 851 | 24.328 | 39.785 | 15.283 | 1.00 | 26.99 |
| ATOM | 293 | N   | ASP | 852 | 22.836 | 41.343 | 15.917 | 1.00 | 30.82 |
| ATOM | 295 | CA  | ASP | 852 | 22.538 | 41.862 | 14.566 | 1.00 | 31.76 |
| ATOM | 296 | CB  | ASP | 852 | 21.050 | 42.186 | 14.386 | 1.00 | 39.33 |
| ATOM | 297 | CG  | ASP | 852 | 20.222 | 40.993 | 13.993 | 1.00 | 47.41 |
| ATOM | 298 | OD1 | ASP | 852 | 19.687 | 40.330 | 14.906 | 1.00 | 54.12 |
| ATOM | 299 | OD2 | ASP | 852 | 20.066 | 40.754 | 12.775 | 1.00 | 53.02 |
| ATOM | 300 | C   | ASP | 852 | 23.265 | 43.204 | 14.506 | 1.00 | 25.97 |
| ATOM | 301 | O   | ASP | 852 | 23.096 | 44.021 | 15.416 | 1.00 | 21.64 |
| ATOM | 302 | N   | ALA | 853 | 24.099 | 43.411 | 13.495 | 1.00 | 20.18 |
| ATOM | 304 | CA  | ALA | 853 | 24.818 | 44.672 | 13.342 | 1.00 | 23.55 |
| ATOM | 305 | CB  | ALA | 853 | 26.305 | 44.440 | 13.292 | 1.00 | 23.32 |
| ATOM | 306 | C   | ALA | 853 | 24.311 | 45.222 | 12.026 | 1.00 | 23.89 |
| ATOM | 307 | O   | ALA | 853 | 24.079 | 44.439 | 11.108 | 1.00 | 26.15 |
| ATOM | 308 | N   | PHE | 854 | 24.044 | 46.526 | 11.936 | 1.00 | 22.87 |

FIG. 7(7)

| | | | | | | | | |
|---|---|---|---|---|---|---|---|---|
| ATOM | 310 | CA | PHE | 854 | 23.529 | 47.059 | 10.680 | 1.00 16.46 |
| ATOM | 311 | CB | PHE | 854 | 22.487 | 48.135 | 10.901 | 1.00 23.71 |
| ATOM | 312 | CG | PHE | 854 | 22.020 | 48.758 | 9.643 | 1.00 27.62 |
| ATOM | 313 | CD1 | PHE | 854 | 22.476 | 50.011 | 9.266 | 1.00 28.26 |
| ATOM | 314 | CD2 | PHE | 854 | 21.205 | 48.052 | 8.771 | 1.00 31.56 |
| ATOM | 315 | CE1 | PHE | 854 | 22.136 | 50.549 | 8.025 | 1.00 30.16 |
| ATOM | 316 | CE2 | PHE | 854 | 20.856 | 48.592 | 7.512 | 1.00 34.04 |
| ATOM | 317 | CZ | PHE | 854 | 21.328 | 49.838 | 7.145 | 1.00 28.32 |
| ATOM | 318 | C | PHE | 854 | 24.618 | 47.569 | 9.794 | 1.00 14.10 |
| ATOM | 319 | O | PHE | 854 | 25.493 | 48.299 | 10.209 | 1.00 17.34 |
| ATOM | 320 | N | GLY | 855 | 24.556 | 47.163 | 8.553 | 1.00 17.45 |
| ATOM | 322 | CA | GLY | 855 | 25.559 | 47.571 | 7.604 | 1.00 18.50 |
| ATOM | 323 | C | GLY | 855 | 26.988 | 47.318 | 8.020 | 1.00 22.65 |
| ATOM | 324 | O | GLY | 855 | 27.806 | 48.193 | 7.777 | 1.00 26.82 |
| ATOM | 325 | N | ILE | 856 | 27.332 | 46.150 | 8.580 | 1.00 23.51 |
| ATOM | 327 | CA | ILE | 856 | 28.740 | 45.886 | 8.983 | 1.00 24.11 |
| ATOM | 328 | CB | ILE | 856 | 28.868 | 44.692 | 9.980 | 1.00 27.72 |
| ATOM | 329 | CG2 | ILE | 856 | 28.535 | 43.370 | 9.259 | 1.00 29.88 |
| ATOM | 330 | CG1 | ILE | 856 | 30.282 | 44.663 | 10.608 | 1.00 23.26 |
| ATOM | 331 | CD1 | ILE | 856 | 30.371 | 44.079 | 12.034 | 1.00 21.70 |
| ATOM | 332 | C | ILE | 856 | 29.704 | 45.665 | 7.805 | 1.00 24.83 |
| ATOM | 333 | O | ILE | 856 | 30.918 | 45.721 | 7.950 | 1.00 28.37 |
| ATOM | 334 | N | ASP | 857 | 29.145 | 45.460 | 6.626 | 1.00 27.69 |
| ATOM | 336 | CA | ASP | 857 | 29.926 | 45.248 | 5.420 | 1.00 31.23 |
| ATOM | 337 | CB | ASP | 857 | 29.566 | 43.891 | 4.838 | 1.00 34.80 |
| ATOM | 338 | CG | ASP | 857 | 28.074 | 43.658 | 4.811 | 1.00 40.03 |
| ATOM | 339 | OD1 | ASP | 857 | 27.328 | 44.597 | 4.448 | 1.00 43.33 |
| ATOM | 340 | OD2 | ASP | 857 | 27.641 | 42.549 | 5.200 | 1.00 46.87 |
| ATOM | 341 | C | ASP | 857 | 29.654 | 46.323 | 4.370 | 1.00 32.81 |
| ATOM | 342 | O | ASP | 857 | 29.721 | 46.040 | 3.183 | 1.00 38.59 |
| ATOM | 343 | N | LYS | 858 | 29.299 | 47.529 | 4.813 | 1.00 34.74 |
| ATOM | 345 | CA | LYS | 858 | 28.987 | 48.690 | 3.946 | 1.00 34.64 |
| ATOM | 346 | CB | LYS | 858 | 30.061 | 48.947 | 2.889 | 1.00 31.38 |
| ATOM | 347 | CG | LYS | 858 | 31.462 | 48.964 | 3.418 | 1.00 34.36 |
| ATOM | 348 | CD | LYS | 858 | 31.605 | 49.890 | 4.603 | 1.00 39.41 |
| ATOM | 349 | CE | LYS | 858 | 33.005 | 49.791 | 5.228 | 1.00 39.87 |
| ATOM | 350 | NZ | LYS | 858 | 34.059 | 50.089 | 4.218 | 1.00 39.89 |
| ATOM | 354 | C | LYS | 858 | 27.629 | 48.709 | 3.254 | 1.00 32.27 |
| ATOM | 355 | O | LYS | 858 | 27.249 | 49.737 | 2.724 | 1.00 35.02 |
| ATOM | 356 | N | THR | 859 | 26.891 | 47.607 | 3.258 | 1.00 32.20 |
| ATOM | 358 | CA | THR | 859 | 25.597 | 47.610 | 2.600 | 1.00 30.11 |
| ATOM | 359 | CB | THR | 859 | 25.355 | 46.332 | 1.785 | 1.00 30.38 |
| ATOM | 360 | OG1 | THR | 859 | 25.365 | 45.187 | 2.641 | 1.00 32.29 |

FIG. 7(8)

| | | | | | | | |
|---|---|---|---|---|---|---|---|
| ATOM | 362 | CG2 | THR | 859 | 26.437 | 46.179 | 0.757 1.00 32.22 |
| ATOM | 363 | C | THR | 859 | 24.450 | 47.839 | 3.546 1.00 28.71 |
| ATOM | 364 | O | THR | 859 | 24.577 | 47.647 | 4.750 1.00 30.55 |
| ATOM | 365 | N | ALA | 860 | 23.303 | 48.201 | 2.989 1.00 30.07 |
| ATOM | 367 | CA | ALA | 860 | 22.123 | 48.474 | 3.784 1.00 28.01 |
| ATOM | 368 | CB | ALA | 860 | 21.141 | 49.253 | 2.928 1.00 23.78 |
| ATOM | 369 | C | ALA | 860 | 21.461 | 47.222 | 4.394 1.00 28.00 |
| ATOM | 370 | O | ALA | 860 | 20.251 | 47.100 | 4.373 1.00 31.77 |
| ATOM | 371 | N | THR | 861 | 22.228 | 46.325 | 5.008 1.00 29.99 |
| ATOM | 373 | CA | THR | 861 | 21.663 | 45.078 | 5.577 1.00 27.77 |
| ATOM | 374 | CB | THR | 861 | 22.186 | 43.857 | 4.808 1.00 20.97 |
| ATOM | 375 | OG1 | THR | 861 | 23.614 | 43.926 | 4.687 1.00 27.23 |
| ATOM | 377 | CG2 | THR | 861 | 21.608 | 43.794 | 3.449 1.00 29.39 |
| ATOM | 378 | C | THR | 861 | 21.986 | 44.790 | 7.055 1.00 31.89 |
| ATOM | 379 | O | THR | 861 | 23.095 | 45.077 | 7.532 1.00 34.73 |
| ATOM | 380 | N | CYS | 862 | 21.037 | 44.183 | 7.770 1.00 34.09 |
| ATOM | 382 | CA | CYS | 862 | 21.250 | 43.805 | 9.178 1.00 31.63 |
| ATOM | 383 | CB | CYS | 862 | 19.922 | 43.756 | 9.943 1.00 27.50 |
| ATOM | 384 | SG | CYS | 862 | 19.863 | 44.908 | 11.327 1.00 41.79 |
| ATOM | 385 | C | CYS | 862 | 21.876 | 42.424 | 9.146 1.00 25.51 |
| ATOM | 386 | O | CYS | 862 | 21.241 | 41.492 | 8.700 1.00 30.38 |
| ATOM | 387 | N | ARG | 863 | 23.136 | 42.307 | 9.541 1.00 27.68 |
| ATOM | 389 | CA | ARG | 863 | 23.839 | 41.025 | 9.532 1.00 28.29 |
| ATOM | 390 | CB | ARG | 863 | 25.211 | 41.210 | 8.882 1.00 36.18 |
| ATOM | 391 | CG | ARG | 863 | 25.775 | 39.945 | 8.275 1.00 48.71 |
| ATOM | 392 | CD | ARG | 863 | 27.282 | 40.034 | 7.943 1.00 58.46 |
| ATOM | 393 | NE | ARG | 863 | 27.824 | 38.721 | 7.550 1.00 65.04 |
| ATOM | 395 | CZ | ARG | 863 | 29.112 | 38.452 | 7.330 1.00 65.66 |
| ATOM | 396 | NH1 | ARG | 863 | 29.482 | 37.219 | 6.985 1.00 67.60 |
| ATOM | 399 | NH2 | ARG | 863 | 30.030 | 39.409 | 7.421 1.00 66.49 |
| ATOM | 402 | C | ARG | 863 | 24.006 | 40.409 | 10.943 1.00 28.34 |
| ATOM | 403 | O | ARG | 863 | 24.337 | 41.125 | 11.904 1.00 24.64 |
| ATOM | 404 | N | THR | 864 | 23.735 | 39.100 | 11.078 1.00 23.23 |
| ATOM | 406 | CA | THR | 864 | 23.900 | 38.426 | 12.364 1.00 18.91 |
| ATOM | 407 | CB | THR | 864 | 23.062 | 37.099 | 12.489 1.00 19.40 |
| ATOM | 408 | OG1 | THR | 864 | 21.672 | 37.435 | 12.547 1.00 24.20 |
| ATOM | 410 | CG2 | THR | 864 | 23.371 | 36.351 | 13.793 1.00 8.83 |
| ATOM | 411 | C | THR | 864 | 25.385 | 38.148 | 12.462 1.00 20.93 |
| ATOM | 412 | O | THR | 864 | 26.001 | 37.736 | 11.468 1.00 20.14 |
| ATOM | 413 | N | VAL | 865 | 25.962 | 38.442 | 13.634 1.00 16.03 |
| ATOM | 415 | CA | VAL | 865 | 27.381 | 38.254 | 13.897 1.00 16.69 |
| ATOM | 416 | CB | VAL | 865 | 28.175 | 39.620 | 13.906 1.00 17.70 |
| ATOM | 417 | CG1 | VAL | 865 | 28.107 | 40.299 | 12.539 1.00 21.22 |

FIG. 7(9)

| | | | | | | | |
|---|---|---|---|---|---|---|---|
| ATOM | 418 | CG2 | VAL | 865 | 27.625 | 40.554 | 14.979 | 1.00 | 20.92 |
| ATOM | 419 | C | VAL | 865 | 27.533 | 37.660 | 15.276 | 1.00 | 15.90 |
| ATOM | 420 | O | VAL | 865 | 26.552 | 37.554 | 15.995 | 1.00 | 16.43 |
| ATOM | 421 | N | ALA | 866 | 28.775 | 37.295 | 15.612 | 1.00 | 16.37 |
| ATOM | 423 | CA | ALA | 866 | 29.210 | 36.753 | 16.910 | 1.00 | 18.08 |
| ATOM | 424 | CB | ALA | 866 | 30.022 | 35.490 | 16.691 | 1.00 | 7.41 |
| ATOM | 425 | C | ALA | 866 | 30.117 | 37.834 | 17.588 | 1.00 | 23.87 |
| ATOM | 426 | O | ALA | 866 | 31.121 | 38.261 | 16.998 | 1.00 | 24.17 |
| ATOM | 427 | N | VAL | 867 | 29.790 | 38.235 | 18.827 | 1.00 | 26.69 |
| ATOM | 429 | CA | VAL | 867 | 30.534 | 39.268 | 19.554 | 1.00 | 20.37 |
| ATOM | 430 | CB | VAL | 867 | 29.592 | 40.365 | 20.088 | 1.00 | 17.71 |
| ATOM | 431 | CG1 | VAL | 867 | 30.361 | 41.586 | 20.519 | 1.00 | 9.32 |
| ATOM | 432 | CG2 | VAL | 867 | 28.635 | 40.753 | 19.027 | 1.00 | 14.57 |
| ATOM | 433 | C | VAL | 867 | 31.320 | 38.748 | 20.728 | 1.00 | 21.67 |
| ATOM | 434 | O | VAL | 867 | 30.784 | 38.085 | 21.606 | 1.00 | 23.57 |
| ATOM | 435 | N | LYS | 868 | 32.616 | 38.982 | 20.694 | 1.00 | 21.65 |
| ATOM | 437 | CA | LYS | 868 | 33.471 | 38.593 | 21.782 | 1.00 | 27.02 |
| ATOM | 438 | CB | LYS | 868 | 34.860 | 38.169 | 21.289 | 1.00 | 29.71 |
| ATOM | 439 | CG | LYS | 868 | 34.842 | 36.963 | 20.405 | 1.00 | 37.08 |
| ATOM | 440 | CD | LYS | 868 | 36.151 | 36.810 | 19.666 | 1.00 | 44.81 |
| ATOM | 441 | CE | LYS | 868 | 36.183 | 35.512 | 18.868 | 1.00 | 45.52 |
| ATOM | 442 | NZ | LYS | 868 | 37.548 | 35.298 | 18.274 | 1.00 | 47.28 |
| ATOM | 446 | C | LYS | 868 | 33.585 | 39.842 | 22.647 | 1.00 | 26.11 |
| ATOM | 447 | O | LYS | 868 | 33.962 | 40.914 | 22.188 | 1.00 | 24.72 |
| ATOM | 448 | N | MET | 869 | 33.184 | 39.721 | 23.888 | 1.00 | 29.77 |
| ATOM | 450 | CA | MET | 869 | 33.299 | 40.821 | 24.803 | 1.00 | 32.95 |
| ATOM | 451 | CB | MET | 869 | 31.958 | 41.491 | 24.996 | 1.00 | 30.57 |
| ATOM | 452 | CG | MET | 869 | 30.900 | 40.542 | 25.463 | 1.00 | 32.29 |
| ATOM | 453 | SD | MET | 869 | 29.348 | 41.157 | 24.961 | 1.00 | 42.68 |
| ATOM | 454 | CE | MET | 869 | 29.251 | 42.663 | 25.919 | 1.00 | 35.32 |
| ATOM | 455 | C | MET | 869 | 33.778 | 40.205 | 26.095 | 1.00 | 40.29 |
| ATOM | 456 | O | MET | 869 | 33.921 | 38.967 | 26.216 | 1.00 | 35.26 |
| ATOM | 457 | N | LEU | 870 | 34.079 | 41.066 | 27.051 | 1.00 | 46.88 |
| ATOM | 459 | CA | LEU | 870 | 34.521 | 40.576 | 28.337 | 1.00 | 51.36 |
| ATOM | 460 | CB | LEU | 870 | 35.544 | 41.549 | 28.937 | 1.00 | 48.55 |
| ATOM | 461 | CG | LEU | 870 | 36.862 | 41.677 | 28.180 | 1.00 | 44.32 |
| ATOM | 462 | CD1 | LEU | 870 | 37.734 | 42.739 | 28.855 | 1.00 | 36.89 |
| ATOM | 463 | CD2 | LEU | 870 | 37.535 | 40.306 | 28.149 | 1.00 | 41.04 |
| ATOM | 464 | C | LEU | 870 | 33.344 | 40.306 | 29.311 | 1.00 | 53.63 |
| ATOM | 465 | O | LEU | 870 | 32.163 | 40.615 | 29.037 | 1.00 | 52.68 |
| ATOM | 466 | N | LYS | 871 | 33.675 | 39.644 | 30.412 | 1.00 | 56.89 |
| ATOM | 468 | CA | LYS | 871 | 32.695 | 39.346 | 31.426 | 1.00 | 58.53 |
| ATOM | 469 | CB | LYS | 871 | 33.083 | 38.077 | 32.169 | 1.00 | 59.89 |

FIG. 7(10)

| | | | | | | | | |
|---|---|---|---|---|---|---|---|---|
| ATOM | 470 | CG | LYS | 871 | 31.903 | 37.220 | 32.546 | 1.00 63.81 |
| ATOM | 471 | CD | LYS | 871 | 31.912 | 35.965 | 31.719 | 1.00 65.43 |
| ATOM | 472 | CE | LYS | 871 | 33.268 | 35.318 | 31.853 | 1.00 70.59 |
| ATOM | 473 | NZ | LYS | 871 | 33.318 | 34.051 | 31.135 | 1.00 76.57 |
| ATOM | 477 | C | LYS | 871 | 32.649 | 40.518 | 32.404 | 1.00 59.44 |
| ATOM | 478 | O | LYS | 871 | 33.582 | 41.342 | 32.464 | 1.00 56.75 |
| ATOM | 479 | N | GLU | 872 | 31.566 | 40.571 | 33.177 | 1.00 61.50 |
| ATOM | 481 | CA | GLU | 872 | 31.357 | 41.618 | 34.177 | 1.00 64.12 |
| ATOM | 482 | CB | GLU | 872 | 29.928 | 41.539 | 34.739 | 1.00 66.85 |
| ATOM | 483 | CG | GLU | 872 | 28.846 | 41.903 | 33.729 | 1.00 71.27 |
| ATOM | 484 | CD | GLU | 872 | 29.060 | 41.218 | 32.387 | 1.00 74.41 |
| ATOM | 485 | OE1 | GLU | 872 | 28.900 | 39.980 | 32.326 | 1.00 76.27 |
| ATOM | 486 | OE2 | GLU | 872 | 29.443 | 41.903 | 31.411 | 1.00 74.20 |
| ATOM | 487 | C | GLU | 872 | 32.387 | 41.424 | 35.288 | 1.00 60.87 |
| ATOM | 488 | O | GLU | 872 | 32.331 | 40.441 | 36.026 | 1.00 61.34 |
| ATOM | 489 | N | GLY | 873 | 33.368 | 42.319 | 35.335 | 1.00 57.40 |
| ATOM | 491 | CA | GLY | 873 | 34.408 | 42.223 | 36.337 | 1.00 53.93 |
| ATOM | 492 | C | GLY | 873 | 35.703 | 41.641 | 35.803 | 1.00 52.30 |
| ATOM | 493 | O | GLY | 873 | 36.518 | 41.103 | 36.563 | 1.00 51.95 |
| ATOM | 494 | N | ALA | 874 | 35.881 | 41.721 | 34.491 | 1.00 51.13 |
| ATOM | 496 | CA | ALA | 874 | 37.090 | 41.217 | 33.862 | 1.00 51.21 |
| ATOM | 497 | CB | ALA | 874 | 36.875 | 41.049 | 32.335 | 1.00 48.57 |
| ATOM | 498 | C | ALA | 874 | 38.270 | 42.172 | 34.199 | 1.00 50.40 |
| ATOM | 499 | O | ALA | 874 | 38.101 | 43.388 | 34.369 | 1.00 48.57 |
| ATOM | 500 | N | THR | 875 | 39.465 | 41.609 | 34.245 | 1.00 48.33 |
| ATOM | 502 | CA | THR | 875 | 40.657 | 42.334 | 34.617 | 1.00 51.59 |
| ATOM | 503 | CB | THR | 875 | 41.572 | 41.428 | 35.447 | 1.00 54.42 |
| ATOM | 504 | OG1 | THR | 875 | 42.677 | 42.184 | 35.937 | 1.00 60.69 |
| ATOM | 506 | CG2 | THR | 875 | 42.107 | 40.280 | 34.593 | 1.00 60.52 |
| ATOM | 507 | C | THR | 875 | 41.455 | 42.830 | 33.448 | 1.00 51.15 |
| ATOM | 508 | O | THR | 875 | 41.395 | 42.263 | 32.372 | 1.00 52.26 |
| ATOM | 509 | N | HIS | 876 | 42.343 | 43.770 | 33.733 | 1.00 53.93 |
| ATOM | 511 | CA | HIS | 876 | 43.215 | 44.392 | 32.737 | 1.00 55.68 |
| ATOM | 512 | CB | HIS | 876 | 44.170 | 45.383 | 33.419 | 1.00 54.06 |
| ATOM | 513 | CG | HIS | 876 | 45.609 | 44.980 | 33.361 | 1.00 56.52 |
| ATOM | 514 | CD2 | HIS | 876 | 46.595 | 45.314 | 32.487 | 1.00 56.83 |
| ATOM | 515 | ND1 | HIS | 876 | 46.191 | 44.149 | 34.297 | 1.00 60.22 |
| ATOM | 517 | CE1 | HIS | 876 | 47.472 | 43.992 | 34.009 | 1.00 62.12 |
| ATOM | 518 | NE2 | HIS | 876 | 47.739 | 44.689 | 32.916 | 1.00 59.66 |
| ATOM | 520 | C | HIS | 876 | 44.003 | 43.385 | 31.898 | 1.00 54.72 |
| ATOM | 521 | O | HIS | 876 | 44.510 | 43.712 | 30.810 | 1.00 54.08 |
| ATOM | 522 | N | SER | 877 | 44.167 | 42.189 | 32.434 | 1.00 52.07 |
| ATOM | 524 | CA | SER | 877 | 44.872 | 41.160 | 31.704 | 1.00 53.73 |

FIG. 7(11)

| | | | | | | | |
|---|---|---|---|---|---|---|---|
| ATOM | 525 | CB | SER | 877 | 45.622 | 40.256 | 32.669 | 1.00 57.58 |
| ATOM | 526 | OG | SER | 877 | 46.559 | 41.054 | 33.379 | 1.00 63.62 |
| ATOM | 528 | C | SER | 877 | 43.880 | 40.410 | 30.810 | 1.00 51.29 |
| ATOM | 529 | O | SER | 877 | 44.227 | 39.962 | 29.715 | 1.00 50.11 |
| ATOM | 530 | N | GLU | 878 | 42.629 | 40.320 | 31.246 | 1.00 47.72 |
| ATOM | 532 | CA | GLU | 878 | 41.620 | 39.696 | 30.410 | 1.00 45.39 |
| ATOM | 533 | CB | GLU | 878 | 40.335 | 39.483 | 31.201 | 1.00 48.19 |
| ATOM | 534 | CG | GLU | 878 | 40.383 | 38.191 | 32.013 | 1.00 60.86 |
| ATOM | 535 | CD | GLU | 878 | 39.304 | 38.086 | 33.092 | 1.00 68.27 |
| ATOM | 536 | OE1 | GLU | 878 | 38.448 | 37.162 | 33.027 | 1.00 70.85 |
| ATOM | 537 | OE2 | GLU | 878 | 39.336 | 38.911 | 34.029 | 1.00 67.92 |
| ATOM | 538 | C | GLU | 878 | 41.448 | 40.702 | 29.277 | 1.00 40.09 |
| ATOM | 539 | O | GLU | 878 | 41.536 | 40.365 | 28.104 | 1.00 38.92 |
| ATOM | 540 | N | HIS | 879 | 41.393 | 41.966 | 29.659 | 1.00 34.60 |
| ATOM | 542 | CA | HIS | 879 | 41.252 | 43.072 | 28.732 | 1.00 36.68 |
| ATOM | 543 | CB | HIS | 879 | 41.070 | 44.392 | 29.505 | 1.00 44.03 |
| ATOM | 544 | CG | HIS | 879 | 40.637 | 45.547 | 28.652 | 1.00 43.54 |
| ATOM | 545 | CD2 | HIS | 879 | 39.403 | 46.025 | 28.364 | 1.00 40.08 |
| ATOM | 546 | ND1 | HIS | 879 | 41.529 | 46.307 | 27.917 | 1.00 39.08 |
| ATOM | 548 | CE1 | HIS | 879 | 40.860 | 47.192 | 27.202 | 1.00 40.82 |
| ATOM | 549 | NE2 | HIS | 879 | 39.572 | 47.045 | 27.452 | 1.00 49.01 |
| ATOM | 551 | C | HIS | 879 | 42.455 | 43.172 | 27.797 | 1.00 34.17 |
| ATOM | 552 | O | HIS | 879 | 42.293 | 43.494 | 26.626 | 1.00 33.65 |
| ATOM | 553 | N | ARG | 880 | 43.664 | 42.993 | 28.319 | 1.00 33.25 |
| ATOM | 555 | CA | ARG | 880 | 44.838 | 43.033 | 27.470 | 1.00 29.84 |
| ATOM | 556 | CB | ARG | 880 | 46.124 | 42.932 | 28.299 | 1.00 36.53 |
| ATOM | 557 | CG | ARG | 880 | 46.615 | 41.470 | 28.452 | 1.00 50.57 |
| ATOM | 558 | CD | ARG | 880 | 48.121 | 41.276 | 28.649 | 1.00 56.95 |
| ATOM | 559 | NE | ARG | 880 | 48.555 | 41.748 | 29.960 | 1.00 63.99 |
| ATOM | 561 | CZ | ARG | 880 | 49.030 | 42.967 | 30.175 | 1.00 66.67 |
| ATOM | 562 | NH1 | ARG | 880 | 49.391 | 43.327 | 31.397 | 1.00 66.45 |
| ATOM | 565 | NH2 | ARG | 880 | 49.170 | 43.813 | 29.157 | 1.00 66.52 |
| ATOM | 568 | C | ARG | 880 | 44.741 | 41.799 | 26.533 | 1.00 29.72 |
| ATOM | 569 | O | ARG | 880 | 45.246 | 41.808 | 25.401 | 1.00 21.81 |
| ATOM | 570 | N | ALA | 881 | 44.070 | 40.747 | 27.006 | 1.00 28.49 |
| ATOM | 572 | CA | ALA | 881 | 43.942 | 39.514 | 26.227 | 1.00 31.72 |
| ATOM | 573 | CB | ALA | 881 | 43.587 | 38.342 | 27.142 | 1.00 31.57 |
| ATOM | 574 | C | ALA | 881 | 42.978 | 39.592 | 25.044 | 1.00 29.98 |
| ATOM | 575 | O | ALA | 881 | 43.319 | 39.154 | 23.944 | 1.00 31.95 |
| ATOM | 576 | N | LEU | 882 | 41.766 | 40.099 | 25.273 | 1.00 27.12 |
| ATOM | 578 | CA | LEU | 882 | 40.804 | 40.248 | 24.193 | 1.00 27.43 |
| ATOM | 579 | CB | LEU | 882 | 39.493 | 40.784 | 24.728 | 1.00 23.93 |
| ATOM | 580 | CG | LEU | 882 | 38.402 | 40.925 | 23.662 | 1.00 25.91 |

FIG. 7(12)

| ATOM | 581 | CD1 | LEU | 882 | 38.435 | 39.722 | 22.743 | 1.00 | 21.91 |
|---|---|---|---|---|---|---|---|---|---|
| ATOM | 582 | CD2 | LEU | 882 | 37.013 | 41.102 | 24.325 | 1.00 | 23.61 |
| ATOM | 583 | C | LEU | 882 | 41.368 | 41.230 | 23.151 | 1.00 | 30.62 |
| ATOM | 584 | O | LEU | 882 | 41.312 | 40.982 | 21.945 | 1.00 | 27.61 |
| ATOM | 585 | N | MET | 883 | 41.940 | 42.325 | 23.643 | 1.00 | 29.74 |
| ATOM | 587 | CA | MET | 883 | 42.548 | 43.364 | 22.808 | 1.00 | 30.75 |
| ATOM | 588 | CB | MET | 883 | 43.001 | 44.516 | 23.738 | 1.00 | 27.47 |
| ATOM | 589 | CG | MET | 883 | 43.432 | 45.828 | 23.084 | 1.00 | 33.64 |
| ATOM | 590 | SD | MET | 883 | 42.313 | 46.592 | 21.882 | 1.00 | 33.18 |
| ATOM | 591 | CE | MET | 883 | 41.031 | 47.285 | 22.943 | 1.00 | 33.54 |
| ATOM | 592 | C | MET | 883 | 43.711 | 42.756 | 21.965 | 1.00 | 29.92 |
| ATOM | 593 | O | MET | 883 | 43.862 | 43.022 | 20.766 | 1.00 | 28.38 |
| ATOM | 594 | N | SER | 884 | 44.501 | 41.893 | 22.588 | 1.00 | 29.75 |
| ATOM | 596 | CA | SER | 884 | 45.597 | 41.231 | 21.912 | 1.00 | 28.29 |
| ATOM | 597 | CB | SER | 884 | 46.343 | 40.391 | 22.923 | 1.00 | 32.03 |
| ATOM | 598 | OG | SER | 884 | 47.220 | 39.502 | 22.270 | 1.00 | 44.59 |
| ATOM | 600 | C | SER | 884 | 45.091 | 40.329 | 20.778 | 1.00 | 29.39 |
| ATOM | 601 | O | SER | 884 | 45.595 | 40.359 | 19.654 | 1.00 | 28.92 |
| ATOM | 602 | N | GLU | 885 | 44.084 | 39.526 | 21.071 | 1.00 | 25.33 |
| ATOM | 604 | CA | GLU | 885 | 43.559 | 38.661 | 20.058 | 1.00 | 27.47 |
| ATOM | 605 | CB | GLU | 885 | 42.563 | 37.692 | 20.661 | 1.00 | 31.61 |
| ATOM | 606 | CG | GLU | 885 | 41.142 | 38.108 | 20.642 | 1.00 | 46.01 |
| ATOM | 607 | CD | GLU | 885 | 40.215 | 36.903 | 20.799 | 1.00 | 55.19 |
| ATOM | 608 | OE1 | GLU | 885 | 40.018 | 36.469 | 21.964 | 1.00 | 58.80 |
| ATOM | 609 | OE2 | GLU | 885 | 39.715 | 36.379 | 19.762 | 1.00 | 54.01 |
| ATOM | 610 | C | GLU | 885 | 42.945 | 39.470 | 18.924 | 1.00 | 28.59 |
| ATOM | 611 | O | GLU | 885 | 42.833 | 38.983 | 17.805 | 1.00 | 26.67 |
| ATOM | 612 | N | LEU | 886 | 42.560 | 40.712 | 19.211 | 1.00 | 27.06 |
| ATOM | 614 | CA | LEU | 886 | 41.994 | 41.594 | 18.205 | 1.00 | 23.75 |
| ATOM | 615 | CB | LEU | 886 | 41.483 | 42.887 | 18.847 | 1.00 | 22.79 |
| ATOM | 616 | CG | LEU | 886 | 41.122 | 44.033 | 17.905 | 1.00 | 17.60 |
| ATOM | 617 | CD1 | LEU | 886 | 39.981 | 43.608 | 16.999 | 1.00 | 11.98 |
| ATOM | 618 | CD2 | LEU | 886 | 40.747 | 45.285 | 18.702 | 1.00 | 18.31 |
| ATOM | 619 | C | LEU | 886 | 43.049 | 41.936 | 17.147 | 1.00 | 24.77 |
| ATOM | 620 | O | LEU | 886 | 42.767 | 41.880 | 15.939 | 1.00 | 22.15 |
| ATOM | 621 | N | LYS | 887 | 44.265 | 42.246 | 17.602 | 1.00 | 25.08 |
| ATOM | 623 | CA | LYS | 887 | 45.384 | 42.613 | 16.722 | 1.00 | 24.94 |
| ATOM | 624 | CB | LYS | 887 | 46.517 | 43.227 | 17.544 | 1.00 | 29.70 |
| ATOM | 625 | CG | LYS | 887 | 46.105 | 44.304 | 18.560 | 1.00 | 30.67 |
| ATOM | 626 | CD | LYS | 887 | 45.556 | 45.551 | 17.895 | 1.00 | 28.99 |
| ATOM | 627 | CE | LYS | 887 | 45.170 | 46.645 | 18.923 | 1.00 | 26.07 |
| ATOM | 628 | NZ | LYS | 887 | 46.354 | 47.216 | 19.621 | 1.00 | 17.59 |
| ATOM | 632 | C | LYS | 887 | 45.921 | 41.407 | 15.925 | 1.00 | 25.59 |

FIG. 7(13)

| | | | | | | | |
|---|---|---|---|---|---|---|---|
| ATOM | 633 | O | LYS | 887 | 46.388 | 41.547 | 14.793 | 1.00 30.23 |
| ATOM | 634 | N | ILE | 888 | 45.917 | 40.235 | 16.542 | 1.00 20.48 |
| ATOM | 636 | CA | ILE | 888 | 46.347 | 39.028 | 15.859 | 1.00 21.46 |
| ATOM | 637 | CB | ILE | 888 | 46.306 | 37.795 | 16.816 | 1.00 22.73 |
| ATOM | 638 | CG2 | ILE | 888 | 46.604 | 36.556 | 16.047 | 1.00 24.05 |
| ATOM | 639 | CG1 | ILE | 888 | 47.355 | 37.929 | 17.937 | 1.00 23.32 |
| ATOM | 640 | CD1 | ILE | 888 | 47.092 | 37.058 | 19.190 | 1.00 18.29 |
| ATOM | 641 | C | ILE | 888 | 45.392 | 38.822 | 14.663 | 1.00 19.51 |
| ATOM | 642 | O | ILE | 888 | 45.834 | 38.710 | 13.529 | 1.00 19.15 |
| ATOM | 643 | N | LEU | 889 | 44.088 | 38.828 | 14.922 | 1.00 15.54 |
| ATOM | 645 | CA | LEU | 889 | 43.078 | 38.677 | 13.872 | 1.00 20.73 |
| ATOM | 646 | CB | LEU | 889 | 41.658 | 38.818 | 14.446 | 1.00 19.41 |
| ATOM | 647 | CG | LEU | 889 | 41.204 | 37.652 | 15.372 | 1.00 22.61 |
| ATOM | 648 | CD1 | LEU | 889 | 39.735 | 37.752 | 15.697 | 1.00 13.49 |
| ATOM | 649 | CD2 | LEU | 889 | 41.500 | 36.263 | 14.764 | 1.00 18.87 |
| ATOM | 650 | C | LEU | 889 | 43.308 | 39.678 | 12.762 | 1.00 24.12 |
| ATOM | 651 | O | LEU | 889 | 43.342 | 39.344 | 11.584 | 1.00 28.65 |
| ATOM | 652 | N | ILE | 890 | 43.461 | 40.931 | 13.138 | 1.00 29.62 |
| ATOM | 654 | CA | ILE | 890 | 43.753 | 41.953 | 12.158 | 1.00 26.41 |
| ATOM | 655 | CB | ILE | 890 | 43.966 | 43.310 | 12.865 | 1.00 24.45 |
| ATOM | 656 | CG2 | ILE | 890 | 44.555 | 44.333 | 11.888 | 1.00 30.36 |
| ATOM | 657 | CG1 | ILE | 890 | 42.645 | 43.825 | 13.438 | 1.00 19.80 |
| ATOM | 658 | CD1 | ILE | 890 | 42.812 | 45.061 | 14.241 | 1.00 14.93 |
| ATOM | 659 | C | ILE | 890 | 45.053 | 41.519 | 11.415 | 1.00 28.37 |
| ATOM | 660 | O | ILE | 890 | 45.126 | 41.553 | 10.191 | 1.00 24.83 |
| ATOM | 661 | N | HIS | 891 | 46.066 | 41.099 | 12.164 | 1.00 27.37 |
| ATOM | 663 | CA | HIS | 891 | 47.309 | 40.659 | 11.567 | 1.00 27.76 |
| ATOM | 664 | CB | HIS | 891 | 48.277 | 40.175 | 12.654 | 1.00 36.80 |
| ATOM | 665 | CG | HIS | 891 | 49.509 | 39.507 | 12.100 | 1.00 47.58 |
| ATOM | 666 | CD2 | HIS | 891 | 50.811 | 39.869 | 12.147 | 1.00 46.38 |
| ATOM | 667 | ND1 | HIS | 891 | 49.450 | 38.394 | 11.276 | 1.00 52.71 |
| ATOM | 669 | CE1 | HIS | 891 | 50.660 | 38.114 | 10.825 | 1.00 50.46 |
| ATOM | 670 | NE2 | HIS | 891 | 51.505 | 38.993 | 11.340 | 1.00 54.62 |
| ATOM | 672 | C | HIS | 891 | 47.098 | 39.536 | 10.537 | 1.00 27.01 |
| ATOM | 673 | O | HIS | 891 | 47.522 | 39.647 | 9.402 | 1.00 32.82 |
| ATOM | 674 | N | ILE | 892 | 46.580 | 38.403 | 10.995 | 1.00 24.99 |
| ATOM | 676 | CA | ILE | 892 | 46.300 | 37.216 | 10.181 | 1.00 23.19 |
| ATOM | 677 | CB | ILE | 892 | 45.233 | 36.282 | 10.907 | 1.00 24.73 |
| ATOM | 678 | CG2 | ILE | 892 | 44.643 | 35.295 | 9.941 | 1.00 20.03 |
| ATOM | 679 | CG1 | ILE | 892 | 45.828 | 35.522 | 12.104 | 1.00 26.32 |
| ATOM | 680 | CD1 | ILE | 892 | 47.015 | 36.222 | 12.787 | 1.00 36.72 |
| ATOM | 681 | C | ILE | 892 | 45.700 | 37.625 | 8.848 | 1.00 22.57 |
| ATOM | 682 | O | ILE | 892 | 46.115 | 37.155 | 7.775 | 1.00 25.20 |

FIG. 7(14)

| | | | | | | | |
|---|---|---|---|---|---|---|---|
| ATOM | 683 | N | GLY | 893 | 44.699 | 38.492 | 8.916 | 1.00 | 23.88 |
| ATOM | 685 | CA | GLY | 893 | 44.034 | 38.910 | 7.702 | 1.00 | 25.37 |
| ATOM | 686 | C | GLY | 893 | 42.794 | 38.080 | 7.403 | 1.00 | 25.54 |
| ATOM | 687 | O | GLY | 893 | 42.303 | 37.326 | 8.224 | 1.00 | 32.60 |
| ATOM | 688 | N | HIS | 894 | 42.327 | 38.149 | 6.176 | 1.00 | 26.97 |
| ATOM | 690 | CA | HIS | 894 | 41.120 | 37.457 | 5.797 | 1.00 | 26.35 |
| ATOM | 691 | CB | HIS | 894 | 40.233 | 38.464 | 5.042 | 1.00 | 31.72 |
| ATOM | 692 | CG | HIS | 894 | 39.114 | 37.833 | 4.274 | 1.00 | 35.68 |
| ATOM | 693 | CD2 | HIS | 894 | 37.818 | 37.609 | 4.608 | 1.00 | 34.18 |
| ATOM | 694 | ND1 | HIS | 894 | 39.271 | 37.346 | 2.989 | 1.00 | 38.36 |
| ATOM | 696 | CE1 | HIS | 894 | 38.121 | 36.854 | 2.568 | 1.00 | 36.24 |
| ATOM | 697 | NE2 | HIS | 894 | 37.224 | 37.004 | 3.527 | 1.00 | 35.86 |
| ATOM | 699 | C | HIS | 894 | 41.253 | 36.182 | 4.958 | 1.00 | 24.38 |
| ATOM | 700 | O | HIS | 894 | 42.045 | 36.108 | 4.007 | 1.00 | 24.24 |
| ATOM | 701 | N | HIS | 895 | 40.426 | 35.202 | 5.280 | 1.00 | 17.00 |
| ATOM | 703 | CA | HIS | 895 | 40.379 | 33.994 | 4.494 | 1.00 | 18.62 |
| ATOM | 704 | CB | HIS | 895 | 41.363 | 32.929 | 4.931 | 1.00 | 15.85 |
| ATOM | 705 | CG | HIS | 895 | 41.446 | 31.814 | 3.943 | 1.00 | 21.47 |
| ATOM | 706 | CD2 | HIS | 895 | 42.076 | 31.737 | 2.745 | 1.00 | 17.93 |
| ATOM | 707 | ND1 | HIS | 895 | 40.675 | 30.676 | 4.042 | 1.00 | 21.96 |
| ATOM | 709 | CE1 | HIS | 895 | 40.819 | 29.956 | 2.938 | 1.00 | 21.22 |
| ATOM | 710 | NE2 | HIS | 895 | 41.663 | 30.578 | 2.137 | 1.00 | 10.16 |
| ATOM | 712 | C | HIS | 895 | 38.979 | 33.467 | 4.626 | 1.00 | 15.66 |
| ATOM | 713 | O | HIS | 895 | 38.396 | 33.656 | 5.663 | 1.00 | 18.76 |
| ATOM | 714 | N | LEU | 896 | 38.419 | 32.865 | 3.567 | 1.00 | 21.74 |
| ATOM | 716 | CA | LEU | 896 | 37.042 | 32.306 | 3.584 | 1.00 | 18.37 |
| ATOM | 717 | CB | LEU | 896 | 36.652 | 31.762 | 2.210 | 1.00 | 17.64 |
| ATOM | 718 | CG | LEU | 896 | 35.297 | 31.068 | 2.218 | 1.00 | 25.15 |
| ATOM | 719 | CD1 | LEU | 896 | 34.218 | 32.077 | 2.454 | 1.00 | 24.41 |
| ATOM | 720 | CD2 | LEU | 896 | 35.042 | 30.342 | 0.934 | 1.00 | 25.59 |
| ATOM | 721 | C | LEU | 896 | 36.867 | 31.172 | 4.569 | 1.00 | 17.58 |
| ATOM | 722 | O | LEU | 896 | 35.783 | 30.937 | 5.068 | 1.00 | 23.11 |
| ATOM | 723 | N | ASN | 897 | 37.952 | 30.475 | 4.849 | 1.00 | 15.99 |
| ATOM | 725 | CA | ASN | 897 | 37.878 | 29.340 | 5.725 | 1.00 | 18.36 |
| ATOM | 726 | CB | ASN | 897 | 38.589 | 28.134 | 5.078 | 1.00 | 20.86 |
| ATOM | 727 | CG | ASN | 897 | 37.928 | 27.689 | 3.747 | 1.00 | 16.88 |
| ATOM | 728 | OD1 | ASN | 897 | 38.567 | 27.692 | 2.694 | 1.00 | 14.51 |
| ATOM | 729 | ND2 | ASN | 897 | 36.639 | 27.346 | 3.799 | 1.00 | 12.11 |
| ATOM | 732 | C | ASN | 897 | 38.293 | 29.541 | 7.188 | 1.00 | 25.65 |
| ATOM | 733 | O | ASN | 897 | 38.648 | 28.556 | 7.858 | 1.00 | 22.22 |
| ATOM | 734 | N | VAL | 898 | 38.357 | 30.800 | 7.660 | 1.00 | 23.53 |
| ATOM | 736 | CA | VAL | 898 | 38.631 | 31.079 | 9.081 | 1.00 | 15.38 |
| ATOM | 737 | CB | VAL | 898 | 40.036 | 31.719 | 9.457 | 1.00 | 11.47 |

FIG. 7(15)

| | | | | | | | | |
|---|---|---|---|---|---|---|---|---|
| ATOM | 738 | CG1 | VAL | 898 | 41.146 | 30.813 | 9.017 | 1.00 14.76 |
| ATOM | 739 | CG2 | VAL | 898 | 40.236 | 33.119 | 8.883 | 1.00 8.71 |
| ATOM | 740 | C | VAL | 898 | 37.475 | 31.959 | 9.477 | 1.00 15.57 |
| ATOM | 741 | O | VAL | 898 | 36.698 | 32.382 | 8.620 | 1.00 17.87 |
| ATOM | 742 | N | VAL | 899 | 37.226 | 32.049 | 10.773 | 1.00 18.55 |
| ATOM | 744 | CA | VAL | 899 | 36.155 | 32.882 | 11.264 | 1.00 20.68 |
| ATOM | 745 | CB | VAL | 899 | 35.757 | 32.487 | 12.720 | 1.00 19.98 |
| ATOM | 746 | CG1 | VAL | 899 | 34.618 | 33.384 | 13.202 | 1.00 18.29 |
| ATOM | 747 | CG2 | VAL | 899 | 35.346 | 31.016 | 12.788 | 1.00 12.67 |
| ATOM | 748 | C | VAL | 899 | 36.807 | 34.272 | 11.244 | 1.00 21.95 |
| ATOM | 749 | O | VAL | 899 | 37.725 | 34.517 | 12.003 | 1.00 21.42 |
| ATOM | 750 | N | ASN | 900 | 36.352 | 35.164 | 10.363 | 1.00 23.43 |
| ATOM | 752 | CA | ASN | 900 | 36.930 | 36.526 | 10.226 | 1.00 23.52 |
| ATOM | 753 | CB | ASN | 900 | 36.737 | 37.061 | 8.803 | 1.00 19.45 |
| ATOM | 754 | CG | ASN | 900 | 37.350 | 36.177 | 7.782 | 1.00 19.58 |
| ATOM | 755 | OD1 | ASN | 900 | 38.578 | 36.087 | 7.667 | 1.00 17.65 |
| ATOM | 756 | ND2 | ASN | 900 | 36.511 | 35.528 | 7.004 | 1.00 20.34 |
| ATOM | 759 | C | ASN | 900 | 36.484 | 37.641 | 11.152 | 1.00 17.00 |
| ATOM | 760 | O | ASN | 900 | 35.343 | 37.704 | 11.598 | 1.00 16.94 |
| ATOM | 761 | N | LEU | 901 | 37.413 | 38.544 | 11.384 | 1.00 17.25 |
| ATOM | 763 | CA | LEU | 901 | 37.167 | 39.733 | 12.160 | 1.00 17.98 |
| ATOM | 764 | CB | LEU | 901 | 38.494 | 40.447 | 12.426 | 1.00 16.80 |
| ATOM | 765 | CG | LEU | 901 | 38.444 | 41.819 | 13.101 | 1.00 14.17 |
| ATOM | 766 | CD1 | LEU | 901 | 38.018 | 41.673 | 14.560 | 1.00 11.71 |
| ATOM | 767 | CD2 | LEU | 901 | 39.782 | 42.435 | 13.008 | 1.00 2.76 |
| ATOM | 768 | C | LEU | 901 | 36.354 | 40.578 | 11.174 | 1.00 20.28 |
| ATOM | 769 | O | LEU | 901 | 36.669 | 40.612 | 9.965 | 1.00 18.06 |
| ATOM | 770 | N | LEU | 902 | 35.280 | 41.180 | 11.686 | 1.00 19.74 |
| ATOM | 772 | CA | LEU | 902 | 34.398 | 42.031 | 10.917 | 1.00 15.84 |
| ATOM | 773 | CB | LEU | 902 | 32.950 | 41.593 | 11.087 | 1.00 11.70 |
| ATOM | 774 | CG | LEU | 902 | 32.615 | 40.230 | 10.473 | 1.00 13.49 |
| ATOM | 775 | CD1 | LEU | 902 | 31.142 | 39.827 | 10.774 | 1.00 13.78 |
| ATOM | 776 | CD2 | LEU | 902 | 32.856 | 40.270 | 8.981 | 1.00 12.15 |
| ATOM | 777 | C | LEU | 902 | 34.566 | 43.486 | 11.345 | 1.00 19.59 |
| ATOM | 778 | O | LEU | 902 | 34.466 | 44.380 | 10.510 | 1.00 23.95 |
| ATOM | 779 | N | GLY | 903 | 34.854 | 43.724 | 12.625 | 1.00 20.15 |
| ATOM | 781 | CA | GLY | 903 | 35.037 | 45.090 | 13.114 | 1.00 21.60 |
| ATOM | 782 | C | GLY | 903 | 35.147 | 45.075 | 14.620 | 1.00 24.02 |
| ATOM | 783 | O | GLY | 903 | 35.070 | 43.991 | 15.194 | 1.00 26.53 |
| ATOM | 784 | N | ALA | 904 | 35.305 | 46.236 | 15.269 | 1.00 25.19 |
| ATOM | 786 | CA | ALA | 904 | 35.411 | 46.293 | 16.740 | 1.00 18.80 |
| ATOM | 787 | CB | ALA | 904 | 36.830 | 46.074 | 17.177 | 1.00 12.62 |
| ATOM | 788 | C | ALA | 904 | 34.886 | 47.559 | 17.386 | 1.00 20.83 |

FIG. 7(16)

| | | | | | | | | |
|---|---|---|---|---|---|---|---|---|
| ATOM | 789 | O | ALA | 904 | 34.789 | 48.616 | 16.765 | 1.00 26.12 |
| ATOM | 790 | N | CYS | 905 | 34.617 | 47.443 | 18.674 | 1.00 21.21 |
| ATOM | 792 | CA | CYS | 905 | 34.128 | 48.530 | 19.493 | 1.00 19.91 |
| ATOM | 793 | CB | CYS | 905 | 32.804 | 48.160 | 20.115 | 1.00 16.08 |
| ATOM | 794 | SG | CYS | 905 | 31.561 | 47.894 | 18.851 | 1.00 15.32 |
| ATOM | 795 | C | CYS | 905 | 35.176 | 48.687 | 20.556 | 1.00 23.00 |
| ATOM | 796 | O | CYS | 905 | 35.245 | 47.890 | 21.486 | 1.00 24.21 |
| ATOM | 797 | N | THR | 906 | 36.042 | 49.674 | 20.361 | 1.00 26.02 |
| ATOM | 799 | CA | THR | 906 | 37.140 | 49.945 | 21.283 | 1.00 29.46 |
| ATOM | 800 | CB | THR | 906 | 38.514 | 49.768 | 20.574 | 1.00 26.67 |
| ATOM | 801 | OG1 | THR | 906 | 38.635 | 50.739 | 19.526 | 1.00 29.06 |
| ATOM | 803 | CG2 | THR | 906 | 38.648 | 48.363 | 20.001 | 1.00 23.13 |
| ATOM | 804 | C | THR | 906 | 37.130 | 51.346 | 21.928 | 1.00 30.07 |
| ATOM | 805 | O | THR | 906 | 37.642 | 51.522 | 23.036 | 1.00 29.29 |
| ATOM | 806 | N | LYS | 907 | 36.582 | 52.332 | 21.228 | 1.00 32.81 |
| ATOM | 808 | CA | LYS | 907 | 36.554 | 53.686 | 21.745 | 1.00 39.38 |
| ATOM | 809 | CB | LYS | 907 | 35.982 | 54.637 | 20.701 | 1.00 41.03 |
| ATOM | 810 | CG | LYS | 907 | 34.536 | 54.432 | 20.386 | 1.00 48.86 |
| ATOM | 811 | CD | LYS | 907 | 34.071 | 55.528 | 19.427 | 1.00 57.25 |
| ATOM | 812 | CE | LYS | 907 | 33.996 | 56.878 | 20.143 | 1.00 63.62 |
| ATOM | 813 | NZ | LYS | 907 | 33.688 | 58.001 | 19.213 | 1.00 68.81 |
| ATOM | 817 | C | LYS | 907 | 35.796 | 53.779 | 23.070 | 1.00 44.43 |
| ATOM | 818 | O | LYS | 907 | 35.094 | 52.867 | 23.442 | 1.00 44.52 |
| ATOM | 819 | N | PRO | 908 | 36.034 | 54.838 | 23.857 | 1.00 49.18 |
| ATOM | 820 | CD | PRO | 908 | 37.147 | 55.794 | 23.712 | 1.00 50.93 |
| ATOM | 821 | CA | PRO | 908 | 35.358 | 55.022 | 25.149 | 1.00 46.86 |
| ATOM | 822 | CB | PRO | 908 | 35.963 | 56.324 | 25.647 | 1.00 49.68 |
| ATOM | 823 | CG | PRO | 908 | 37.387 | 56.216 | 25.143 | 1.00 51.43 |
| ATOM | 824 | C | PRO | 908 | 33.852 | 55.145 | 25.036 | 1.00 44.06 |
| ATOM | 825 | O | PRO | 908 | 33.345 | 55.600 | 24.008 | 1.00 44.40 |
| ATOM | 826 | N | GLY | 909 | 33.154 | 54.772 | 26.110 | 1.00 41.44 |
| ATOM | 828 | CA | GLY | 909 | 31.698 | 54.842 | 26.135 | 1.00 37.38 |
| ATOM | 829 | C | GLY | 909 | 30.999 | 53.502 | 26.035 | 1.00 38.26 |
| ATOM | 830 | O | GLY | 909 | 29.778 | 53.439 | 25.751 | 1.00 40.07 |
| ATOM | 831 | N | GLY | 910 | 31.753 | 52.424 | 26.264 | 1.00 36.39 |
| ATOM | 833 | CA | GLY | 910 | 31.178 | 51.087 | 26.190 | 1.00 34.35 |
| ATOM | 834 | C | GLY | 910 | 32.180 | 49.961 | 26.360 | 1.00 31.85 |
| ATOM | 835 | O | GLY | 910 | 33.394 | 50.235 | 26.528 | 1.00 27.95 |
| ATOM | 836 | N | PRO | 911 | 31.710 | 48.686 | 26.319 | 1.00 27.95 |
| ATOM | 837 | CD | PRO | 911 | 30.280 | 48.339 | 26.197 | 1.00 28.51 |
| ATOM | 838 | CA | PRO | 911 | 32.511 | 47.463 | 26.467 | 1.00 25.21 |
| ATOM | 839 | CB | PRO | 911 | 31.438 | 46.393 | 26.724 | 1.00 27.44 |
| ATOM | 840 | CG | PRO | 911 | 30.315 | 46.840 | 25.891 | 1.00 22.45 |

FIG. 7(17)

| ATOM | 841 | C | PRO | 911 | 33.340 | 47.118 | 25.234 | 1.00 | 22.33 |
|---|---|---|---|---|---|---|---|---|---|
| ATOM | 842 | O | PRO | 911 | 32.903 | 47.366 | 24.124 | 1.00 | 23.57 |
| ATOM | 843 | N | LEU | 912 | 34.548 | 46.581 | 25.430 | 1.00 | 22.75 |
| ATOM | 845 | CA | LEU | 912 | 35.412 | 46.177 | 24.308 | 1.00 | 23.22 |
| ATOM | 846 | CB | LEU | 912 | 36.778 | 45.685 | 24.812 | 1.00 | 23.67 |
| ATOM | 847 | CG | LEU | 912 | 38.095 | 45.759 | 24.005 | 1.00 | 24.34 |
| ATOM | 848 | CD1 | LEU | 912 | 38.988 | 44.618 | 24.490 | 1.00 | 20.11 |
| ATOM | 849 | CD2 | LEU | 912 | 37.906 | 45.745 | 22.477 | 1.00 | 12.72 |
| ATOM | 850 | C | LEU | 912 | 34.692 | 45.010 | 23.627 | 1.00 | 22.56 |
| ATOM | 851 | O | LEU | 912 | 34.342 | 44.029 | 24.283 | 1.00 | 17.69 |
| ATOM | 852 | N | MET | 913 | 34.417 | 45.142 | 22.334 | 1.00 | 24.19 |
| ATOM | 854 | CA | MET | 913 | 33.724 | 44.085 | 21.617 | 1.00 | 21.51 |
| ATOM | 855 | CB | MET | 913 | 32.264 | 44.456 | 21.429 | 1.00 | 22.09 |
| ATOM | 856 | CG | MET | 913 | 31.489 | 44.461 | 22.728 | 1.00 | 22.26 |
| ATOM | 857 | SD | MET | 913 | 29.829 | 45.009 | 22.484 | 1.00 | 24.17 |
| ATOM | 858 | CE | MET | 913 | 30.127 | 46.676 | 22.205 | 1.00 | 20.40 |
| ATOM | 859 | C | MET | 913 | 34.386 | 43.768 | 20.295 | 1.00 | 20.42 |
| ATOM | 860 | O | MET | 913 | 34.701 | 44.657 | 19.519 | 1.00 | 21.08 |
| ATOM | 861 | N | VAL | 914 | 34.703 | 42.491 | 20.102 | 1.00 | 23.72 |
| ATOM | 863 | CA | VAL | 914 | 35.354 | 42.001 | 18.891 | 1.00 | 20.24 |
| ATOM | 864 | CB | VAL | 914 | 36.614 | 41.170 | 19.232 | 1.00 | 16.92 |
| ATOM | 865 | CG1 | VAL | 914 | 37.254 | 40.637 | 17.958 | 1.00 | 19.36 |
| ATOM | 866 | CG2 | VAL | 914 | 37.629 | 42.055 | 19.972 | 1.00 | 13.30 |
| ATOM | 867 | C | VAL | 914 | 34.296 | 41.210 | 18.132 | 1.00 | 19.70 |
| ATOM | 868 | O | VAL | 914 | 33.836 | 40.191 | 18.587 | 1.00 | 26.45 |
| ATOM | 869 | N | ILE | 915 | 33.844 | 41.775 | 17.026 | 1.00 | 19.86 |
| ATOM | 871 | CA | ILE | 915 | 32.806 | 41.212 | 16.179 | 1.00 | 20.42 |
| ATOM | 872 | CB | ILE | 915 | 32.034 | 42.384 | 15.455 | 1.00 | 18.44 |
| ATOM | 873 | CG2 | ILE | 915 | 30.721 | 41.909 | 14.869 | 1.00 | 12.35 |
| ATOM | 874 | CG1 | ILE | 915 | 31.756 | 43.531 | 16.426 | 1.00 | 17.60 |
| ATOM | 875 | CD1 | ILE | 915 | 31.358 | 44.822 | 15.735 | 1.00 | 15.14 |
| ATOM | 876 | C | ILE | 915 | 33.457 | 40.287 | 15.115 | 1.00 | 23.98 |
| ATOM | 877 | O | ILE | 915 | 34.361 | 40.722 | 14.373 | 1.00 | 23.30 |
| ATOM | 878 | N | VAL | 916 | 33.054 | 39.011 | 15.075 | 1.00 | 20.08 |
| ATOM | 880 | CA | VAL | 916 | 33.594 | 38.089 | 14.077 | 1.00 | 17.64 |
| ATOM | 881 | CB | VAL | 916 | 34.543 | 37.003 | 14.680 | 1.00 | 9.09 |
| ATOM | 882 | CG1 | VAL | 916 | 35.703 | 37.685 | 15.350 | 1.00 | 5.05 |
| ATOM | 883 | CG2 | VAL | 916 | 33.817 | 36.126 | 15.678 | 1.00 | 10.26 |
| ATOM | 884 | C | VAL | 916 | 32.422 | 37.486 | 13.342 | 1.00 | 17.74 |
| ATOM | 885 | O | VAL | 916 | 31.275 | 37.790 | 13.664 | 1.00 | 20.02 |
| ATOM | 886 | N | GLU | 917 | 32.684 | 36.702 | 12.303 | 1.00 | 14.74 |
| ATOM | 888 | CA | GLU | 917 | 31.589 | 36.073 | 11.577 | 1.00 | 13.03 |
| ATOM | 889 | CB | GLU | 917 | 32.120 | 35.409 | 10.332 | 1.00 | 14.06 |

FIG. 7(18)

| ATOM | 890 | CG | GLU | 917 | 32.946 | 36.348 | 9.464 | 1.00 | 24.11 |
|------|-----|-----|-----|-----|--------|--------|-------|------|-------|
| ATOM | 891 | CD | GLU | 917 | 33.543 | 35.651 | 8.258 | 1.00 | 26.52 |
| ATOM | 892 | OE1 | GLU | 917 | 33.060 | 35.904 | 7.139 | 1.00 | 27.67 |
| ATOM | 893 | OE2 | GLU | 917 | 34.480 | 34.841 | 8.425 | 1.00 | 28.39 |
| ATOM | 894 | C | GLU | 917 | 30.853 | 35.051 | 12.434 | 1.00 | 14.78 |
| ATOM | 895 | O | GLU | 917 | 31.445 | 34.344 | 13.234 | 1.00 | 14.35 |
| ATOM | 896 | N | PHE | 918 | 29.557 | 34.958 | 12.229 | 1.00 | 19.12 |
| ATOM | 898 | CA | PHE | 918 | 28.688 | 34.042 | 12.966 | 1.00 | 18.07 |
| ATOM | 899 | CB | PHE | 918 | 27.334 | 34.721 | 13.168 | 1.00 | 18.48 |
| ATOM | 900 | CG | PHE | 918 | 26.275 | 33.840 | 13.748 | 1.00 | 17.83 |
| ATOM | 901 | CD1 | PHE | 918 | 26.328 | 33.456 | 15.081 | 1.00 | 18.65 |
| ATOM | 902 | CD2 | PHE | 918 | 25.213 | 33.400 | 12.953 | 1.00 | 21.10 |
| ATOM | 903 | CE1 | PHE | 918 | 25.336 | 32.639 | 15.613 | 1.00 | 18.12 |
| ATOM | 904 | CE2 | PHE | 918 | 24.210 | 32.580 | 13.473 | 1.00 | 14.29 |
| ATOM | 905 | CZ | PHE | 918 | 24.274 | 32.201 | 14.799 | 1.00 | 17.78 |
| ATOM | 906 | C | PHE | 918 | 28.487 | 32.805 | 12.113 | 1.00 | 18.83 |
| ATOM | 907 | O | PHE | 918 | 28.081 | 32.917 | 10.964 | 1.00 | 11.61 |
| ATOM | 908 | N | CYS | 919 | 28.761 | 31.635 | 12.676 | 1.00 | 19.49 |
| ATOM | 910 | CA | CYS | 919 | 28.590 | 30.372 | 11.947 | 1.00 | 19.00 |
| ATOM | 911 | CB | CYS | 919 | 29.855 | 29.566 | 12.069 | 1.00 | 16.78 |
| ATOM | 912 | SG | CYS | 919 | 31.225 | 30.428 | 11.325 | 1.00 | 16.84 |
| ATOM | 913 | C | CYS | 919 | 27.383 | 29.659 | 12.556 | 1.00 | 21.18 |
| ATOM | 914 | O | CYS | 919 | 27.474 | 29.135 | 13.676 | 1.00 | 20.69 |
| ATOM | 915 | N | LYS | 920 | 26.269 | 29.653 | 11.818 | 1.00 | 18.06 |
| ATOM | 917 | CA | LYS | 920 | 24.998 | 29.130 | 12.318 | 1.00 | 28.13 |
| ATOM | 918 | CB | LYS | 920 | 23.799 | 29.581 | 11.459 | 1.00 | 25.17 |
| ATOM | 919 | CG | LYS | 920 | 23.595 | 28.799 | 10.207 | 1.00 | 33.78 |
| ATOM | 920 | CD | LYS | 920 | 22.658 | 29.509 | 9.250 | 1.00 | 40.32 |
| ATOM | 921 | CE | LYS | 920 | 21.261 | 29.706 | 9.829 | 1.00 | 51.94 |
| ATOM | 922 | NZ | LYS | 920 | 20.343 | 30.396 | 8.845 | 1.00 | 56.09 |
| ATOM | 926 | C | LYS | 920 | 24.813 | 27.679 | 12.700 | 1.00 | 28.53 |
| ATOM | 927 | O | LYS | 920 | 24.020 | 27.405 | 13.592 | 1.00 | 31.57 |
| ATOM | 928 | N | PHE | 921 | 25.533 | 26.757 | 12.078 | 1.00 | 24.89 |
| ATOM | 930 | CA | PHE | 921 | 25.328 | 25.362 | 12.409 | 1.00 | 21.12 |
| ATOM | 931 | CB | PHE | 921 | 25.497 | 24.518 | 11.171 | 1.00 | 20.75 |
| ATOM | 932 | CG | PHE | 921 | 24.588 | 24.917 | 10.084 | 1.00 | 22.95 |
| ATOM | 933 | CD1 | PHE | 921 | 23.224 | 24.734 | 10.219 | 1.00 | 27.55 |
| ATOM | 934 | CD2 | PHE | 921 | 25.077 | 25.564 | 8.975 | 1.00 | 29.40 |
| ATOM | 935 | CE1 | PHE | 921 | 22.362 | 25.205 | 9.269 | 1.00 | 35.42 |
| ATOM | 936 | CE2 | PHE | 921 | 24.237 | 26.041 | 8.013 | 1.00 | 32.24 |
| ATOM | 937 | CZ | PHE | 921 | 22.869 | 25.870 | 8.154 | 1.00 | 38.81 |
| ATOM | 938 | C | PHE | 921 | 26.158 | 24.823 | 13.535 | 1.00 | 21.23 |
| ATOM | 939 | O | PHE | 921 | 26.002 | 23.664 | 13.900 | 1.00 | 22.74 |

FIG. 7(19)

| | | | | | | | | |
|---|---|---|---|---|---|---|---|---|
| ATOM | 940 | N | GLY | 922 | 27.047 | 25.659 | 14.065 | 1.00 18.39 |
| ATOM | 942 | CA | GLY | 922 | 27.906 | 25.257 | 15.172 | 1.00 17.62 |
| ATOM | 943 | C | GLY | 922 | 29.115 | 24.455 | 14.759 | 1.00 18.42 |
| ATOM | 944 | O | GLY | 922 | 29.331 | 24.230 | 13.581 | 1.00 20.81 |
| ATOM | 945 | N | ASN | 923 | 29.903 | 24.011 | 15.729 | 1.00 22.93 |
| ATOM | 947 | CA | ASN | 923 | 31.092 | 23.223 | 15.430 | 1.00 24.85 |
| ATOM | 948 | CB | ASN | 923 | 31.867 | 22.837 | 16.705 | 1.00 29.68 |
| ATOM | 949 | CG | ASN | 923 | 31.212 | 21.710 | 17.493 | 1.00 39.14 |
| ATOM | 950 | OD1 | ASN | 923 | 31.252 | 20.550 | 17.087 | 1.00 41.11 |
| ATOM | 951 | ND2 | ASN | 923 | 30.662 | 22.038 | 18.660 | 1.00 35.87 |
| ATOM | 954 | C | ASN | 923 | 30.818 | 22.019 | 14.523 | 1.00 21.09 |
| ATOM | 955 | O | ASN | 923 | 29.685 | 21.566 | 14.370 | 1.00 20.59 |
| ATOM | 956 | N | LEU | 924 | 31.867 | 21.523 | 13.896 | 1.00 21.13 |
| ATOM | 958 | CA | LEU | 924 | 31.740 | 20.431 | 12.957 | 1.00 22.85 |
| ATOM | 959 | CB | LEU | 924 | 33.019 | 20.377 | 12.126 | 1.00 23.67 |
| ATOM | 960 | CG | LEU | 924 | 33.019 | 19.462 | 10.920 | 1.00 17.22 |
| ATOM | 961 | CD1 | LEU | 924 | 31.776 | 19.699 | 10.125 | 1.00 18.21 |
| ATOM | 962 | CD2 | LEU | 924 | 34.268 | 19.729 | 10.095 | 1.00 23.82 |
| ATOM | 963 | C | LEU | 924 | 31.414 | 19.062 | 13.558 | 1.00 22.65 |
| ATOM | 964 | O | LEU | 924 | 30.601 | 18.326 | 13.013 | 1.00 26.13 |
| ATOM | 965 | N | SER | 925 | 31.035 | 18.742 | 14.687 | 1.00 20.06 |
| ATOM | 967 | CA | SER | 925 | 31.853 | 17.463 | 15.383 | 1.00 25.99 |
| ATOM | 968 | CB | SER | 925 | 32.741 | 17.400 | 16.623 | 1.00 27.28 |
| ATOM | 969 | OG | SER | 925 | 32.426 | 16.272 | 17.416 | 1.00 32.86 |
| ATOM | 971 | C | SER | 925 | 30.432 | 17.217 | 15.812 | 1.00 26.73 |
| ATOM | 972 | O | SER | 925 | 29.863 | 16.148 | 15.552 | 1.00 30.93 |
| ATOM | 973 | N | THR | 926 | 29.892 | 18.190 | 16.534 | 1.00 24.48 |
| ATOM | 975 | CA | THR | 926 | 28.535 | 18.129 | 16.996 | 1.00 19.27 |
| ATOM | 976 | CB | THR | 926 | 28.258 | 19.336 | 17.901 | 1.00 16.05 |
| ATOM | 977 | OG1 | THR | 926 | 29.230 | 19.374 | 18.951 | 1.00 18.42 |
| ATOM | 979 | CG2 | THR | 926 | 26.927 | 19.216 | 18.550 | 1.00 13.93 |
| ATOM | 980 | C | THR | 926 | 27.610 | 18.048 | 15.758 | 1.00 20.47 |
| ATOM | 981 | O | THR | 926 | 26.654 | 17.258 | 15.711 | 1.00 25.12 |
| ATOM | 982 | N | TYR | 927 | 27.961 | 18.760 | 14.701 | 1.00 18.97 |
| ATOM | 984 | CA | TYR | 927 | 27.128 | 18.715 | 13.515 | 1.00 20.97 |
| ATOM | 985 | CB | TYR | 927 | 27.597 | 19.720 | 12.464 | 1.00 18.52 |
| ATOM | 986 | CG | TYR | 927 | 26.708 | 19.683 | 11.230 | 1.00 18.69 |
| ATOM | 987 | CD1 | TYR | 927 | 25.391 | 20.196 | 11.266 | 1.00 14.64 |
| ATOM | 988 | CE1 | TYR | 927 | 24.567 | 20.173 | 10.125 | 1.00 13.73 |
| ATOM | 989 | CD2 | TYR | 927 | 27.173 | 19.138 | 10.031 | 1.00 22.28 |
| ATOM | 990 | CE2 | TYR | 927 | 26.347 | 19.104 | 8.879 | 1.00 24.92 |
| ATOM | 991 | CZ | TYR | 927 | 25.058 | 19.626 | 8.944 | 1.00 16.40 |
| ATOM | 992 | OH | TYR | 927 | 24.285 | 19.600 | 7.819 | 1.00 23.87 |

FIG. 7(20)

| | | | | | | | | |
|---|---|---|---|---|---|---|---|---|
| ATOM | 994  | C   | TYR | 927 | 27.118 | 17.343 | 12.855 | 1.00 23.85 |
| ATOM | 995  | O   | TYR | 927 | 26.078 | 16.860 | 12.428 | 1.00 24.11 |
| ATOM | 996  | N   | LEU | 928 | 28.313 | 16.793 | 12.665 | 1.00 28.91 |
| ATOM | 998  | CA  | LEU | 928 | 28.513 | 15.495 | 12.020 | 1.00 31.09 |
| ATOM | 999  | CB  | LEU | 928 | 30.017 | 15.192 | 11.863 | 1.00 27.50 |
| ATOM | 1000 | CG  | LEU | 928 | 30.813 | 16.159 | 10.953 | 1.00 24.21 |
| ATOM | 1001 | CD1 | LEU | 928 | 32.302 | 15.880 | 11.065 | 1.00 24.38 |
| ATOM | 1002 | CD2 | LEU | 928 | 30.343 | 16.097 |  9.514 | 1.00 12.63 |
| ATOM | 1003 | C   | LEU | 928 | 27.801 | 14.369 | 12.747 | 1.00 31.00 |
| ATOM | 1004 | O   | LEU | 928 | 27.164 | 13.540 | 12.117 | 1.00 31.53 |
| ATOM | 1005 | N   | ARG | 929 | 27.883 | 14.351 | 14.067 | 1.00 34.05 |
| ATOM | 1007 | CA  | ARG | 929 | 27.193 | 13.316 | 14.833 | 1.00 40.50 |
| ATOM | 1008 | CB  | ARG | 929 | 27.406 | 13.552 | 16.325 | 1.00 41.71 |
| ATOM | 1009 | CG  | ARG | 929 | 28.358 | 12.605 | 16.969 | 1.00 40.42 |
| ATOM | 1010 | CD  | ARG | 929 | 29.253 | 13.359 | 17.908 | 1.00 49.36 |
| ATOM | 1011 | NE  | ARG | 929 | 28.521 | 13.947 | 19.020 | 1.00 62.28 |
| ATOM | 1013 | CZ  | ARG | 929 | 28.946 | 14.985 | 19.749 | 1.00 65.86 |
| ATOM | 1014 | NH1 | ARG | 929 | 28.178 | 15.432 | 20.753 | 1.00 66.98 |
| ATOM | 1017 | NH2 | ARG | 929 | 30.122 | 15.573 | 19.492 | 1.00 58.39 |
| ATOM | 1020 | C   | ARG | 929 | 25.678 | 13.304 | 14.529 | 1.00 42.76 |
| ATOM | 1021 | O   | ARG | 929 | 25.075 | 12.234 | 14.370 | 1.00 44.84 |
| ATOM | 1022 | N   | SER | 930 | 25.089 | 14.498 | 14.412 | 1.00 41.42 |
| ATOM | 1024 | CA  | SER | 930 | 23.663 | 14.677 | 14.150 | 1.00 37.04 |
| ATOM | 1025 | CB  | SER | 930 | 23.324 | 16.151 | 14.250 | 1.00 38.80 |
| ATOM | 1026 | OG  | SER | 930 | 23.662 | 16.816 | 13.041 | 1.00 37.58 |
| ATOM | 1028 | C   | SER | 930 | 23.226 | 14.226 | 12.774 | 1.00 38.41 |
| ATOM | 1029 | O   | SER | 930 | 22.034 | 14.254 | 12.451 | 1.00 43.98 |
| ATOM | 1030 | N   | LYS | 931 | 24.179 | 13.865 | 11.936 | 1.00 37.60 |
| ATOM | 1032 | CA  | LYS | 931 | 23.845 | 13.472 | 10.590 | 1.00 38.82 |
| ATOM | 1033 | CB  | LYS | 931 | 24.575 | 14.387 |  9.606 | 1.00 43.10 |
| ATOM | 1034 | CG  | LYS | 931 | 24.388 | 15.864 |  9.884 | 1.00 45.62 |
| ATOM | 1035 | CD  | LYS | 931 | 22.999 | 16.302 |  9.487 | 1.00 49.49 |
| ATOM | 1036 | CE  | LYS | 931 | 22.901 | 16.444 |  7.985 | 1.00 46.94 |
| ATOM | 1037 | NZ  | LYS | 931 | 21.501 | 16.690 |  7.568 | 1.00 49.54 |
| ATOM | 1041 | C   | LYS | 931 | 24.136 | 12.011 | 10.264 | 1.00 39.02 |
| ATOM | 1042 | O   | LYS | 931 | 23.991 | 11.615 |  9.111 | 1.00 42.79 |
| ATOM | 1043 | N   | ARG | 932 | 24.522 | 11.199 | 11.247 | 1.00 37.44 |
| ATOM | 1045 | CA  | ARG | 932 | 24.793 |  9.776 | 10.971 | 1.00 38.33 |
| ATOM | 1046 | CB  | ARG | 932 | 25.149 |  9.020 | 12.244 | 1.00 33.55 |
| ATOM | 1047 | CG  | ARG | 932 | 26.456 |  9.461 | 12.798 | 1.00 33.92 |
| ATOM | 1048 | CD  | ARG | 932 | 26.812 |  8.729 | 14.043 | 1.00 35.88 |
| ATOM | 1049 | NE  | ARG | 932 | 28.223 |  8.929 | 14.368 | 1.00 43.26 |
| ATOM | 1051 | CZ  | ARG | 932 | 28.720 |  8.909 | 15.604 | 1.00 45.56 |

FIG. 7(21)

| | | | | | | | | |
|---|---|---|---|---|---|---|---|---|
| ATOM | 1052 | NH1 | ARG | 932 | 30.018 | 9.098 | 15.809 | 1.00 47.32 |
| ATOM | 1055 | NH2 | ARG | 932 | 27.916 | 8.725 | 16.645 | 1.00 53.04 |
| ATOM | 1058 | C | ARG | 932 | 23.621 | 9.087 | 10.273 | 1.00 41.54 |
| ATOM | 1059 | O | ARG | 932 | 23.821 | 8.135 | 9.532 | 1.00 41.31 |
| ATOM | 1060 | N | ASN | 933 | 22.412 | 9.582 | 10.536 | 1.00 44.37 |
| ATOM | 1062 | CA | ASN | 933 | 21.181 | 9.069 | 9.956 | 1.00 47.14 |
| ATOM | 1063 | CB | ASN | 933 | 19.974 | 9.453 | 10.824 | 1.00 54.55 |
| ATOM | 1064 | CG | ASN | 933 | 19.783 | 8.545 | 12.050 | 1.00 57.14 |
| ATOM | 1065 | OD1 | ASN | 933 | 20.622 | 7.693 | 12.369 | 1.00 54.11 |
| ATOM | 1066 | ND2 | ASN | 933 | 18.668 | 8.752 | 12.757 | 1.00 57.76 |
| ATOM | 1069 | C | ASN | 933 | 20.974 | 9.680 | 8.589 | 1.00 49.60 |
| ATOM | 1070 | O | ASN | 933 | 20.260 | 9.125 | 7.753 | 1.00 55.62 |
| ATOM | 1071 | N | GLU | 934 | 21.494 | 10.888 | 8.403 | 1.00 52.11 |
| ATOM | 1073 | CA | GLU | 934 | 21.365 | 11.580 | 7.122 | 1.00 52.39 |
| ATOM | 1074 | CB | GLU | 934 | 20.859 | 13.007 | 7.323 | 1.00 56.14 |
| ATOM | 1075 | CG | GLU | 934 | 19.434 | 13.095 | 7.822 | 1.00 59.40 |
| ATOM | 1076 | CD | GLU | 934 | 19.332 | 13.686 | 9.211 | 1.00 63.97 |
| ATOM | 1077 | OE1 | GLU | 934 | 18.427 | 13.250 | 9.953 | 1.00 69.17 |
| ATOM | 1078 | OE2 | GLU | 934 | 20.138 | 14.580 | 9.563 | 1.00 64.27 |
| ATOM | 1079 | C | GLU | 934 | 22.677 | 11.593 | 6.332 | 1.00 50.45 |
| ATOM | 1080 | O | GLU | 934 | 23.188 | 12.663 | 5.961 | 1.00 50.70 |
| ATOM | 1081 | N | PHE | 935 | 23.205 | 10.396 | 6.070 | 1.00 46.25 |
| ATOM | 1083 | CA | PHE | 935 | 24.440 | 10.225 | 5.325 | 1.00 41.20 |
| ATOM | 1084 | CB | PHE | 935 | 25.638 | 10.121 | 6.268 | 1.00 40.97 |
| ATOM | 1085 | CG | PHE | 935 | 26.923 | 9.800 | 5.555 | 1.00 39.81 |
| ATOM | 1086 | CD1 | PHE | 935 | 27.327 | 8.478 | 5.378 | 1.00 34.65 |
| ATOM | 1087 | CD2 | PHE | 935 | 27.676 | 10.815 | 4.970 | 1.00 33.02 |
| ATOM | 1088 | CE1 | PHE | 935 | 28.455 | 8.180 | 4.617 | 1.00 32.30 |
| ATOM | 1089 | CE2 | PHE | 935 | 28.793 | 10.515 | 4.218 | 1.00 29.96 |
| ATOM | 1090 | CZ | PHE | 935 | 29.181 | 9.201 | 4.037 | 1.00 29.08 |
| ATOM | 1091 | C | PHE | 935 | 24.474 | 9.006 | 4.412 | 1.00 40.49 |
| ATOM | 1092 | O | PHE | 935 | 24.394 | 7.871 | 4.865 | 1.00 40.47 |
| ATOM | 1093 | N | VAL | 936 | 24.694 | 9.237 | 3.133 | 1.00 38.66 |
| ATOM | 1095 | CA | VAL | 936 | 24.809 | 8.138 | 2.208 | 1.00 43.29 |
| ATOM | 1096 | CB | VAL | 936 | 23.663 | 8.113 | 1.221 | 1.00 40.39 |
| ATOM | 1097 | CG1 | VAL | 936 | 23.739 | 9.312 | 0.280 | 1.00 34.50 |
| ATOM | 1098 | CG2 | VAL | 936 | 23.720 | 6.841 | 0.444 | 1.00 42.47 |
| ATOM | 1099 | C | VAL | 936 | 26.087 | 8.436 | 1.438 | 1.00 49.63 |
| ATOM | 1100 | O | VAL | 936 | 26.322 | 9.585 | 1.081 | 1.00 55.64 |
| ATOM | 1101 | N | PRO | 937 | 26.960 | 7.433 | 1.222 | 1.00 50.29 |
| ATOM | 1102 | CD | PRO | 937 | 26.966 | 6.087 | 1.822 | 1.00 49.69 |
| ATOM | 1103 | CA | PRO | 937 | 28.207 | 7.669 | 0.483 | 1.00 50.65 |
| ATOM | 1104 | CB | PRO | 937 | 28.676 | 6.260 | 0.177 | 1.00 46.68 |

FIG. 7(22)

| | | | | | | | |
|---|---|---|---|---|---|---|---|
| ATOM | 1105 | CG | PRO | 937 | 28.378 | 5.582 | 1.493 1.00 47.42 |
| ATOM | 1106 | C | PRO | 937 | 28.019 | 8.501 | -0.774 1.00 53.83 |
| ATOM | 1107 | O | PRO | 937 | 28.644 | 9.558 | -0.937 1.00 53.64 |
| ATOM | 1108 | N | TYR | 938 | 27.153 | 8.046 | -1.660 1.00 54.91 |
| ATOM | 1110 | CA | TYR | 938 | 26.918 | 8.803 | -2.859 1.00 62.52 |
| ATOM | 1111 | CB | TYR | 938 | 27.580 | 8.161 | -4.080 1.00 67.73 |
| ATOM | 1120 | C | TYR | 938 | 25.443 | 8.800 | -3.059 1.00 67.31 |
| ATOM | 1121 | O | TYR | 938 | 24.722 | 8.082 | -2.361 1.00 66.13 |
| ATOM | 1122 | N | LYS | 939 | 25.027 | 9.601 | -4.038 1.00 75.30 |
| ATOM | 1124 | CA | LYS | 939 | 23.639 | 9.770 | -4.445 1.00 81.21 |
| ATOM | 1125 | CB | LYS | 939 | 23.209 | 11.254 | -4.284 1.00 80.04 |
| ATOM | 1126 | C | LYS | 939 | 23.543 | 9.331 | -5.921 1.00 87.24 |
| ATOM | 1127 | O | LYS | 939 | 24.582 | 9.384 | -6.646 1.00 90.23 |
| ATOM | 1129 | CB | ASP | 998 | 17.986 | 15.692 | 3.023 1.00 53.00 |
| ATOM | 1130 | C | ASP | 998 | 20.489 | 15.723 | 3.377 1.00 55.33 |
| ATOM | 1131 | O | ASP | 998 | 21.051 | 16.058 | 4.426 1.00 56.29 |
| ATOM | 1134 | N | ASP | 998 | 19.408 | 16.931 | 1.400 1.00 54.52 |
| ATOM | 1136 | CA | ASP | 998 | 19.279 | 16.514 | 2.829 1.00 55.12 |
| ATOM | 1137 | N | PHE | 999 | 20.900 | 14.687 | 2.653 1.00 52.90 |
| ATOM | 1139 | CA | PHE | 999 | 21.984 | 13.834 | 3.111 1.00 46.86 |
| ATOM | 1140 | CB | PHE | 999 | 21.841 | 12.420 | 2.528 1.00 51.05 |
| ATOM | 1141 | CG | PHE | 999 | 20.897 | 11.537 | 3.296 1.00 55.62 |
| ATOM | 1142 | CD1 | PHE | 999 | 21.249 | 10.236 | 3.606 1.00 56.12 |
| ATOM | 1143 | CD2 | PHE | 999 | 19.671 | 12.022 | 3.751 1.00 60.98 |
| ATOM | 1144 | CE1 | PHE | 999 | 20.397 | 9.422 | 4.368 1.00 61.93 |
| ATOM | 1145 | CE2 | PHE | 999 | 18.816 | 11.222 | 4.509 1.00 61.09 |
| ATOM | 1146 | CZ | PHE | 999 | 19.183 | 9.917 | 4.820 1.00 60.64 |
| ATOM | 1147 | C | PHE | 999 | 23.373 | 14.302 | 2.837 1.00 41.06 |
| ATOM | 1148 | O | PHE | 999 | 23.632 | 14.937 | 1.820 1.00 36.04 |
| ATOM | 1149 | N | LEU | 1000 | 24.238 | 14.057 | 3.812 1.00 37.57 |
| ATOM | 1151 | CA | LEU | 1000 | 25.651 | 14.326 | 3.652 1.00 36.08 |
| ATOM | 1152 | CB | LEU | 1000 | 26.401 | 14.306 | 4.985 1.00 35.67 |
| ATOM | 1153 | CG | LEU | 1000 | 25.923 | 15.286 | 6.057 1.00 36.23 |
| ATOM | 1154 | CD1 | LEU | 1000 | 26.941 | 15.370 | 7.201 1.00 29.94 |
| ATOM | 1155 | CD2 | LEU | 1000 | 25.707 | 16.654 | 5.435 1.00 38.66 |
| ATOM | 1156 | C | LEU | 1000 | 26.089 | 13.139 | 2.756 1.00 35.16 |
| ATOM | 1157 | O | LEU | 1000 | 25.330 | 12.167 | 2.569 1.00 32.68 |
| ATOM | 1158 | N | THR | 1001 | 27.292 | 13.228 | 2.201 1.00 29.92 |
| ATOM | 1160 | CA | THR | 1001 | 27.803 | 12.236 | 1.285 1.00 25.42 |
| ATOM | 1161 | CB | THR | 1001 | 27.396 | 12.560 | -0.178 1.00 30.10 |

FIG. 7(23)

| | | | | | | | | |
|---|---|---|---|---|---|---|---|---|
| ATOM | 1162 | OG1 | THR | 1001 | 28.055 | 13.771 | -0.605 | 1.00 33.54 |
| ATOM | 1164 | CG2 | THR | 1001 | 25.878 | 12.741 | -0.326 | 1.00 29.24 |
| ATOM | 1165 | C | THR | 1001 | 29.303 | 12.388 | 1.338 | 1.00 27.68 |
| ATOM | 1166 | O | THR | 1001 | 29.805 | 13.303 | 1.985 | 1.00 28.02 |
| ATOM | 1167 | N | LEU | 1002 | 30.020 | 11.552 | 0.592 | 1.00 26.85 |
| ATOM | 1169 | CA | LEU | 1002 | 31.454 | 11.636 | 0.572 | 1.00 24.39 |
| ATOM | 1170 | CB | LEU | 1002 | 32.044 | 10.545 | -0.298 | 1.00 22.71 |
| ATOM | 1171 | CG | LEU | 1002 | 32.269 | 9.304 | 0.573 | 1.00 27.80 |
| ATOM | 1172 | CD1 | LEU | 1002 | 32.727 | 8.142 | -0.280 | 1.00 27.11 |
| ATOM | 1173 | CD2 | LEU | 1002 | 33.295 | 9.592 | 1.670 | 1.00 24.64 |
| ATOM | 1174 | C | LEU | 1002 | 31.908 | 12.995 | 0.099 | 1.00 26.97 |
| ATOM | 1175 | O | LEU | 1002 | 32.967 | 13.459 | 0.506 | 1.00 26.84 |
| ATOM | 1176 | N | GLU | 1003 | 31.063 | 13.682 | -0.666 | 1.00 27.89 |
| ATOM | 1178 | CA | GLU | 1003 | 31.428 | 15.000 | -1.185 | 1.00 28.02 |
| ATOM | 1179 | CB | GLU | 1003 | 30.419 | 15.503 | -2.208 | 1.00 32.50 |
| ATOM | 1180 | CG | GLU | 1003 | 30.988 | 16.624 | -3.077 | 1.00 37.49 |
| ATOM | 1181 | CD | GLU | 1003 | 31.915 | 16.121 | -4.170 | 1.00 38.89 |
| ATOM | 1182 | OE1 | GLU | 1003 | 33.065 | 15.743 | -3.886 | 1.00 43.61 |
| ATOM | 1183 | OE2 | GLU | 1003 | 31.488 | 16.102 | -5.331 | 1.00 46.97 |
| ATOM | 1184 | C | GLU | 1003 | 31.591 | 16.044 | -0.117 | 1.00 25.24 |
| ATOM | 1185 | O | GLU | 1003 | 32.485 | 16.885 | -0.211 | 1.00 26.57 |
| ATOM | 1186 | N | HIS | 1004 | 30.748 | 15.953 | 0.913 | 1.00 23.16 |
| ATOM | 1188 | CA | HIS | 1004 | 30.746 | 16.884 | 2.040 | 1.00 19.58 |
| ATOM | 1189 | CB | HIS | 1004 | 29.508 | 16.719 | 2.912 | 1.00 19.12 |
| ATOM | 1190 | CG | HIS | 1004 | 28.227 | 17.024 | 2.208 | 1.00 23.47 |
| ATOM | 1191 | CD2 | HIS | 1004 | 27.173 | 17.784 | 2.570 | 1.00 23.78 |
| ATOM | 1192 | ND1 | HIS | 1004 | 27.911 | 16.508 | 0.964 | 1.00 27.88 |
| ATOM | 1194 | CE1 | HIS | 1004 | 26.718 | 16.936 | 0.596 | 1.00 20.57 |
| ATOM | 1195 | NE2 | HIS | 1004 | 26.246 | 17.710 | 1.554 | 1.00 23.61 |
| ATOM | 1197 | C | HIS | 1004 | 31.940 | 16.631 | 2.885 | 1.00 21.64 |
| ATOM | 1198 | O | HIS | 1004 | 32.753 | 17.508 | 3.075 | 1.00 25.00 |
| ATOM | 1199 | N | LEU | 1005 | 32.055 | 15.419 | 3.394 | 1.00 23.11 |
| ATOM | 1201 | CA | LEU | 1005 | 33.186 | 15.072 | 4.222 | 1.00 23.79 |
| ATOM | 1202 | CB | LEU | 1005 | 33.131 | 13.581 | 4.589 | 1.00 24.17 |
| ATOM | 1203 | CG | LEU | 1005 | 32.183 | 13.199 | 5.743 | 1.00 27.48 |
| ATOM | 1204 | CD1 | LEU | 1005 | 31.030 | 14.150 | 5.821 | 1.00 25.44 |
| ATOM | 1205 | CD2 | LEU | 1005 | 31.679 | 11.771 | 5.627 | 1.00 22.50 |
| ATOM | 1206 | C | LEU | 1005 | 34.506 | 15.467 | 3.558 | 1.00 20.41 |
| ATOM | 1207 | O | LEU | 1005 | 35.361 | 16.034 | 4.206 | 1.00 21.82 |
| ATOM | 1208 | N | ILE | 1006 | 34.668 | 15.212 | 2.264 | 1.00 19.50 |

FIG. 7(24)

| | | | | | | | |
|---|---|---|---|---|---|---|---|
| ATOM | 1210 | CA | ILE | 1006 | 35.914 | 15.589 | 1.609 | 1.00 | 18.77 |
| ATOM | 1211 | CB | ILE | 1006 | 36.128 | 14.806 | 0.276 | 1.00 | 16.46 |
| ATOM | 1212 | CG2 | ILE | 1006 | 37.602 | 14.777 | -0.103 | 1.00 | 12.82 |
| ATOM | 1213 | CG1 | ILE | 1006 | 35.718 | 13.341 | 0.441 | 1.00 | 20.16 |
| ATOM | 1214 | CD1 | ILE | 1006 | 35.961 | 12.446 | -0.834 | 1.00 | 11.88 |
| ATOM | 1215 | C | ILE | 1006 | 35.998 | 17.136 | 1.377 | 1.00 | 22.88 |
| ATOM | 1216 | O | ILE | 1006 | 37.113 | 17.730 | 1.431 | 1.00 | 21.25 |
| ATOM | 1217 | N | CYS | 1007 | 34.854 | 17.788 | 1.108 | 1.00 | 21.47 |
| ATOM | 1219 | CA | CYS | 1007 | 34.860 | 19.240 | 0.909 | 1.00 | 21.66 |
| ATOM | 1220 | CB | CYS | 1007 | 33.522 | 19.825 | 0.431 | 1.00 | 24.87 |
| ATOM | 1221 | SG | CYS | 1007 | 33.760 | 21.544 | -0.085 | 1.00 | 30.17 |
| ATOM | 1222 | C | CYS | 1007 | 35.247 | 19.953 | 2.196 | 1.00 | 22.22 |
| ATOM | 1223 | O | CYS | 1007 | 36.024 | 20.905 | 2.158 | 1.00 | 25.94 |
| ATOM | 1224 | N | TYR | 1008 | 34.691 | 19.527 | 3.331 | 1.00 | 20.53 |
| ATOM | 1226 | CA | TYR | 1008 | 35.030 | 20.132 | 4.617 | 1.00 | 17.94 |
| ATOM | 1227 | CB | TYR | 1008 | 34.248 | 19.493 | 5.758 | 1.00 | 18.61 |
| ATOM | 1228 | CG | TYR | 1008 | 32.753 | 19.488 | 5.626 | 1.00 | 17.97 |
| ATOM | 1229 | CD1 | TYR | 1008 | 32.019 | 18.455 | 6.175 | 1.00 | 16.67 |
| ATOM | 1230 | CE1 | TYR | 1008 | 30.641 | 18.462 | 6.158 | 1.00 | 22.78 |
| ATOM | 1231 | CD2 | TYR | 1008 | 32.059 | 20.549 | 5.031 | 1.00 | 22.19 |
| ATOM | 1232 | CE2 | TYR | 1008 | 30.646 | 20.569 | 5.011 | 1.00 | 20.60 |
| ATOM | 1233 | CZ | TYR | 1008 | 29.949 | 19.513 | 5.579 | 1.00 | 23.22 |
| ATOM | 1234 | OH | TYR | 1008 | 28.574 | 19.454 | 5.551 | 1.00 | 18.30 |
| ATOM | 1236 | C | TYR | 1008 | 36.537 | 19.945 | 4.883 | 1.00 | 18.55 |
| ATOM | 1237 | O | TYR | 1008 | 37.217 | 20.917 | 5.256 | 1.00 | 20.35 |
| ATOM | 1238 | N | SER | 1009 | 37.056 | 18.726 | 4.642 | 1.00 | 14.74 |
| ATOM | 1240 | CA | SER | 1009 | 38.476 | 18.409 | 4.852 | 1.00 | 13.39 |
| ATOM | 1241 | CB | SER | 1009 | 38.810 | 16.962 | 4.473 | 1.00 | 17.24 |
| ATOM | 1242 | OG | SER | 1009 | 38.018 | 16.001 | 5.152 | 1.00 | 26.04 |
| ATOM | 1244 | C | SER | 1009 | 39.310 | 19.309 | 3.985 | 1.00 | 16.36 |
| ATOM | 1245 | O | SER | 1009 | 40.317 | 19.864 | 4.446 | 1.00 | 20.21 |
| ATOM | 1246 | N | PHE | 1010 | 38.953 | 19.375 | 2.699 | 1.00 | 20.97 |
| ATOM | 1248 | CA | PHE | 1010 | 39.654 | 20.246 | 1.742 | 1.00 | 23.34 |
| ATOM | 1249 | CB | PHE | 1010 | 38.985 | 20.126 | 0.365 | 1.00 | 18.83 |
| ATOM | 1250 | CG | PHE | 1010 | 39.605 | 21.002 | -0.685 | 1.00 | 17.13 |
| ATOM | 1251 | CD1 | PHE | 1010 | 38.830 | 21.940 | -1.370 | 1.00 | 13.94 |
| ATOM | 1252 | CD2 | PHE | 1010 | 40.979 | 20.918 | -0.968 | 1.00 | 17.85 |
| ATOM | 1253 | CE1 | PHE | 1010 | 39.410 | 22.804 | -2.339 | 1.00 | 16.30 |
| ATOM | 1254 | CE2 | PHE | 1010 | 41.569 | 21.763 | -1.917 | 1.00 | 17.15 |
| ATOM | 1255 | CZ | PHE | 1010 | 40.772 | 22.714 | -2.608 | 1.00 | 18.02 |

FIG. 7(25)

| ATOM | 1256 | C   | PHE | 1010 | 39.688 | 21.746 | 2.242  | 1.00 | 22.02 |
|------|------|-----|-----|------|--------|--------|--------|------|-------|
| ATOM | 1257 | O   | PHE | 1010 | 40.749 | 22.390 | 2.298  | 1.00 | 23.00 |
| ATOM | 1258 | N   | GLN | 1011 | 38.535 | 22.271 | 2.643  | 1.00 | 19.25 |
| ATOM | 1260 | CA  | GLN | 1011 | 38.418 | 23.640 | 3.159  | 1.00 | 19.07 |
| ATOM | 1261 | CB  | GLN | 1011 | 36.980 | 23.945 | 3.480  | 1.00 | 12.84 |
| ATOM | 1262 | CG  | GLN | 1011 | 36.117 | 24.005 | 2.270  | 1.00 | 6.53  |
| ATOM | 1263 | CD  | GLN | 1011 | 34.713 | 24.371 | 2.659  | 1.00 | 18.81 |
| ATOM | 1264 | OE1 | GLN | 1011 | 34.490 | 25.382 | 3.347  | 1.00 | 21.22 |
| ATOM | 1265 | NE2 | GLN | 1011 | 33.760 | 23.525 | 2.302  | 1.00 | 26.88 |
| ATOM | 1268 | C   | GLN | 1011 | 39.262 | 23.894 | 4.394  | 1.00 | 18.28 |
| ATOM | 1269 | O   | GLN | 1011 | 39.840 | 24.982 | 4.543  | 1.00 | 19.80 |
| ATOM | 1270 | N   | VAL | 1012 | 39.270 | 22.934 | 5.319  | 1.00 | 11.82 |
| ATOM | 1272 | CA  | VAL | 1012 | 40.110 | 23.063 | 6.500  | 1.00 | 13.54 |
| ATOM | 1273 | CB  | VAL | 1012 | 39.825 | 21.936 | 7.528  | 1.00 | 15.67 |
| ATOM | 1274 | CG1 | VAL | 1012 | 40.686 | 22.107 | 8.795  | 1.00 | 10.56 |
| ATOM | 1275 | CG2 | VAL | 1012 | 38.370 | 21.948 | 7.901  | 1.00 | 14.92 |
| ATOM | 1276 | C   | VAL | 1012 | 41.618 | 23.068 | 6.068  | 1.00 | 16.72 |
| ATOM | 1277 | O   | VAL | 1012 | 42.448 | 23.782 | 6.665  | 1.00 | 20.48 |
| ATOM | 1278 | N   | ALA | 1013 | 42.001 | 22.291 | 5.051  | 1.00 | 15.90 |
| ATOM | 1280 | CA  | ALA | 1013 | 43.401 | 22.352 | 4.602  | 1.00 | 17.77 |
| ATOM | 1281 | CB  | ALA | 1013 | 43.732 | 21.206 | 3.638  | 1.00 | 10.59 |
| ATOM | 1282 | C   | ALA | 1013 | 43.685 | 23.755 | 3.963  | 1.00 | 15.74 |
| ATOM | 1283 | O   | ALA | 1013 | 44.764 | 24.302 | 4.139  | 1.00 | 17.49 |
| ATOM | 1284 | N   | LYS | 1014 | 42.718 | 24.342 | 3.244  | 1.00 | 17.18 |
| ATOM | 1286 | CA  | LYS | 1014 | 42.866 | 25.706 | 2.665  | 1.00 | 15.11 |
| ATOM | 1287 | CB  | LYS | 1014 | 41.557 | 26.152 | 2.020  | 1.00 | 23.73 |
| ATOM | 1288 | CG  | LYS | 1014 | 41.146 | 25.474 | 0.748  | 1.00 | 23.57 |
| ATOM | 1289 | CD  | LYS | 1014 | 41.963 | 26.033 | -0.354 | 1.00 | 26.38 |
| ATOM | 1290 | CE  | LYS | 1014 | 41.172 | 25.978 | -1.617 | 1.00 | 38.71 |
| ATOM | 1291 | NZ  | LYS | 1014 | 42.034 | 26.404 | -2.776 | 1.00 | 50.36 |
| ATOM | 1295 | C   | LYS | 1014 | 43.105 | 26.678 | 3.823  | 1.00 | 11.16 |
| ATOM | 1296 | O   | LYS | 1014 | 44.066 | 27.452 | 3.818  | 1.00 | 13.85 |
| ATOM | 1297 | N   | GLY | 1015 | 42.210 | 26.590 | 4.816  | 1.00 | 10.82 |
| ATOM | 1299 | CA  | GLY | 1015 | 42.250 | 27.403 | 6.017  | 1.00 | 12.48 |
| ATOM | 1300 | C   | GLY | 1015 | 43.584 | 27.327 | 6.715  | 1.00 | 17.17 |
| ATOM | 1301 | O   | GLY | 1015 | 44.124 | 28.349 | 7.130  | 1.00 | 19.92 |
| ATOM | 1302 | N   | MET | 1016 | 44.159 | 26.128 | 6.763  | 1.00 | 17.82 |
| ATOM | 1304 | CA  | MET | 1016 | 45.426 | 25.927 | 7.439  | 1.00 | 15.78 |
| ATOM | 1305 | CB  | MET | 1016 | 45.516 | 24.488 | 7.925  | 1.00 | 17.77 |
| ATOM | 1306 | CG  | MET | 1016 | 44.538 | 24.156 | 9.057  | 1.00 | 15.19 |
| ATOM | 1307 | SD  | MET | 1016 | 44.931 | 24.991 | 10.623 | 1.00 | 15.49 |

FIG. 7(26)

| | | | | | | | |
|---|---|---|---|---|---|---|---|
| ATOM | 1308 | CE  | MET | 1016 | 46.642 24.894 10.658 | 1.00 |  5.63 |
| ATOM | 1309 | C   | MET | 1016 | 46.625 26.321  6.618 | 1.00 | 14.62 |
| ATOM | 1310 | O   | MET | 1016 | 47.680 26.667  7.163 | 1.00 | 15.76 |
| ATOM | 1311 | N   | GLU | 1017 | 46.487 26.208  5.305 | 1.00 | 14.65 |
| ATOM | 1313 | CA  | GLU | 1017 | 47.552 26.608  4.384 | 1.00 | 21.43 |
| ATOM | 1314 | CB  | GLU | 1017 | 47.177 26.195  2.947 | 1.00 | 21.43 |
| ATOM | 1315 | CG  | GLU | 1017 | 48.162 26.622  1.878 | 1.00 | 22.82 |
| ATOM | 1316 | CD  | GLU | 1017 | 47.634 26.421  0.436 | 1.00 | 27.12 |
| ATOM | 1317 | OE1 | GLU | 1017 | 46.457 26.769  0.141 | 1.00 | 24.95 |
| ATOM | 1318 | OE2 | GLU | 1017 | 48.418 25.927 -0.424 | 1.00 | 32.93 |
| ATOM | 1319 | C   | GLU | 1017 | 47.667 28.145  4.535 | 1.00 | 18.38 |
| ATOM | 1320 | O   | GLU | 1017 | 48.760 28.668  4.593 | 1.00 | 17.43 |
| ATOM | 1321 | N   | PHE | 1018 | 46.526 28.839  4.677 | 1.00 | 19.09 |
| ATOM | 1323 | CA  | PHE | 1018 | 46.509 30.295  4.894 | 1.00 | 20.74 |
| ATOM | 1324 | CB  | PHE | 1018 | 45.067 30.848  4.870 | 1.00 | 27.18 |
| ATOM | 1325 | CG  | PHE | 1018 | 44.942 32.338  5.248 | 1.00 | 25.91 |
| ATOM | 1326 | CD1 | PHE | 1018 | 44.477 32.718  6.521 | 1.00 | 26.19 |
| ATOM | 1327 | CD2 | PHE | 1018 | 45.300 33.345  4.348 | 1.00 | 25.16 |
| ATOM | 1328 | CE1 | PHE | 1018 | 44.381 34.059  6.890 | 1.00 | 27.10 |
| ATOM | 1329 | CE2 | PHE | 1018 | 45.208 34.708  4.712 | 1.00 | 28.34 |
| ATOM | 1330 | CZ  | PHE | 1018 | 44.754 35.064  5.982 | 1.00 | 26.60 |
| ATOM | 1331 | C   | PHE | 1018 | 47.179 30.663  6.216 | 1.00 | 18.20 |
| ATOM | 1332 | O   | PHE | 1018 | 48.139 31.430  6.228 | 1.00 | 15.08 |
| ATOM | 1333 | N   | LEU | 1019 | 46.676 30.122  7.328 | 1.00 | 16.94 |
| ATOM | 1335 | CA  | LEU | 1019 | 47.259 30.414  8.654 | 1.00 | 19.44 |
| ATOM | 1336 | CB  | LEU | 1019 | 46.673 29.533  9.754 | 1.00 | 22.88 |
| ATOM | 1337 | CG  | LEU | 1019 | 45.238 29.773 10.165 | 1.00 | 24.41 |
| ATOM | 1338 | CD1 | LEU | 1019 | 44.956 28.916 11.388 | 1.00 | 24.01 |
| ATOM | 1339 | CD2 | LEU | 1019 | 45.084 31.277 10.485 | 1.00 | 25.61 |
| ATOM | 1340 | C   | LEU | 1019 | 48.736 30.173  8.660 | 1.00 | 19.44 |
| ATOM | 1341 | O   | LEU | 1019 | 49.493 30.896  9.316 | 1.00 | 18.98 |
| ATOM | 1342 | N   | ALA | 1020 | 49.135 29.076  8.023 | 1.00 | 19.45 |
| ATOM | 1344 | CA  | ALA | 1020 | 50.545 28.747  7.961 | 1.00 | 22.29 |
| ATOM | 1345 | CB  | ALA | 1020 | 50.748 27.350  7.397 | 1.00 | 21.86 |
| ATOM | 1346 | C   | ALA | 1020 | 51.252 29.829  7.115 | 1.00 | 26.13 |
| ATOM | 1347 | O   | ALA | 1020 | 52.348 30.257  7.471 | 1.00 | 25.25 |
| ATOM | 1348 | N   | SER | 1021 | 50.600 30.323  6.050 | 1.00 | 29.72 |
| ATOM | 1350 | CA  | SER | 1021 | 51.194 31.384  5.219 | 1.00 | 27.59 |
| ATOM | 1351 | CB  | SER | 1021 | 50.289 31.754  4.026 | 1.00 | 23.95 |

FIG. 7(27)

| ATOM | 1352 | OG | SER | 1021 | 49.252 | 32.662 | 4.349 | 1.00 | 22.60 |
|------|------|-----|-----|------|--------|--------|-------|------|-------|
| ATOM | 1354 | C | SER | 1021 | 51.469 | 32.614 | 6.109 | 1.00 | 32.83 |
| ATOM | 1355 | O | SER | 1021 | 52.570 | 33.172 | 6.073 | 1.00 | 36.57 |
| ATOM | 1356 | N | ARG | 1022 | 50.513 | 32.957 | 6.981 | 1.00 | 31.88 |
| ATOM | 1358 | CA | ARG | 1022 | 50.645 | 34.093 | 7.901 | 1.00 | 22.64 |
| ATOM | 1359 | CB | ARG | 1022 | 49.294 | 34.483 | 8.465 | 1.00 | 17.89 |
| ATOM | 1360 | CG | ARG | 1022 | 48.254 | 34.691 | 7.420 | 1.00 | 17.72 |
| ATOM | 1361 | CD | ARG | 1022 | 48.648 | 35.816 | 6.468 | 1.00 | 18.00 |
| ATOM | 1362 | NE | ARG | 1022 | 49.714 | 36.666 | 6.993 | 1.00 | 31.94 |
| ATOM | 1364 | CZ | ARG | 1022 | 49.625 | 37.980 | 7.168 | 1.00 | 30.72 |
| ATOM | 1365 | NH1 | ARG | 1022 | 50.653 | 38.644 | 7.662 | 1.00 | 23.85 |
| ATOM | 1368 | NH2 | ARG | 1022 | 48.508 | 38.620 | 6.862 | 1.00 | 40.00 |
| ATOM | 1371 | C | ARG | 1022 | 51.563 | 33.787 | 9.056 | 1.00 | 24.84 |
| ATOM | 1372 | O | ARG | 1022 | 51.718 | 34.612 | 9.960 | 1.00 | 23.27 |
| ATOM | 1373 | N | LYS | 1023 | 52.115 | 32.576 | 9.061 | 1.00 | 23.84 |
| ATOM | 1375 | CA | LYS | 1023 | 53.039 | 32.137 | 10.094 | 1.00 | 23.59 |
| ATOM | 1376 | CB | LYS | 1023 | 54.237 | 33.067 | 10.196 | 1.00 | 22.44 |
| ATOM | 1377 | C | LYS | 1023 | 52.404 | 31.899 | 11.456 | 1.00 | 25.21 |
| ATOM | 1378 | O | LYS | 1023 | 53.054 | 32.024 | 12.504 | 1.00 | 28.54 |
| ATOM | 1379 | N | CYS | 1024 | 51.164 | 31.435 | 11.411 | 1.00 | 20.82 |
| ATOM | 1381 | CA | CYS | 1024 | 50.404 | 31.114 | 12.595 | 1.00 | 28.12 |
| ATOM | 1382 | CB | CYS | 1024 | 48.982 | 31.709 | 12.472 | 1.00 | 30.32 |
| ATOM | 1383 | SG | CYS | 1024 | 48.936 | 33.504 | 12.847 | 1.00 | 33.73 |
| ATOM | 1384 | C | CYS | 1024 | 50.388 | 29.576 | 12.729 | 1.00 | 32.20 |
| ATOM | 1385 | O | CYS | 1024 | 50.636 | 28.882 | 11.756 | 1.00 | 38.70 |
| ATOM | 1386 | N | ILE | 1025 | 50.167 | 29.057 | 13.934 | 1.00 | 30.55 |
| ATOM | 1388 | CA | ILE | 1025 | 50.123 | 27.619 | 14.216 | 1.00 | 33.60 |
| ATOM | 1389 | CB | ILE | 1025 | 51.406 | 27.169 | 14.970 | 1.00 | 36.10 |
| ATOM | 1390 | CG2 | ILE | 1025 | 51.223 | 25.807 | 15.619 | 1.00 | 38.88 |
| ATOM | 1391 | CG1 | ILE | 1025 | 52.585 | 27.121 | 13.988 | 1.00 | 38.38 |
| ATOM | 1392 | CD1 | ILE | 1025 | 53.913 | 27.422 | 14.604 | 1.00 | 34.51 |
| ATOM | 1393 | C | ILE | 1025 | 48.891 | 27.526 | 15.104 | 1.00 | 33.66 |
| ATOM | 1394 | O | ILE | 1025 | 48.751 | 28.301 | 16.034 | 1.00 | 41.71 |
| ATOM | 1395 | N | HIS | 1026 | 47.958 | 26.643 | 14.797 | 1.00 | 31.27 |
| ATOM | 1397 | CA | HIS | 1026 | 46.742 | 26.570 | 15.589 | 1.00 | 27.97 |
| ATOM | 1398 | CB | HIS | 1026 | 45.691 | 25.745 | 14.861 | 1.00 | 23.43 |
| ATOM | 1399 | CG | HIS | 1026 | 44.283 | 26.091 | 15.229 | 1.00 | 30.06 |
| ATOM | 1400 | CD2 | HIS | 1026 | 43.342 | 26.801 | 14.560 | 1.00 | 33.43 |
| ATOM | 1401 | ND1 | HIS | 1026 | 43.680 | 25.659 | 16.393 | 1.00 | 24.53 |

FIG. 7(28)

| | | | | | | | |
|---|---|---|---|---|---|---|---|
| ATOM | 1403 | CE1 | HIS | 1026 | 42.428 | 26.085 | 16.424 | 1.00 | 26.31 |
| ATOM | 1404 | NE2 | HIS | 1026 | 42.199 | 26.781 | 15.321 | 1.00 | 29.05 |
| ATOM | 1406 | C | HIS | 1026 | 46.901 | 26.086 | 17.036 | 1.00 | 30.13 |
| ATOM | 1407 | O | HIS | 1026 | 46.335 | 26.681 | 17.955 | 1.00 | 37.96 |
| ATOM | 1408 | N | ARG | 1027 | 47.662 | 25.024 | 17.244 | 1.00 | 26.58 |
| ATOM | 1410 | CA | ARG | 1027 | 47.872 | 24.429 | 18.583 | 1.00 | 31.87 |
| ATOM | 1411 | CB | ARG | 1027 | 48.235 | 25.483 | 19.666 | 1.00 | 20.17 |
| ATOM | 1412 | C | ARG | 1027 | 46.762 | 23.449 | 19.055 | 1.00 | 31.55 |
| ATOM | 1413 | O | ARG | 1027 | 47.047 | 22.477 | 19.742 | 1.00 | 38.11 |
| ATOM | 1414 | N | ASP | 1028 | 45.528 | 23.629 | 18.597 | 1.00 | 30.85 |
| ATOM | 1416 | CA | ASP | 1028 | 44.466 | 22.698 | 18.955 | 1.00 | 26.34 |
| ATOM | 1417 | CB | ASP | 1028 | 43.788 | 23.098 | 20.248 | 1.00 | 32.60 |
| ATOM | 1418 | CG | ASP | 1028 | 42.847 | 22.020 | 20.755 | 1.00 | 35.64 |
| ATOM | 1419 | OD1 | ASP | 1028 | 41.692 | 22.346 | 21.096 | 1.00 | 36.08 |
| ATOM | 1420 | OD2 | ASP | 1028 | 43.267 | 20.842 | 20.790 | 1.00 | 40.39 |
| ATOM | 1421 | C | ASP | 1028 | 43.435 | 22.565 | 17.841 | 1.00 | 26.23 |
| ATOM | 1422 | O | ASP | 1028 | 42.276 | 22.926 | 17.998 | 1.00 | 23.40 |
| ATOM | 1423 | N | LEU | 1029 | 43.884 | 22.034 | 16.708 | 1.00 | 24.88 |
| ATOM | 1425 | CA | LEU | 1029 | 43.053 | 21.842 | 15.533 | 1.00 | 23.16 |
| ATOM | 1426 | CB | LEU | 1029 | 43.958 | 21.772 | 14.299 | 1.00 | 18.78 |
| ATOM | 1427 | CG | LEU | 1029 | 43.221 | 21.714 | 12.965 | 1.00 | 20.21 |
| ATOM | 1428 | CD1 | LEU | 1029 | 42.349 | 22.952 | 12.812 | 1.00 | 15.13 |
| ATOM | 1429 | CD2 | LEU | 1029 | 44.249 | 21.601 | 11.827 | 1.00 | 22.91 |
| ATOM | 1430 | C | LEU | 1029 | 42.237 | 20.562 | 15.700 | 1.00 | 25.25 |
| ATOM | 1431 | O | LEU | 1029 | 42.765 | 19.473 | 15.591 | 1.00 | 30.47 |
| ATOM | 1432 | N | ALA | 1030 | 40.949 | 20.703 | 15.957 | 1.00 | 25.99 |
| ATOM | 1434 | CA | ALA | 1030 | 40.062 | 19.574 | 16.182 | 1.00 | 25.19 |
| ATOM | 1435 | CB | ALA | 1030 | 39.872 | 19.387 | 17.679 | 1.00 | 24.55 |
| ATOM | 1436 | C | ALA | 1030 | 38.761 | 20.007 | 15.558 | 1.00 | 27.35 |
| ATOM | 1437 | O | ALA | 1030 | 38.611 | 21.202 | 15.302 | 1.00 | 33.46 |
| ATOM | 1438 | N | ALA | 1031 | 37.797 | 19.094 | 15.379 | 1.00 | 25.19 |
| ATOM | 1440 | CA | ALA | 1031 | 36.508 | 19.451 | 14.752 | 1.00 | 22.16 |
| ATOM | 1441 | CB | ALA | 1031 | 35.772 | 18.210 | 14.270 | 1.00 | 21.71 |
| ATOM | 1442 | C | ALA | 1031 | 35.551 | 20.353 | 15.536 | 1.00 | 20.96 |
| ATOM | 1443 | O | ALA | 1031 | 34.639 | 20.950 | 14.944 | 1.00 | 21.36 |
| ATOM | 1444 | N | ARG | 1032 | 35.712 | 20.388 | 16.859 | 1.00 | 22.49 |
| ATOM | 1446 | CA | ARG | 1032 | 34.898 | 21.246 | 17.736 | 1.00 | 27.01 |
| ATOM | 1447 | CB | ARG | 1032 | 35.157 | 20.945 | 19.220 | 1.00 | 25.22 |
| ATOM | 1448 | CG | ARG | 1032 | 36.534 | 21.451 | 19.707 | 1.00 | 34.44 |
| ATOM | 1449 | CD | ARG | 1032 | 37.150 | 20.503 | 20.770 | 1.00 | 46.39 |

FIG. 7(29)

| | | | | | | | |
|---|---|---|---|---|---|---|---|
| ATOM | 1450 | NE | ARG | 1032 | 38.554 | 20.752 | 21.158 1.00 41.28 |
| ATOM | 1452 | CZ | ARG | 1032 | 39.464 | 19.799 | 21.352 1.00 32.28 |
| ATOM | 1453 | NH1 | ARG | 1032 | 40.677 | 20.129 | 21.709 1.00 27.74 |
| ATOM | 1456 | NH2 | ARG | 1032 | 39.178 | 18.524 | 21.148 1.00 31.24 |
| ATOM | 1459 | C | ARG | 1032 | 35.296 | 22.708 | 17.482 1.00 25.91 |
| ATOM | 1460 | O | ARG | 1032 | 34.601 | 23.605 | 17.935 1.00 30.23 |
| ATOM | 1461 | N | ASN | 1033 | 36.451 | 22.911 | 16.840 1.00 20.90 |
| ATOM | 1463 | CA | ASN | 1033 | 37.008 | 24.222 | 16.495 1.00 15.77 |
| ATOM | 1464 | CB | ASN | 1033 | 38.497 | 24.290 | 16.813 1.00 18.29 |
| ATOM | 1465 | CG | ASN | 1033 | 38.760 | 24.160 | 18.254 1.00 20.60 |
| ATOM | 1466 | OD1 | ASN | 1033 | 37.891 | 24.445 | 19.067 1.00 29.84 |
| ATOM | 1467 | ND2 | ASN | 1033 | 39.929 | 23.677 | 18.601 1.00 18.08 |
| ATOM | 1470 | C | ASN | 1033 | 36.839 | 24.535 | 15.019 1.00 19.29 |
| ATOM | 1471 | O | ASN | 1033 | 37.619 | 25.303 | 14.450 1.00 17.18 |
| ATOM | 1472 | N | ILE | 1034 | 35.934 | 23.822 | 14.366 1.00 17.56 |
| ATOM | 1474 | CA | ILE | 1034 | 35.631 | 24.092 | 12.972 1.00 17.92 |
| ATOM | 1475 | CB | ILE | 1034 | 35.813 | 22.868 | 12.091 1.00 15.66 |
| ATOM | 1476 | CG2 | ILE | 1034 | 35.364 | 23.192 | 10.647 1.00 12.61 |
| ATOM | 1477 | CG1 | ILE | 1034 | 37.247 | 22.349 | 12.221 1.00 10.08 |
| ATOM | 1478 | CD1 | ILE | 1034 | 38.312 | 23.384 | 11.994 1.00 18.10 |
| ATOM | 1479 | C | ILE | 1034 | 34.147 | 24.381 | 13.075 1.00 21.87 |
| ATOM | 1480 | O | ILE | 1034 | 33.410 | 23.592 | 13.669 1.00 26.72 |
| ATOM | 1481 | N | LEU | 1035 | 33.711 | 25.524 | 12.575 1.00 21.91 |
| ATOM | 1483 | CA | LEU | 1035 | 32.311 | 25.883 | 12.670 1.00 19.45 |
| ATOM | 1484 | CB | LEU | 1035 | 32.190 | 27.310 | 13.181 1.00 18.73 |
| ATOM | 1485 | CG | LEU | 1035 | 32.102 | 27.454 | 14.691 1.00 21.53 |
| ATOM | 1486 | CD1 | LEU | 1035 | 33.019 | 26.518 | 15.456 1.00 8.66 |
| ATOM | 1487 | CD2 | LEU | 1035 | 32.391 | 28.881 | 15.016 1.00 19.34 |
| ATOM | 1488 | C | LEU | 1035 | 31.700 | 25.764 | 11.316 1.00 20.15 |
| ATOM | 1489 | O | LEU | 1035 | 32.377 | 25.977 | 10.310 1.00 21.51 |
| ATOM | 1490 | N | LEU | 1036 | 30.429 | 25.390 | 11.275 1.00 24.13 |
| ATOM | 1492 | CA | LEU | 1036 | 29.745 | 25.237 | 10.006 1.00 26.96 |
| ATOM | 1493 | CB | LEU | 1036 | 29.027 | 23.882 | 9.909 1.00 20.57 |
| ATOM | 1494 | CG | LEU | 1036 | 28.149 | 23.631 | 8.681 1.00 17.23 |
| ATOM | 1495 | CD1 | LEU | 1036 | 28.877 | 23.617 | 7.360 1.00 7.53 |
| ATOM | 1496 | CD2 | LEU | 1036 | 27.566 | 22.306 | 8.900 1.00 18.85 |
| ATOM | 1497 | C | LEU | 1036 | 28.827 | 26.432 | 9.755 1.00 31.45 |
| ATOM | 1498 | O | LEU | 1036 | 27.953 | 26.794 | 10.557 1.00 29.93 |
| ATOM | 1499 | N | SER | 1037 | 29.094 | 27.061 | 8.628 1.00 34.52 |
| ATOM | 1501 | CA | SER | 1037 | 28.410 | 28.248 | 8.215 1.00 37.11 |

FIG. 7(30)

| | | | | | | | |
|---|---|---|---|---|---|---|---|
| ATOM | 1502 | CB  | SER 1037 | 29.448 | 29.220 | 7.632 | 1.00 41.11 |
| ATOM | 1503 | OG  | SER 1037 | 28.879 | 30.439 | 7.193 | 1.00 44.80 |
| ATOM | 1505 | C   | SER 1037 | 27.367 | 27.890 | 7.209 | 1.00 39.39 |
| ATOM | 1506 | O   | SER 1037 | 27.045 | 26.735 | 7.024 | 1.00 42.14 |
| ATOM | 1507 | N   | GLU 1038 | 26.884 | 28.912 | 6.531 | 1.00 44.94 |
| ATOM | 1509 | CA  | GLU 1038 | 25.845 | 28.806 | 5.534 | 1.00 50.37 |
| ATOM | 1510 | CB  | GLU 1038 | 25.685 | 30.152 | 4.792 | 1.00 56.15 |
| ATOM | 1511 | CG  | GLU 1038 | 25.599 | 31.391 | 5.676 | 1.00 55.19 |
| ATOM | 1512 | CD  | GLU 1038 | 24.518 | 31.270 | 6.708 | 1.00 59.42 |
| ATOM | 1513 | OE1 | GLU 1038 | 23.464 | 30.637 | 6.419 | 1.00 58.62 |
| ATOM | 1514 | OE2 | GLU 1038 | 24.736 | 31.806 | 7.816 | 1.00 63.52 |
| ATOM | 1515 | C   | GLU 1038 | 25.954 | 27.672 | 4.518 | 1.00 51.35 |
| ATOM | 1516 | O   | GLU 1038 | 25.619 | 26.521 | 4.816 | 1.00 57.04 |
| ATOM | 1517 | N   | LYS 1039 | 26.414 | 27.997 | 3.317 | 1.00 46.28 |
| ATOM | 1519 | CA  | LYS 1039 | 26.467 | 27.021 | 2.251 | 1.00 43.05 |
| ATOM | 1520 | CB  | LYS 1039 | 26.455 | 27.729 | 0.898 | 1.00 41.05 |
| ATOM | 1521 | C   | LYS 1039 | 27.689 | 26.155 | 2.401 | 1.00 44.31 |
| ATOM | 1522 | O   | LYS 1039 | 28.687 | 26.358 | 1.697 | 1.00 50.06 |
| ATOM | 1523 | N   | ASN 1040 | 27.611 | 25.210 | 3.339 | 1.00 37.02 |
| ATOM | 1525 | CA  | ASN 1040 | 28.701 | 24.283 | 3.630 | 1.00 32.65 |
| ATOM | 1526 | CB  | ASN 1040 | 28.647 | 23.041 | 2.761 | 1.00 31.69 |
| ATOM | 1527 | CG  | ASN 1040 | 27.641 | 22.061 | 3.267 | 1.00 31.29 |
| ATOM | 1528 | OD1 | ASN 1040 | 26.740 | 21.693 | 2.553 | 1.00 38.80 |
| ATOM | 1529 | ND2 | ASN 1040 | 27.749 | 21.680 | 4.530 | 1.00 36.05 |
| ATOM | 1532 | C   | ASN 1040 | 30.096 | 24.844 | 3.656 | 1.00 28.45 |
| ATOM | 1533 | O   | ASN 1040 | 31.079 | 24.162 | 3.300 | 1.00 26.00 |
| ATOM | 1534 | N   | VAL 1041 | 30.174 | 26.101 | 4.073 | 1.00 23.77 |
| ATOM | 1536 | CA  | VAL 1041 | 31.447 | 26.739 | 4.207 | 1.00 16.56 |
| ATOM | 1537 | CB  | VAL 1041 | 31.382 | 28.274 | 3.940 | 1.00 16.16 |
| ATOM | 1538 | CG1 | VAL 1041 | 32.709 | 28.948 | 4.315 | 1.00 8.57 |
| ATOM | 1539 | CG2 | VAL 1041 | 31.124 | 28.509 | 2.470 | 1.00 6.79 |
| ATOM | 1540 | C   | VAL 1041 | 31.726 | 26.382 | 5.646 | 1.00 15.50 |
| ATOM | 1541 | O   | VAL 1041 | 30.825 | 26.333 | 6.485 | 1.00 9.73 |
| ATOM | 1542 | N   | VAL 1042 | 32.967 | 26.022 | 5.883 | 1.00 18.82 |
| ATOM | 1544 | CA  | VAL 1042 | 33.431 | 25.607 | 7.185 | 1.00 19.76 |
| ATOM | 1545 | CB  | VAL 1042 | 33.907 | 24.110 | 7.051 | 1.00 22.19 |
| ATOM | 1546 | CG1 | VAL 1042 | 35.439 | 23.993 | 7.041 | 1.00 18.66 |
| ATOM | 1547 | CG2 | VAL 1042 | 33.247 | 23.242 | 8.100 | 1.00 22.95 |
| ATOM | 1548 | C   | VAL 1042 | 34.580 | 26.607 | 7.483 | 1.00 20.50 |
| ATOM | 1549 | O   | VAL 1042 | 35.348 | 26.960 | 6.575 | 1.00 17.75 |

FIG. 7(31)

| | | | | | | | | |
|---|---|---|---|---|---|---|---|---|
| ATOM | 1550 | N | LYS | 1043 | 34.675 | 27.082 | 8.726 | 1.00 18.30 |
| ATOM | 1552 | CA | LYS | 1043 | 35.679 | 28.070 | 9.103 | 1.00 17.43 |
| ATOM | 1553 | CB | LYS | 1043 | 34.977 | 29.420 | 9.277 | 1.00 17.68 |
| ATOM | 1554 | CG | LYS | 1043 | 34.202 | 29.845 | 8.031 | 1.00 19.19 |
| ATOM | 1555 | CD | LYS | 1043 | 33.560 | 31.228 | 8.186 | 1.00 26.86 |
| ATOM | 1556 | CE | LYS | 1043 | 33.270 | 31.885 | 6.820 | 1.00 18.32 |
| ATOM | 1557 | NZ | LYS | 1043 | 34.353 | 32.806 | 6.425 | 1.00 22.63 |
| ATOM | 1561 | C | LYS | 1043 | 36.373 | 27.687 | 10.399 | 1.00 18.35 |
| ATOM | 1562 | O | LYS | 1043 | 35.709 | 27.235 | 11.330 | 1.00 17.37 |
| ATOM | 1563 | N | ILE | 1044 | 37.692 | 27.880 | 10.461 | 1.00 17.47 |
| ATOM | 1565 | CA | ILE | 1044 | 38.504 | 27.558 | 11.645 | 1.00 21.49 |
| ATOM | 1566 | CB | ILE | 1044 | 40.010 | 27.390 | 11.267 | 1.00 20.48 |
| ATOM | 1567 | CG2 | ILE | 1044 | 40.896 | 27.250 | 12.502 | 1.00 15.75 |
| ATOM | 1568 | CG1 | ILE | 1044 | 40.221 | 26.237 | 10.300 | 1.00 14.66 |
| ATOM | 1569 | CD1 | ILE | 1044 | 41.584 | 26.344 | 9.669 | 1.00 12.76 |
| ATOM | 1570 | C | ILE | 1044 | 38.432 | 28.735 | 12.626 | 1.00 30.73 |
| ATOM | 1571 | O | ILE | 1044 | 38.370 | 29.888 | 12.207 | 1.00 31.68 |
| ATOM | 1572 | N | CYS | 1045 | 38.454 | 28.436 | 13.918 | 1.00 38.50 |
| ATOM | 1574 | CA | CYS | 1045 | 38.437 | 29.444 | 14.968 | 1.00 48.73 |
| ATOM | 1575 | CB | CYS | 1045 | 37.027 | 29.586 | 15.558 | 1.00 50.35 |
| ATOM | 1576 | SG | CYS | 1045 | 36.259 | 28.069 | 16.173 | 1.00 59.69 |
| ATOM | 1577 | C | CYS | 1045 | 39.473 | 29.041 | 16.033 | 1.00 54.63 |
| ATOM | 1578 | O | CYS | 1045 | 39.981 | 27.912 | 15.986 | 1.00 54.88 |
| ATOM | 1579 | N | ASP | 1046 | 39.811 | 29.954 | 16.956 | 1.00 64.20 |
| ATOM | 1581 | CA | ASP | 1046 | 40.816 | 29.700 | 18.021 | 1.00 69.98 |
| ATOM | 1582 | CB | ASP | 1046 | 40.454 | 28.407 | 18.788 | 1.00 72.94 |
| ATOM | 1583 | CG | ASP | 1046 | 41.338 | 28.165 | 20.009 | 1.00 75.40 |
| ATOM | 1584 | OD1 | ASP | 1046 | 40.930 | 28.584 | 21.110 | 1.00 77.66 |
| ATOM | 1585 | OD2 | ASP | 1046 | 42.428 | 27.547 | 19.878 | 1.00 75.18 |
| ATOM | 1586 | C | ASP | 1046 | 42.219 | 29.580 | 17.354 | 1.00 74.21 |
| ATOM | 1587 | O | ASP | 1046 | 43.183 | 29.036 | 17.940 | 1.00 74.94 |
| ATOM | 1588 | N | PHE | 1047 | 42.307 | 30.205 | 16.171 | 1.00 75.46 |
| ATOM | 1590 | CA | PHE | 1047 | 43.462 | 30.212 | 15.245 | 1.00 71.53 |
| ATOM | 1591 | CB | PHE | 1047 | 42.919 | 30.267 | 13.790 | 1.00 72.10 |
| ATOM | 1592 | CG | PHE | 1047 | 41.906 | 31.381 | 13.526 | 1.00 71.34 |
| ATOM | 1593 | CD1 | PHE | 1047 | 42.139 | 32.327 | 12.526 | 1.00 74.26 |
| ATOM | 1594 | CD2 | PHE | 1047 | 40.747 | 31.501 | 14.284 | 1.00 69.46 |
| ATOM | 1595 | CE1 | PHE | 1047 | 41.242 | 33.367 | 12.293 | 1.00 70.87 |
| ATOM | 1596 | CE2 | PHE | 1047 | 39.847 | 32.533 | 14.066 | 1.00 67.97 |
| ATOM | 1597 | CZ | PHE | 1047 | 40.096 | 33.467 | 13.068 | 1.00 71.41 |

FIG. 7(32)

| | | | | | | | | |
|---|---|---|---|---|---|---|---|---|
| ATOM | 1598 | C | PHE | 1047 | 44.681 | 31.163 | 15.426 | 1.00 67.78 |
| ATOM | 1599 | O | PHE | 1047 | 44.507 | 32.345 | 15.797 | 1.00 63.26 |
| ATOM | 1601 | CB | ASP | 1064 | 29.579 | 17.003 | 25.123 | 1.00 69.86 |
| ATOM | 1602 | CG | ASP | 1064 | 30.534 | 16.464 | 24.050 | 1.00 69.93 |
| ATOM | 1603 | OD1 | ASP | 1064 | 31.028 | 15.321 | 24.179 | 1.00 71.35 |
| ATOM | 1604 | OD2 | ASP | 1064 | 30.776 | 17.189 | 23.063 | 1.00 71.45 |
| ATOM | 1605 | C | ASP | 1064 | 31.511 | 17.821 | 26.539 | 1.00 64.90 |
| ATOM | 1606 | O | ASP | 1064 | 31.512 | 19.029 | 26.788 | 1.00 64.09 |
| ATOM | 1609 | N | ASP | 1064 | 29.229 | 17.550 | 27.534 | 1.00 67.30 |
| ATOM | 1611 | CA | ASP | 1064 | 30.204 | 17.019 | 26.533 | 1.00 67.58 |
| ATOM | 1612 | N | ALA | 1065 | 32.617 | 17.135 | 26.278 | 1.00 61.87 |
| ATOM | 1614 | CA | ALA | 1065 | 33.932 | 17.759 | 26.244 | 1.00 58.06 |
| ATOM | 1615 | CB | ALA | 1065 | 34.479 | 17.935 | 27.650 | 1.00 56.61 |
| ATOM | 1616 | C | ALA | 1065 | 34.888 | 16.915 | 25.397 | 1.00 57.97 |
| ATOM | 1617 | O | ALA | 1065 | 34.491 | 15.906 | 24.788 | 1.00 56.86 |
| ATOM | 1618 | N | ARG | 1066 | 36.155 | 17.313 | 25.400 | 1.00 54.64 |
| ATOM | 1620 | CA | ARG | 1066 | 37.182 | 16.664 | 24.607 | 1.00 50.99 |
| ATOM | 1621 | CB | ARG | 1066 | 37.538 | 17.539 | 23.393 | 1.00 49.53 |
| ATOM | 1622 | CG | ARG | 1066 | 36.459 | 17.608 | 22.335 | 1.00 52.76 |
| ATOM | 1623 | CD | ARG | 1066 | 36.866 | 16.805 | 21.125 | 1.00 57.63 |
| ATOM | 1624 | NE | ARG | 1066 | 35.847 | 16.645 | 20.093 | 1.00 57.02 |
| ATOM | 1626 | CZ | ARG | 1066 | 35.976 | 17.033 | 18.824 | 1.00 55.63 |
| ATOM | 1627 | NH1 | ARG | 1066 | 34.984 | 16.797 | 17.995 | 1.00 57.63 |
| ATOM | 1630 | NH2 | ARG | 1066 | 37.046 | 17.691 | 18.385 | 1.00 40.52 |
| ATOM | 1633 | C | ARG | 1066 | 38.428 | 16.513 | 25.427 | 1.00 49.01 |
| ATOM | 1634 | O | ARG | 1066 | 38.652 | 17.274 | 26.364 | 1.00 46.29 |
| ATOM | 1635 | N | LEU | 1067 | 39.251 | 15.546 | 25.041 | 1.00 46.48 |
| ATOM | 1637 | CA | LEU | 1067 | 40.510 | 15.320 | 25.709 | 1.00 45.62 |
| ATOM | 1638 | CB | LEU | 1067 | 40.703 | 13.840 | 26.073 | 1.00 45.53 |
| ATOM | 1639 | CG | LEU | 1067 | 41.335 | 13.519 | 27.441 | 1.00 44.07 |
| ATOM | 1640 | CD1 | LEU | 1067 | 42.236 | 12.322 | 27.273 | 1.00 37.52 |
| ATOM | 1641 | CD2 | LEU | 1067 | 42.109 | 14.710 | 28.057 | 1.00 39.60 |
| ATOM | 1642 | C | LEU | 1067 | 41.530 | 15.778 | 24.677 | 1.00 42.00 |
| ATOM | 1643 | O | LEU | 1067 | 41.983 | 15.010 | 23.832 | 1.00 41.05 |
| ATOM | 1644 | N | PRO | 1068 | 41.854 | 17.072 | 24.698 | 1.00 41.22 |
| ATOM | 1645 | CD | PRO | 1068 | 41.265 | 18.104 | 25.584 | 1.00 34.16 |
| ATOM | 1646 | CA | PRO | 1068 | 42.817 | 17.661 | 23.761 | 1.00 38.41 |
| ATOM | 1647 | CB | PRO | 1068 | 42.919 | 19.104 | 24.277 | 1.00 36.08 |
| ATOM | 1648 | CG | PRO | 1068 | 41.496 | 19.355 | 24.828 | 1.00 29.23 |
| ATOM | 1649 | C | PRO | 1068 | 44.197 | 16.961 | 23.571 | 1.00 35.36 |

FIG. 7(33)

```
ATOM  1650 O   PRO 1068    44.932 17.258 22.623 1.00 37.80
ATOM  1651 N   LEU 1069    44.552 16.040 24.455 1.00 33.98
ATOM  1653 CA  LEU 1069    45.829 15.337 24.333 1.00 35.06
ATOM  1654 CB  LEU 1069    46.092 14.517 25.601 1.00 37.80
ATOM  1655 CG  LEU 1069    47.228 13.497 25.488 1.00 40.67
ATOM  1656 CD1 LEU 1069    48.599 14.156 25.752 1.00 36.35
ATOM  1657 CD2 LEU 1069    46.939 12.333 26.445 1.00 40.75
ATOM  1658 C   LEU 1069    45.776 14.397 23.121 1.00 34.16
ATOM  1659 O   LEU 1069    46.787 14.115 22.461 1.00 32.14
ATOM  1660 N   LYS 1070    44.571 13.916 22.859 1.00 28.95
ATOM  1662 CA  LYS 1070    44.280 13.014 21.765 1.00 28.17
ATOM  1663 CB  LYS 1070    42.828 12.569 21.911 1.00 22.17
ATOM  1664 CG  LYS 1070    42.553 11.730 23.144 1.00 22.02
ATOM  1665 CD  LYS 1070    41.085 11.317 23.107 1.00 24.17
ATOM  1666 CE  LYS 1070    40.851  9.908 23.646 1.00 29.35
ATOM  1667 NZ  LYS 1070    39.444  9.436 23.439 1.00 35.82
ATOM  1671 C   LYS 1070    44.518 13.582 20.340 1.00 29.26
ATOM  1672 O   LYS 1070    44.368 12.867 19.344 1.00 27.81
ATOM  1673 N   TRP 1071    44.862 14.865 20.260 1.00 27.00
ATOM  1675 CA  TRP 1071    45.086 15.550 18.995 1.00 27.37
ATOM  1676 CB  TRP 1071    44.191 16.827 18.882 1.00 20.67
ATOM  1677 CG  TRP 1071    42.724 16.551 18.545 1.00 20.12
ATOM  1678 CD2 TRP 1071    41.685 16.138 19.451 1.00 17.97
ATOM  1679 CE2 TRP 1071    40.524 15.892 18.675 1.00 13.02
ATOM  1680 CE3 TRP 1071    41.628 15.944 20.838 1.00 23.76
ATOM  1681 CD1 TRP 1071    42.153 16.560 17.304 1.00 19.50
ATOM  1682 NE1 TRP 1071    40.834 16.155 17.373 1.00 13.62
ATOM  1684 CZ2 TRP 1071    39.342 15.465 19.233 1.00 16.22
ATOM  1685 CZ3 TRP 1071    40.439 15.511 21.396 1.00 20.67
ATOM  1686 CH2 TRP 1071    39.321 15.273 20.594 1.00 19.47
ATOM  1687 C   TRP 1071    46.523 15.961 18.889 1.00 26.26
ATOM  1688 O   TRP 1071    46.948 16.465 17.842 1.00 28.70
ATOM  1689 N   MET 1072    47.278 15.713 19.959 1.00 24.85
ATOM  1691 CA  MET 1072    48.676 16.119 20.034 1.00 22.67
ATOM  1692 CB  MET 1072    49.066 16.317 21.487 1.00 31.30
ATOM  1693 CG  MET 1072    48.328 17.416 22.229 1.00 34.64
ATOM  1694 SD  MET 1072    48.977 17.610 23.948 1.00 35.65
ATOM  1695 CE  MET 1072    50.667 17.842 23.669 1.00 27.97
ATOM  1696 C   MET 1072    49.697 15.215 19.388 1.00 25.43
ATOM  1697 O   MET 1072    49.798 14.029 19.729 1.00 21.51
```

FIG. 7(34)

| | | | | | | | | |
|---|---|---|---|---|---|---|---|---|
| ATOM | 1698 | N | ALA | 1073 | 50.545 | 15.800 | 18.547 | 1.00 25.55 |
| ATOM | 1700 | CA | ALA | 1073 | 51.571 | 15.024 | 17.874 | 1.00 29.80 |
| ATOM | 1701 | CB | ALA | 1073 | 52.369 | 15.912 | 16.958 | 1.00 22.65 |
| ATOM | 1702 | C | ALA | 1073 | 52.448 | 14.453 | 18.989 | 1.00 34.88 |
| ATOM | 1703 | O | ALA | 1073 | 52.431 | 14.970 | 20.115 | 1.00 39.38 |
| ATOM | 1704 | N | PRO | 1074 | 53.183 | 13.355 | 18.724 | 1.00 36.01 |
| ATOM | 1705 | CD | PRO | 1074 | 53.087 | 12.450 | 17.570 | 1.00 31.55 |
| ATOM | 1706 | CA | PRO | 1074 | 54.040 | 12.771 | 19.769 | 1.00 36.24 |
| ATOM | 1707 | CB | PRO | 1074 | 54.544 | 11.485 | 19.115 | 1.00 34.34 |
| ATOM | 1708 | CG | PRO | 1074 | 53.415 | 11.137 | 18.193 | 1.00 31.88 |
| ATOM | 1709 | C | PRO | 1074 | 55.189 | 13.670 | 20.288 | 1.00 37.13 |
| ATOM | 1710 | O | PRO | 1074 | 55.570 | 13.575 | 21.447 | 1.00 34.58 |
| ATOM | 1711 | N | GLU | 1075 | 55.746 | 14.533 | 19.440 | 1.00 37.40 |
| ATOM | 1713 | CA | GLU | 1075 | 56.813 | 15.422 | 19.884 | 1.00 40.62 |
| ATOM | 1714 | CB | GLU | 1075 | 57.598 | 15.990 | 18.707 | 1.00 33.55 |
| ATOM | 1715 | CG | GLU | 1075 | 56.853 | 16.957 | 17.844 | 1.00 39.40 |
| ATOM | 1716 | CD | GLU | 1075 | 55.952 | 16.300 | 16.828 | 1.00 43.14 |
| ATOM | 1717 | OE1 | GLU | 1075 | 55.965 | 15.055 | 16.720 | 1.00 49.09 |
| ATOM | 1718 | OE2 | GLU | 1075 | 55.228 | 17.040 | 16.124 | 1.00 44.63 |
| ATOM | 1719 | C | GLU | 1075 | 56.239 | 16.546 | 20.757 | 1.00 42.73 |
| ATOM | 1720 | O | GLU | 1075 | 56.903 | 17.061 | 21.639 | 1.00 44.76 |
| ATOM | 1721 | N | THR | 1076 | 54.982 | 16.888 | 20.524 | 1.00 46.13 |
| ATOM | 1723 | CA | THR | 1076 | 54.304 | 17.923 | 21.283 | 1.00 46.22 |
| ATOM | 1724 | CB | THR | 1076 | 52.991 | 18.319 | 20.605 | 1.00 43.95 |
| ATOM | 1725 | OG1 | THR | 1076 | 53.245 | 18.666 | 19.230 | 1.00 46.46 |
| ATOM | 1727 | CG2 | THR | 1076 | 52.361 | 19.481 | 21.334 | 1.00 43.93 |
| ATOM | 1728 | C | THR | 1076 | 53.991 | 17.378 | 22.662 | 1.00 47.62 |
| ATOM | 1729 | O | THR | 1076 | 54.175 | 18.057 | 23.650 | 1.00 52.45 |
| ATOM | 1730 | N | ILE | 1077 | 53.442 | 16.173 | 22.717 | 1.00 47.96 |
| ATOM | 1732 | CA | ILE | 1077 | 53.123 | 15.528 | 23.980 | 1.00 46.99 |
| ATOM | 1733 | CB | ILE | 1077 | 52.496 | 14.151 | 23.720 | 1.00 46.43 |
| ATOM | 1734 | CG2 | ILE | 1077 | 52.691 | 13.232 | 24.895 | 1.00 46.16 |
| ATOM | 1735 | CG1 | ILE | 1077 | 51.024 | 14.306 | 23.384 | 1.00 44.29 |
| ATOM | 1736 | CD1 | ILE | 1077 | 50.336 | 13.010 | 23.163 | 1.00 46.43 |
| ATOM | 1737 | C | ILE | 1077 | 54.418 | 15.345 | 24.767 | 1.00 51.37 |
| ATOM | 1738 | O | ILE | 1077 | 54.473 | 15.577 | 25.974 | 1.00 52.53 |
| ATOM | 1739 | N | PHE | 1078 | 55.458 | 14.931 | 24.058 | 1.00 53.41 |
| ATOM | 1741 | CA | PHE | 1078 | 56.750 | 14.696 | 24.672 | 1.00 58.94 |
| ATOM | 1742 | CB | PHE | 1078 | 57.506 | 13.570 | 23.925 | 1.00 60.74 |
| ATOM | 1743 | CG | PHE | 1078 | 56.901 | 12.184 | 24.124 | 1.00 57.84 |

FIG. 7(35)

| | | | | | | | | |
|---|---|---|---|---|---|---|---|---|
| ATOM | 1744 | CD1 | PHE | 1078 | 56.068 | 11.612 | 23.169 | 1.00 54.09 |
| ATOM | 1745 | CD2 | PHE | 1078 | 57.127 | 11.483 | 25.298 | 1.00 58.64 |
| ATOM | 1746 | CE1 | PHE | 1078 | 55.478 | 10.380 | 23.381 | 1.00 53.82 |
| ATOM | 1747 | CE2 | PHE | 1078 | 56.539 | 10.254 | 25.514 | 1.00 57.20 |
| ATOM | 1748 | CZ | PHE | 1078 | 55.711 | 9.703 | 24.555 | 1.00 55.07 |
| ATOM | 1749 | C | PHE | 1078 | 57.574 | 15.981 | 24.767 | 1.00 63.98 |
| ATOM | 1750 | O | PHE | 1078 | 57.433 | 16.738 | 25.736 | 1.00 67.06 |
| ATOM | 1751 | N | ASP | 1079 | 58.356 | 16.274 | 23.724 | 1.00 66.97 |
| ATOM | 1753 | CA | ASP | 1079 | 59.215 | 17.472 | 23.678 | 1.00 68.09 |
| ATOM | 1754 | CB | ASP | 1079 | 60.225 | 17.402 | 22.501 | 1.00 66.89 |
| ATOM | 1755 | CG | ASP | 1079 | 60.174 | 16.082 | 21.714 | 1.00 69.02 |
| ATOM | 1756 | OD1 | ASP | 1079 | 60.254 | 16.156 | 20.474 | 1.00 71.23 |
| ATOM | 1757 | OD2 | ASP | 1079 | 60.089 | 14.980 | 22.308 | 1.00 69.71 |
| ATOM | 1758 | C | ASP | 1079 | 58.434 | 18.806 | 23.599 | 1.00 67.74 |
| ATOM | 1759 | O | ASP | 1079 | 59.011 | 19.848 | 23.266 | 1.00 66.85 |
| ATOM | 1760 | N | ARG | 1080 | 57.137 | 18.747 | 23.926 | 1.00 68.20 |
| ATOM | 1762 | CA | ARG | 1080 | 56.173 | 19.858 | 23.898 | 1.00 66.60 |
| ATOM | 1763 | CB | ARG | 1080 | 55.997 | 20.496 | 25.279 | 1.00 67.64 |
| ATOM | 1764 | CG | ARG | 1080 | 54.529 | 20.758 | 25.638 | 1.00 71.26 |
| ATOM | 1765 | CD | ARG | 1080 | 53.823 | 19.481 | 26.096 | 1.00 73.66 |
| ATOM | 1766 | NE | ARG | 1080 | 52.364 | 19.610 | 26.226 | 1.00 75.75 |
| ATOM | 1768 | CZ | ARG | 1080 | 51.642 | 18.981 | 27.157 | 1.00 74.86 |
| ATOM | 1769 | NH1 | ARG | 1080 | 50.321 | 19.134 | 27.211 | 1.00 69.96 |
| ATOM | 1772 | NH2 | ARG | 1080 | 52.247 | 18.212 | 28.060 | 1.00 72.78 |
| ATOM | 1775 | C | ARG | 1080 | 56.305 | 20.920 | 22.801 | 1.00 63.93 |
| ATOM | 1776 | O | ARG | 1080 | 55.861 | 22.069 | 22.955 | 1.00 61.93 |
| ATOM | 1777 | N | VAL | 1081 | 56.863 | 20.510 | 21.667 | 1.00 61.30 |
| ATOM | 1779 | CA | VAL | 1081 | 57.034 | 21.413 | 20.545 | 1.00 58.53 |
| ATOM | 1780 | CB | VAL | 1081 | 58.202 | 20.951 | 19.584 | 1.00 60.54 |
| ATOM | 1781 | CG1 | VAL | 1081 | 59.304 | 20.266 | 20.370 | 1.00 62.35 |
| ATOM | 1782 | CG2 | VAL | 1081 | 57.701 | 20.043 | 18.455 | 1.00 55.04 |
| ATOM | 1783 | C | VAL | 1081 | 55.713 | 21.481 | 19.771 | 1.00 56.90 |
| ATOM | 1784 | O | VAL | 1081 | 55.052 | 20.452 | 19.560 | 1.00 57.43 |
| ATOM | 1785 | N | TYR | 1082 | 55.287 | 22.699 | 19.435 | 1.00 51.51 |
| ATOM | 1787 | CA | TYR | 1082 | 54.078 | 22.909 | 18.641 | 1.00 41.08 |
| ATOM | 1788 | CB | TYR | 1082 | 53.092 | 23.847 | 19.332 | 1.00 37.59 |
| ATOM | 1789 | CG | TYR | 1082 | 52.275 | 23.238 | 20.442 | 1.00 32.41 |
| ATOM | 1790 | CD1 | TYR | 1082 | 52.800 | 23.135 | 21.721 | 1.00 38.13 |
| ATOM | 1791 | CE1 | TYR | 1082 | 52.043 | 22.663 | 22.781 | 1.00 38.73 |
| ATOM | 1792 | CD2 | TYR | 1082 | 50.961 | 22.843 | 20.234 | 1.00 27.91 |

FIG. 7(36)

| | | | | | | | | |
|---|---|---|---|---|---|---|---|---|
| ATOM | 1793 | CE2 | TYR | 1082 | 50.189 | 22.374 | 21.287 | 1.00 33.59 |
| ATOM | 1794 | CZ  | TYR | 1082 | 50.739 | 22.290 | 22.572 | 1.00 36.82 |
| ATOM | 1795 | OH  | TYR | 1082 | 50.001 | 21.874 | 23.679 | 1.00 39.60 |
| ATOM | 1797 | C   | TYR | 1082 | 54.591 | 23.598 | 17.410 | 1.00 34.81 |
| ATOM | 1798 | O   | TYR | 1082 | 55.240 | 24.608 | 17.545 | 1.00 33.62 |
| ATOM | 1799 | N   | THR | 1083 | 54.394 | 22.997 | 16.236 | 1.00 34.71 |
| ATOM | 1801 | CA  | THR | 1083 | 54.819 | 23.573 | 14.946 | 1.00 30.90 |
| ATOM | 1802 | CB  | THR | 1083 | 56.106 | 22.894 | 14.384 | 1.00 29.46 |
| ATOM | 1803 | OG1 | THR | 1083 | 55.789 | 21.598 | 13.837 | 1.00 30.18 |
| ATOM | 1805 | CG2 | THR | 1083 | 57.159 | 22.768 | 15.486 | 1.00 21.74 |
| ATOM | 1806 | C   | THR | 1083 | 53.678 | 23.371 | 13.946 | 1.00 27.79 |
| ATOM | 1807 | O   | THR | 1083 | 52.651 | 22.777 | 14.293 | 1.00 28.80 |
| ATOM | 1808 | N   | ILE | 1084 | 53.804 | 23.869 | 12.721 | 1.00 24.37 |
| ATOM | 1810 | CA  | ILE | 1084 | 52.700 | 23.615 | 11.797 | 1.00 27.69 |
| ATOM | 1811 | CB  | ILE | 1084 | 52.739 | 24.381 | 10.465 | 1.00 28.65 |
| ATOM | 1812 | CG2 | ILE | 1084 | 51.450 | 25.166 | 10.284 | 1.00 29.19 |
| ATOM | 1813 | CG1 | ILE | 1084 | 53.977 | 25.259 | 10.361 | 1.00 37.75 |
| ATOM | 1814 | CD1 | ILE | 1084 | 55.235 | 24.517 |  9.985 | 1.00 46.61 |
| ATOM | 1815 | C   | ILE | 1084 | 52.689 | 22.143 | 11.459 | 1.00 26.44 |
| ATOM | 1816 | O   | ILE | 1084 | 51.627 | 21.589 | 11.173 | 1.00 24.29 |
| ATOM | 1817 | N   | GLN | 1085 | 53.861 | 21.507 | 11.518 | 1.00 25.11 |
| ATOM | 1819 | CA  | GLN | 1085 | 53.920 | 20.097 | 11.188 | 1.00 24.39 |
| ATOM | 1820 | CB  | GLN | 1085 | 55.315 | 19.612 | 10.823 | 1.00 27.61 |
| ATOM | 1821 | CG  | GLN | 1085 | 55.753 | 20.012 |  9.411 | 1.00 33.25 |
| ATOM | 1822 | CD  | GLN | 1085 | 54.653 | 19.826 |  8.347 | 1.00 34.07 |
| ATOM | 1823 | OE1 | GLN | 1085 | 53.943 | 20.779 |  8.004 | 1.00 41.60 |
| ATOM | 1824 | NE2 | GLN | 1085 | 54.546 | 18.632 |  7.797 | 1.00 28.88 |
| ATOM | 1827 | C   | GLN | 1085 | 53.296 | 19.267 | 12.258 | 1.00 23.23 |
| ATOM | 1828 | O   | GLN | 1085 | 52.900 | 18.141 | 11.981 | 1.00 25.97 |
| ATOM | 1829 | N   | SER | 1086 | 53.195 | 19.798 | 13.480 | 1.00 20.86 |
| ATOM | 1831 | CA  | SER | 1086 | 52.488 | 19.040 | 14.507 | 1.00 18.08 |
| ATOM | 1832 | CB  | SER | 1086 | 53.044 | 19.256 | 15.926 | 1.00 20.91 |
| ATOM | 1833 | OG  | SER | 1086 | 52.870 | 20.559 | 16.440 | 1.00 21.60 |
| ATOM | 1835 | C   | SER | 1086 | 50.962 | 19.336 | 14.353 | 1.00 20.67 |
| ATOM | 1836 | O   | SER | 1086 | 50.138 | 18.531 | 14.806 | 1.00 13.79 |
| ATOM | 1837 | N   | ASP | 1087 | 50.602 | 20.415 | 13.609 | 1.00 18.68 |
| ATOM | 1839 | CA  | ASP | 1087 | 49.190 | 20.793 | 13.324 | 1.00 11.08 |
| ATOM | 1840 | CB  | ASP | 1087 | 49.038 | 22.249 | 12.805 | 1.00 21.08 |
| ATOM | 1841 | CG  | ASP | 1087 | 48.845 | 23.287 | 13.920 | 1.00 23.79 |
| ATOM | 1842 | OD1 | ASP | 1087 | 49.348 | 24.407 | 13.745 | 1.00 31.01 |

FIG. 7(37)

| | | | | | | | |
|---|---|---|---|---|---|---|---|
| ATOM | 1843 | OD2 | ASP | 1087 | 48.212 | 23.013 | 14.967 | 1.00 | 28.91 |
| ATOM | 1844 | C   | ASP | 1087 | 48.632 | 19.860 | 12.261 | 1.00 | 11.16 |
| ATOM | 1845 | O   | ASP | 1087 | 47.406 | 19.640 | 12.177 | 1.00 | 12.65 |
| ATOM | 1846 | N   | VAL | 1088 | 49.520 | 19.390 | 11.390 | 1.00 | 9.61 |
| ATOM | 1848 | CA  | VAL | 1088 | 49.181 | 18.404 | 10.345 | 1.00 | 13.37 |
| ATOM | 1849 | CB  | VAL | 1088 | 50.351 | 18.195 | 9.389  | 1.00 | 15.40 |
| ATOM | 1850 | CG1 | VAL | 1088 | 50.057 | 17.067 | 8.486  | 1.00 | 14.68 |
| ATOM | 1851 | CG2 | VAL | 1088 | 50.609 | 19.477 | 8.587  | 1.00 | 10.67 |
| ATOM | 1852 | C   | VAL | 1088 | 48.839 | 17.061 | 11.014 | 1.00 | 13.67 |
| ATOM | 1853 | O   | VAL | 1088 | 47.897 | 16.387 | 10.618 | 1.00 | 15.00 |
| ATOM | 1854 | N   | TRP | 1089 | 49.618 | 16.668 | 12.015 | 1.00 | 12.30 |
| ATOM | 1856 | CA  | TRP | 1089 | 49.301 | 15.460 | 12.748 | 1.00 | 12.96 |
| ATOM | 1857 | CB  | TRP | 1089 | 50.236 | 15.279 | 13.960 | 1.00 | 16.98 |
| ATOM | 1858 | CG  | TRP | 1089 | 49.764 | 14.195 | 14.887 | 1.00 | 18.14 |
| ATOM | 1859 | CD2 | TRP | 1089 | 50.325 | 12.884 | 15.031 | 1.00 | 18.48 |
| ATOM | 1860 | CE2 | TRP | 1089 | 49.476 | 12.162 | 15.893 | 1.00 | 20.05 |
| ATOM | 1861 | CE3 | TRP | 1089 | 51.460 | 12.245 | 14.503 | 1.00 | 22.61 |
| ATOM | 1862 | CD1 | TRP | 1089 | 48.640 | 14.215 | 15.657 | 1.00 | 18.89 |
| ATOM | 1863 | NE1 | TRP | 1089 | 48.451 | 12.995 | 16.255 | 1.00 | 19.54 |
| ATOM | 1865 | CZ2 | TRP | 1089 | 49.725 | 10.839 | 16.249 | 1.00 | 20.08 |
| ATOM | 1866 | CZ3 | TRP | 1089 | 51.709 | 10.927 | 14.855 | 1.00 | 17.00 |
| ATOM | 1867 | CH2 | TRP | 1089 | 50.846 | 10.243 | 15.722 | 1.00 | 23.71 |
| ATOM | 1868 | C   | TRP | 1089 | 47.873 | 15.711 | 13.207 | 1.00 | 14.68 |
| ATOM | 1869 | O   | TRP | 1089 | 46.987 | 14.958 | 12.842 | 1.00 | 20.33 |
| ATOM | 1870 | N   | SER | 1090 | 47.636 | 16.823 | 13.923 | 1.00 | 18.59 |
| ATOM | 1872 | CA  | SER | 1090 | 46.287 | 17.209 | 14.413 | 1.00 | 15.54 |
| ATOM | 1873 | CB  | SER | 1090 | 46.297 | 18.603 | 15.043 | 1.00 | 12.20 |
| ATOM | 1874 | OG  | SER | 1090 | 47.066 | 18.621 | 16.237 | 1.00 | 18.86 |
| ATOM | 1876 | C   | SER | 1090 | 45.256 | 17.190 | 13.309 | 1.00 | 16.50 |
| ATOM | 1877 | O   | SER | 1090 | 44.128 | 16.691 | 13.487 | 1.00 | 18.14 |
| ATOM | 1878 | N   | PHE | 1091 | 45.635 | 17.745 | 12.158 | 1.00 | 23.35 |
| ATOM | 1880 | CA  | PHE | 1091 | 44.746 | 17.776 | 10.997 | 1.00 | 20.78 |
| ATOM | 1881 | CB  | PHE | 1091 | 45.445 | 18.399 | 9.786  | 1.00 | 17.07 |
| ATOM | 1882 | CG  | PHE | 1091 | 44.533 | 18.524 | 8.598  | 1.00 | 21.98 |
| ATOM | 1883 | CD1 | PHE | 1091 | 43.396 | 19.347 | 8.666  | 1.00 | 17.34 |
| ATOM | 1884 | CD2 | PHE | 1091 | 44.740 | 17.754 | 7.460  | 1.00 | 19.42 |
| ATOM | 1885 | CE1 | PHE | 1091 | 42.485 | 19.398 | 7.641  | 1.00 | 15.43 |
| ATOM | 1886 | CE2 | PHE | 1091 | 43.829 | 17.792 | 6.421  | 1.00 | 18.06 |
| ATOM | 1887 | CZ  | PHE | 1091 | 42.693 | 18.618 | 6.509  | 1.00 | 19.76 |
| ATOM | 1888 | C   | PHE | 1091 | 44.306 | 16.332 | 10.667 | 1.00 | 17.25 |

FIG. 7(38)

| | | | | | | | |
|---|---|---|---|---|---|---|---|
| ATOM | 1889 | O | PHE | 1091 | 43.147 | 16.077 | 10.334 1.00 15.79 |
| ATOM | 1890 | N | GLY | 1092 | 45.258 | 15.408 | 10.812 1.00 19.49 |
| ATOM | 1892 | CA | GLY | 1092 | 45.042 | 13.988 | 10.577 1.00 18.11 |
| ATOM | 1893 | C | GLY | 1092 | 44.029 | 13.429 | 11.544 1.00 19.35 |
| ATOM | 1894 | O | GLY | 1092 | 43.235 | 12.581 | 11.137 1.00 24.23 |
| ATOM | 1895 | N | VAL | 1093 | 44.073 | 13.836 | 12.819 1.00 18.53 |
| ATOM | 1897 | CA | VAL | 1093 | 43.055 | 13.392 | 13.788 1.00 20.09 |
| ATOM | 1898 | CB | VAL | 1093 | 43.389 | 13.752 | 15.298 1.00 15.18 |
| ATOM | 1899 | CG1 | VAL | 1093 | 42.421 | 13.051 | 16.187 1.00 17.08 |
| ATOM | 1900 | CG2 | VAL | 1093 | 44.778 | 13.310 | 15.698 1.00 11.27 |
| ATOM | 1901 | C | VAL | 1093 | 41.661 | 13.971 | 13.376 1.00 22.42 |
| ATOM | 1902 | O | VAL | 1093 | 40.649 | 13.253 | 13.396 1.00 26.19 |
| ATOM | 1903 | N | LEU | 1094 | 41.618 | 15.235 | 12.938 1.00 23.95 |
| ATOM | 1905 | CA | LEU | 1094 | 40.363 | 15.893 | 12.484 1.00 19.63 |
| ATOM | 1906 | CB | LEU | 1094 | 40.667 | 17.338 | 12.050 1.00 25.24 |
| ATOM | 1907 | CG | LEU | 1094 | 39.587 | 18.420 | 11.974 1.00 27.30 |
| ATOM | 1908 | CD1 | LEU | 1094 | 40.136 | 19.497 | 11.113 1.00 28.26 |
| ATOM | 1909 | CD2 | LEU | 1094 | 38.265 | 17.929 | 11.385 1.00 27.54 |
| ATOM | 1910 | C | LEU | 1094 | 39.775 | 15.146 | 11.280 1.00 16.12 |
| ATOM | 1911 | O | LEU | 1094 | 38.555 | 15.002 | 11.129 1.00 16.14 |
| ATOM | 1912 | N | LEU | 1095 | 40.631 | 14.766 | 10.348 1.00 16.30 |
| ATOM | 1914 | CA | LEU | 1095 | 40.155 | 14.003 | 9.195 1.00 17.98 |
| ATOM | 1915 | CB | LEU | 1095 | 41.321 | 13.538 | 8.317 1.00 16.52 |
| ATOM | 1916 | CG | LEU | 1095 | 41.981 | 14.536 | 7.386 1.00 14.88 |
| ATOM | 1917 | CD1 | LEU | 1095 | 42.807 | 13.734 | 6.399 1.00 11.81 |
| ATOM | 1918 | CD2 | LEU | 1095 | 40.931 | 15.401 | 6.639 1.00 21.08 |
| ATOM | 1919 | C | LEU | 1095 | 39.437 | 12.770 | 9.722 1.00 17.52 |
| ATOM | 1920 | O | LEU | 1095 | 38.324 | 12.448 | 9.270 1.00 16.23 |
| ATOM | 1921 | N | TRP | 1096 | 40.077 | 12.105 | 10.697 1.00 14.50 |
| ATOM | 1923 | CA | TRP | 1096 | 39.509 | 10.916 | 11.304 1.00 14.02 |
| ATOM | 1924 | CB | TRP | 1096 | 40.452 | 10.330 | 12.337 1.00 13.21 |
| ATOM | 1925 | CG | TRP | 1096 | 40.010 | 8.992 | 12.850 1.00 18.93 |
| ATOM | 1926 | CD2 | TRP | 1096 | 39.016 | 8.732 | 13.856 1.00 24.77 |
| ATOM | 1927 | CE2 | TRP | 1096 | 38.952 | 7.319 | 14.020 1.00 27.07 |
| ATOM | 1928 | CE3 | TRP | 1096 | 38.178 | 9.546 | 14.647 1.00 29.39 |
| ATOM | 1929 | CD1 | TRP | 1096 | 40.483 | 7.781 | 12.460 1.00 21.28 |
| ATOM | 1930 | NE1 | TRP | 1096 | 39.854 | 6.770 | 13.154 1.00 18.61 |
| ATOM | 1932 | CZ2 | TRP | 1096 | 38.075 | 6.700 | 14.954 1.00 28.21 |
| ATOM | 1933 | CZ3 | TRP | 1096 | 37.303 | 8.927 | 15.581 1.00 29.42 |
| ATOM | 1934 | CH2 | TRP | 1096 | 37.266 | 7.511 | 15.719 1.00 27.60 |

FIG. 7(39)

| | | | | | | | | |
|---|---|---|---|---|---|---|---|---|
| ATOM | 1935 | C | TRP | 1096 | 38.159 | 11.236 | 11.927 | 1.00 18.94 |
| ATOM | 1936 | O | TRP | 1096 | 37.212 | 10.439 | 11.826 | 1.00 22.31 |
| ATOM | 1937 | N | GLU | 1097 | 38.046 | 12.385 | 12.592 | 1.00 23.97 |
| ATOM | 1939 | CA | GLU | 1097 | 36.754 | 12.750 | 13.195 | 1.00 21.61 |
| ATOM | 1940 | CB | GLU | 1097 | 36.823 | 14.012 | 14.041 | 1.00 26.60 |
| ATOM | 1941 | CG | GLU | 1097 | 37.880 | 14.065 | 15.109 | 1.00 21.55 |
| ATOM | 1942 | CD | GLU | 1097 | 37.795 | 15.380 | 15.800 | 1.00 23.56 |
| ATOM | 1943 | OE1 | GLU | 1097 | 36.726 | 15.591 | 16.393 | 1.00 21.97 |
| ATOM | 1944 | OE2 | GLU | 1097 | 38.741 | 16.208 | 15.706 | 1.00 20.79 |
| ATOM | 1945 | C | GLU | 1097 | 35.744 | 13.010 | 12.116 | 1.00 19.15 |
| ATOM | 1946 | O | GLU | 1097 | 34.549 | 12.766 | 12.304 | 1.00 28.35 |
| ATOM | 1947 | N | ILE | 1098 | 36.190 | 13.565 | 11.001 | 1.00 17.99 |
| ATOM | 1949 | CA | ILE | 1098 | 35.244 | 13.821 | 9.915 | 1.00 17.98 |
| ATOM | 1950 | CB | ILE | 1098 | 35.862 | 14.650 | 8.732 | 1.00 13.59 |
| ATOM | 1951 | CG2 | ILE | 1098 | 34.880 | 14.725 | 7.568 | 1.00 13.47 |
| ATOM | 1952 | CG1 | ILE | 1098 | 36.169 | 16.074 | 9.181 | 1.00 11.46 |
| ATOM | 1953 | CD1 | ILE | 1098 | 36.691 | 16.960 | 8.074 | 1.00 9.72 |
| ATOM | 1954 | C | ILE | 1098 | 34.645 | 12.529 | 9.372 | 1.00 16.07 |
| ATOM | 1955 | O | ILE | 1098 | 33.444 | 12.445 | 9.171 | 1.00 18.22 |
| ATOM | 1956 | N | PHE | 1099 | 35.460 | 11.499 | 9.171 | 1.00 20.11 |
| ATOM | 1958 | CA | PHE | 1099 | 34.925 | 10.257 | 8.601 | 1.00 18.95 |
| ATOM | 1959 | CB | PHE | 1099 | 35.909 | 9.660 | 7.625 | 1.00 16.86 |
| ATOM | 1960 | CG | PHE | 1099 | 36.269 | 10.584 | 6.517 | 1.00 12.61 |
| ATOM | 1961 | CD1 | PHE | 1099 | 37.308 | 11.468 | 6.671 | 1.00 14.37 |
| ATOM | 1962 | CD2 | PHE | 1099 | 35.522 | 10.624 | 5.362 | 1.00 18.03 |
| ATOM | 1963 | CE1 | PHE | 1099 | 37.595 | 12.369 | 5.717 | 1.00 13.66 |
| ATOM | 1964 | CE2 | PHE | 1099 | 35.811 | 11.553 | 4.378 | 1.00 16.05 |
| ATOM | 1965 | CZ | PHE | 1099 | 36.843 | 12.418 | 4.568 | 1.00 17.86 |
| ATOM | 1966 | C | PHE | 1099 | 34.368 | 9.201 | 9.551 | 1.00 23.18 |
| ATOM | 1967 | O | PHE | 1099 | 34.111 | 8.070 | 9.149 | 1.00 22.90 |
| ATOM | 1968 | N | SER | 1100 | 34.274 | 9.553 | 10.825 | 1.00 26.68 |
| ATOM | 1970 | CA | SER | 1100 | 33.652 | 8.690 | 11.820 | 1.00 24.51 |
| ATOM | 1971 | CB | SER | 1100 | 34.504 | 8.572 | 13.079 | 1.00 25.60 |
| ATOM | 1972 | OG | SER | 1100 | 34.826 | 9.842 | 13.625 | 1.00 29.76 |
| ATOM | 1974 | C | SER | 1100 | 32.398 | 9.465 | 12.145 | 1.00 26.92 |
| ATOM | 1975 | O | SER | 1100 | 31.765 | 9.211 | 13.157 | 1.00 31.32 |
| ATOM | 1976 | N | LEU | 1101 | 32.018 | 10.387 | 11.251 | 1.00 28.15 |
| ATOM | 1978 | CA | LEU | 1101 | 30.860 | 11.241 | 11.453 | 1.00 24.97 |
| ATOM | 1979 | CB | LEU | 1101 | 29.556 | 10.557 | 11.015 | 1.00 22.00 |
| ATOM | 1980 | CG | LEU | 1101 | 29.423 | 10.410 | 9.495 | 1.00 25.66 |

FIG. 7(40)

| | | | | | | | | |
|---|---|---|---|---|---|---|---|---|
| ATOM | 1981 | CD1 | LEU | 1101 | 28.060 | 9.866 | 9.127 | 1.00 22.23 |
| ATOM | 1982 | CD2 | LEU | 1101 | 29.632 | 11.768 | 8.829 | 1.00 32.30 |
| ATOM | 1983 | C | LEU | 1101 | 30.771 | 11.779 | 12.888 | 1.00 26.64 |
| ATOM | 1984 | O | LEU | 1101 | 29.793 | 11.552 | 13.580 | 1.00 31.34 |
| ATOM | 1985 | N | GLY | 1102 | 31.828 | 12.446 | 13.336 | 1.00 24.93 |
| ATOM | 1987 | CA | GLY | 1102 | 31.836 | 13.057 | 14.650 | 1.00 28.61 |
| ATOM | 1988 | C | GLY | 1102 | 32.129 | 12.293 | 15.917 | 1.00 32.38 |
| ATOM | 1989 | O | GLY | 1102 | 31.647 | 12.693 | 16.950 | 1.00 35.69 |
| ATOM | 1990 | N | ALA | 1103 | 33.004 | 11.291 | 15.876 | 1.00 35.95 |
| ATOM | 1992 | CA | ALA | 1103 | 33.354 | 10.500 | 17.060 | 1.00 31.27 |
| ATOM | 1993 | CB | ALA | 1103 | 33.515 | 9.041 | 16.672 | 1.00 36.15 |
| ATOM | 1994 | C | ALA | 1103 | 34.625 | 10.972 | 17.747 | 1.00 34.29 |
| ATOM | 1995 | O | ALA | 1103 | 35.382 | 11.788 | 17.190 | 1.00 36.92 |
| ATOM | 1996 | N | SER | 1104 | 34.886 | 10.417 | 18.934 | 1.00 33.11 |
| ATOM | 1998 | CA | SER | 1104 | 36.087 | 10.744 | 19.715 | 1.00 35.13 |
| ATOM | 1999 | CB | SER | 1104 | 35.906 | 10.422 | 21.207 | 1.00 38.40 |
| ATOM | 2000 | OG | SER | 1104 | 34.719 | 10.964 | 21.765 | 1.00 50.36 |
| ATOM | 2002 | C | SER | 1104 | 37.216 | 9.852 | 19.249 | 1.00 34.54 |
| ATOM | 2003 | O | SER | 1104 | 37.039 | 8.640 | 19.167 | 1.00 33.44 |
| ATOM | 2004 | N | PRO | 1105 | 38.395 | 10.434 | 18.963 | 1.00 32.93 |
| ATOM | 2005 | CD | PRO | 1105 | 38.678 | 11.877 | 18.972 | 1.00 31.54 |
| ATOM | 2006 | CA | PRO | 1105 | 39.571 | 9.693 | 18.513 | 1.00 29.88 |
| ATOM | 2007 | CB | PRO | 1105 | 40.633 | 10.781 | 18.465 | 1.00 22.24 |
| ATOM | 2008 | CG | PRO | 1105 | 39.883 | 11.965 | 18.079 | 1.00 28.04 |
| ATOM | 2009 | C | PRO | 1105 | 39.919 | 8.659 | 19.582 | 1.00 32.54 |
| ATOM | 2010 | O | PRO | 1105 | 39.480 | 8.795 | 20.731 | 1.00 28.79 |
| ATOM | 2011 | N | TYR | 1106 | 40.700 | 7.648 | 19.196 | 1.00 34.52 |
| ATOM | 2013 | CA | TYR | 1106 | 41.148 | 6.564 | 20.085 | 1.00 39.62 |
| ATOM | 2014 | CB | TYR | 1106 | 42.374 | 6.994 | 20.896 | 1.00 37.66 |
| ATOM | 2015 | CG | TYR | 1106 | 43.496 | 7.566 | 20.059 | 1.00 39.50 |
| ATOM | 2016 | CD1 | TYR | 1106 | 43.690 | 8.957 | 19.976 | 1.00 37.50 |
| ATOM | 2017 | CE1 | TYR | 1106 | 44.655 | 9.518 | 19.143 | 1.00 35.61 |
| ATOM | 2018 | CD2 | TYR | 1106 | 44.315 | 6.739 | 19.293 | 1.00 34.54 |
| ATOM | 2019 | CE2 | TYR | 1106 | 45.305 | 7.290 | 18.446 | 1.00 38.80 |
| ATOM | 2020 | CZ | TYR | 1106 | 45.466 | 8.686 | 18.373 | 1.00 38.23 |
| ATOM | 2021 | OH | TYR | 1106 | 46.412 | 9.240 | 17.520 | 1.00 31.37 |
| ATOM | 2023 | C | TYR | 1106 | 40.022 | 6.128 | 21.016 | 1.00 47.24 |
| ATOM | 2024 | O | TYR | 1106 | 40.100 | 6.296 | 22.247 | 1.00 46.94 |
| ATOM | 2025 | N | PRO | 1107 | 38.947 | 5.570 | 20.431 | 1.00 52.30 |
| ATOM | 2026 | CD | PRO | 1107 | 38.880 | 5.234 | 18.996 | 1.00 52.76 |

FIG. 7(41)

| ATOM | 2027 | CA  | PRO | 1107 | 37.750 | 5.088  | 21.125 | 1.00 | 55.67 |
|------|------|-----|-----|------|--------|--------|--------|------|-------|
| ATOM | 2028 | CB  | PRO | 1107 | 37.078 | 4.223  | 20.066 | 1.00 | 55.09 |
| ATOM | 2029 | CG  | PRO | 1107 | 37.420 | 4.931  | 18.797 | 1.00 | 52.62 |
| ATOM | 2030 | C   | PRO | 1107 | 38.035 | 4.300  | 22.408 | 1.00 | 60.55 |
| ATOM | 2031 | O   | PRO | 1107 | 38.668 | 3.231  | 22.377 | 1.00 | 60.88 |
| ATOM | 2032 | N   | GLY | 1108 | 37.631 | 4.894  | 23.533 | 1.00 | 62.85 |
| ATOM | 2034 | CA  | GLY | 1108 | 37.790 | 4.284  | 24.845 | 1.00 | 63.10 |
| ATOM | 2035 | C   | GLY | 1108 | 39.171 | 3.783  | 25.228 | 1.00 | 61.44 |
| ATOM | 2036 | O   | GLY | 1108 | 39.319 | 3.010  | 26.178 | 1.00 | 63.49 |
| ATOM | 2037 | N   | VAL | 1109 | 40.181 | 4.228  | 24.498 | 1.00 | 58.31 |
| ATOM | 2039 | CA  | VAL | 1109 | 41.548 | 3.835  | 24.766 | 1.00 | 55.54 |
| ATOM | 2040 | CB  | VAL | 1109 | 42.430 | 4.181  | 23.580 | 1.00 | 54.11 |
| ATOM | 2041 | CG1 | VAL | 1109 | 43.857 | 3.787  | 23.857 | 1.00 | 51.33 |
| ATOM | 2042 | CG2 | VAL | 1109 | 41.875 | 3.528  | 22.306 | 1.00 | 54.09 |
| ATOM | 2043 | C   | VAL | 1109 | 42.006 | 4.657  | 25.949 | 1.00 | 57.04 |
| ATOM | 2044 | O   | VAL | 1109 | 41.492 | 5.749  | 26.163 | 1.00 | 57.18 |
| ATOM | 2045 | N   | LYS | 1110 | 42.969 | 4.140  | 26.711 | 1.00 | 59.43 |
| ATOM | 2047 | CA  | LYS | 1110 | 43.497 | 4.849  | 27.880 | 1.00 | 60.27 |
| ATOM | 2048 | CB  | LYS | 1110 | 43.928 | 3.842  | 28.936 | 1.00 | 63.70 |
| ATOM | 2049 | C   | LYS | 1110 | 44.664 | 5.796  | 27.538 | 1.00 | 60.52 |
| ATOM | 2050 | O   | LYS | 1110 | 45.570 | 5.410  | 26.780 | 1.00 | 61.06 |
| ATOM | 2051 | N   | ILE | 1111 | 44.665 | 7.006  | 28.115 | 1.00 | 58.79 |
| ATOM | 2053 | CA  | ILE | 1111 | 45.732 | 7.987  | 27.859 | 1.00 | 60.01 |
| ATOM | 2054 | CB  | ILE | 1111 | 45.236 | 9.441  | 27.886 | 1.00 | 63.41 |
| ATOM | 2055 | CG2 | ILE | 1111 | 44.517 | 9.798  | 26.596 | 1.00 | 58.31 |
| ATOM | 2056 | CG1 | ILE | 1111 | 44.413 | 9.688  | 29.145 | 1.00 | 69.87 |
| ATOM | 2057 | CD1 | ILE | 1111 | 44.341 | 11.144 | 29.528 | 1.00 | 75.64 |
| ATOM | 2058 | C   | ILE | 1111 | 46.949 | 7.891  | 28.781 | 1.00 | 58.91 |
| ATOM | 2059 | O   | ILE | 1111 | 47.670 | 8.862  | 28.992 | 1.00 | 59.56 |
| ATOM | 2060 | N   | ASP | 1112 | 47.187 | 6.697  | 29.299 | 1.00 | 60.43 |
| ATOM | 2062 | CA  | ASP | 1112 | 48.312 | 6.407  | 30.173 | 1.00 | 56.25 |
| ATOM | 2063 | CB  | ASP | 1112 | 48.318 | 4.919  | 30.421 | 1.00 | 59.88 |
| ATOM | 2064 | CG  | ASP | 1112 | 48.273 | 4.131  | 29.122 | 1.00 | 67.87 |
| ATOM | 2065 | OD1 | ASP | 1112 | 47.179 | 3.893  | 28.564 | 1.00 | 71.34 |
| ATOM | 2066 | OD2 | ASP | 1112 | 49.348 | 3.765  | 28.628 | 1.00 | 72.11 |
| ATOM | 2067 | C   | ASP | 1112 | 49.612 | 6.795  | 29.489 | 1.00 | 54.37 |
| ATOM | 2068 | O   | ASP | 1112 | 49.634 | 7.066  | 28.284 | 1.00 | 50.67 |
| ATOM | 2069 | N   | GLU | 1113 | 50.710 | 6.741  | 30.236 | 1.00 | 55.36 |
| ATOM | 2071 | CA  | GLU | 1113 | 52.024 | 7.089  | 29.683 | 1.00 | 55.99 |
| ATOM | 2072 | CB  | GLU | 1113 | 53.051 | 7.374  | 30.806 | 1.00 | 58.69 |

FIG. 7(42)

| | | | | | | | | |
|---|---|---|---|---|---|---|---|---|
| ATOM | 2073 | C | GLU | 1113 | 52.552 | 6.015 | 28.726 | 1.00 54.42 |
| ATOM | 2074 | O | GLU | 1113 | 53.624 | 6.175 | 28.126 | 1.00 51.91 |
| ATOM | 2075 | N | GLU | 1114 | 51.822 | 4.903 | 28.627 | 1.00 51.54 |
| ATOM | 2077 | CA | GLU | 1114 | 52.192 | 3.819 | 27.719 | 1.00 54.36 |
| ATOM | 2078 | CB | GLU | 1114 | 51.873 | 2.452 | 28.322 | 1.00 56.43 |
| ATOM | 2079 | CG | GLU | 1114 | 53.072 | 1.749 | 28.948 | 1.00 63.29 |
| ATOM | 2080 | CD | GLU | 1114 | 53.996 | 2.661 | 29.772 | 1.00 67.36 |
| ATOM | 2081 | OE1 | GLU | 1114 | 55.153 | 2.870 | 29.329 | 1.00 67.34 |
| ATOM | 2082 | OE2 | GLU | 1114 | 53.590 | 3.127 | 30.873 | 1.00 68.20 |
| ATOM | 2083 | C | GLU | 1114 | 51.440 | 4.031 | 26.412 | 1.00 52.22 |
| ATOM | 2084 | O | GLU | 1114 | 51.830 | 3.514 | 25.360 | 1.00 51.74 |
| ATOM | 2085 | N | PHE | 1115 | 50.383 | 4.840 | 26.486 | 1.00 49.67 |
| ATOM | 2087 | CA | PHE | 1115 | 49.603 | 5.175 | 25.320 | 1.00 44.59 |
| ATOM | 2088 | CB | PHE | 1115 | 48.400 | 6.013 | 25.688 | 1.00 44.73 |
| ATOM | 2089 | CG | PHE | 1115 | 47.918 | 6.890 | 24.579 | 1.00 49.93 |
| ATOM | 2090 | CD1 | PHE | 1115 | 48.140 | 8.270 | 24.621 | 1.00 50.02 |
| ATOM | 2091 | CD2 | PHE | 1115 | 47.251 | 6.344 | 23.477 | 1.00 53.38 |
| ATOM | 2092 | CE1 | PHE | 1115 | 47.704 | 9.098 | 23.577 | 1.00 52.88 |
| ATOM | 2093 | CE2 | PHE | 1115 | 46.805 | 7.158 | 22.425 | 1.00 51.00 |
| ATOM | 2094 | CZ | PHE | 1115 | 47.033 | 8.535 | 22.474 | 1.00 54.64 |
| ATOM | 2095 | C | PHE | 1115 | 50.582 | 5.981 | 24.507 | 1.00 46.08 |
| ATOM | 2096 | O | PHE | 1115 | 50.929 | 5.572 | 23.402 | 1.00 47.48 |
| ATOM | 2097 | N | CYS | 1116 | 51.127 | 7.047 | 25.101 | 1.00 43.91 |
| ATOM | 2099 | CA | CYS | 1116 | 52.109 | 7.898 | 24.404 | 1.00 45.79 |
| ATOM | 2100 | CB | CYS | 1116 | 52.473 | 9.113 | 25.247 | 1.00 44.47 |
| ATOM | 2101 | SG | CYS | 1116 | 51.129 | 9.723 | 26.295 | 1.00 64.10 |
| ATOM | 2102 | C | CYS | 1116 | 53.392 | 7.140 | 24.019 | 1.00 46.03 |
| ATOM | 2103 | O | CYS | 1116 | 54.232 | 7.667 | 23.279 | 1.00 46.86 |
| ATOM | 2104 | N | ARG | 1117 | 53.536 | 5.911 | 24.529 | 1.00 44.91 |
| ATOM | 2106 | CA | ARG | 1117 | 54.688 | 5.069 | 24.237 | 1.00 41.89 |
| ATOM | 2107 | CB | ARG | 1117 | 54.882 | 4.001 | 25.308 | 1.00 43.78 |
| ATOM | 2108 | CG | ARG | 1117 | 56.237 | 3.298 | 25.233 | 1.00 45.19 |
| ATOM | 2109 | CD | ARG | 1117 | 56.189 | 1.905 | 25.856 | 1.00 47.09 |
| ATOM | 2110 | NE | ARG | 1117 | 55.490 | 0.922 | 25.021 | 1.00 49.55 |
| ATOM | 2112 | CZ | ARG | 1117 | 54.329 | 0.337 | 25.336 | 1.00 51.59 |
| ATOM | 2113 | NH1 | ARG | 1117 | 53.783 | -0.547 | 24.506 | 1.00 51.49 |
| ATOM | 2116 | NH2 | ARG | 1117 | 53.695 | 0.649 | 26.461 | 1.00 47.17 |
| ATOM | 2119 | C | ARG | 1117 | 54.370 | 4.389 | 22.927 | 1.00 38.98 |
| ATOM | 2120 | O | ARG | 1117 | 55.156 | 4.455 | 21.996 | 1.00 42.49 |
| ATOM | 2121 | N | ARG | 1118 | 53.206 | 3.751 | 22.860 | 1.00 35.52 |

FIG. 7(43)

| | | | | | | | | |
|---|---|---|---|---|---|---|---|---|
| ATOM | 2123 | CA | ARG | 1118 | 52.745 | 3.072 | 21.649 | 1.00 36.78 |
| ATOM | 2124 | CB | ARG | 1118 | 51.330 | 2.559 | 21.880 | 1.00 31.14 |
| ATOM | 2125 | CG | ARG | 1118 | 51.216 | 1.675 | 23.068 | 1.00 34.41 |
| ATOM | 2126 | CD | ARG | 1118 | 49.766 | 1.587 | 23.535 | 1.00 45.83 |
| ATOM | 2127 | NE | ARG | 1118 | 48.897 | 0.750 | 22.693 | 1.00 53.41 |
| ATOM | 2129 | CZ | ARG | 1118 | 47.564 | 0.658 | 22.826 | 1.00 55.58 |
| ATOM | 2130 | NH1 | ARG | 1118 | 46.862 | -0.144 | 22.025 | 1.00 56.70 |
| ATOM | 2133 | NH2 | ARG | 1118 | 46.921 | 1.380 | 23.745 | 1.00 55.55 |
| ATOM | 2136 | C | ARG | 1118 | 52.742 | 4.067 | 20.471 | 1.00 38.92 |
| ATOM | 2137 | O | ARG | 1118 | 53.331 | 3.835 | 19.400 | 1.00 38.28 |
| ATOM | 2138 | N | LEU | 1119 | 52.063 | 5.186 | 20.711 | 1.00 40.67 |
| ATOM | 2140 | CA | LEU | 1119 | 51.912 | 6.295 | 19.779 | 1.00 36.71 |
| ATOM | 2141 | CB | LEU | 1119 | 51.192 | 7.416 | 20.540 | 1.00 32.46 |
| ATOM | 2142 | CG | LEU | 1119 | 50.238 | 8.508 | 20.049 | 1.00 25.91 |
| ATOM | 2143 | CD1 | LEU | 1119 | 51.047 | 9.651 | 19.564 | 1.00 19.62 |
| ATOM | 2144 | CD2 | LEU | 1119 | 49.250 | 7.993 | 19.024 | 1.00 22.26 |
| ATOM | 2145 | C | LEU | 1119 | 53.301 | 6.728 | 19.245 | 1.00 38.89 |
| ATOM | 2146 | O | LEU | 1119 | 53.469 | 6.960 | 18.047 | 1.00 43.59 |
| ATOM | 2147 | N | LYS | 1120 | 54.315 | 6.771 | 20.099 | 1.00 42.22 |
| ATOM | 2149 | CA | LYS | 1120 | 55.649 | 7.152 | 19.640 | 1.00 41.56 |
| ATOM | 2150 | CB | LYS | 1120 | 56.523 | 7.548 | 20.813 | 1.00 42.85 |
| ATOM | 2151 | CG | LYS | 1120 | 57.467 | 8.670 | 20.467 | 1.00 52.51 |
| ATOM | 2152 | CD | LYS | 1120 | 58.407 | 8.989 | 21.620 | 1.00 60.23 |
| ATOM | 2153 | CE | LYS | 1120 | 59.298 | 10.206 | 21.321 | 1.00 69.72 |
| ATOM | 2154 | NZ | LYS | 1120 | 58.605 | 11.557 | 21.283 | 1.00 76.23 |
| ATOM | 2158 | C | LYS | 1120 | 56.351 | 6.050 | 18.825 | 1.00 43.73 |
| ATOM | 2159 | O | LYS | 1120 | 57.287 | 6.342 | 18.073 | 1.00 47.49 |
| ATOM | 2160 | N | GLU | 1121 | 55.892 | 4.800 | 18.966 | 1.00 43.94 |
| ATOM | 2162 | CA | GLU | 1121 | 56.453 | 3.636 | 18.262 | 1.00 41.07 |
| ATOM | 2163 | CB | GLU | 1121 | 56.415 | 2.395 | 19.147 | 1.00 48.40 |
| ATOM | 2164 | CG | GLU | 1121 | 57.553 | 2.283 | 20.112 | 1.00 58.39 |
| ATOM | 2165 | CD | GLU | 1121 | 57.183 | 1.451 | 21.309 | 1.00 64.79 |
| ATOM | 2166 | OE1 | GLU | 1121 | 56.403 | 0.483 | 21.119 | 1.00 67.43 |
| ATOM | 2167 | OE2 | GLU | 1121 | 57.657 | 1.778 | 22.431 | 1.00 67.24 |
| ATOM | 2168 | C | GLU | 1121 | 55.739 | 3.284 | 16.968 | 1.00 39.16 |
| ATOM | 2169 | O | GLU | 1121 | 56.224 | 2.423 | 16.216 | 1.00 39.90 |
| ATOM | 2170 | N | GLY | 1122 | 54.525 | 3.805 | 16.781 | 1.00 31.72 |
| ATOM | 2172 | CA | GLY | 1122 | 53.838 | 3.550 | 15.531 | 1.00 22.36 |
| ATOM | 2173 | C | GLY | 1122 | 52.427 | 3.064 | 15.646 | 1.00 19.85 |
| ATOM | 2174 | O | GLY | 1122 | 51.791 | 2.779 | 14.633 | 1.00 18.01 |

FIG. 7(44)

| | | | | | | | |
|---|---|---|---|---|---|---|---|
| ATOM | 2175 | N | THR | 1123 | 51.918 | 2.946 | 16.860 1.00 16.84 |
| ATOM | 2177 | CA | THR | 1123 | 50.535 | 2.502 | 16.989 1.00 22.17 |
| ATOM | 2178 | CB | THR | 1123 | 50.209 | 2.144 | 18.469 1.00 29.75 |
| ATOM | 2179 | OG1 | THR | 1123 | 51.148 | 1.174 | 18.971 1.00 31.60 |
| ATOM | 2181 | CG2 | THR | 1123 | 48.794 | 1.587 | 18.591 1.00 31.44 |
| ATOM | 2182 | C | THR | 1123 | 49.653 | 3.673 | 16.453 1.00 23.74 |
| ATOM | 2183 | O | THR | 1123 | 49.940 | 4.850 | 16.721 1.00 18.73 |
| ATOM | 2184 | N | ARG | 1124 | 48.597 | 3.354 | 15.701 1.00 22.93 |
| ATOM | 2186 | CA | ARG | 1124 | 47.735 | 4.379 | 15.125 1.00 17.39 |
| ATOM | 2187 | CB | ARG | 1124 | 48.094 | 4.680 | 13.670 1.00 17.70 |
| ATOM | 2188 | CG | ARG | 1124 | 49.478 | 5.192 | 13.406 1.00 14.57 |
| ATOM | 2189 | CD | ARG | 1124 | 49.713 | 6.484 | 14.040 1.00 14.31 |
| ATOM | 2190 | NE | ARG | 1124 | 51.046 | 6.935 | 13.684 1.00 10.98 |
| ATOM | 2192 | CZ | ARG | 1124 | 52.067 | 6.988 | 14.533 1.00 16.02 |
| ATOM | 2193 | NH1 | ARG | 1124 | 51.861 | 6.604 | 15.775 1.00 10.96 |
| ATOM | 2196 | NH2 | ARG | 1124 | 53.269 | 7.468 | 14.163 1.00 8.74 |
| ATOM | 2199 | C | ARG | 1124 | 46.317 | 3.893 | 15.096 1.00 16.31 |
| ATOM | 2200 | O | ARG | 1124 | 46.085 | 2.698 | 15.022 1.00 20.38 |
| ATOM | 2201 | N | MET | 1125 | 45.380 | 4.847 | 15.081 1.00 21.15 |
| ATOM | 2203 | CA | MET | 1125 | 43.943 | 4.570 | 15.023 1.00 23.81 |
| ATOM | 2204 | CB | MET | 1125 | 43.158 | 5.870 | 15.012 1.00 16.88 |
| ATOM | 2205 | CG | MET | 1125 | 42.783 | 6.397 | 16.380 1.00 17.08 |
| ATOM | 2206 | SD | MET | 1125 | 41.656 | 7.825 | 16.270 1.00 25.19 |
| ATOM | 2207 | CE | MET | 1125 | 42.908 | 9.123 | 15.776 1.00 17.02 |
| ATOM | 2208 | C | MET | 1125 | 43.604 | 3.789 | 13.749 1.00 29.80 |
| ATOM | 2209 | O | MET | 1125 | 44.298 | 3.923 | 12.748 1.00 33.37 |
| ATOM | 2210 | N | ARG | 1126 | 42.576 | 2.953 | 13.806 1.00 36.07 |
| ATOM | 2212 | CA | ARG | 1126 | 42.116 | 2.183 | 12.668 1.00 36.36 |
| ATOM | 2213 | CB | ARG | 1126 | 41.465 | 0.859 | 13.154 1.00 40.10 |
| ATOM | 2214 | CG | ARG | 1126 | 40.257 | 1.021 | 14.061 1.00 54.46 |
| ATOM | 2215 | CD | ARG | 1126 | 38.956 | 1.268 | 13.263 1.00 65.08 |
| ATOM | 2216 | NE | ARG | 1126 | 37.839 | 1.758 | 14.091 1.00 72.39 |
| ATOM | 2218 | CZ | ARG | 1126 | 36.545 | 1.753 | 13.740 1.00 74.53 |
| ATOM | 2219 | NH1 | ARG | 1126 | 35.636 | 2.233 | 14.588 1.00 78.72 |
| ATOM | 2222 | NH2 | ARG | 1126 | 36.140 | 1.267 | 12.562 1.00 74.28 |
| ATOM | 2225 | C | ARG | 1126 | 41.124 | 3.094 | 11.888 1.00 32.52 |
| ATOM | 2226 | O | ARG | 1126 | 40.706 | 4.117 | 12.380 1.00 34.88 |
| ATOM | 2227 | N | ALA | 1127 | 40.760 | 2.725 | 10.676 1.00 29.80 |
| ATOM | 2229 | CA | ALA | 1127 | 39.888 | 3.508 | 9.812 1.00 29.83 |
| ATOM | 2230 | CB | ALA | 1127 | 39.743 | 2.782 | 8.460 1.00 32.24 |

FIG. 7(45)

| | | | | | | | | |
|---|---|---|---|---|---|---|---|---|
| ATOM | 2231 | C | ALA | 1127 | 38.518 | 3.697 | 10.415 | 1.00 34.29 |
| ATOM | 2232 | O | ALA | 1127 | 37.944 | 2.727 | 10.881 | 1.00 39.95 |
| ATOM | 2233 | N | PRO | 1128 | 37.943 | 4.934 | 10.335 | 1.00 34.66 |
| ATOM | 2234 | CD | PRO | 1128 | 38.477 | 6.142 | 9.685 | 1.00 35.04 |
| ATOM | 2235 | CA | PRO | 1128 | 36.612 | 5.251 | 10.871 | 1.00 31.59 |
| ATOM | 2236 | CB | PRO | 1128 | 36.511 | 6.776 | 10.669 | 1.00 32.56 |
| ATOM | 2237 | CG | PRO | 1128 | 37.819 | 7.222 | 10.499 | 1.00 31.06 |
| ATOM | 2238 | C | PRO | 1128 | 35.648 | 4.597 | 9.916 | 1.00 33.99 |
| ATOM | 2239 | O | PRO | 1128 | 35.975 | 4.429 | 8.749 | 1.00 38.28 |
| ATOM | 2240 | N | ASP | 1129 | 34.416 | 4.371 | 10.344 | 1.00 31.98 |
| ATOM | 2242 | CA | ASP | 1129 | 33.425 | 3.728 | 9.489 | 1.00 34.11 |
| ATOM | 2243 | CB | ASP | 1129 | 32.157 | 3.432 | 10.277 | 1.00 29.91 |
| ATOM | 2244 | CG | ASP | 1129 | 32.447 | 2.811 | 11.623 | 1.00 34.04 |
| ATOM | 2245 | OD1 | ASP | 1129 | 33.519 | 2.172 | 11.805 | 1.00 35.22 |
| ATOM | 2246 | OD2 | ASP | 1129 | 31.597 | 2.976 | 12.515 | 1.00 36.43 |
| ATOM | 2247 | C | ASP | 1129 | 33.061 | 4.360 | 8.158 | 1.00 35.75 |
| ATOM | 2248 | O | ASP | 1129 | 32.441 | 3.699 | 7.312 | 1.00 38.26 |
| ATOM | 2249 | N | TYR | 1130 | 33.444 | 5.613 | 7.925 | 1.00 32.58 |
| ATOM | 2251 | CA | TYR | 1130 | 33.056 | 6.200 | 6.649 | 1.00 34.86 |
| ATOM | 2252 | CB | TYR | 1130 | 32.067 | 7.332 | 6.888 | 1.00 38.26 |
| ATOM | 2253 | CG | TYR | 1130 | 30.996 | 6.960 | 7.889 | 1.00 37.51 |
| ATOM | 2254 | CD1 | TYR | 1130 | 31.208 | 7.153 | 9.245 | 1.00 36.44 |
| ATOM | 2255 | CE1 | TYR | 1130 | 30.249 | 6.853 | 10.148 | 1.00 40.00 |
| ATOM | 2256 | CD2 | TYR | 1130 | 29.787 | 6.442 | 7.468 | 1.00 39.18 |
| ATOM | 2257 | CE2 | TYR | 1130 | 28.813 | 6.143 | 8.360 | 1.00 34.53 |
| ATOM | 2258 | CZ | TYR | 1130 | 29.050 | 6.353 | 9.709 | 1.00 39.16 |
| ATOM | 2259 | OH | TYR | 1130 | 28.120 | 6.147 | 10.690 | 1.00 47.34 |
| ATOM | 2261 | C | TYR | 1130 | 34.136 | 6.657 | 5.732 | 1.00 34.80 |
| ATOM | 2262 | O | TYR | 1130 | 33.853 | 7.257 | 4.694 | 1.00 27.05 |
| ATOM | 2263 | N | THR | 1131 | 35.388 | 6.414 | 6.108 | 1.00 37.58 |
| ATOM | 2265 | CA | THR | 1131 | 36.457 | 6.829 | 5.238 | 1.00 38.70 |
| ATOM | 2266 | CB | THR | 1131 | 37.783 | 6.598 | 5.763 | 1.00 39.57 |
| ATOM | 2267 | OG1 | THR | 1131 | 37.775 | 5.417 | 6.564 | 1.00 51.23 |
| ATOM | 2269 | CG2 | THR | 1131 | 38.250 | 7.775 | 6.481 | 1.00 49.58 |
| ATOM | 2270 | C | THR | 1131 | 36.476 | 6.071 | 3.955 | 1.00 38.19 |
| ATOM | 2271 | O | THR | 1131 | 35.913 | 4.967 | 3.808 | 1.00 38.82 |
| ATOM | 2272 | N | THR | 1132 | 37.297 | 6.649 | 3.104 | 1.00 31.58 |
| ATOM | 2274 | CA | THR | 1132 | 37.638 | 6.148 | 1.836 | 1.00 27.37 |
| ATOM | 2275 | CB | THR | 1132 | 37.591 | 7.302 | 0.887 | 1.00 18.06 |
| ATOM | 2276 | OG1 | THR | 1132 | 36.274 | 7.366 | 0.348 | 1.00 29.75 |

FIG. 7(46)

| | | | | | | | |
|---|---|---|---|---|---|---|---|
| ATOM | 2278 | CG2 | THR | 1132 | 38.528 | 7.126 | -0.161 1.00 32.09 |
| ATOM | 2279 | C | THR | 1132 | 39.064 | 5.634 | 2.159 1.00 31.18 |
| ATOM | 2280 | O | THR | 1132 | 39.678 | 6.088 | 3.149 1.00 37.35 |
| ATOM | 2281 | N | PRO | 1133 | 39.543 | 4.601 | 1.439 1.00 29.49 |
| ATOM | 2282 | CD | PRO | 1133 | 38.884 | 3.875 | 0.336 1.00 28.18 |
| ATOM | 2283 | CA | PRO | 1133 | 40.876 | 4.065 | 1.686 1.00 23.60 |
| ATOM | 2284 | CB | PRO | 1133 | 41.029 | 2.998 | 0.604 1.00 29.05 |
| ATOM | 2285 | CG | PRO | 1133 | 39.640 | 2.581 | 0.319 1.00 28.36 |
| ATOM | 2286 | C | PRO | 1133 | 41.917 | 5.122 | 1.500 1.00 22.87 |
| ATOM | 2287 | O | PRO | 1133 | 42.944 | 5.119 | 2.182 1.00 30.07 |
| ATOM | 2288 | N | GLU | 1134 | 41.700 | 5.983 | 0.511 1.00 18.80 |
| ATOM | 2290 | CA | GLU | 1134 | 42.656 | 7.049 | 0.264 1.00 22.21 |
| ATOM | 2291 | CB | GLU | 1134 | 42.594 | 7.573 | -1.160 1.00 26.28 |
| ATOM | 2292 | CG | GLU | 1134 | 41.214 | 7.564 | -1.765 1.00 40.23 |
| ATOM | 2293 | CD | GLU | 1134 | 40.901 | 6.347 | -2.617 1.00 42.05 |
| ATOM | 2294 | OE1 | GLU | 1134 | 41.727 | 6.004 | -3.504 1.00 44.65 |
| ATOM | 2295 | OE2 | GLU | 1134 | 39.799 | 5.779 | -2.453 1.00 44.07 |
| ATOM | 2296 | C | GLU | 1134 | 42.547 | 8.164 | 1.300 1.00 21.07 |
| ATOM | 2297 | O | GLU | 1134 | 43.528 | 8.877 | 1.543 1.00 20.78 |
| ATOM | 2298 | N | MET | 1135 | 41.375 | 8.304 | 1.940 1.00 20.24 |
| ATOM | 2300 | CA | MET | 1135 | 41.233 | 9.304 | 2.996 1.00 16.52 |
| ATOM | 2301 | CB | MET | 1135 | 39.775 | 9.658 | 3.319 1.00 17.57 |
| ATOM | 2302 | CG | MET | 1135 | 39.158 | 10.807 | 2.420 1.00 15.02 |
| ATOM | 2303 | SD | MET | 1135 | 40.199 | 12.320 | 2.187 1.00 20.17 |
| ATOM | 2304 | CE | MET | 1135 | 40.632 | 12.648 | 3.877 1.00 13.20 |
| ATOM | 2305 | C | MET | 1135 | 41.974 | 8.751 | 4.191 1.00 20.41 |
| ATOM | 2306 | O | MET | 1135 | 42.772 | 9.461 | 4.787 1.00 25.79 |
| ATOM | 2307 | N | TYR | 1136 | 41.836 | 7.448 | 4.445 1.00 20.30 |
| ATOM | 2309 | CA | TYR | 1136 | 42.565 | 6.817 | 5.540 1.00 17.65 |
| ATOM | 2310 | CB | TYR | 1136 | 42.082 | 5.394 | 5.832 1.00 21.89 |
| ATOM | 2311 | CG | TYR | 1136 | 42.786 | 4.775 | 7.041 1.00 26.17 |
| ATOM | 2312 | CD1 | TYR | 1136 | 42.702 | 5.353 | 8.325 1.00 20.81 |
| ATOM | 2313 | CE1 | TYR | 1136 | 43.364 | 4.781 | 9.427 1.00 17.33 |
| ATOM | 2314 | CD2 | TYR | 1136 | 43.554 | 3.612 | 6.900 1.00 26.03 |
| ATOM | 2315 | CE2 | TYR | 1136 | 44.225 | 3.034 | 7.998 1.00 12.75 |
| ATOM | 2316 | CZ | TYR | 1136 | 44.124 | 3.615 | 9.245 1.00 16.64 |
| ATOM | 2317 | OH | TYR | 1136 | 44.791 | 2.999 | 10.281 1.00 17.57 |
| ATOM | 2319 | C | TYR | 1136 | 44.077 | 6.847 | 5.267 1.00 14.28 |
| ATOM | 2320 | O | TYR | 1136 | 44.892 | 7.066 | 6.179 1.00 19.62 |
| ATOM | 2321 | N | GLN | 1137 | 44.479 | 6.693 | 4.022 1.00 12.55 |

FIG. 7(47)

| ATOM | 2323 | CA | GLN | 1137 | 45.903 | 6.777 | 3.758 | 1.00 | 16.34 |
|---|---|---|---|---|---|---|---|---|---|
| ATOM | 2324 | CB | GLN | 1137 | 46.218 | 6.412 | 2.325 | 1.00 | 18.36 |
| ATOM | 2325 | CG | GLN | 1137 | 47.702 | 6.654 | 1.945 | 1.00 | 21.79 |
| ATOM | 2326 | CD | GLN | 1137 | 48.613 | 5.655 | 2.561 | 1.00 | 14.21 |
| ATOM | 2327 | OE1 | GLN | 1137 | 48.416 | 4.469 | 2.381 | 1.00 | 22.64 |
| ATOM | 2328 | NE2 | GLN | 1137 | 49.571 | 6.111 | 3.344 | 1.00 | 18.97 |
| ATOM | 2331 | C | GLN | 1137 | 46.415 | 8.193 | 4.041 | 1.00 | 20.40 |
| ATOM | 2332 | O | GLN | 1137 | 47.598 | 8.378 | 4.391 | 1.00 | 25.11 |
| ATOM | 2333 | N | THR | 1138 | 45.564 | 9.194 | 3.807 | 1.00 | 18.65 |
| ATOM | 2335 | CA | THR | 1138 | 45.939 | 10.568 | 4.068 | 1.00 | 15.52 |
| ATOM | 2336 | CB | THR | 1138 | 44.921 | 11.507 | 3.538 | 1.00 | 19.97 |
| ATOM | 2337 | OG1 | THR | 1138 | 44.797 | 11.257 | 2.144 | 1.00 | 18.74 |
| ATOM | 2339 | CG2 | THR | 1138 | 45.381 | 12.939 | 3.722 | 1.00 | 21.70 |
| ATOM | 2340 | C | THR | 1138 | 46.111 | 10.721 | 5.566 | 1.00 | 12.73 |
| ATOM | 2341 | O | THR | 1138 | 47.067 | 11.344 | 6.010 | 1.00 | 18.83 |
| ATOM | 2342 | N | MET | 1139 | 45.233 | 10.118 | 6.352 | 1.00 | 9.32 |
| ATOM | 2344 | CA | MET | 1139 | 45.402 | 10.151 | 7.809 | 1.00 | 12.25 |
| ATOM | 2345 | CB | MET | 1139 | 44.295 | 9.349 | 8.480 | 1.00 | 13.21 |
| ATOM | 2346 | CG | MET | 1139 | 42.967 | 10.007 | 8.354 | 1.00 | 5.60 |
| ATOM | 2347 | SD | MET | 1139 | 41.708 | 8.982 | 9.003 | 1.00 | 17.66 |
| ATOM | 2348 | CE | MET | 1139 | 40.510 | 9.337 | 7.925 | 1.00 | 2.00 |
| ATOM | 2349 | C | MET | 1139 | 46.773 | 9.567 | 8.198 | 1.00 | 15.96 |
| ATOM | 2350 | O | MET | 1139 | 47.573 | 10.237 | 8.855 | 1.00 | 17.30 |
| ATOM | 2351 | N | LEU | 1140 | 47.058 | 8.333 | 7.770 | 1.00 | 15.29 |
| ATOM | 2353 | CA | LEU | 1140 | 48.357 | 7.735 | 8.081 | 1.00 | 14.20 |
| ATOM | 2354 | CB | LEU | 1140 | 48.542 | 6.409 | 7.326 | 1.00 | 6.27 |
| ATOM | 2355 | CG | LEU | 1140 | 47.511 | 5.373 | 7.745 | 1.00 | 15.42 |
| ATOM | 2356 | CD1 | LEU | 1140 | 47.656 | 4.103 | 6.927 | 1.00 | 8.64 |
| ATOM | 2357 | CD2 | LEU | 1140 | 47.648 | 5.103 | 9.246 | 1.00 | 14.99 |
| ATOM | 2358 | C | LEU | 1140 | 49.518 | 8.684 | 7.751 | 1.00 | 17.20 |
| ATOM | 2359 | O | LEU | 1140 | 50.552 | 8.691 | 8.442 | 1.00 | 18.73 |
| ATOM | 2360 | N | ASP | 1141 | 49.396 | 9.413 | 6.644 | 1.00 | 20.16 |
| ATOM | 2362 | CA | ASP | 1141 | 50.442 | 10.374 | 6.229 | 1.00 | 19.52 |
| ATOM | 2363 | CB | ASP | 1141 | 50.139 | 10.963 | 4.851 | 1.00 | 20.89 |
| ATOM | 2364 | CG | ASP | 1141 | 50.228 | 9.942 | 3.772 | 1.00 | 25.01 |
| ATOM | 2365 | OD1 | ASP | 1141 | 50.537 | 8.765 | 4.074 | 1.00 | 30.17 |
| ATOM | 2366 | OD2 | ASP | 1141 | 49.994 | 10.321 | 2.624 | 1.00 | 26.42 |
| ATOM | 2367 | C | ASP | 1141 | 50.627 | 11.521 | 7.207 | 1.00 | 15.10 |
| ATOM | 2368 | O | ASP | 1141 | 51.762 | 11.905 | 7.502 | 1.00 | 8.73 |
| ATOM | 2369 | N | CYS | 1142 | 49.504 | 12.101 | 7.637 | 1.00 | 10.75 |

FIG. 7(48)

| | | | | | | | | |
|---|---|---|---|---|---|---|---|---|
| ATOM | 2371 | CA | CYS | 1142 | 49.516 | 13.196 | 8.590 | 1.00 13.88 |
| ATOM | 2372 | CB | CYS | 1142 | 48.110 | 13.776 | 8.739 | 1.00 17.83 |
| ATOM | 2373 | SG | CYS | 1142 | 47.414 | 14.574 | 7.291 | 1.00 17.66 |
| ATOM | 2374 | C | CYS | 1142 | 50.042 | 12.717 | 9.961 | 1.00 15.52 |
| ATOM | 2375 | O | CYS | 1142 | 50.545 | 13.513 | 10.734 | 1.00 16.31 |
| ATOM | 2376 | N | TRP | 1143 | 49.883 | 11.424 | 10.266 | 1.00 20.06 |
| ATOM | 2378 | CA | TRP | 1143 | 50.344 | 10.830 | 11.528 | 1.00 17.66 |
| ATOM | 2379 | CB | TRP | 1143 | 49.393 | 9.727 | 11.991 | 1.00 15.44 |
| ATOM | 2380 | CG | TRP | 1143 | 48.041 | 10.236 | 12.273 | 1.00 14.25 |
| ATOM | 2381 | CD2 | TRP | 1143 | 46.814 | 9.495 | 12.233 | 1.00 18.13 |
| ATOM | 2382 | CE2 | TRP | 1143 | 45.774 | 10.401 | 12.540 | 1.00 12.59 |
| ATOM | 2383 | CE3 | TRP | 1143 | 46.490 | 8.143 | 11.966 | 1.00 16.02 |
| ATOM | 2384 | CD1 | TRP | 1143 | 47.710 | 11.514 | 12.605 | 1.00 7.90 |
| ATOM | 2385 | NE1 | TRP | 1143 | 46.355 | 11.618 | 12.768 | 1.00 13.52 |
| ATOM | 2387 | CZ2 | TRP | 1143 | 44.425 | 10.012 | 12.592 | 1.00 8.83 |
| ATOM | 2388 | CZ3 | TRP | 1143 | 45.155 | 7.755 | 12.017 | 1.00 11.61 |
| ATOM | 2389 | CH2 | TRP | 1143 | 44.133 | 8.691 | 12.327 | 1.00 16.83 |
| ATOM | 2390 | C | TRP | 1143 | 51.765 | 10.281 | 11.442 | 1.00 23.22 |
| ATOM | 2391 | O | TRP | 1143 | 52.208 | 9.507 | 12.298 | 1.00 27.31 |
| ATOM | 2392 | N | HIS | 1144 | 52.510 | 10.722 | 10.440 | 1.00 24.48 |
| ATOM | 2394 | CA | HIS | 1144 | 53.876 | 10.280 | 10.299 | 1.00 26.08 |
| ATOM | 2395 | CB | HIS | 1144 | 54.495 | 10.859 | 9.023 | 1.00 19.25 |
| ATOM | 2396 | CG | HIS | 1144 | 55.791 | 10.214 | 8.654 | 1.00 18.57 |
| ATOM | 2397 | CD2 | HIS | 1144 | 56.923 | 10.003 | 9.374 | 1.00 14.60 |
| ATOM | 2398 | ND1 | HIS | 1144 | 56.016 | 9.657 | 7.415 | 1.00 19.61 |
| ATOM | 2400 | CE1 | HIS | 1144 | 57.231 | 9.133 | 7.387 | 1.00 19.99 |
| ATOM | 2401 | NE2 | HIS | 1144 | 57.803 | 9.332 | 8.562 | 1.00 15.04 |
| ATOM | 2403 | C | HIS | 1144 | 54.710 | 10.671 | 11.542 | 1.00 32.65 |
| ATOM | 2404 | O | HIS | 1144 | 54.626 | 11.795 | 12.031 | 1.00 31.70 |
| ATOM | 2405 | N | GLY | 1145 | 55.541 | 9.734 | 12.016 | 1.00 37.26 |
| ATOM | 2407 | CA | GLY | 1145 | 56.393 | 9.970 | 13.168 | 1.00 31.32 |
| ATOM | 2408 | C | GLY | 1145 | 57.251 | 11.212 | 13.001 | 1.00 35.04 |
| ATOM | 2409 | O | GLY | 1145 | 57.372 | 11.989 | 13.942 | 1.00 38.42 |
| ATOM | 2410 | N | GLU | 1146 | 57.915 | 11.373 | 11.852 | 1.00 34.51 |
| ATOM | 2412 | CA | GLU | 1146 | 58.735 | 12.577 | 11.598 | 1.00 37.16 |
| ATOM | 2413 | CB | GLU | 1146 | 59.871 | 12.303 | 10.627 | 1.00 37.16 |
| ATOM | 2414 | CG | GLU | 1146 | 61.093 | 11.742 | 11.292 | 1.00 50.26 |
| ATOM | 2415 | CD | GLU | 1146 | 61.186 | 10.243 | 11.110 | 1.00 54.17 |
| ATOM | 2416 | OE1 | GLU | 1146 | 61.158 | 9.509 | 12.125 | 1.00 55.25 |
| ATOM | 2417 | OE2 | GLU | 1146 | 61.280 | 9.804 | 9.938 | 1.00 59.09 |

FIG. 7(49)

| ATOM | 2418 | C   | GLU | 1146 | 57.910 | 13.742 | 11.052 | 1.00 | 36.46 |
|------|------|-----|-----|------|--------|--------|--------|------|-------|
| ATOM | 2419 | O   | GLU | 1146 | 57.378 | 13.665 | 9.934  | 1.00 | 35.72 |
| ATOM | 2420 | N   | PRO | 1147 | 57.861 | 14.868 | 11.791 | 1.00 | 34.09 |
| ATOM | 2421 | CD  | PRO | 1147 | 58.490 | 15.147 | 13.099 | 1.00 | 33.72 |
| ATOM | 2422 | CA  | PRO | 1147 | 57.082 | 16.020 | 11.336 | 1.00 | 29.77 |
| ATOM | 2423 | CB  | PRO | 1147 | 57.446 | 17.106 | 12.351 | 1.00 | 27.86 |
| ATOM | 2424 | CG  | PRO | 1147 | 57.668 | 16.334 | 13.619 | 1.00 | 26.72 |
| ATOM | 2425 | C   | PRO | 1147 | 57.436 | 16.417 | 9.922  | 1.00 | 27.04 |
| ATOM | 2426 | O   | PRO | 1147 | 56.559 | 16.784 | 9.158  | 1.00 | 30.21 |
| ATOM | 2427 | N   | SER | 1148 | 58.698 | 16.255 | 9.551  | 1.00 | 22.56 |
| ATOM | 2429 | CA  | SER | 1148 | 59.177 | 16.616 | 8.210  | 1.00 | 24.23 |
| ATOM | 2430 | CB  | SER | 1148 | 60.707 | 16.724 | 8.203  | 1.00 | 27.40 |
| ATOM | 2431 | OG  | SER | 1148 | 61.314 | 15.477 | 8.545  | 1.00 | 36.19 |
| ATOM | 2433 | C   | SER | 1148 | 58.743 | 15.674 | 7.101  | 1.00 | 21.41 |
| ATOM | 2434 | O   | SER | 1148 | 58.890 | 15.964 | 5.913  | 1.00 | 24.41 |
| ATOM | 2435 | N   | GLN | 1149 | 58.272 | 14.508 | 7.485  | 1.00 | 25.45 |
| ATOM | 2437 | CA  | GLN | 1149 | 57.831 | 13.547 | 6.497  | 1.00 | 26.28 |
| ATOM | 2438 | CB  | GLN | 1149 | 58.224 | 12.142 | 6.946  | 1.00 | 32.79 |
| ATOM | 2439 | CG  | GLN | 1149 | 59.705 | 11.907 | 6.958  | 1.00 | 25.96 |
| ATOM | 2440 | CD  | GLN | 1149 | 60.279 | 12.196 | 5.622  | 1.00 | 32.77 |
| ATOM | 2441 | OE1 | GLN | 1149 | 59.765 | 11.744 | 4.591  | 1.00 | 36.63 |
| ATOM | 2442 | NE2 | GLN | 1149 | 61.312 | 13.007 | 5.604  | 1.00 | 37.86 |
| ATOM | 2445 | C   | GLN | 1149 | 56.327 | 13.670 | 6.278  | 1.00 | 23.40 |
| ATOM | 2446 | O   | GLN | 1149 | 55.783 | 13.145 | 5.306  | 1.00 | 23.12 |
| ATOM | 2447 | N   | ARG | 1150 | 55.662 | 14.339 | 7.215  | 1.00 | 22.72 |
| ATOM | 2449 | CA  | ARG | 1150 | 54.226 | 14.581 | 7.132  | 1.00 | 17.86 |
| ATOM | 2450 | CB  | ARG | 1150 | 53.721 | 15.243 | 8.392  | 1.00 | 16.38 |
| ATOM | 2451 | CG  | ARG | 1150 | 54.161 | 14.532 | 9.598  | 1.00 | 13.96 |
| ATOM | 2452 | CD  | ARG | 1150 | 53.285 | 14.903 | 10.728 | 1.00 | 15.08 |
| ATOM | 2453 | NE  | ARG | 1150 | 53.632 | 14.090 | 11.879 | 1.00 | 24.55 |
| ATOM | 2455 | CZ  | ARG | 1150 | 54.066 | 14.564 | 13.040 | 1.00 | 27.63 |
| ATOM | 2456 | NH1 | ARG | 1150 | 54.192 | 15.871 | 13.230 | 1.00 | 27.18 |
| ATOM | 2459 | NH2 | ARG | 1150 | 54.423 | 13.717 | 13.991 | 1.00 | 29.34 |
| ATOM | 2462 | C   | ARG | 1150 | 54.025 | 15.559 | 6.008  | 1.00 | 16.82 |
| ATOM | 2463 | O   | ARG | 1150 | 54.913 | 16.382 | 5.715  | 1.00 | 13.09 |
| ATOM | 2464 | N   | PRO | 1151 | 52.873 | 15.464 | 5.320  | 1.00 | 18.01 |
| ATOM | 2465 | CD  | PRO | 1151 | 51.793 | 14.453 | 5.320  | 1.00 | 6.32  |
| ATOM | 2466 | CA  | PRO | 1151 | 52.726 | 16.442 | 4.240  | 1.00 | 18.95 |
| ATOM | 2467 | CB  | PRO | 1151 | 51.489 | 15.948 | 3.492  | 1.00 | 16.01 |
| ATOM | 2468 | CG  | PRO | 1151 | 50.726 | 15.092 | 4.520  | 1.00 | 10.59 |

FIG. 7(50)

| | | | | | | | | |
|---|---|---|---|---|---|---|---|---|
| ATOM | 2469 | C   | PRO | 1151 | 52.574 | 17.861 |  4.805 | 1.00 18.27 |
| ATOM | 2470 | O   | PRO | 1151 | 52.422 | 18.039 |  6.006 | 1.00 19.70 |
| ATOM | 2471 | N   | THR | 1152 | 52.763 | 18.860 |  3.958 | 1.00 19.16 |
| ATOM | 2473 | CA  | THR | 1152 | 52.604 | 20.251 |  4.366 | 1.00 14.92 |
| ATOM | 2474 | CB  | THR | 1152 | 53.511 | 21.138 |  3.560 | 1.00 13.80 |
| ATOM | 2475 | OG1 | THR | 1152 | 53.146 | 21.080 |  2.163 | 1.00 17.02 |
| ATOM | 2477 | CG2 | THR | 1152 | 54.918 | 20.697 |  3.764 | 1.00  5.40 |
| ATOM | 2478 | C   | THR | 1152 | 51.196 | 20.571 |  3.979 | 1.00 13.16 |
| ATOM | 2479 | O   | THR | 1152 | 50.682 | 19.905 |  3.084 | 1.00 19.18 |
| ATOM | 2480 | N   | PHE | 1153 | 50.561 | 21.572 |  4.599 | 1.00 14.62 |
| ATOM | 2482 | CA  | PHE | 1153 | 49.176 | 21.910 |  4.224 | 1.00 12.87 |
| ATOM | 2483 | CB  | PHE | 1153 | 48.588 | 23.023 |  5.083 | 1.00 11.95 |
| ATOM | 2484 | CG  | PHE | 1153 | 48.157 | 22.558 |  6.422 | 1.00  9.67 |
| ATOM | 2485 | CD1 | PHE | 1153 | 47.037 | 21.740 |  6.560 | 1.00 14.91 |
| ATOM | 2486 | CD2 | PHE | 1153 | 48.891 | 22.857 |  7.533 | 1.00 15.01 |
| ATOM | 2487 | CE1 | PHE | 1153 | 46.660 | 21.215 |  7.802 | 1.00  9.44 |
| ATOM | 2488 | CE2 | PHE | 1153 | 48.529 | 22.340 |  8.789 | 1.00 13.43 |
| ATOM | 2489 | CZ  | PHE | 1153 | 47.405 | 21.513 |  8.913 | 1.00  8.41 |
| ATOM | 2490 | C   | PHE | 1153 | 49.073 | 22.253 |  2.750 | 1.00 16.98 |
| ATOM | 2491 | O   | PHE | 1153 | 48.078 | 21.927 |  2.114 | 1.00 21.60 |
| ATOM | 2492 | N   | SER | 1154 | 50.116 | 22.841 |  2.168 | 1.00 15.39 |
| ATOM | 2494 | CA  | SER | 1154 | 50.031 | 23.123 |  0.754 | 1.00 17.55 |
| ATOM | 2495 | CB  | SER | 1154 | 51.251 | 23.868 |  0.254 | 1.00 25.28 |
| ATOM | 2496 | OG  | SER | 1154 | 51.244 | 25.190 |  0.776 | 1.00 33.35 |
| ATOM | 2498 | C   | SER | 1154 | 49.850 | 21.815 |  0.022 | 1.00 20.26 |
| ATOM | 2499 | O   | SER | 1154 | 48.932 | 21.704 | -0.798 | 1.00 23.74 |
| ATOM | 2500 | N   | GLU | 1155 | 50.670 | 20.808 |  0.347 | 1.00 19.47 |
| ATOM | 2502 | CA  | GLU | 1155 | 50.534 | 19.493 | -0.307 | 1.00 16.55 |
| ATOM | 2503 | CB  | GLU | 1155 | 51.588 | 18.513 |  0.188 | 1.00 19.82 |
| ATOM | 2504 | CG  | GLU | 1155 | 52.932 | 18.773 | -0.486 | 1.00 20.20 |
| ATOM | 2505 | CD  | GLU | 1155 | 54.128 | 18.210 |  0.249 | 1.00 23.11 |
| ATOM | 2506 | OE1 | GLU | 1155 | 55.226 | 18.377 | -0.312 | 1.00 35.76 |
| ATOM | 2507 | OE2 | GLU | 1155 | 54.009 | 17.631 |  1.359 | 1.00 21.09 |
| ATOM | 2508 | C   | GLU | 1155 | 49.153 | 18.918 | -0.107 | 1.00 16.59 |
| ATOM | 2509 | O   | GLU | 1155 | 48.548 | 18.414 | -1.055 | 1.00 21.37 |
| ATOM | 2510 | N   | LEU | 1156 | 48.619 | 19.034 |  1.101 | 1.00 16.01 |
| ATOM | 2512 | CA  | LEU | 1156 | 47.272 | 18.532 |  1.375 | 1.00 18.06 |
| ATOM | 2513 | CB  | LEU | 1156 | 46.969 | 18.521 |  2.875 | 1.00 15.74 |
| ATOM | 2514 | CG  | LEU | 1156 | 47.688 | 17.493 |  3.759 | 1.00 11.35 |
| ATOM | 2515 | CD1 | LEU | 1156 | 47.786 | 18.049 |  5.201 | 1.00  2.08 |

FIG. 7(51)

| | | | | | | | |
|---|---|---|---|---|---|---|---|
| ATOM | 2516 | CD2 | LEU | 1156 | 46.927 | 16.150 | 3.708 1.00 14.36 |
| ATOM | 2517 | C | LEU | 1156 | 46.165 | 19.287 | 0.638 1.00 20.03 |
| ATOM | 2518 | O | LEU | 1156 | 45.105 | 18.711 | 0.355 1.00 26.86 |
| ATOM | 2519 | N | VAL | 1157 | 46.354 | 20.570 | 0.355 1.00 21.44 |
| ATOM | 2521 | CA | VAL | 1157 | 45.303 | 21.283 | -0.362 1.00 21.15 |
| ATOM | 2522 | CB | VAL | 1157 | 45.513 | 22.801 | -0.381 1.00 21.33 |
| ATOM | 2523 | CG1 | VAL | 1157 | 44.569 | 23.453 | -1.368 1.00 15.98 |
| ATOM | 2524 | CG2 | VAL | 1157 | 45.198 | 23.340 | 0.974 1.00 13.87 |
| ATOM | 2525 | C | VAL | 1157 | 45.270 | 20.721 | -1.760 1.00 22.88 |
| ATOM | 2526 | O | VAL | 1157 | 44.198 | 20.508 | -2.333 1.00 25.54 |
| ATOM | 2527 | N | GLU | 1158 | 46.445 | 20.400 | -2.282 1.00 23.10 |
| ATOM | 2529 | CA | GLU | 1158 | 46.503 | 19.815 | -3.603 1.00 27.24 |
| ATOM | 2530 | CB | GLU | 1158 | 47.922 | 19.756 | -4.115 1.00 32.82 |
| ATOM | 2531 | CG | GLU | 1158 | 47.969 | 18.978 | -5.404 1.00 44.73 |
| ATOM | 2532 | CD | GLU | 1158 | 49.187 | 19.268 | -6.212 1.00 51.53 |
| ATOM | 2533 | OE1 | GLU | 1158 | 49.007 | 19.887 | -7.292 1.00 54.31 |
| ATOM | 2534 | OE2 | GLU | 1158 | 50.298 | 18.869 | -5.765 1.00 51.10 |
| ATOM | 2535 | C | GLU | 1158 | 45.939 | 18.403 | -3.643 1.00 26.42 |
| ATOM | 2536 | O | GLU | 1158 | 45.167 | 18.051 | -4.546 1.00 25.91 |
| ATOM | 2537 | N | HIS | 1159 | 46.347 | 17.591 | -2.669 1.00 26.36 |
| ATOM | 2539 | CA | HIS | 1159 | 45.897 | 16.226 | -2.611 1.00 21.52 |
| ATOM | 2540 | CB | HIS | 1159 | 46.674 | 15.444 | -1.576 1.00 25.28 |
| ATOM | 2541 | CG | HIS | 1159 | 46.322 | 13.991 | -1.545 1.00 24.66 |
| ATOM | 2542 | CD2 | HIS | 1159 | 46.408 | 13.030 | -2.497 1.00 24.44 |
| ATOM | 2543 | ND1 | HIS | 1159 | 45.749 | 13.387 | -0.452 1.00 21.30 |
| ATOM | 2545 | CE1 | HIS | 1159 | 45.489 | 12.125 | -0.731 1.00 23.16 |
| ATOM | 2546 | NE2 | HIS | 1159 | 45.879 | 11.884 | -1.961 1.00 19.88 |
| ATOM | 2548 | C | HIS | 1159 | 44.402 | 16.104 | -2.391 1.00 21.56 |
| ATOM | 2549 | O | HIS | 1159 | 43.741 | 15.311 | -3.066 1.00 22.19 |
| ATOM | 2550 | N | LEU | 1160 | 43.852 | 16.874 | -1.456 1.00 20.25 |
| ATOM | 2552 | CA | LEU | 1160 | 42.408 | 16.832 | -1.209 1.00 17.66 |
| ATOM | 2553 | CB | LEU | 1160 | 42.111 | 17.502 | 0.130 1.00 17.84 |
| ATOM | 2554 | CG | LEU | 1160 | 42.676 | 16.760 | 1.352 1.00 20.17 |
| ATOM | 2555 | CD1 | LEU | 1160 | 42.472 | 17.542 | 2.619 1.00 21.45 |
| ATOM | 2556 | CD2 | LEU | 1160 | 41.992 | 15.454 | 1.512 1.00 19.45 |
| ATOM | 2557 | C | LEU | 1160 | 41.566 | 17.418 | -2.395 1.00 17.71 |
| ATOM | 2558 | O | LEU | 1160 | 40.426 | 17.030 | -2.624 1.00 15.39 |
| ATOM | 2559 | N | GLY | 1161 | 42.130 | 18.356 | -3.153 1.00 23.52 |
| ATOM | 2561 | CA | GLY | 1161 | 41.434 | 18.879 | -4.322 1.00 21.37 |
| ATOM | 2562 | C | GLY | 1161 | 41.342 | 17.741 | -5.346 1.00 23.91 |

FIG. 7(52)

| | | |
|---|---|---|
| ATOM | 2563 O   GLY 1161 | 40.295 17.526 -5.971 1.00 23.05 |
| ATOM | 2564 N   ASN 1162 | 42.439 16.997 -5.520 1.00 21.49 |
| ATOM | 2566 CA  ASN 1162 | 42.428 15.854 -6.428 1.00 22.31 |
| ATOM | 2567 CB  ASN 1162 | 43.771 15.109 -6.427 1.00 22.34 |
| ATOM | 2568 CG  ASN 1162 | 44.904 15.888 -7.062 1.00 20.03 |
| ATOM | 2569 OD1 ASN 1162 | 44.705 16.903 -7.701 1.00 28.17 |
| ATOM | 2570 ND2 ASN 1162 | 46.117 15.401 -6.873 1.00 32.22 |
| ATOM | 2573 C   ASN 1162 | 41.356 14.851 -5.969 1.00 23.05 |
| ATOM | 2574 O   ASN 1162 | 40.570 14.378 -6.769 1.00 26.11 |
| ATOM | 2575 N   LEU 1163 | 41.360 14.490 -4.688 1.00 21.05 |
| ATOM | 2577 CA  LEU 1163 | 40.405 13.523 -4.166 1.00 19.91 |
| ATOM | 2578 CB  LEU 1163 | 40.695 13.172 -2.689 1.00 19.18 |
| ATOM | 2579 CG  LEU 1163 | 41.675 12.042 -2.275 1.00 18.62 |
| ATOM | 2580 CD1 LEU 1163 | 42.959 12.120 -3.020 1.00 24.35 |
| ATOM | 2581 CD2 LEU 1163 | 41.983 12.043 -0.804 1.00 14.82 |
| ATOM | 2582 C   LEU 1163 | 39.015 14.038 -4.331 1.00 19.71 |
| ATOM | 2583 O   LEU 1163 | 38.110 13.318 -4.767 1.00 23.11 |
| ATOM | 2584 N   LEU 1164 | 38.860 15.328 -4.121 1.00 25.91 |
| ATOM | 2586 CA  LEU 1164 | 37.533 15.941 -4.226 1.00 29.28 |
| ATOM | 2587 CB  LEU 1164 | 37.603 17.388 -3.726 1.00 31.25 |
| ATOM | 2588 CG  LEU 1164 | 36.348 18.176 -3.371 1.00 25.75 |
| ATOM | 2589 CD1 LEU 1164 | 35.429 17.396 -2.435 1.00 31.52 |
| ATOM | 2590 CD2 LEU 1164 | 7.018 15.866 -5.653 1.00 30.07 |
| ATOM | 2592 O   LEU 1164 | 35.953 15.330 -5.903 1.00 32.61 |
| ATOM | 2593 N   GLN 1165 | 37.810 16.344 -6.598 1.00 33.76 |
| ATOM | 2595 CA  GLN 1165 | 37.423 16.317 -8.003 1.00 39.95 |
| ATOM | 2596 CB  GLN 1165 | 38.451 17.048 -8.855 1.00 46.90 |
| ATOM | 2597 CG  GLN 1165 | 38.758 18.474 -8.480 1.00 49.81 |
| ATOM | 2598 CD  GLN 1165 | 39.874 19.024 -9.348 1.00 56.23 |
| ATOM | 2599 OE1 GLN 1165 | 41.056 18.945 -8.997 1.00 55.97 |
| ATOM | 2600 NE2 GLN 1165 | 39.508 19.536 -10.518 1.00 60.66 |
| ATOM | 2603 C   GLN 1165 | 37.304 14.898 -8.554 1.00 39.33 |
| ATOM | 2604 O   GLN 1165 | 36.652 14.685 -9.568 1.00 42.09 |
| ATOM | 2605 N   ALA 1166 | 38.059 13.965 -7.988 1.00 36.82 |
| ATOM | 2607 CA  ALA 1166 | 37.994 12.586 -8.441 1.00 34.66 |
| ATOM | 2608 CB  ALA 1166 | 39.096 11.748 -7.814 1.00 32.78 |
| ATOM | 2609 C   ALA 1166 | 36.640 12.103 -7.991 1.00 36.63 |
| ATOM | 2610 O   ALA 1166 | 35.969 11.381 -8.713 1.00 39.47 |
| ATOM | 2611 N   ASN 1167 | 36.226 12.532 -6.800 1.00 40.01 |
| ATOM | 2613 CA  ASN 1167 | 34.911 12.158 -6.264 1.00 42.40 |

FIG. 7(53)

| | | | | | | | |
|---|---|---|---|---|---|---|---|
| ATOM | 2614 | CB | ASN | 1167 | 34.641 | 12.878 | -4.919 | 1.00 | 42.99 |
| ATOM | 2615 | CG | ASN | 1167 | 33.354 | 12.409 | -4.242 | 1.00 | 40.80 |
| ATOM | 2616 | OD1 | ASN | 1167 | 32.306 | 13.046 | -4.348 | 1.00 | 40.18 |
| ATOM | 2617 | ND2 | ASN | 1167 | 33.436 | 11.294 | -3.532 | 1.00 | 36.58 |
| ATOM | 2620 | C | ASN | 1167 | 33.822 | 12.498 | -7.299 | 1.00 | 41.88 |
| ATOM | 2621 | O | ASN | 1167 | 32.837 | 11.789 | -7.391 | 1.00 | 41.83 |
| ATOM | 2622 | N | ALA | 1168 | 34.057 | 13.558 | -8.085 | 1.00 | 45.09 |
| ATOM | 2624 | CA | ALA | 1168 | 33.187 | 14.065 | -9.160 | 1.00 | 46.02 |
| ATOM | 2625 | CB | ALA | 1168 | 32.507 | 12.933 | -9.929 | 1.00 | 45.92 |
| ATOM | 2626 | C | ALA | 1168 | 32.181 | 15.123 | -8.728 | 1.00 | 48.61 |
| ATOM | 2628 | O | ALA | 1168 | 32.627 | 16.233 | -8.363 | 1.00 | 50.20 |
| ATOM | 2629 | O | HOH | 1 | 46.858 | 21.496 | 16.690 | 1.00 | 23.54 |
| ATOM | 2632 | O | HOH | 2 | 49.904 | 21.605 | 17.271 | 1.00 | 36.65 |
| ATOM | 2635 | O | HOH | 3 | 49.682 | 18.133 | 17.657 | 1.00 | 50.47 |
| ATOM | 2638 | O | HOH | 4 | 56.606 | 19.394 | 15.202 | 1.00 | 25.28 |
| ATOM | 2641 | O | HOH | 5 | 57.215 | 21.949 | 11.395 | 1.00 | 37.66 |
| ATOM | 2644 | O | HOH | 6 | 56.082 | 25.850 | 12.933 | 1.00 | 34.63 |
| ATOM | 2647 | O | HOH | 7 | 52.355 | 23.016 | 6.377 | 1.00 | 21.45 |
| ATOM | 2650 | O | HOH | 8 | 51.153 | 27.376 | 4.088 | 1.00 | 29.93 |
| ATOM | 2653 | O | HOH | 9 | 44.820 | 28.454 | 1.120 | 1.00 | 16.47 |
| ATOM | 2656 | O | HOH | 10 | 46.377 | 38.321 | 5.198 | 1.00 | 31.93 |
| ATOM | 2659 | O | HOH | 11 | 43.987 | 38.133 | 3.129 | 1.00 | 52.41 |
| ATOM | 2662 | O | HOH | 12 | 53.321 | 40.451 | 6.702 | 1.00 | 31.88 |
| ATOM | 2665 | O | HOH | 13 | 44.977 | 49.530 | 8.305 | 1.00 | 44.56 |
| ATOM | 2668 | O | HOH | 14 | 44.379 | 43.338 | 7.798 | 1.00 | 31.72 |
| ATOM | 2671 | O | HOH | 15 | 39.477 | 40.232 | 8.468 | 1.00 | 36.65 |
| ATOM | 2674 | O | HOH | 16 | 41.987 | 36.751 | 10.646 | 1.00 | 23.26 |
| ATOM | 2677 | O | HOH | 17 | 41.711 | 41.873 | 6.802 | 1.00 | 34.79 |
| ATOM | 2680 | O | HOH | 18 | 29.514 | 24.656 | 18.739 | 1.00 | 31.43 |
| ATOM | 2683 | O | HOH | 19 | 27.493 | 22.351 | 15.517 | 1.00 | 42.03 |
| ATOM | 2686 | O | HOH | 20 | 24.345 | 20.097 | 15.325 | 1.00 | 24.92 |
| ATOM | 2689 | O | HOH | 21 | 32.381 | 18.452 | 20.520 | 1.00 | 75.12 |
| ATOM | 2692 | O | HOH | 22 | 31.071 | 8.282 | 19.507 | 1.00 | 31.68 |
| ATOM | 2695 | O | HOH | 23 | 33.001 | 7.742 | 21.598 | 1.00 | 38.67 |
| ATOM | 2698 | O | HOH | 24 | 34.802 | 6.439 | 18.667 | 1.00 | 34.24 |
| ATOM | 2701 | O | HOH | 25 | 32.273 | 6.932 | 14.174 | 1.00 | 41.21 |
| ATOM | 2704 | O | HOH | 26 | 34.059 | 5.245 | 12.870 | 1.00 | 49.30 |
| ATOM | 2707 | O | HOH | 27 | 38.059 | 3.432 | 4.799 | 1.00 | 63.69 |
| ATOM | 2710 | O | HOH | 28 | 41.089 | 1.841 | 4.421 | 1.00 | 42.86 |
| ATOM | 2713 | O | HOH | 29 | 45.081 | 9.234 | -0.557 | 1.00 | 39.97 |

FIG. 7(54)

| | | | | | | | | |
|---|---|---|---|---|---|---|---|---|
| ATOM | 2716 | O | HOH | 30 | 47.301 | 11.215 | 1.271 | 1.00 58.47 |
| ATOM | 2719 | O | HOH | 31 | 50.046 | 14.055 | 0.168 | 1.00 37.58 |
| ATOM | 2722 | O | HOH | 32 | 54.425 | 8.937 | 4.821 | 1.00 36.74 |
| ATOM | 2725 | O | HOH | 33 | 52.279 | 7.099 | 5.152 | 1.00 13.04 |
| ATOM | 2728 | O | HOH | 34 | 53.025 | 7.510 | 7.740 | 1.00 25.53 |
| ATOM | 2731 | O | HOH | 35 | 50.852 | 6.818 | 10.462 | 1.00 18.29 |
| ATOM | 2734 | O | HOH | 36 | 46.448 | 7.762 | 15.254 | 1.00 9.08 |
| ATOM | 2737 | O | HOH | 37 | 47.326 | 3.930 | 20.460 | 1.00 34.16 |
| ATOM | 2740 | O | HOH | 38 | 48.264 | 12.367 | 20.804 | 1.00 22.14 |
| ATOM | 2743 | O | HOH | 39 | 44.276 | 8.193 | 24.312 | 1.00 40.52 |
| ATOM | 2746 | O | HOH | 40 | 37.491 | 11.237 | 25.975 | 1.00 38.71 |
| ATOM | 2749 | O | HOH | 41 | 37.592 | 13.565 | 23.164 | 1.00 44.55 |
| ATOM | 2752 | O | HOH | 42 | 34.887 | 12.418 | 26.235 | 1.00 50.96 |
| ATOM | 2755 | O | HOH | 43 | 24.823 | 15.933 | 17.377 | 1.00 33.72 |
| ATOM | 2758 | O | HOH | 44 | 23.302 | 7.532 | 7.049 | 1.00 57.56 |
| ATOM | 2761 | O | HOH | 45 | 29.954 | 11.864 | -3.109 | 1.00 38.05 |
| ATOM | 2764 | O | HOH | 46 | 42.099 | 3.812 | 18.044 | 1.00 40.12 |
| ATOM | 2767 | O | HOH | 47 | 38.653 | 0.737 | 18.003 | 1.00 37.30 |
| ATOM | 2770 | O | HOH | 48 | 34.169 | 14.465 | 16.707 | 1.00 20.01 |
| ATOM | 2773 | O | HOH | 49 | 37.055 | 32.622 | 16.570 | 1.00 31.20 |
| ATOM | 2776 | O | HOH | 50 | 29.361 | 31.729 | 15.460 | 1.00 21.90 |
| ATOM | 2779 | O | HOH | 51 | 25.866 | 31.495 | 10.192 | 1.00 24.50 |
| ATOM | 2782 | O | HOH | 52 | 23.411 | 32.276 | 10.616 | 1.00 68.85 |
| ATOM | 2785 | O | HOH | 53 | 22.135 | 37.404 | 8.648 | 1.00 40.22 |
| ATOM | 2788 | O | HOH | 54 | 28.356 | 36.997 | 10.747 | 1.00 22.41 |
| ATOM | 2791 | O | HOH | 55 | 29.650 | 33.190 | 8.897 | 1.00 31.98 |
| ATOM | 2794 | O | HOH | 56 | 34.801 | 35.904 | 3.297 | 1.00 59.73 |
| ATOM | 2797 | O | HOH | 57 | 24.341 | 20.715 | 4.934 | 1.00 28.10 |
| ATOM | 2800 | O | HOH | 58 | 37.439 | 20.236 | 25.832 | 1.00 33.07 |
| ATOM | 2803 | O | HOH | 59 | 32.675 | 51.977 | 19.122 | 1.00 33.52 |
| ATOM | 2806 | O | HOH | 60 | 32.722 | 54.003 | 14.118 | 1.00 25.01 |
| ATOM | 2809 | O | HOH | 61 | 29.691 | 54.769 | 22.004 | 1.00 27.32 |
| ATOM | 2812 | O | HOH | 62 | 21.347 | 47.577 | 14.711 | 1.00 27.85 |
| ATOM | 2815 | O | HOH | 63 | 25.640 | 44.257 | 7.516 | 1.00 24.71 |
| ATOM | 2818 | O | HOH | 64 | 24.686 | 40.916 | 3.785 | 1.00 55.13 |
| ATOM | 2821 | O | HOH | 65 | 33.825 | 48.721 | 10.105 | 1.00 39.11 |
| ATOM | 2824 | O | HOH | 66 | 39.855 | 54.415 | 18.247 | 1.00 50.97 |
| ATOM | 2827 | O | HOH | 67 | 36.001 | 50.053 | 7.081 | 1.00 68.99 |
| ATOM | 2830 | O | HOH | 68 | 37.973 | 50.651 | 5.331 | 1.00 32.12 |
| ATOM | 2833 | O | HOH | 69 | 40.220 | 53.227 | 6.506 | 1.00 15.02 |

FIG. 7(55)

| | | | | | | | | |
|---|---|---|---|---|---|---|---|---|
| ATOM | 2836 | O | HOH | 70 | 42.258 | 51.833 | 6.993 | 1.00 21.05 |
| ATOM | 2839 | O | HOH | 71 | 36.813 | 55.217 | 13.035 | 1.00 46.29 |
| ATOM | 2842 | O | HOH | 72 | 37.030 | 55.879 | 15.712 | 1.00 39.36 |
| ATOM | 2845 | O | HOH | 73 | 23.054 | 45.061 | 23.607 | 1.00 51.11 |
| ATOM | 2848 | O | HOH | 74 | 27.075 | 54.516 | 6.971 | 1.00 51.66 |
| ATOM | 2851 | O | HOH | 75 | 21.634 | 54.039 | 13.651 | 1.00 36.36 |
| ATOM | 2854 | O | HOH | 76 | 45.158 | 47.529 | 30.699 | 1.00 56.11 |
| ATOM | 2857 | O | HOH | 77 | 44.469 | 45.246 | 36.699 | 1.00 36.50 |
| ATOM | 2860 | O | HOH | 78 | 45.882 | 41.717 | 36.085 | 1.00 28.57 |
| ATOM | 2863 | O | HOH | 79 | 49.406 | 41.527 | 34.292 | 1.00 65.94 |
| ATOM | 2866 | O | HOH | 80 | 36.134 | 49.719 | 26.101 | 1.00 63.80 |
| ATOM | 2869 | O | HOH | 81 | 26.884 | 28.564 | 16.554 | 1.00 49.20 |
| ATOM | 2872 | O | HOH | 82 | 22.079 | 10.131 | 13.444 | 1.00 56.45 |
| ATOM | 2875 | O | HOH | 83 | 41.225 | 4.655 | 30.464 | 1.00 58.98 |
| ATOM | 2878 | O | HOH | 84 | 47.309 | 1.568 | 10.326 | 1.00 21.69 |
| ATOM | 2881 | O | HOH | 85 | 56.613 | 18.335 | 6.527 | 1.00 33.97 |
| ATOM | 2884 | O | HOH | 86 | 56.196 | 16.855 | 3.275 | 1.00 47.24 |
| ATOM | 2887 | O | HOH | 87 | 54.826 | 22.813 | 0.598 | 1.00 33.50 |
| ATOM | 2890 | O | HOH | 88 | 52.962 | 21.915 | -2.351 | 1.00 66.62 |
| ATOM | 2893 | O | HOH | 89 | 47.896 | 24.242 | -3.714 | 1.00 40.99 |
| ATOM | 2896 | O | HOH | 90 | 40.295 | 22.360 | 25.551 | 1.00 39.81 |
| ATOM | 2899 | O | HOH | 91 | 40.188 | 3.202 | 15.661 | 1.00 45.97 |
| ATOM | 2902 | O | HOH | 92 | 45.159 | 2.965 | 19.553 | 1.00 44.25 |
| ATOM | 2905 | O | HOH | 93 | 36.591 | 7.772 | 23.374 | 1.00 68.23 |
| ATOM | 2908 | O | HOH | 94 | 34.274 | 5.197 | 22.878 | 1.00 51.62 |
| ATOM | 2911 | O | HOH | 95 | 41.935 | 7.033 | 29.073 | 1.00 63.23 |
| ATOM | 2914 | O | HOH | 96 | 20.731 | 12.105 | 14.716 | 1.00 54.80 |
| ATOM | 2917 | O | HOH | 97 | 23.147 | 13.682 | 17.882 | 1.00 50.81 |
| ATOM | 2920 | O | HOH | 98 | 35.515 | 9.509 | -3.558 | 1.00 56.70 |
| ATOM | 2923 | O | HOH | 99 | 38.933 | 9.503 | -1.231 | 1.00 32.18 |
| ATOM | 2926 | O | HOH | 100 | 51.814 | 24.438 | 3.703 | 1.00 52.00 |
| ATOM | 2929 | O | HOH | 101 | 51.670 | 28.690 | 0.838 | 1.00 42.41 |
| ATOM | 2932 | O | HOH | 102 | 46.536 | 30.610 | 1.750 | 1.00 45.80 |
| ATOM | 2935 | O | HOH | 103 | 45.165 | 34.214 | 0.818 | 1.00 46.46 |
| ATOM | 2938 | O | HOH | 104 | 42.695 | 35.194 | 1.055 | 1.00 25.82 |
| ATOM | 2941 | O | HOH | 105 | 39.689 | 33.418 | 0.723 | 1.00 31.99 |
| ATOM | 2944 | O | HOH | 106 | 23.962 | 38.119 | 27.549 | 1.00 47.89 |
| ATOM | 2947 | O | HOH | 107 | 25.343 | 40.908 | 27.379 | 1.00 54.09 |
| ATOM | 2950 | O | HOH | 108 | 20.307 | 35.738 | 19.866 | 1.00 32.61 |
| ATOM | 2953 | O | HOH | 109 | 28.085 | 54.303 | 18.810 | 1.00 61.58 |

FIG. 7(56)

| | | | | | | | |
|---|---|---|---|---|---|---|---|
| ATOM | 2956 | O | HOH | 110 | 29.849 56.131 16.966 | 1.00 | 37.29 |
| ATOM | 2959 | O | HOH | 111 | 31.503 58.023 14.735 | 1.00 | 46.45 |
| ATOM | 2962 | O | HOH | 112 | 35.212 55.981 10.499 | 1.00 | 92.07 |
| ATOM | 2965 | O | HOH | 113 | 36.530 55.812 6.656 | 1.00 | 30.72 |
| ATOM | 2968 | O | HOH | 114 | 50.045 41.251 26.059 | 1.00 | 82.26 |
| ATOM | 2971 | O | HOH | 115 | 25.153 36.460 9.054 | 1.00 | 50.86 |
| ATOM | 2974 | O | HOH | 116 | 31.749 32.705 15.359 | 1.00 | 30.04 |
| ATOM | 2977 | O | HOH | 117 | 30.213 3.806 4.940 | 1.00 | 39.74 |
| ATOM | 2980 | O | HOH | 118 | 36.511 1.159 7.275 | 1.00 | 41.62 |
| ATOM | 2983 | O | HOH | 119 | 27.155 4.637 5.224 | 1.00 | 79.92 |
| ATOM | 2986 | O | HOH | 120 | 57.319 11.287 3.459 | 1.00 | 33.02 |
| ATOM | 2989 | O | HOH | 121 | 52.121 12.483 1.755 | 1.00 | 45.55 |
| ATOM | 2992 | O | HOH | 122 | 47.613 14.088 -5.021 | 1.00 | 41.01 |
| ATOM | 2995 | O | HOH | 123 | 57.550 26.628 16.551 | 1.00 | 30.62 |
| ATOM | 2998 | O | HOH | 124 | 32.338 10.125 23.559 | 1.00 | 35.48 |
| ATOM | 3001 | O | HOH | 125 | 31.065 5.698 3.273 | 1.00 | 42.74 |
| ATOM | 3004 | O | HOH | 126 | 32.603 4.523 1.410 | 1.00 | 33.30 |
| ATOM | 3007 | O | HOH | 127 | 34.394 2.617 4.702 | 1.00 | 42.12 |
| ATOM | 3010 | O | HOH | 128 | 37.961 10.373 -4.287 | 1.00 | 47.57 |
| ATOM | 3013 | O | HOH | 129 | 42.215 11.947 -6.970 | 1.00 | 45.13 |
| ATOM | 3016 | O | HOH | 130 | 46.307 8.952 -4.280 | 1.00 | 70.02 |
| ATOM | 3019 | O | HOH | 131 | 50.369 17.388 -3.277 | 1.00 | 42.22 |
| ATOM | 3022 | O | HOH | 132 | 47.231 21.866 22.930 | 1.00 | 50.84 |
| ATOM | 3025 | O | HOH | 133 | 45.362 17.669 27.147 | 1.00 | 48.06 |
| ATOM | 3028 | O | HOH | 134 | 27.005 23.141 18.124 | 1.00 | 49.65 |
| ATOM | 3031 | O | HOH | 135 | 45.726 12.511 -6.453 | 1.00 | 45.31 |
| ATOM | 3034 | O | HOH | 136 | 46.998 11.755 18.088 | 1.00 | 37.38 |
| ATOM | 3037 | O | HOH | 137 | 39.706 37.699 9.894 | 1.00 | 40.71 |
| ATOM | 3040 | O | HOH | 138 | 18.768 48.678 17.798 | 1.00 | 74.62 |
| ATOM | 3043 | O | HOH | 139 | 43.641 47.080 26.762 | 1.00 | 44.64 |
| ATOM | 3046 | O | HOH | 140 | 32.593 53.980 16.744 | 1.00 | 43.95 |
| ATOM | 3049 | O | HOH | 141 | 34.726 55.568 14.399 | 1.00 | 45.86 |
| ATOM | 3052 | O | HOH | 142 | 30.551 53.227 19.638 | 1.00 | 35.99 |
| ATOM | 3055 | O | HOH | 143 | 26.370 55.161 14.300 | 1.00 | 33.09 |
| ATOM | 3058 | O | HOH | 144 | 24.547 55.803 6.815 | 1.00 | 58.70 |
| ATOM | 3061 | O | HOH | 145 | 36.217 52.574 3.221 | 1.00 | 68.48 |
| ATOM | 3064 | O | HOH | 146 | 39.065 54.455 4.595 | 1.00 | 48.85 |
| ATOM | 3067 | O | HOH | 147 | 45.130 40.725 5.433 | 1.00 | 62.58 |
| ATOM | 3070 | O | HOH | 148 | 33.453 43.988 7.386 | 1.00 | 41.59 |
| ATOM | 3073 | O | HOH | 149 | 36.626 45.045 6.144 | 1.00 | 54.04 |

FIG. 7(57)

| | | | | | | | | |
|---|---|---|---|---|---|---|---|---|
| ATOM | 3076 | O | HOH | 150 | 19.458 | 36.977 | 14.386 | 1.00 56.50 |
| ATOM | 3079 | O | HOH | 151 | 19.502 | 40.993 | 17.850 | 1.00 43.35 |
| ATOM | 3082 | O | HOH | 152 | 39.793 | 38.257 | 27.760 | 1.00 63.31 |
| ATOM | 3085 | O | HOH | 153 | 40.730 | 53.944 | 20.682 | 1.00 49.91 |
| ATOM | 3088 | O | HOH | 154 | 45.371 | 49.402 | 5.710 | 1.00 41.53 |
| ATOM | 3091 | O | HOH | 155 | 49.114 | 26.038 | 11.482 | 1.00 34.43 |
| ATOM | 3094 | O | HOH | 156 | 54.085 | 28.403 | 10.828 | 1.00 28.60 |
| ATOM | 3097 | O | HOH | 157 | 18.729 | 14.990 | 12.752 | 1.00 44.66 |
| ATOM | 3100 | O | HOH | 158 | 27.500 | 2.046 | 10.138 | 1.00 47.88 |
| ATOM | 3103 | O | HOH | 159 | 23.505 | 7.763 | 16.082 | 1.00 45.49 |
| ATOM | 3106 | O | HOH | 160 | 38.101 | 22.326 | 23.406 | 1.00 43.42 |
| ATOM | 3109 | O | HOH | 161 | 36.788 | 33.961 | 0.261 | 1.00 59.95 |
| ATOM | 3112 | O | HOH | 162 | 19.380 | 27.777 | 6.595 | 1.00 56.29 |
| ATOM | 3115 | O | HOH | 163 | 33.583 | 33.343 | 17.339 | 1.00 68.25 |
| ATOM | 3118 | O | HOH | 164 | 43.221 | 53.467 | 17.853 | 1.00 62.89 |
| ATOM | 3121 | O | HOH | 165 | 28.154 | 41.110 | 29.042 | 1.00 61.19 |
| ATOM | 3124 | O | HOH | 166 | 44.877 | 47.914 | 12.583 | 1.00 21.27 |
| ATOM | 3127 | O | HOH | 167 | 46.589 | 45.908 | 14.329 | 1.00 39.48 |
| ATOM | 3130 | O | HOH | 168 | 48.235 | 43.490 | 14.297 | 1.00 46.88 |
| ATOM | 3133 | O | HOH | 169 | 47.834 | 0.528 | 14.762 | 1.00 74.55 |
| ATOM | 3136 | O | HOH | 170 | 48.711 | -2.009 | 16.386 | 1.00 52.45 |
| ATOM | 3139 | O | HOH | 171 | 41.210 | 0.396 | 17.381 | 1.00 58.05 |
| ATOM | 3142 | O | HOH | 172 | 43.837 | 1.538 | 17.483 | 1.00 72.30 |
| ATOM | 3145 | O | HOH | 173 | 41.780 | -2.478 | 14.396 | 1.00 47.15 |
| ATOM | 3148 | O | HOH | 174 | 31.466 | 11.699 | 21.418 | 1.00 45.99 |
| ATOM | 3151 | O | HOH | 175 | 35.046 | 14.218 | 20.429 | 1.00 39.37 |
| ATOM | 3154 | O | HOH | 176 | 22.639 | 26.143 | 4.324 | 1.00 36.80 |
| ATOM | 3157 | O | HOH | 177 | 26.114 | 24.452 | 6.028 | 1.00 31.04 |
| ATOM | 3160 | O | HOH | 178 | 28.927 | 30.687 | 4.252 | 1.00 41.38 |
| ATOM | 3163 | O | HOH | 179 | 23.899 | 6.610 | 18.621 | 1.00 56.43 |
| ATOM | 3166 | O | HOH | 180 | 53.386 | 11.969 | 4.493 | 1.00 39.86 |
| ATOM | 3169 | O | HOH | 181 | 30.051 | 43.727 | 0.910 | 1.00 47.97 |
| ATOM | 3172 | O | HOH | 182 | 31.659 | 49.099 | 8.149 | 1.00 52.84 |

```
                              SEQUENCE LISTING

<160> NUMBER OF SEQ ID NOS: 12

<210> SEQ ID NO 1
   <211> LENGTH: 31
   <212> TYPE: DNA
   <213> ORGANISM: Homo sapiens

<400> SEQUENCE: 1
cagcatatgg atccagatga actcccattg g                                  31

<210> SEQ ID NO 2
   <211> LENGTH: 34
   <212> TYPE: DNA
   <213> ORGANISM: Homo sapiens

<400> SEQUENCE: 2
gcggtcgact taaacaggag gagagctcag tgtg                               34

<210> SEQ ID NO 3
   <211> LENGTH: 33
   <212> TYPE: DNA
   <213> ORGANISM: Homo sapiens

<400> SEQUENCE: 3
gcacatatgg aacgactgcc ttatgatgcc agc                                33

<210> SEQ ID NO 4
   <211> LENGTH: 38
   <212> TYPE: DNA
   <213> ORGANISM: Homo sapiens

<400> SEQUENCE: 4
cctgtcgact tatccagaat cctcttccat gctcaaag                           38

<210> SEQ ID NO 5
   <211> LENGTH: 317
   <212> TYPE: PRT
   <213> ORGANISM: Homo sapiens

<400> SEQUENCE: 5

Met Asp Pro Asp Glu Leu Pro Leu Asp Glu His Cys Glu Arg Leu Pro
    1               5                  10                  15

Tyr Asp Ala Ser Lys Trp Glu Phe Pro Arg Asp Arg Leu Lys Leu Gly
                   20                  25                  30

Lys Pro Leu Gly Arg Gly Ala Phe Gly Gln Val Ile Glu Ala Asp Ala
                   35                  40                  45
```

```
Phe Gly Ile Asp Lys Thr Ala Thr Cys Arg Thr Val Ala Val Lys Met
        50                  55                  60

Leu Lys Glu Gly Ala Thr His Ser Glu His Arg Ala Leu Met Ser Glu
 65                  70                  75                  80

Leu Lys Ile Leu Ile His Ile Gly His His Leu Asn Val Val Asn Leu
                 85                  90                  95

Leu Gly Ala Cys Thr Lys Pro Gly Gly Pro Leu Met Val Ile Val Glu
                100                 105                 110

Phe Cys Lys Phe Gly Asn Leu Ser Thr Tyr Leu Arg Ser Lys Arg Asn
            115                 120                 125

Glu Phe Val Pro Tyr Lys Glu Ala Pro Glu Asp Leu Tyr Lys Asp Phe
        130                 135                 140

Leu Thr Leu Glu His Leu Leu Ile Cys Tyr Ser Phe Gln Val Ala Lys
145                 150                 155                 160

Gly Met Glu Phe Leu Ala Ser Arg Lys Cys Ile His Arg Asp Leu Ala
                165                 170                 175

Ala Arg Asn Ile Leu Leu Ser Glu Lys Asn Val Val Lys Ile Cys Asp
            180                 185                 190

Phe Gly Leu Ala Arg Asp Ile Tyr Lys Asp Pro Asp Tyr Val Arg Lys
        195                 200                 205

Gly Asp Ala Arg Leu Pro Leu Lys Trp Met Ala Pro Glu Thr Ile Phe
210                 215                 220

Asp Arg Val Tyr Thr Ile Gln Ser Asp Val Trp Ser Phe Gly Val Leu
225                 230                 235                 240

Leu Trp Glu Ile Phe Ser Leu Gly Ala Ser Pro Tyr Pro Gly Val Lys
                245                 250                 255

Ile Asp Glu Glu Phe Cys Arg Arg Leu Lys Glu Gly Thr Arg Met Arg
            260                 265                 270

Ala Pro Asp Tyr Thr Thr Pro Glu Met Tyr Gln Thr Met Leu Asp Cys
        275                 280                 285

Trp His Gly Glu Pro Ser Gln Arg Pro Thr Phe Ser Glu Leu Val Glu
    290                 295                 300

His Leu Gly Asn Leu Leu Gln Ala Asn Ala Gln Gln Asp
305                 310                 315

<210> SEQ ID NO 6
<211> LENGTH: 386
<212> TYPE: PRT
<213> ORGANISM: E. coli

<400> SEQUENCE: 6

Asp Pro Met Gln Leu Pro Tyr Asp Ser Arg Trp Glu Phe Pro Arg Asp
 1               5                  10                  15

Gly Leu Val Leu Gly Arg Val Leu Gly Ser Gly Ala Phe Gly Lys Val
                20                  25                  30

Val Glu Gly Thr Ala Tyr Gly Leu Ser Arg Ser Gln Pro Val Met Lys
            35                  40                  45

Val Ala Val Lys Met Leu Lys Pro Thr Ala Arg Ser Ser Glu Lys Gln
        50                  55                  60

Ala Leu Met Ser Glu Leu Lys Ile Met Thr His Leu Gly Pro His Leu
 65                  70                  75                  80

Asn Ile Val Asn Leu Leu Gly Ala Cys Thr Lys Ser Gly Pro Ile Tyr
                 85                  90                  95

Ile Ile Thr Glu Tyr Cys Phe Tyr Gly Asp Leu Val Asn Tyr Leu His
                100                 105                 110
```

-continued

```
Lys Asn Arg Asp Ser Phe Leu Ser His His Pro Glu Lys Pro Lys Lys
            115                 120                 125

Glu Leu Asp Ile Phe Gly Leu Asn Pro Ala Asp Glu Ser Thr Arg Ser
        130                 135                 140

Tyr Val Ile Leu Ser Phe Glu Asn Asn Gly Asp Tyr Met Asp Met Lys
145                 150                 155                 160

Gln Ala Asp Thr Thr Gln Tyr Val Pro Met Leu Glu Arg Lys Glu Val
                165                 170                 175

Ser Lys Tyr Ser Asp Ile Gln Arg Ser Leu Tyr Asp Arg Pro Ala Ser
            180                 185                 190

Tyr Lys Lys Lys Ser Met Leu Asp Ser Glu Val Lys Asn Leu Leu Ser
        195                 200                 205

Asp Asp Asn Ser Glu Gly Leu Thr Leu Leu Asp Leu Leu Ser Phe Thr
210                 215                 220

Tyr Gln Val Ala Arg Gly Met Glu Phe Leu Ala Ser Lys Asn Cys Val
225                 230                 235                 240

His Arg Asp Leu Ala Ala Arg Asn Val Leu Leu Ala Gln Gly Lys Ile
                245                 250                 255

Val Lys Ile Cys Asp Phe Gly Leu Ala Arg Asp Ile Met His Asp Ser
            260                 265                 270

Asn Tyr Val Ser Lys Gly Ser Thr Phe Leu Pro Val Lys Trp Met Ala
        275                 280                 285

Pro Glu Ser Ile Phe Asp Asn Leu Tyr Thr Thr Leu Ser Asp Val Trp
290                 295                 300

Ser Tyr Gly Ile Leu Leu Trp Glu Ile Phe Ser Leu Gly Gly Thr Pro
305                 310                 315                 320

Tyr Pro Gly Met Met Val Asp Ser Thr Phe Tyr Asn Lys Ile Lys Ser
                325                 330                 335

Gly Tyr Arg Met Ala Lys Pro Asp His Ala Thr Ser Glu Val Tyr Glu
            340                 345                 350

Ile Met Val Lys Cys Trp Asn Ser Glu Pro Glu Lys Arg Pro Ser Phe
        355                 360                 365

Tyr His Leu Ser Glu Ile Val Glu Asn Leu Leu Pro Gly Gln Tyr Lys
370                 375                 380

Lys Ser
385

<210> SEQ ID NO 7
<211> LENGTH: 310
<212> TYPE: PRT
<213> ORGANISM: Homo sapiens

<400> SEQUENCE: 7

Met Leu Ala Gly Val Ser Glu Tyr Glu Leu Pro Glu Asp Pro Arg Trp
1               5                   10                  15

Glu Leu Pro Arg Asp Arg Leu Val Leu Gly Lys Pro Leu Gly Glu Gly
            20                  25                  30

Cys Phe Gly Gln Val Val Leu Ala Glu Ala Ile Gly Leu Asp Lys Asp
        35                  40                  45

Lys Pro Asn Arg Val Thr Lys Val Ala Val Lys Met Leu Lys Ser Asp
    50                  55                  60

Ala Thr Glu Lys Asp Leu Ser Asp Leu Ile Ser Glu Met Glu Met Met
65                  70                  75                  80

Lys Met Ile Gly Lys His Lys Asn Ile Ile Asn Leu Leu Gly Ala Cys
                85                  90                  95
```

```
Thr Gln Asp Gly Pro Leu Tyr Val Ile Val Glu Tyr Ala Ser Lys Gly
            100                 105                 110
Asn Leu Arg Glu Tyr Leu Gln Ala Arg Arg Pro Pro Gly Leu Glu Tyr
            115                 120                 125
Cys Tyr Asn Pro Ser His Asn Pro Glu Glu Gln Leu Ser Ser Lys Asp
            130                 135                 140
Leu Val Ser Cys Ala Tyr Gln Val Ala Arg Gly Met Glu Tyr Leu Ala
145                 150                 155                 160
Ser Lys Lys Cys Ile His Arg Asp Leu Ala Ala Arg Asn Val Leu Val
                    165                 170                 175
Thr Glu Asp Asn Val Met Lys Ile Ala Asp Phe Gly Leu Ala Arg Asp
            180                 185                 190
Ile His His Ile Asp Tyr Tyr Lys Lys Thr Thr Asn Gly Arg Leu Pro
            195                 200                 205
Val Lys Trp Met Ala Pro Glu Ala Leu Phe Asp Arg Ile Tyr Thr His
            210                 215                 220
Gln Ser Asp Val Trp Ser Phe Gly Val Leu Leu Trp Glu Ile Phe Thr
225                 230                 235                 240
Leu Gly Gly Ser Pro Tyr Pro Gly Val Pro Val Glu Glu Leu Phe Lys
                    245                 250                 255
Leu Leu Lys Glu Gly His Arg Met Asp Lys Pro Ser Asn Cys Thr Asn
            260                 265                 270
Glu Leu Tyr Met Met Met Arg Asp Cys Trp His Ala Val Pro Ser Gln
            275                 280                 285
Arg Pro Thr Phe Lys Gln Leu Val Glu Asp Leu Asp Arg Ile Val Ala
            290                 295                 300
Leu Thr Ser Asn Gln Glu
305                 310

<210> SEQ ID NO 8
<211> LENGTH: 297
<212> TYPE: PRT
<213> ORGANISM: Homo sapiens

<400> SEQUENCE: 8

Val Phe Pro Cys Ser Val Tyr Val Pro Asp Glu Trp Glu Val Ser Arg
  1                 5                  10                  15
Glu Lys Ile Thr Leu Leu Arg Glu Leu Gly Gln Gly Ser Phe Gly Met
            20                  25                  30
Val Tyr Glu Gly Asn Ala Arg Asp Ile Ile Lys Gly Glu Ala Glu Thr
            35                  40                  45
Arg Val Ala Val Lys Thr Val Asn Glu Ser Ala Ser Leu Arg Glu Arg
        50                  55                  60
Ile Glu Phe Leu Asn Glu Ala Ser Val Met Lys Gly Phe Thr Cys His
65                  70                  75                  80
His Val Val Arg Leu Leu Gly Val Val Ser Lys Gly Gln Pro Thr Leu
                    85                  90                  95
Val Val Met Glu Leu Met Ala His Gly Asp Leu Lys Ser Tyr Leu Arg
            100                 105                 110
Ser Leu Arg Pro Glu Ala Glu Asn Asn Pro Gly Arg Pro Pro Pro Thr
            115                 120                 125
Leu Gln Glu Met Ile Gln Met Ala Ala Glu Ile Ala Asp Gly Met Ala
            130                 135                 140
Tyr Leu Asn Ala Lys Lys Phe Val His Arg Asp Leu Ala Ala Arg Asn
145                 150                 155                 160
```

-continued

```
Cys Met Val Ala His Asp Phe Thr Val Lys Ile Gly Asp Phe Gly Met
                165                 170                 175

Thr Arg Asp Ile Tyr Glu Thr Asp Tyr Tyr Arg Lys Gly Gly Lys Gly
            180                 185                 190

Leu Leu Pro Val Arg Trp Met Ala Pro Glu Ser Leu Lys Asp Gly Val
        195                 200                 205

Phe Thr Thr Ser Ser Asp Met Trp Ser Phe Gly Val Val Leu Trp Glu
    210                 215                 220

Ile Thr Ser Leu Ala Glu Gln Pro Tyr Gln Gly Leu Ser Asn Glu Gln
225                 230                 235                 240

Val Leu Lys Phe Val Met Asp Gly Gly Tyr Leu Asp Gln Pro Asp Asn
                245                 250                 255

Cys Pro Glu Arg Val Thr Asp Leu Met Arg Met Cys Trp Gln Phe Asn
            260                 265                 270

Pro Asn Met Arg Pro Thr Phe Leu Glu Ile Val Asn Leu Leu Lys Asp
        275                 280                 285

Asp Leu His Pro Ser Phe Pro Glu Val
    290                 295

<210> SEQ ID NO 9
<211> LENGTH: 367
<212> TYPE: PRT
<213> ORGANISM: Homo sapiens

<400> SEQUENCE: 9

Met Asp Pro Asp Glu Val Pro Leu Asp Glu Gln Cys Glu Arg Leu Pro
  1               5                  10                  15

Tyr Asp Ala Ser Lys Trp Glu Phe Ala Arg Glu Arg Leu Lys Leu Gly
             20                  25                  30

Lys Ser Leu Gly Arg Gly Ala Phe Gly Lys Val Val Gln Ala Ser Ala
         35                  40                  45

Phe Gly Ile Lys Lys Ser Pro Thr Cys Arg Thr Val Ala Val Lys Met
     50                  55                  60

Leu Lys Glu Gly Ala Thr Ala Ser Glu Tyr Lys Ala Leu Met Thr Glu
 65                  70                  75                  80

Leu Lys Ile Leu Thr His Ile Gly His His Leu Asn Val Val Asn Leu
                 85                  90                  95

Leu Gly Ala Cys Thr Lys Gln Gly Gly Pro Leu Met Val Ile Val Glu
            100                 105                 110

Tyr Cys Lys Tyr Gly Asn Leu Ser Asn Tyr Leu Lys Ser Lys Arg Asp
        115                 120                 125

Leu Phe Phe Leu Asn Lys Asp Ala Ala Leu His Met Glu Pro Lys Lys
    130                 135                 140

Glu Lys Met Glu Pro Gly Leu Glu Gln Gly Lys Lys Pro Arg Leu Asp
145                 150                 155                 160

Ser Val Thr Ser Ser Glu Ser Phe Ala Ser Gly Phe Gln Glu Asp
                165                 170                 175

Lys Ser Leu Ser Asp Val Glu Glu Glu Asp Ser Asp Gly Phe Tyr
            180                 185                 190

Lys Glu Pro Ile Thr Met Glu Asp Leu Ile Ser Tyr Ser Phe Gln Val
        195                 200                 205

Ala Arg Gly Met Glu Phe Leu Ser Arg Lys Cys Ile His Arg Asp
    210                 215                 220

Leu Ala Ala Arg Asn Ile Leu Leu Ser Glu Asn Asn Val Val Lys Ile
225                 230                 235                 240
```

```
Cys Asp Phe Gly Leu Ala Arg Asp Ile Tyr Lys Asn Pro Asp Tyr Val
                245                 250                 255

Arg Lys Gly Asp Thr Arg Leu Pro Leu Lys Trp Met Ala Pro Glu Ser
            260                 265                 270

Ile Phe Asp Lys Ile Tyr Ser Thr Lys Ser Asp Val Trp Ser Tyr Gly
        275                 280                 285

Val Leu Leu Trp Glu Ile Phe Ser Leu Gly Gly Ser Pro Tyr Pro Gly
    290                 295                 300

Val Gln Met Asp Glu Asp Phe Cys Ser Arg Leu Arg Glu Gly Met Arg
305                 310                 315                 320

Met Arg Ala Pro Glu Tyr Ser Thr Pro Glu Ile Tyr Gln Ile Met Leu
                325                 330                 335

Asp Cys Trp His Arg Asp Pro Lys Glu Arg Pro Arg Phe Ala Glu Leu
            340                 345                 350

Val Glu Lys Leu Gly Asp Leu Leu Gln Ala Asn Val Gln Gln Asp
        355                 360                 365

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 10
ctcagcagga ttgataagac tacattgttc                                              30

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 11
gaatttgtcc cctacaagga agctcctgaa gatctg                                       36

<210> SEQ ID NO 12
<211> LENGTH: 367
<212> TYPE: PRT
<213> ORGANISM: Homo sapiens

<400> SEQUENCE: 12

Met Asp Pro Asp Glu Leu Pro Leu Asp Glu His Cys Glu Arg Leu Pro
  1               5                  10                  15

Tyr Asp Ala Ser Lys Trp Glu Phe Pro Arg Asp Arg Leu Lys Leu Gly
                 20                  25                  30

Lys Pro Leu Gly Arg Gly Ala Phe Gly Gln Val Ile Glu Ala Asp Ala
             35                  40                  45

Phe Gly Ile Asp Lys Thr Ala Thr Cys Arg Thr Val Ala Val Lys Met
         50                  55                  60

Leu Lys Glu Gly Ala Thr His Ser Glu His Arg Ala Leu Met Ser Glu
 65                  70                  75                  80

Leu Lys Ile Leu Ile His Ile Gly His His Leu Asn Val Val Asn Leu
                 85                  90                  95

Leu Gly Ala Cys Thr Lys Pro Gly Gly Pro Leu Met Val Ile Val Glu
            100                 105                 110
```

-continued

```
Phe Cys Lys Phe Gly Asn Leu Ser Thr Tyr Leu Arg Ser Lys Arg Asn
        115                 120                 125

Glu Phe Val Pro Tyr Lys Thr Lys Gly Ala Arg Phe Arg Gln Gly Lys
        130                 135                 140

Asp Tyr Val Gly Ala Ile Pro Val Asp Leu Lys Arg Arg Leu Asp Ser
145                 150                 155                 160

Ile Thr Ser Ser Gln Ser Ser Ala Ser Ser Gly Phe Val Glu Glu Lys
                165                 170                 175

Ser Leu Ser Asp Val Glu Glu Glu Ala Pro Glu Asp Leu Tyr Lys
                180                 185                 190

Asp Phe Leu Thr Leu Glu His Leu Leu Ile Cys Tyr Ser Phe Gln Val
        195                 200                 205

Ala Lys Gly Met Glu Phe Leu Ala Ser Arg Lys Cys Ile His Arg Asp
        210                 215                 220

Leu Ala Ala Arg Asn Ile Leu Leu Ser Glu Lys Asn Val Val Lys Ile
225                 230                 235                 240

Cys Asp Phe Gly Leu Ala Arg Asp Ile Tyr Lys Asp Pro Asp Tyr Val
                245                 250                 255

Arg Lys Gly Asp Ala Arg Leu Pro Leu Lys Trp Met Ala Pro Glu Thr
                260                 265                 270

Ile Phe Asp Arg Val Tyr Thr Ile Gln Ser Asp Val Trp Ser Phe Gly
        275                 280                 285

Val Leu Leu Trp Glu Ile Phe Ser Leu Gly Ala Ser Pro Tyr Pro Gly
        290                 295                 300

Val Lys Ile Asp Glu Glu Phe Cys Arg Arg Leu Lys Glu Gly Thr Arg
305                 310                 315                 320

Met Arg Ala Pro Asp Tyr Thr Thr Pro Glu Met Tyr Gln Thr Met Leu
                325                 330                 335

Asp Cys Trp His Gly Glu Pro Ser Gln Arg Pro Thr Phe Ser Glu Leu
                340                 345                 350

Val Glu His Leu Gly Asn Leu Leu Gln Ala Asn Ala Gln Gln Asp
        355                 360                 365
```

MODIFICATIONS OF THE VEGF RECEPTOR-2 PROTEIN AND METHODS OF USE

This application claims the benefit of Provisional Application Ser. No. 60/009,503, filed Sep. 8, 1998, hereby incorporated by reference in its entirety.

TECHNICAL FIELD AND INDUSTRIAL APPLICABILITY OF INVENTION

The present invention discloses the isolation of a key portion of the catalytic kinase region of vascular endothelial growth factor receptor 2 or VEGFR-2 through cloning, sequencing and x-ray crystallography. Also disclosed is the deletion of various amino acid residues from an area of the catalytic region called the kinase insert domain (KID). The resulting polypeptide retains comparable in vitro kinase activity to that of the wild-type KID and is not necessary for the catalytic activity of the polypeptide, and more importantly, allows complete crystallization of the protein such that it may be characterized by X-ray crystallography. The present invention further discloses x-ray crystallography data useful for identification and construction of therapeutic compounds in the treatment of various disease conditions associated with VEGFR-2.

BACKGROUND OF THE INVENTION

Many physiological events including embryogenesis, organ development, estrus, and wound healing require vascular growth and remodeling (Folkman et al., (1992) *J. Biol. Chem.* 267, 10931–10934; Risau, W. (1995) *FASEB J.* 9, 926–933.). In addition to these beneficial processes, angiogenesis is also involved in the proliferation of disease states such as tumor growth, metastasis, psoriasis, rheumatoid arthritis, macular degeneration and retinopathy (Pepper, M. S., (1996) *Vasc. Med.* 1, 259–266; Kuiper et al., (1998) *Pharmacol. Res.* 37, 1–16, 1998; Kumar and Fidler, (1998) *In Vivo*18, 27–34; Szekanecz et al., (1998) *J. Investig. Med.* 46, 27–41; Tolentino and Adamis, (1988) *Int. Ophthalmol. Clin.* 38, 77–94. Of the signaling pathways known to influence vascular formation, these involving vascular endothelial growth factor (VEGF) have been shown to be essential and selective for vascular endothelial cells (Dvorak et al., (1995) *Am. J. Path.* 146, 1029–1039; Thomas, K., (1996) *J. Biol. Chem.* 271, 603–606; Ferrara N. and Davis-Smyth, (1997) *Endocrine Rev.* 18, 4–25). The therapeutic potential of inhibiting the VEGF pathway has been directly demonstrated by anti-VEGF monoclonal antibodies which were active against a variety of human tumors (Borgstrom et al, (1996) *Cancer Res.* 56, 4032–4039) and ischemic retinal disease (Adamis et al., (1996) *Arch. Ophthalmol.* 114, 66–71).

Normal vasculogenesis and angiogenesis play important roles in a variety of physiological processes such as embryonic development, wound healing, organ regeneration and female reproductive processes such as follicle development in the corpus luteum during ovulation and placental growth after pregnancy (Folkman & Shing, 1992). Uncontrolled vasculogenesis and/or angiogenesis has been associated with diseases, such as diabetes, as well as malignant solid tumors that rely on vascularization for growth. Klagsburn & Soker, (1993) *Current Biology* 3(10):699–702; Folkham, (1991) *J. Natl., Cancer Inst.* 82:4–6; Weidner, et al., (1991) *New Engl. J. Med.* 324:1–5.

Several polypeptides with in vitro endothelial cell growth promoting activity have been identified. Examples include acidic and basic fibroblastic growth factor (FGF), vascular endothelial growth factor (VEGF)and placental growth factor. Unlike FGF, VEGF has recently been reported to be an endothelial cell specific mitogen (Ferrara & Henzel, (1989) *Biochem. Biophys. Res. Comm.* 161:851–858; Vaisman et al., (1990) *J. Biol. Chem.* 265:19461–19566).

Thus, identification of the specific receptors to which VEGF binds is important to understanding of the regulation of endothelial cell proliferation. Two structurally related tyrosine kinases have been identified to bind VEGF with high affinity: the flt-1 receptor (Shibuya et al., (1990) *Oncogene* 5:519–524; De Vries et al., (1992) *Science* 255:989–991) and the KDR/FLK-1receptor, discussed herein. Consequently, it had been surmised that RTKs may have a role in the modulation and regulation of endothelial cell proliferation.

Recent disclosures, such as information set forth in U.S. patent application Ser. Nos. 08/193,829, 08/038,596 and 07/975,750, strongly suggest that VEGF is not only responsible for endothelial cell proliferation, but also is the prime regulator of normal and pathological angiogenesis. See generally, Klagsbum & Soker, (1993) *Current Biology* 3:699–702; Houck, et al., (1992) *J. Biol. Chem* 267:26031–26037.

VEGF is a homodimeric cytokine that is expressed in at least four splice-variant forms of 121–206 residues (Ferrara and Davis-Smyth, 1997). Vascular endothelial cells express at least two high-affinity receptors for VEGF: VEGF-R1/Flt-1 and VEGFR-2/KDR. VEGF-R1 and VEGFR-2 are receptor tyrosine kinases each comprised of an extracellular domain that contains 7 immunoglobulin-like segments and binds VEGF, a short membrane spanning region, and a cytosolic domain possessing tyrosine kinase activity. The kinase domain directly follows the extracellular and juxtamembrane regions and is itself followed by another domain (post-kinase domain), which may function in binding of other proteins for signal transduction. These two receptors appear to have different signaling pathways and functions with VEGFR-2 being of primary importance in mitosis of endothelial cells (Waltenberger et al., (1994) *J. Biol. Chem.* 269, 26988–26995; Seetharm et al., (1995) *Oncogene* 10, 135–147; Shalaby et al., (1995) *Nature* 376, 576–579).

Both FGF and VEGF are potent angiogenic factors which induce formation of new capillary blood vessels. Transfection of human breast carcinoma cell line MCF-7 with FGF resulted in cell lines that form progressively growing and metastatic tumors when injected (s.c.) into nude mice. FGF may play a critical role in progression of breast tumors to an estrogen-independent, anti-estrogen resistant metastatic phenotype (McLeskey et al., (1993) *Cancer Res.* 53: 2168–2177). Breast tumor cells exhibited increased neovascularization, increased spontaneous metastasis and more rapid growth in vivo than did the non-transfected tumors. FGF has been shown to be transforming in NIH-3T3 cells and implicated in tumorigenesis and metastasis of mouse mammary tumors. FGF overexpression conferred a tumorigenic phenotype on a human adrenal carcinoma cell line suggesting that FGF's may also play a role in the transformation of epithelial cells. Polyclonal neutralizing antibodies to FGF inhibited tumor growth in Balb/c nude mice transplanted with K1000 cells (transfected with the leader sequence of bFGF) which form tumors in these mice (Hori et al., (1991) *Cancer Res.* 51: 6180–9184).

Due to the role of FGF in neovascularization, tumorigenesis and metastasis, there is a need in the art for FGF inhibitors as potent anti-cancer agents that exert their anti-FGF activity by preventing intracellular signaling of FGF.

VEGF, by contrast, is an endothelial cell-specific mitogen and an angiogenesis inducer that is released by a variety of tumor cells and expressed in human tumor cells in situ. Unlike FGF, transfection of cell lines with a cDNA sequence encoding VEGF, did not promote transformation, but did facilitate tumor growth in vivo (Ferrara, N., and Davis-Smyth, T. (1997)). Furthermore, administration of a polyclonal antibody which neutralized VEGF also inhibited growth of human rhabdomyosarcoma, glioblastoma multiforme and leiomyosarcoma cell lines in nude mice (Kim et al., (1993) Nature 362: 841–843).

In view of the importance of receptor tyrosine kinases (RTKs) to the control, regulation and modulation of endothelial cell proliferation and potentially vasculogenesis and/or angiogenesis, many attempts have been made to identify RTK "inhibitors" using a variety of approaches, including the use of mutant ligands (U.S. Pat. No. 4,966,849), soluble receptors and antibodies (Application No. WO 94/10202; Kendall & Thomas, (1994) Proc. Natl. Acad. Sci. 90:10705–09; Kim, et al., 1993), RNA ligands (Jellinek, et al., (1994) Biochemistry 3:10450–56), protein kinase C inhibitors (Schuchter, et al., (1991) Cancer Res. 51:682–687); Takano, et al., (1993) Mol. Bio. Cell 4:358A; Kinsella, et al., (1992) Exp. Cell Res. 199:56–62; Wright, et al., (1992) J. Cellular Phys. 152:448–57) and tyrosine kinase inhibitors (WO 94/03427; WO 92/21660; WO 91/15495; WO 94/14808; U.S. Pat. No. 5,330,992; Mariani, et al., (1994) Proc. Am. Assoc. Cancer Res. 35:2268).

More recently, attempts have been made to identify small molecules which act as tyrosine kinase inhibitors. For example, bis monocyclic, bicyclic or heterocyclic aryl compounds (PCT WO 92/20642), vinylene-azaindole derivatives (PCT WO 94/14808) and 1-cyclopropyl-4-pyridyl-quinolones (U.S. Pat. No. 5,330,992) have been described generally as tyrosine kinase inhibitors. Styryl compounds (U.S. Pat. No. 5,217,999), styryl-substituted pyridyl compounds (U.S. Pat. No. 5,302,606), certain quinazoline derivatives (EP Application No. 0 566 266 A1), selenoindoles and selenides (PCT WO 94/03427), tricyclic polyhydroxylic compounds (PCT WO 92/21660) and benzylphosphonic acid compounds (PCT WO 91/15495) have been described as compounds for use as tyrosine kinase inhibitors for use in the treatment of cancer. None of these compounds, however, have been previously associated with the enzymatic function of the VEGFR-2 receptor. Likewise, none of these compounds have been associated with regulation of vasculogenesis and/or angiogenesis.

Therefore, there is a need in the art to develop small molecule antagonists of the PDGF, FGF, EGF and VEGF pathways individually or as a group. Moreover, if these cytokines signal through a common second messenger pathway within the cell, such antagonists will have broad therapeutic activity to treat or prevent the progression of a broad array of diseases, such as coronary restenosis, tumor-associated angiogenesis, atherosclerosis, autoimmune diseases, acute inflammation, certain kidney diseases associated with proliferation of glomerular or mesangial cells, and ocular diseases associated with retinal vessel proliferation. The present invention was made by discovering a common signaling mechanism, a group of active therapeutic agents, shown to be active by a large number of and variety of predictive assays, and discovering a common intracellular signaling intermediate.

Based on sequence homology and overall domain structure, VEGFRs belong to the platelet-derived growth factor receptor family (PDGFR) which also includes PDGFRα, PDGFRβ, the stem cell growth factor receptor (c-kit), and the colony stimulating factor-1 receptor (CSF-1 R/c-fms) (van der Geer et al., (1994) Ann. Rev. Cell Biol. 10, 251–337). Compared to other protein kinases, members of this family contain an insert of approximately 65–97 residues, termed the kinase insert domain (KID), within the catalytic kinase domain relative to other protein kinases. Within the PDGFR family the KIDs are of varying length and low sequence homology. Deletion or mutation of the KID from PDGFRα, PDGFRβ, c-kit, and CSF-1 R have indicated that this domain is not necessary for intrinsic kinase activity but that it is important for the binding of other proteins involved in signal transduction, via autophosphorylation of KID tyrosine residues (Taylor et al., (1989) EMBO J. 8, 2029–2037; Heidaran et al., (1991) Mol. Cell. Biol. 11, 134–142; Yu et al., (1991) Mol. Cell. Biol. 11, 3780–3785; Kazlauskas et al., (1992) Mol. Cell. Biol. 12, 2534–2544; Lev et al., (1992) Proc. Natl. Acad. Sci. USA 89, 678–682; Reedjik et al., (1992) EMBO J. 11, 1365–1372; Bazenet et al., (1996) Mol. Cell. Biol. 16, 6926–6936). Although the signaling pathways and the specific role of the KID are still not fully determined for VEGFRs, the VEGFR-2 KID does contain two tyrosines which are known to be autophosphorylation sites (Dougher-Vermazen et al., (1994) Biochem. Biophys. Res. Comm. 205, 728–738).

Since the determination of the first cyclic AMP-dependent protein kinase (cAPK) structure (Knighton et al., (1991) Science 253, 407–413) a variety of protein kinase structures have been reported (reviewed in Johnson et al., (1996) Cell 85,149–158). Among the receptor protein lyrosine kinases (RTKs), structures of the kinase domain of the insulin receptor (IRK) (Hubbard, et al., (1994) Nature 372, 746–754; Hubbard, (1997) EMBO J. 16, 5572–5581) and the fibroblast growth factor receptor-1 (FGFR1) (Mohammadi et al., (1996) Cell 86, 577–87; Mohammadi et al., (1997) Science 276, 955–960) have been determined.

SUMMARY OF THE INVENTION

The present invention discloses the generation, kinetic characterization, and structure determination of a modified kinase domain of the VEGFR-2 protein, containing 18 residues of the 68 residue kinase insert domain (KID). This 2.4 Å crystal structure of the phosphorylated VEGFR-2 catalytic domain is the first reported structure of a kinase domain of the PDGFR family. This structure provides insights into the orientation of the KID domain of VEGFR-2 which may be relevant to other PDGFR family members. Furthermore, as inhibition of VEGFR-2 kinase has broad clinical applications, this structure provides a three-dimensional description of the target for structure-based design of small molecule VEGFR-2 inhibitors as therapeutic agents.

It is an object of the present invention to disclose an effective method for screening candidate compounds that are specifically agonists or antagonists of various proteins which can be included in the receptor tyrosine kinase family (RTK) by crystallizing RTKs and particularly the VEGFR-2 receptor in order to use molecular modeling of the x-ray crystallography data to model the binding of candidate compounds.

There is disclosed a method for designing and screening potentially therapeutic compounds with activities such as: (1) inhibiting new blood vessel formation that is useful for treating or preventing progression of diabetic retinopathy, cavernous hemangiomas, Kaposi's sarcoma, tumors composed of endothelial-like cells, and growth of cancer cells by preventing their development of a new blood supply: (2) suppressing development of kidney diseases due to cytokine induced proliferation of mesangial cells and/or glomerular epithelial cells that is useful for treating or preventing progression of diabetic glomerulosclerosis and other glomerulonephritis of various types and etiologies; (3) preventing joint destruction accompanying rheumatoid arthritis due to proliferation of synovial cells; (4) suppressing manifestations of psoriasis due to proliferation of keratinocytes and accumulation of inflammatory cells; (5) suppressing accelerated atherogenesis involved in restenosis of coronary vessels or other arterial vessels following angioplasty; (6) suppressing atherogenesis, coronary artery disease and other vasculopathies due to atherogenesis; and (7) suppressing tumor growth via paracrine or autocrine mediated responses to other cytokines such as PDGF, FGF EGF or VEGF that is useful for treating or preventing progression of tumors such as breast cancer stimulated through overexpression of her-2-neu receptor, wherein the inventive method comprises administering a compound that inhibits signal transduction.

The present invention is useful in developing methods that are used in the iterative drug design process. The process identifies potential agonists and antagonists to VEGFR-2 by de novo design of novel drug candidate molecules which bind to the VEGFR-2 receptor to improve their potency. The x-ray crystallographic coordinates disclosed herein, will allow generation of 3-dimensional models of the catalytic site and drug binding site of the VEGFR-2 protein.

De novo design primarily consists of the generation of molecules via the use of computer programs which build and link fragments or atoms into a site based upon steric and electrostatic complementarity, without reference to substrate analog structures. The drug design process begins after the structure of a target RTK is solved to at least a resolution of 2.8 Å. Refinement of the structure to a resolution of 2.5 Å or better, with "fixed" water molecules in place provides more optimal conditions to undertake drug design.

It is another object of this invention to identify KIDs of proteins in the RTK family and develop deletions in said KiDs such that the proteins will be crystallizable and suitable for measurement by x-ray crystallographic means.

It is a further object of this invention to disclose a process whereby KID regions from a member of the RTK family of genes such as PDGERs, VEGFRs and others are modified by deletion of amino acids from the KID regions so as to impart favorable physical characteristics of the resulting polypeptide product. Examples of such favorable physical characteristics are increased solubility, greater stability to temperature variations making the polypeptide suitable for analysis by nuclear magnetic resonance, high throughput screening, biochemical characterizations, x-ray crystallography, calorimetry and other diagnostic means.

It is yet another object of this invention to developing screening methods used in the drug design process of potential agonists and antagonists to proteins in the RTK family by de novo design of novel drug candidate molecules with potentially nanomolar potencies. The x-ray crystallographic coordinates disclosed based on the deletion mutated KIDs and various other deletions of said proteins in the RTK family, will allow generation of 3-dimensional models of the active binding site of the proteins in the RTK family.

BRIEF DESCRIPTION OF THE DRAWINGS

FIG. 1. Secondary structure assignments (as given by Procheck) for the catalytic domain of VEGFR2 and sequence alignment with other representative receptor tyrosine kinases. α helices are designated as αB-αI, β strands are designated as β1–β8. The site of 50 residue deletion in VEGFR2Δ50 (SEQ ID No: 5) is indicated by |. The site of the E990V mutation in VEGFR2D50 (SEQ ID No: 5) is denoted by an *. Sequences are from: VEGFR2 (SEQ ID No: 12) (reported here); FGFR1 (SEQ ID No: 7) (Swiss protein database #P11362); IRK (SEQ ID No: 8) (EMBL protein database #A18657; numbering as in Mohammadi et al., 1996); VEGFR1 (SEQ ID No: 9) (Swiss protein database #P17948); PDGFRα (SEQ ID No: 6) (Swiss protein database #P17948).

FIG. 7. Resulting X-ray crystallography coordinates for VEGFR-2 based on the method disclosed in the crystallization and data collection section.

DETAILED DESCRIPTION AND PREFERRED EMBODIMENTS OF THE INVENTION

Cloning of the VEGFR-2 Protein

Figure 2A:
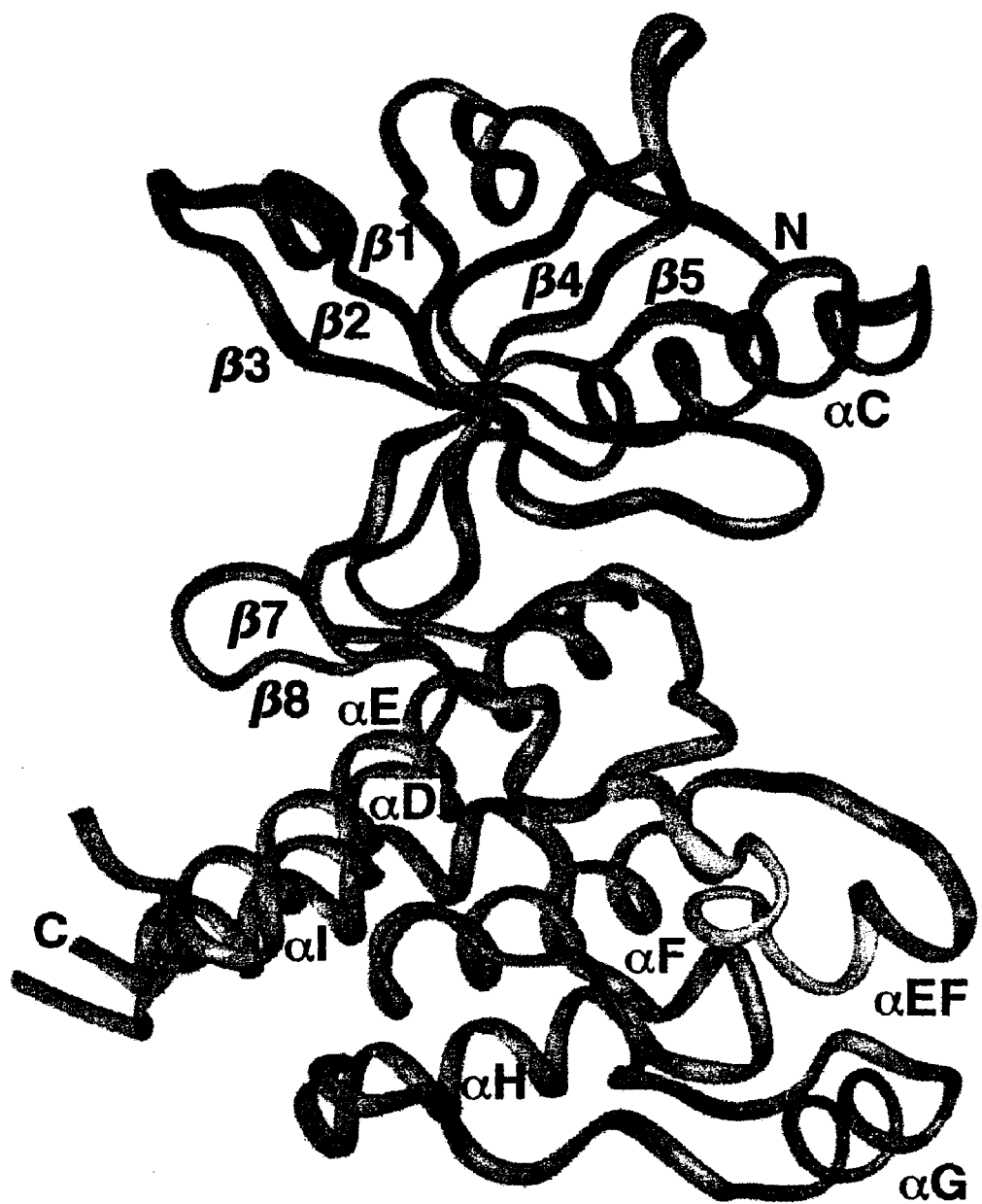
FIG. 2. Overall fold of VEGFR2Δ50P(SEQ ID No: 5), FGFR1, and IRKP. Backbone representation of structures of the kinase domains of (A) VEGFR2 (VEGFR2Δ50P(SEQ ID No: 5)), (B) FGFR1 (molecule A of PDB entry 1 FGK, Mohammadi et al., 1996), and (C) IRKP (PDB entry 1IR3, Hubbard et al., 1997). The views shown in A, B, and C are identical views generated from superpositions of the C-terminal domains. The positions of the termini are denoted by N and C. The nucleotide-binding loop (orange), kinase insert domain (pink), and activation loop (yellow) are highlighted. In (C) the bound AMP-PNP is shown in green and the peptide substrate is shown in red. Figure prepared with INSIGHT II.

The coding sequence (Terman et al., (1992) *Biochem Biophys. Res. Commun.* 187, 1579–86) for the cytoplasmic domain of the VEGFR-2 was amplified by PCR (Mullis et al., (1992). *Biotechnology* 24, 17–27) from a human aorta cDNA pool (Clontech Palo Alto, Calif.). Two overlapping sequences were amplified independently. Vcyt (residues M806-V1356), which represented the entire cytoplasmic domain, and Vcat (residues C817M-G1191), with boundaries based upon a primary amino acid sequence alignment with the insulin receptor kinase catalytic domain (Wei et al., (1995) *J. Biol. Chem.* 270, 8122–8130).

The PCR oligonucleotide primer sequences for Vcyt were:

Vcyt5 5'-CAGCATATGGATCCAGATGAACTCCCAT-TGG-3' (SEQ ID No: 1) and

Vcyt3 5'-GCGGTCGACTTAAACAGGAGGAGAGCT-CAGTGTG-3' (SEQ ID No: 2).

The PCR oligonucleotide primer sequences for the Vcat were:

Vcat5 5'-GCACATATGGAACGACTGCCTTATGATGC-CAGC-3' (SEQ ID No: 3) and

Vcat3 5'-CCTGTCGACTTATCCAGAATCCTCTTCC-ATGCTCAAAG-5' (SEQ ID No: 4).

The amplified DNA was digested with the restriction enzymes NdeI and SalI, ligated into the *E. coli* plasmid pET24a (Novagen Madison, Wis.) and sequence verified. When compared to the original VEGFR-2 sequence in Genbank, (Accession number 346345) two nucleotide differences were noted that resulted in codon changes (Glu848-Val and Asn835-Lys) in both Vcyt and Vcat. Our sequence agrees with subsequent VEGFR-2 Genbank submissions (Accession numbers 2655412 and 3132833).

Mutations were introduced by oligonucleotide site directed mutagenesis (Kunkel, 1985) using the Muta-Gene in vitro Mutagenesis Kit from (Bio-Rad Hercules, Calif.). The Vcat DNA fragment was subcloned from the pET24a vector using an NdeI-XhoI digest into the vector pMGH4 (Schoner et al., 1986, Kan et al., 1992) and this vector was used to generate the ssDNA uracil template (minus strand) in *E. coli* strain CJ236 supplied in the kit. An oligo (SEQ ID No: 10) (5'-CTCAGCAGGATTGATAAGACTACATTG-TTC-3') was designed to create a construct (Vcat(ΔG1172-G1191)) which truncated the C-terminus to residue D1171. Another oligo (SEQ ID No: 11) (5'-GAATTTGTCCCCT-ACAAGGAAGCTCCTGAAGATCTG-3') was designed to delete the central 50 residues (residues T940-E989) of the insert kinase domain, based on a sequence alignment with FGFR1 (Mohammadi et al, 1996). Sequence analysis detected an inadvertent Glu990-Val mutation. All DNA modification and restriction enzymes were purchased from New England Biolabs and oligonucleotides were urchased form Genosys Biotechnology.

The VEGFR2Δ50 construct (SEQ ID No: 5) was made in several steps to combine the necessary utations into the baculovirus expression vector pAcSG2 (Pharmingen San Diego, Calif.). Step 1; the coding region for Vcyt was PCR subcloned from the pET24a vector into the NcoI-KpnI sites of vector pAcSG2. Step2; a 2358bp ScaI-BglII DNA fragment from plasmid pMGH4-Vcat (ΔT940-E989, E990V) was ligated to a 1695bp BglII-ScaI DNA fragment from pMGH4-Vcat (ΔG1172-G1191) creating a pMGH4-Vcat (ΔT940-E989,E990V,ΔG1172-G1191) vector. Step 3; a 913bp BstEII-EagI DNA fragment a pMGH4-Vcat (ΔT940-E989,E990V,ΔG1172-G1191) was ligated to a 3290bp EagI-BstEII DNA fragment from pAcSG2-Vcyt creating pAcSG2-Vcyt (ΔT940-E989,E990V,ΔG1172-G1191), also referred to as VEGFR2Δ50(SEQ ID No: 5. This final construct was sequenced verified through the entire coding region and confirmed to contain only these known mutations from the wild-type sequence (sequence shown in FIG. 1).

DNA encoding VEGFR2Δ50 (SEQ ID No: 5) was transfected into Sf9 cells with linearized baculovirus DNA according to the protocol of the manufacturer (Pharmingen San Diego, Calif.). Single plaques were isolated from this transfection and high titer stocks generated. All stocks were examined by isolation of baculoviral DNA and PCR amplification of the insert using the polyhedron forward and reverse primers (Invitrogen). Sf21 cells were infected at 1–1.5 million cells/mL at MOI=5 for 72 hours and harvested by centrifugation.

Purification of VEGFR2Δ50 From Sf21 Cells

Cell pellets were lysed by dounce homogenization and sonication in 20 mM Tris pH 8.0, 20 mM NaCl, 5 mM DTT, and 5% (v/v) glycerol. The lysate was centrifuged for 50 minutes at 35,000 rpm in a Ti45 rotor. The soluble fraction was loaded onto a 40 ml Q-30 anion exchange column (Pharmacia) and eluted with a 20 mM to 600 mM NaCl gradient in 20 mM Tris pH 8.0, 5 mM DTT, and 5% (v/v) glycerol over 20 column volumes. VEGFR2Δ50 (SEQ ID No: 5) protein was pooled by SDS-PAGE gel analysis and by the presence of kinase activity as measured against gastrin substrate peptide substrate (Boehringer Mannheim). Pooled material was loaded onto a 40 mL hydroxyapatite (Bio-Rad) column and washed extensively with 20 mM Tris pH 8.0, 50 mM NaCl, 5 mM DTT, and 5% glycerol. Protein was eluted using a 500 mL linear gradient from 0 to 50 mM potassium phosphate pH 8.0, 50 mM NaCl, 5 mM DTT, and 5% glycerol. VEGFR2Δ50 (SEQ ID No: 5) protein was pooled by SDS-PAGE gel analysis and by the presence of kinase activity as measured against the gastrin peptide. Material from this column was then diluted 1:1 with 20 mM Tris pH 8.0, 20 mM NaCl, 5 mM DTT, and 5% glycerol and loaded onto an 8 mL Q-15 anion exchange column (Pharmacia). Protein was eluted using with a 180 mL linear NaCl gradient (20 mM-175 mM) in 20 mM Tris pH 8.0, 5 mM DTT, and 5% glycerol. VEGFR2Δ50 (SEQ ID No: 5) protein was pooled as described above. 4M $(NH_4)_2SO4$ was added to the pool to final concentration of 0.6 M and the pool loaded onto a 10 mL HP-phenyl sepharose column (Pharmacia). VEGFR2Δ50 (SEQ ID No: 5) protein was eluted using a 200 mL linear reverse gradient from 0.6 M to 0 M $(NH_4)_2SO4$ in 20 mM Tris and 5 mM DTT. Purified VEGFR2Δ50 protein was buffer exchanged into 50 mM Hepes pH 7.5, 10 mM DTT, 10 % glycerol, and 25 mM NaCl over a 500 ml G-25 column (Pharmacia) and concentrated to 1 mg protein/mL through a 10 kD cutoff polysulfone membrane (Amicon). Final material was aliquoted and flash frozen in liquid $N_2$ and stored at −70° C.

Kinetic Assays

The coupled spectrophotometric assays were done with purified VEGFR2Δ50 protein (SEQ ID No: 5) that was autophosphorylated under conditions: protein (4 mM), ATP (3 mM), $MgCl_2$ (40 mM), DTT (5 mM), in Hepes (100 mM), 10% glycerol, pH 7.5 at 4° C. for 1 hour.

Coupled Spectrophotometric Assay for the Forward Direction

Tyrosine kinase assays were monitored using a Beckman DU 650 Spectrophotometer. Production of ADP was coupled to oxidation of NADH using phosphoenolpyruvate (PEP) through the actions of pyruvate kinase (PK) and lactic dehydrogenase (LDH). The oxidation of NADH was monitored by following the decrease in absorbance at 340 nm ($e_{340}$=6.22 cm$^{-1}$ mM$^{-1}$). Typical reaction solutions contained: 1 mM PEP, 250 mM NADH, 50 units of LDH/mL, 20 units of PK/mL, 5 mM DTT, in 200 mM Hepes, pH 7.5 and varying concentrations of poly($E_4Y_1$) (Sigma), ATP and $MgCl_2$. Assays were initiated with 40 nM of VEGFR2Δ50 protein (SEQ ID No: 5).

Coupled Spectrophotometric Assay for the Reverse Reaction

ATP generation was coupled to production of NADH via the action of hexokinase (HK) and glucose-6-phosphate dehydrogenase (G6PD). In this assay, HK catalyzes the conversion of ATP to ADP and glucose-6-phosphate. Glucose-6-phosphate is then oxidized to D-6-phosphogluconopyranose-1,5-lactone by G6PD with concomitant reduction of NAD to NADH which can be monitored at 340 nm. Typical assay solution contained: glucose (10 mM), NAD (40 mM), DTT (5 mM), $MgCl_2$ (4 mM), HK (15 unit/mL), G6PD (15 units/mL) and indicated concentrations of ADP and phospho-poly($E_4Y$). The reactions were initiated with addition of VEGFR2Δ50 protein (SEQ ID No: 5) (600–900 nM).

Evaluation of Potential Agonists and Antagonists of the VEGFR2Δ50 Protein

Based on the above spectrophotometric and kinetic assays, one can evaluate potential candidate agonists or antagonists of the VEGFR2Δ50 protein (SEQ ID No: 5) by addition of the candidate compounds to the above assay in a competition. As stated above, the kinetics of the activity of the VEGFR2Δ50 protein (SEQ ID No: 5) were measured against the gastrin peptide. The activity in the presence and absence of a candidate compound is measured and the resulting kinetic data is compared. The affinity of the candidate for the receptor will be reflected in the shift to the right of the kinetic curves indicating a competitive antagonist or with a decrease in the maximum activity, which would indicate a non-competitive antagonism. Conversely, a shift to the left of the kinetic curves would indicate a competitive agonist to the VEGFR2Δ50 protein. See generally, Bourne, H. R., et al. in, (1987) *Basic & Clinical Pharmacology* (Katzung, et al., eds) (Ch. 3) 9–22.

In Vitro Autophosphorylation Of VEGFR2Δ50 for Crystallization and Mass Spectrometry.

Aliquots of frozen VEGFR2Δ50 protein (SEQ ID No: 5) were thawed by immersion in cold $H_2O$ and pooled at 4° C. $MgCl_2$ and ATP were added to 26 mM and 4 mM, respectively. VEGFR2Δ50 (SEQ ID No: 5) was incubated at 4° C. for 1 hour. This material (VEGFR2Δ50P) was then buffer exchanged into a solution of 10 mM Hepes 7.5, 10 mM DTT, and 10 mM NaCl and concentrated using a Centriprep-10 (Amicon) to 5 mg protein/mL.

Mass Spectrometry

Trypsin digestion:. Trypsin digestions of purified VEGFR2Δ50 (SEQ ID No: 5) and VEGFR2Δ50P were conducted at 37° C. suing 0.37 mg/ML protein in 25 mM $NH_4HCO_3$ at pH. 7.7 with a reaction volume of 100 μL for two days.

MALDI/MS. MALDI-MS analyses were performed in a Voyager-Elite, time-of-flight mass spectrometer with delayed extraction (PerSeptive Biosystems, Inc., Framingham, Mass.). A volume of 1 μL of digested protein sample was mixed with 1 μL of matrix (a-cyano-4-hydroxycinnamic acid) in a solution of 50% (v/v) solution of acetonitrile and 0.25% (w/w) trifluoroacetic acid in water. Samples were irradiated with a nitrogen laser operated at 337 nm.

NanoESI-MS. NanoESI-MS analyses were performed on a triple quadrapole mass spectrometer (PE Sciex API III, Alberta, Canada) modified with a NanoESI source from Protana A/S, (Denmark). The ESI voltage was set at 700 V and the orifice settings were maintained at 100 V. 3 μL of digested protein was mixed with 7 μL of methanol and 0.5 μL formic acid and then 4 μL of this sample was injected into the mass spectrometer. Ion scans were used to obtain the sequence of phosphopeptides.

Crystallization and Data Collection

Purified phosphorylated VEGFR2Δ50 was concentrated on average to 5 mg protein/mL using a Centricon-10 centrifugal concentrator. Crystals were grown by the hanging drop vapor diffusion method at 4° C. Drops containing 2 μL of protein solution and 2 μL of a mother liquor solution (100 mM Hepes at pH 7.2, 2 M $(NH_4)_2SO_{4,}$, and 2% (v/v) monomethylether polyethylene glycol mW=550) were equilibrated above a 1 mL reservoir of the mother liquor solution to which 50 mM β-mercaptoethanol had been added. Crystals appeared after 3–4 days and grew to as large as 0.3×0.2×0.5 mm over 21 days.

X-ray diffraction data sets were collected using a Rigaku RU-200 rotating anode X-ray generator (CuKα) operated at 50 kV and 100 mA and equipped with Supper focusing mirrors and a MAR345 MAR Research image plate detector. Data collection on frozen crystals was done by transferring a crystal into a cryoprotectant solution (100 mM Hepes at pH 7.2, 2.2 M $(NH_4)_2SO_4$, 0.6 M sucrose, 0.55 M glucose, and 2% (v/v) monomethylether polyethylene glycol MW=550), flash freezing the crystal in liquid nitrogen, and then transferring the frozen crystal into a stream of nitrogen at −186° C. Data was integrated and scaled using DENZO and SCALEPACK (Otwinowski, 1993) Data collection statistics are given in Table 2.

Initial protein phases were obtained using the AMoRe molecular replacement program (Navaza, 1994), molecule 1 of the FGFR1 structure (Mohammadi et al., 1996; PDB entry 1FGK) as a search probe, and the nativel data set. The correct solution was achieved by including the FGFR1 sidechains and removing from mobile residues of the activation loop (640–660), the N-terminus (464–467), a short loop (517–520), and the C-terminus (760–762) from the search model. The correct solution was the top peak in the rotation and translation functions with a correlation coefficient of 0.31. Rigid body refinement in AMoRe improved the solution to a correlation coefficient of 0.49 and an R-factor of 46.3% in the 12.0–4.0 Å resolution range. The correctness of this solution was cross-checked by calculation of a difference Fourier with a $KAu(CN)_2$ derivative. This derivative was generated by soaking a crystal for 3 days in reservoir solution containing 0.5 mM $KAu(CN)_2$ and then increasing the heavy atom concentration to 5 mM and soaking for an additional 64 hours. Scaling of data sets, Patterson calculations, Fourier calculations, and the generation of phases were done using Xtalview (McRee et al., 1992)

Refinement of the model was done using Xplor version 3.1 (Brünger, 1992). Calculation of electron density maps and model fitting was done using XtalView (McRee et al., 1992) Refinement was begun using a data set collected at 4°

C. (native2) and was completed using a data set (native3) collected at −186° C. The final R-factor is 20.2% for data in the range 8–2.4 Å (Fo>2δ). The average B value for all atoms is 31.8 Å$^2$ for protein atoms and 42.8 Å$^2$ for water molecules. The final model includes residues 820–939, 998–1047, and 1064–1168; of these residues the sidechains of K838, R842, F845, K939, D998, K1023, R1027, Y1038, K1039, K1110, and E1113 could not be modeled beyond Cα due to a lack of interpretable density. Analysis of main-chain torsion angles as done using PROCHECK (Laskowski et al., 1993) shows of the 275 residues in the model none occur in the disallowed region and only 4 occur in the generously allowed region of a Ramachandran plot. 182 water molecules were fit to electron density peaks which were greater than 3 δ and were located in positions to make reasonable hydrogen bonds to the protein or other water molecules.

Superpositions of various kinase structures was done using the graphics program Insight II (Molecular Simulations Inc, San Diego, Calif.).

Example 1—Structure Determinations

The tyrosine kinase domain of human VEGFR-2 lacking the 50 central residues of the 68 residues of the KID was expressed in a baculovirus/insect cell system. Of the 1356 residues of full-length VEGFR-2 this construct (VEGFR2Δ50(SEQ ID No: 5)) contains residues 806–939 and 990–1171 of the cytosolic domain (FIG. 1). VEGFR2Δ50 (SEQ ID No: 5) also contains one point mutation (E990V) within the KID relative to wild-type VEGFR-2.

In addition to catalyzing its autophosphorylation, VEGFR2Δ50 (SEQ ID No: 5) is also capable of catalyzing phosphorylation of a poly($E_4Y$) exogenous substrate. Detailed kinetic analysis (Table 1) revealed that its kinetic parameters were nearly identical to that of a comparable VEGFR-2 protein construct containing the entire KID (Parast et al., in press). These results taken together indicate that VEGFR2Δ50 (SEQ ID No: 5) is a fully active functional enzyme. Therefore, deletion of 50 central residues of the KID has no observed effect on the catalytic steps of the phosphotransfer reaction. It was also determined that deletion of more than 60 amino acids from the KID region did cause a diminishment in the activity of the enzyme.

TABLE 1

Kinetic constants of VEGFR2Δ50 (SEQ ID NO: 5)

| Substrate | $K_M$ (mM) | $k_{cat}$ (s$^{-1}$) | $k_{cat}/K_M$ (s$^{-1}$M$^{-1}$) |
|---|---|---|---|
| Forward Reaction | | | |
| MgATP | 0.153 | 13.3 | 87 × 10$^3$ |
| poly ($E_4Y$) | 2.1 | | 63 × 10$^2$ |
| Mg$^{2+}$ | 6.8 | | 20 × 10$^2$ |
| Reverse Reaction | | | |
| MgADP | 0.056 | 0.13 | 23 × 10$^2$ |
| P-poly ($E_4Y$) | 1.0 | | 13 × 10$^1$ |

The VEGFR-2 KID sequence is hydrophilic and highly charged, containing 6 lysine, 5 arginine, 8 glutamic acid, and 5 aspartic acid residues (FIG. 1). Initially several protein constructs containing the VEGFR-2 catalytic domain with the entire KID were generated. After exhaustive attempts to crystallize these protein constructs failed to yield even marginal crystals, the VEGFR2Δ50 construct (SEQ ID No: 5) was created to test the idea that the highly charged KID was interfering with crystallization. As determined by dynamic light scattering this VEGFR2Δ50 construct (SEQ ID No: 5), which eliminated 14 charged residues, exhibited markedly better stability to temperature and protein concentration than protein constructs containing the entire KID.

For crystallization, purified VEGFR2Δ50 (SEQ ID No: 5) was autophosphorylated in vitro by incubation with MgATP. Matrix-assisted laser desorption ionization (MALDI) and nanoelectrospray ionization (NanoESI) mass spectrometry analysis of full-length phosphorylated VEGFR2Δ50 (VEGFR2Δ50P) protein (SEQ ID No: 5) and tryptically digested peptides indicates phosphorylation of Y1059 using the autophosphorylation conditions described here. Crystals diffracting to 2.2 Å were obtained of VEGFR2Δ50P (SEQ ID No: 5) in an unligated state. The crystals belong to the orthorhombic space group $P2_12_12_1$ with one VEGFR2Δ50P (SEQ ID No: 5) molecule in the asymmetric unit. Initial crystallographic phases were determined by molecular replacement using the structure of the unphosphorylated kinase domain of FGFR1 (Mohammadi et al., 1996) as a search model. The correctness of the molecular replacement solution was cross-checked using a gold cyanide derivative. The derivative data, however, was not used for phase calculations of electron density maps used to build the model. The structure has been refined to an R-factor of 20.2% for 8–2.4Å data (Fo>2δ). VEGFR2Δ50P (SEQ ID No: 5) residues for which backbone atoms were not modeled due to disorder include the N-terminal residues 806–819, residues 990–997 of the KID, residues 1048–1063 of the activation loop, and residues 1169–1171 of the C-terminus. Structure determination statistics are included in Table 2.

TABLE 2

VEGFR2Δ50P (SEQ ID NO:5) structure determination statistics

| Data Set | Native (3) | Native (1) | Native (2) | KAu(CN)$_2$ |
|---|---|---|---|---|
| Data resolution (Å) | 15–2.2 | 20–3.0 | 15–2.4 | 15.3.1 |
| $R_{sym}$ (%) | 5.2$^a$ (19,6)$^b$ | 8.4 (19.2) | 7.0 (21.9) | 7.1 (19.5) |
| Completeness (%) | 93.0 (81.0) | 97.5 (98.4) | 98.8 (98.8) | 96.5 (95.0) |
| Temperature (° C.) | −186 | room (~21) | 4 | 4 |
| Unit cell a (Å) | 95.41 | 97.10 | 98.52 | 97.71 |
| Unit cell b (Å) | 96.04 | 96.94 | 96.50 | 96.97 |
| Unit cell c (Å) | 38.22 | 38.63 | 38.56 | 38.52 |
| Refinement resolution (Å) | 8–2.4 | — | — | — |
| Refined R (%) | 20.2$^{c,d}$ | — | — | — |

$^a$R$_{sym}$ = Σ$_{hkl}$Σ$_i$|$_i$ (hkl)-</(hkl)>|/Σ$_{hkl}$Σ$_i$/$_i$ (hkl)
$^b$Value in parenthesis is for highest (resolution shell)
$^c$R = Σ$_{hkl}$ |F$_O$(hkl)| − |F$_C$(hkl)| |/Σ$_{hkl}$|F$_O$(hkl)|
where F$_O$ and F$_C$ are the observed and calculated structure factors, respectively (F$_O$ > 2δ)
$^d$Model includes 275 protein residues and 182 water molecules Overall Kinase Fold Analogous to previously reported structures of both serine/threonine and tyrosine protein kinases, VEGFR2Δ50P (SEQ ID No: 5) is folded into two lobes with catalysis of phosphotransfer taking place in a cleft between the two lobes (reviewed in Cox et al., 1994; Johnson et al., 1996) A C α trace of the VEGFR2Δ50P (SEQ ID No: 5) structure is shown in FIG. 2a. Kinase secondary structural elements are designated (FIG. 1) according to the convention originally given for cAPK (Knighton et al., 1991). The N-terminal lobe (approximately residues 820–920) folds into a twisted β sheet with one α helix (αC). The β structure comprises five antiparallel strands (β1–β5), three of which (β1–β3) are highly curved and curl over the other two strands (β4–β5). The larger C-terminal domain (approximately residues 921–313) contains two antiparallel β strands (β7–β8), which lie at the top of the C-terminal domain adjacent to the N-terminal, β-sheet. Seven α-helices (αD, αE, αE-F, αG, αH, αI) form the remaining core of the C-terminal domain. Like other kinases, VEGFR2Δ50P (SEQ ID No: 5) contains two functionally important loop regions: the glycine-rich nucleotide binding loop (residues 841–846), the catalytic loop (residues 1026–1033) and the activation loop (residues 1046–1075) (FIGS. 1 and 2a).

Of the reported kinase structures, the VEGFR2Δ50P (SEQ ID No: 5) structure resembles most closely that of the catalytic domain of FGFR1 (Mohammadi et al., 1996; PDB entry 1 FGK) with which it shares approximately 55% sequence identity (FIG. 1). Since the two molecules in the crystallographic asymmetric unit of the FGFR1 structure solution are very similar, comparisons to VEGFR2Δ50P (SEQ ID No: 5) (SEQ ID No: 5) will primarily be described only for FGFR1 molecule A. Least squares superposition of 82 Cα positions of (β1–β5) of the N-terminal lobe or 152 Cα positions residues (αD, αE, αF, αG, αH, αI ) of the C-terminal lobe between FGFR1 and VEGFR2Δ50P (SEQ ID No: 5) result in respective rms deviations of 0.40 Å and 0.52 Å. A relative rotation of approximately 5° between the two lobes results in the interlobe cleft of VEGFR2Δ50P (SEQ ID No: 5) being slightly larger and more open. Measurement of distances between equivalent Cα's (K523 and R675 of FGFR1, S877 and R1080 of VEGFR2Δ50P (SEQ ID No: 5)) at the ends of the cleft reveal that this distance is 25.3 Å in VEGFR2Δ50P (SEQ ID No: 5) as compared to 23.2 Å in FGFR1. This is however a minor difference, as compared to much larger relative lobe rotations observed among kinase structures in various ligation and phosphorylation states (Johnson et al., 1996) Cell 85, 149–158). For example, the inter-lobe orientation seen here for VEGFR2Δ50P (SEQ ID No: 5) is in an approximately 20° more open conformation than that seen in the ternary complex structure of the phosphorylated kinase domain of IRK bound to the ATP analog AMP-PNP and a peptide substrate (Hubbard, (1997) EMBO J. 16, 5572–5581; PDB entry 1IR3) (FIG. 2c).

Figure 2B:
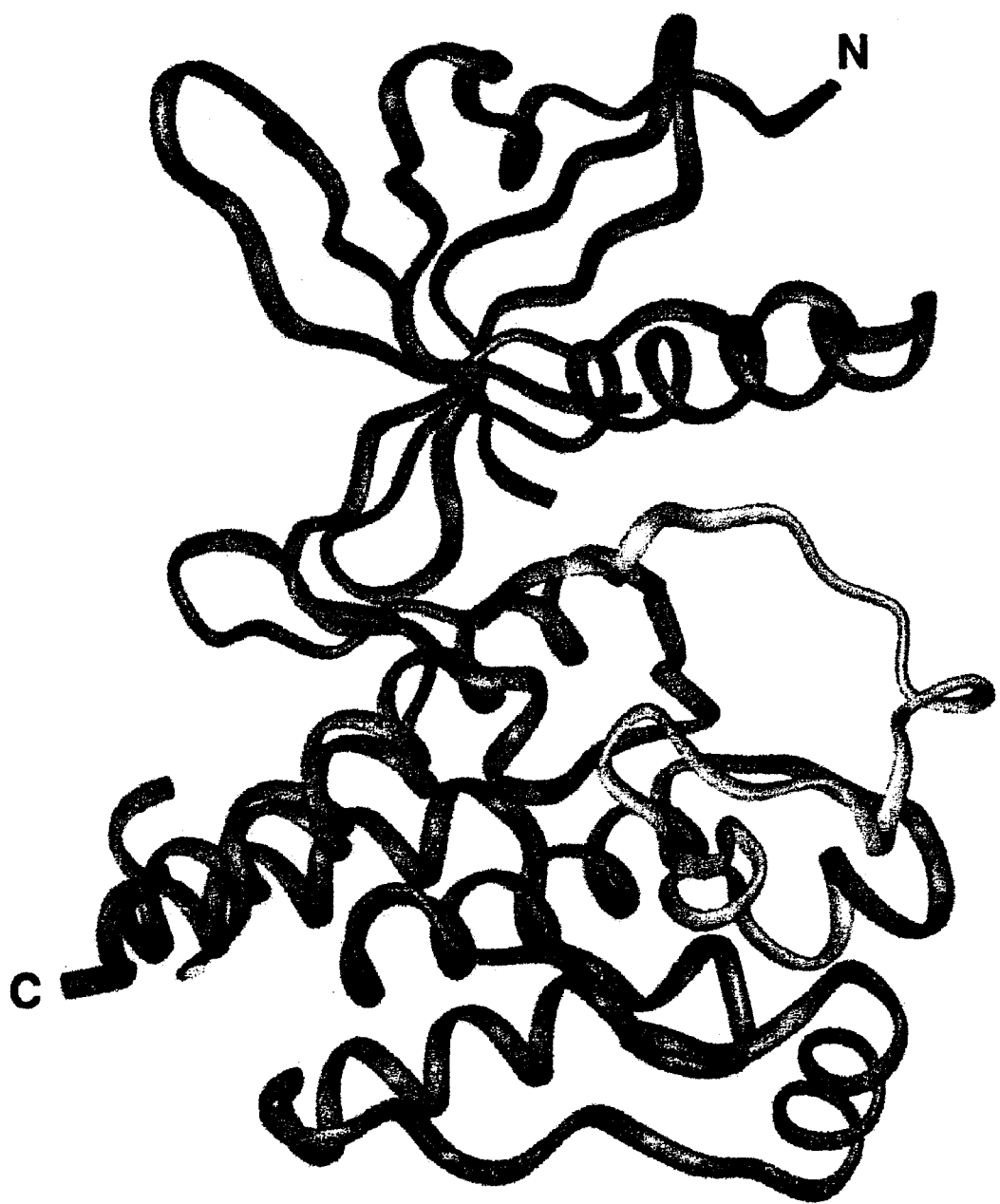
Figure 2C:
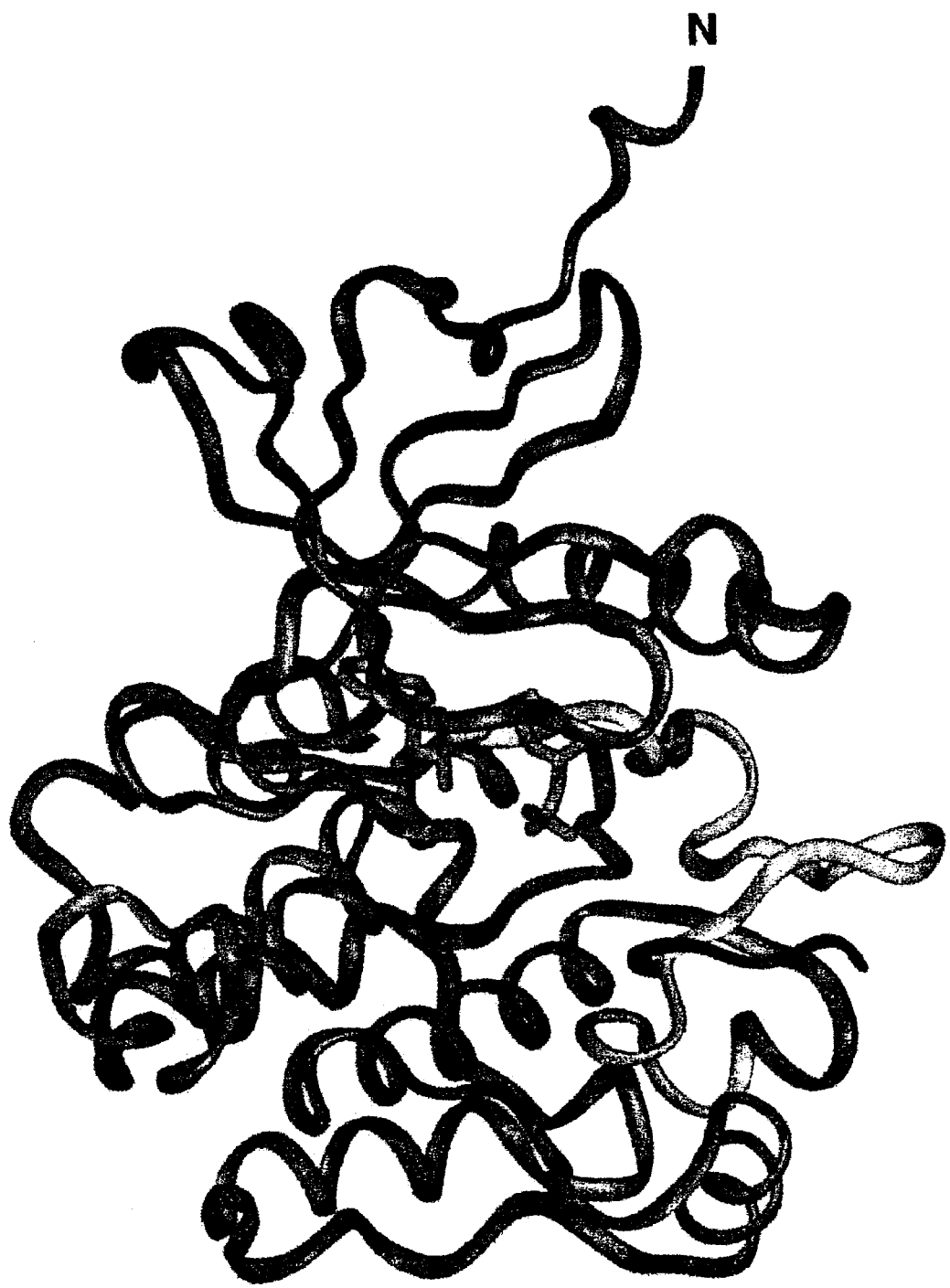

While the β-strand positions of the N-terminal lobe agree well between VEGFR2Δ50P (SEQ ID No: 5) and FGFR1, the structures do diverge significantly at the N-terminal residues preceding the first conserved region starting at residue W827 (FIGS. 2a and 2b). The first 14 residues (M806–E819) of VEGFR2Δ50P (SEQ ID No: 5) are completely disordered and the next seven residues (L820–R826) form an extended loop structure. It is likely that residues 806–819 do not form part of the active kinase region but are instead part of, or are adjacent to, the juxtamembrane region of VEGFR-2. Residues 820–826 do seem to be part of the kinase domain, although a flexible one, as analogous residues are also ordered in the structures of FGFR1, IRK, and the non-receptor tyrosine kinase Lck (Yamaguchi and Hendrickson, (1996) Nature 384, 484–489). Other differences between the VEGFR2Δ50P (SEQ ID No: 5) structure and other kinase structures occur at the kinase insert domain and the activation loop (discussed below).

Catalytic loop and ATP binding site

Figure 3A:
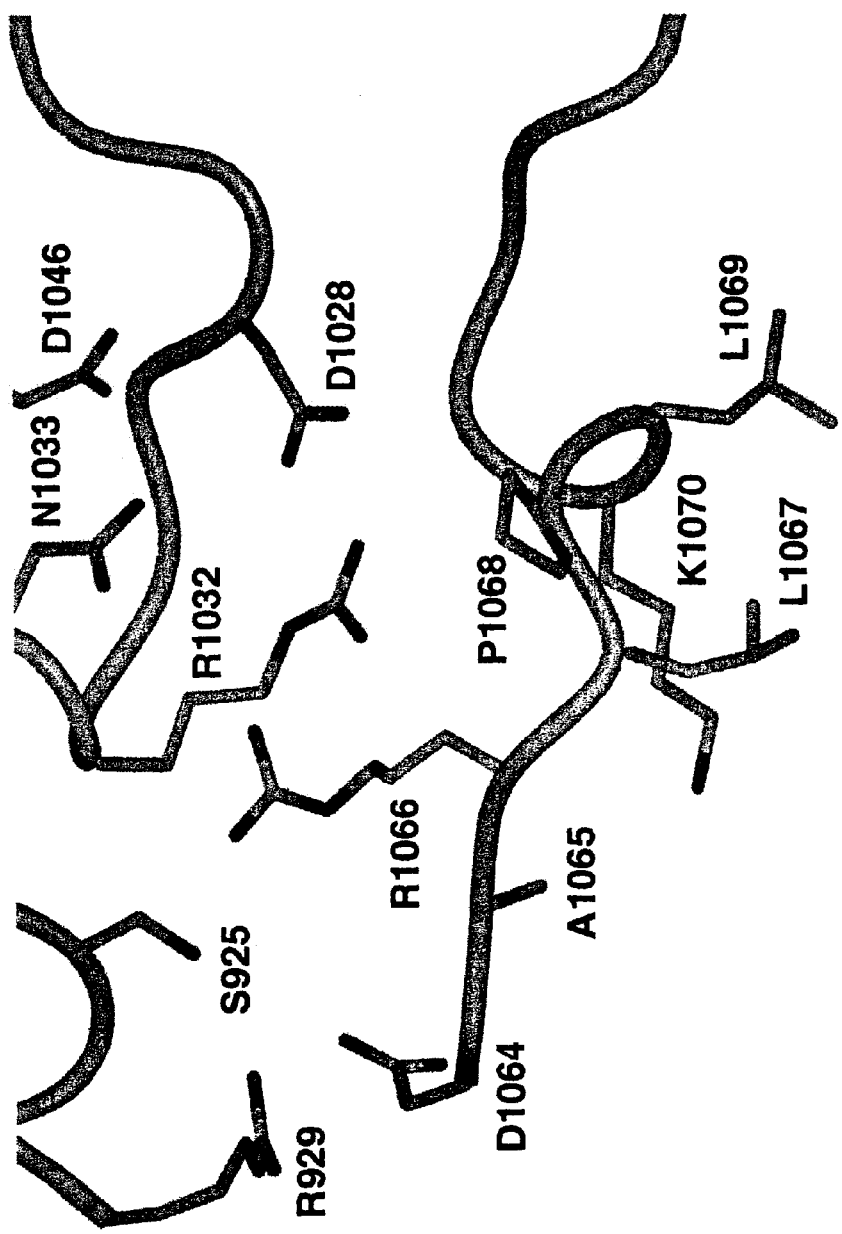
FIG. 3. Catalytic site of VEGFR2Δ50P (SEQ ID No: 5) and IRKP. Cross section of the catalytic site of (A) VEGFR2Δ50P (SEQ ID No: 5) and (B) IRKP (PDB entry 1 IR3; Hubbard et al., 1997) structures. Atoms are colored by element type: carbon (green), oxygen (red), nitrogen (blue), sulfur (yellow), phosphorous (pink),and magnesium ion (orange). (A) includes only protein atoms. (B) includes protein atoms, AMP-PNP atoms, and $Mg^{2+}$ ions. Figure generated using INSIGHT II.
Figure 3B:
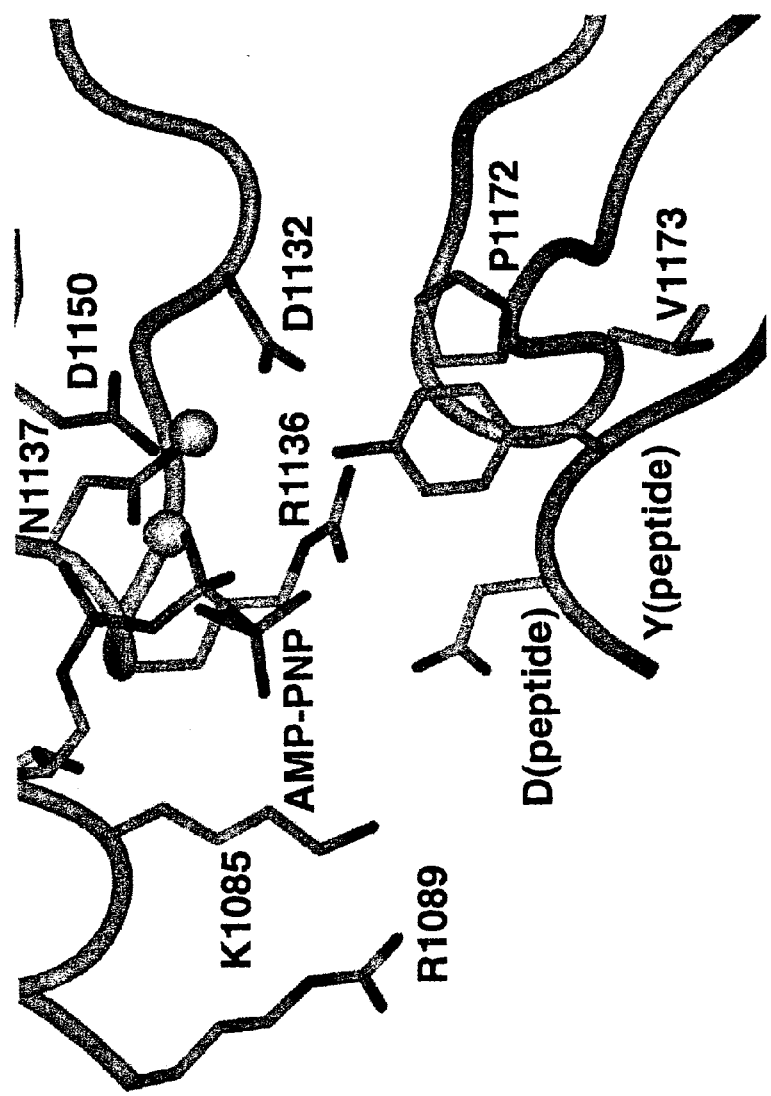

In protein kinases, the loop between αE and β7 has been termed the catalytic loop as it contains an invariant aspartic acid (D1028) that is believed to function as a catalytic base in the phosphotransfer reaction (Johnson et al., 1996). This aspartic acid is part of a stretch of residues (H1026–N1033) whose sequence HRDLAARN is highly conserved among protein tyrosine kinases. In VEGFR2Δ50P (SEQ ID No: 5) the backbone position and most sidechain positions of this loop are similar to those in the unliganded FGFR1 and ternary phosphorylated IRK (IRKP) complex structures. As seen in these previous structures the sidechain carboxylate of the catalytic loop aspartic acid (D1028) is hydrogen bonded to the sidechains of the conserved arginine (R1032) and asparagine (N1033) (FIG. 3).

The ATP binding site of protein kinases lies at the cleft between the N and C-terminal lobes (FIG. 2c). For VEGFR2Δ50P (SEQ ID No: 5), the residues forming this site consist primarily of residues E917–N923, joining the two lobes, and residues L840–1849 which include parts of β1, β2, and the glycine-rich loop of G841–G846. The glycine-rich loop, also referred to as the nucleotide binding loop, is a flexible segment whose position differs among kinase structures in various activated and liganded states. In VEGFR2Δ50P (SEQ ID No: 5) this loop is fairly well ordered and all atoms could be modeled with the exception of the sidechains of R842 and F845. The relative position and conformation of this loop is similar to that observed in the unligated FGFR1 structure. However, this position is markedly different from that in the IRKP ternary complex structure in which the approximately 20° relative rotation of the N and C-terminal lobes results in the glycine-rich loop being 5 Å closer to the C-terminal lobe than in VEGFR2Δ50P (SEQ ID No: 5) structure.

Figure 4:
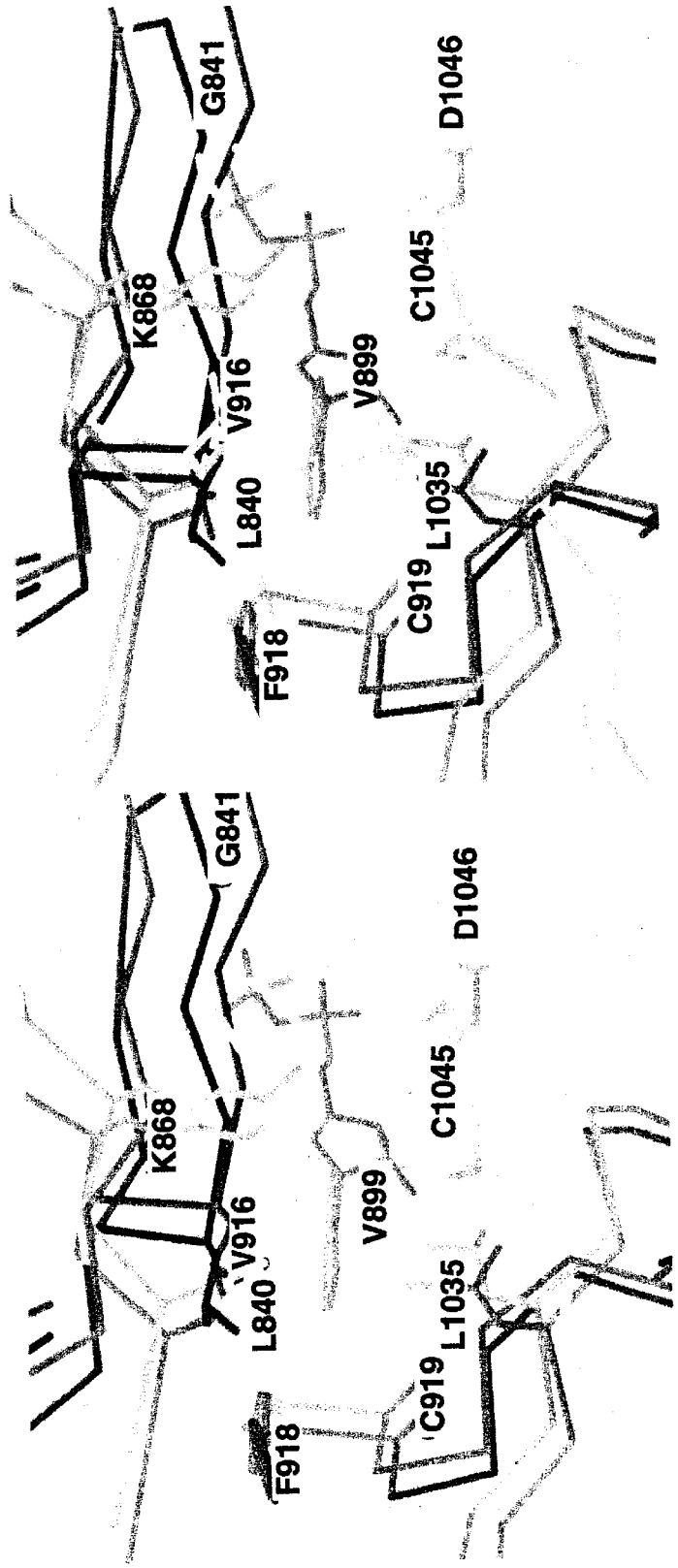
FIG. 4. Nucleotide binding site of VEGFR2Δ50P (SEQ ID No: 5) and FGFR1. Stereo view showing Cα trace and some sidechains of a superposition of the nucleotide binding sites of the VEGFR2Δ50P (SEQ ID No: 5) and the FGFR1-(AMP-PCP) complex (molecule B, Mohammadi et al., 1996) structures. The superposition was done using Cα positions of helices (D,E,F,G,H, and I) of the C-terminal lobes. Carbon atoms of VEGFR2Δ50P (SEQ ID No: 5) are shown in yellow and carbon atoms of FGFR1 are shown in purple. The coloring for other protein atoms is: oxygen (red), nitrogen (blue), and sulfur (green). The AMP-PCP in the FGFR1 structure is depicted in orange. Labels correspond to VEGFR2Δ50P (SEQ ID No: 5) residues. Figure created with Xfit (McRee et al., (1992) *J. Mol. Graph.* 10, 44–46.).

In reported kinase structures with bound ATP or an ATP analog, the adenine ring makes two conserved hydrogen bonds with the protein backbone. In the structure of FGFR1 with AMP-PCP bound (Mohammadi et al., 1996) these hydrogen bonds are between the adenine $NH_2$ and the backbone C=0 of E562 (E917 VEGFR2Δ50P(SEQ ID No: 5)) and between the adenine N1 and the backbone NH of A546 (C919 VEGFR2Δ50P(SEQ ID No: 5)). Although the structure presented here does not contain a bound nucleotide, the similarities in the positions of these backbone atoms to those in FGFR1 indicate that these hydrogen bonds would be formed in a VEGFR2Δ50P(SEQ ID No: 5)-ATP complex and therefore the adenine is expected to bind in a similar position (FIG. 4).

Variation in the ATP-binding sites of kinases involved in disease is of considerable importance in the design of selective ATP-competitive inhibitors as therapeutics. A comparison of the ATP binding sites of FGFR1 and VEGFR2Δ50P (SEQ ID No: 5) reveals that while the overall architecture of the site is conserved, several sequence differences result in differences in the shape of the accessible area for ligand binding. Specific sequence differences between FGFR1 and VEGFR-2 in this site include: V899 (I545 FGFR1), F918 (Y563 FGFR1), C919 (A564 FGFR1), and C1045 (A640 FGFR1) (FIG. 4). Similarly, comparison to the ternary IRKP complex structure reveals variation in the adenine site at V916 (M1076 IRK), F918(L1078), C919 (M1079 IRK), L1035 (M1139 IRK), and C1045 (G1149 IRK). Even greater sequence and structural variation in the adenine site is seen when the VEGFR2Δ50P (SEQ ID No: 5) structure is compared to serine/threonine kinase structures, suggesting that these differences are useful in the design of selective ATP-competitive inhibitors.

Activation loop

Protein kinases contain a large flexible loop, referred to as the activation loop (A-loop) whose conformation is postulated to regulate kinase activity (FIG. 2). In many kinases the conformation of the AL is controlled by the phosphorylation of specific A-loop residues (Johnson et al., 1996). The loop can be generally defined as beginning with the conserved residues DFG and ending at the conserved APE sequence (Johnson et al., 1996). In VEGFR-2 this segment corresponds to D1046–E1075 and contains two tyrosines (Y1054 and Y1059). Both Y1054 and Y1059 were found to be autophosphorylation sites when the cytosolic domain of VEGFR-2 was expressed in *E. coli* (Dougher-Vermazen et al., 1994). Using the in vitro autophosphorylation protocol described here for VEGFR2Δ50(SEQ ID No: 5), a stable phosphorylation site is indicated at Y1059, however no evidence of phosphorylation of Y1054 was detected.

In this unliganded VEGFR2Δ50P (SEQ ID No: 5) structure presented here, the A-loop appears quite mobile and interpretable electron density was not present for most of the central portion of the loop (G1048–G1063). This disorder is consistent with mobility of the A-loop deduced from other kinase structures. For example, of the two molecules in the asymmetric unit of the unphosphorylated FGFR1 kinase structure the center of the A-loop has relatively high temperature factors in molecule A and is completely disordered in molecule B. Although residues 1048–1063 could not be modeled in VEGFR2Δ50P (SEQ ID No: 5), unambiguous electron density was present for residues D1064–E1075, clearly indicating that these residues adopt a conformation similar to that observed in the unphosphorylated FGFR1 structure. The segment of D1064–P1068 has an extended structure that lies adjacent to the catalytic residues D1028 and R1032 (FIG. 3a). Comparison to the structure of the (MgAMP-PNP)-peptide-IRKP complex structure indicates that the position of R1066–P1068 in this VEGFR2Δ50P (SEQ ID No: 5) structure is inhibitory to substrate binding. P1066 occupies equivalent space allocated to the tyrosine sidechain of the peptide substrate in the ternary IRK3P complex structure. The conformation of residues L1069–E1075 is similar to that in the ternary IRKP complex structure, however there is a complete directional change at P1068 (P1172 IRK) between the two structures. In the IRK structure residues N-terminal to this proline are directed toward aEF while in VEGFR2Δ50P (SEQ ID No: 5) they are directed toward αD on the opposite side of the protein (FIGS. 2 and 3).

Despite the phosphorylation of Y1059 prior to crystallization, the conformation seen here for residues D1064–P1068 is similar to the inhibitory conformation observed for analogous residues in the unphosphorylated FGFR1 structure. Y1059 in VEGFR2Δ50 (SEQ ID No: 5) corresponds to a relatively conserved phosphorylation site among protein tyrosine kinases. In the ternary IRKP complex structure and the phosphorylated lymphocyte kinase (Lck) structure (Yamaguchi and Hendrickson, 1996) the tyrosine at this position (Y1163 IRK, Y394 Lck) is phosphorylated and the A-loop has a non-inhibitory conformation similar to that observed in a phosphorylated cAPK ternary complex structure (Zheng et al., 1993). The interactions the phosphate group at this position makes with other protein residues are believed to help stabilize an A-loop conformation that allows substrate and ATP binding (Johnson et al., 1996; Hubbard, 1997). However, since this VEGFR2Δ50P (SEQ ID No: 5) structure described here does not exhibit a similar open A-loop conformation but rather has an inhibitory conformation with much of the loop disordered it is possible that the monophosphorylated A-loop of VEGFR2Δ50P (SEQ ID No: 5) exists in a dynamic equilibrium involving several conformations and that the conformation observed here is the one most favored in this crystal environment.

Kinase Insert Domain:

The kinase insert domain occurs in the kinase C-terminal lobe and connects helices αD and αE. In VEGFR-2 this region corresponds to a 68 residue stretch from N933 to L1000 (FIG. 1). The lack of effect on intrinsic kinase activity (noted above) of deletion of residues T940–E989 is perhaps not surprising as the ends of the KID domain occur relatively far away (approximately 35–40 Å) from the catalytic site and on the opposite side of the protein from the position of the activation loop (FIG. 2). These results are consistent with those for the CSF-1 receptor kinase in which deletion of 58 of the 64 residues of the CSF-1 KID only decreased it's ability to phosphorylate a peptide substrate by 10% (Taylor et al., 1989). Deletion of the entire 98 residues of βPDGFR, however, resulted in an 80% decrease in kinase activity towards a peptide substrate (Severinsson et al., (1990) *Mol. Cell. Biol.* 10, 801–809). Thus, the present invention allows for the production of a synthetic catalytic linker which recognizes that the majority of KID is not required for catalysis but rather only a small number of residues must be present to form a linker between αD and αE so as to maintain a competent kinase structure.

Figure 5:
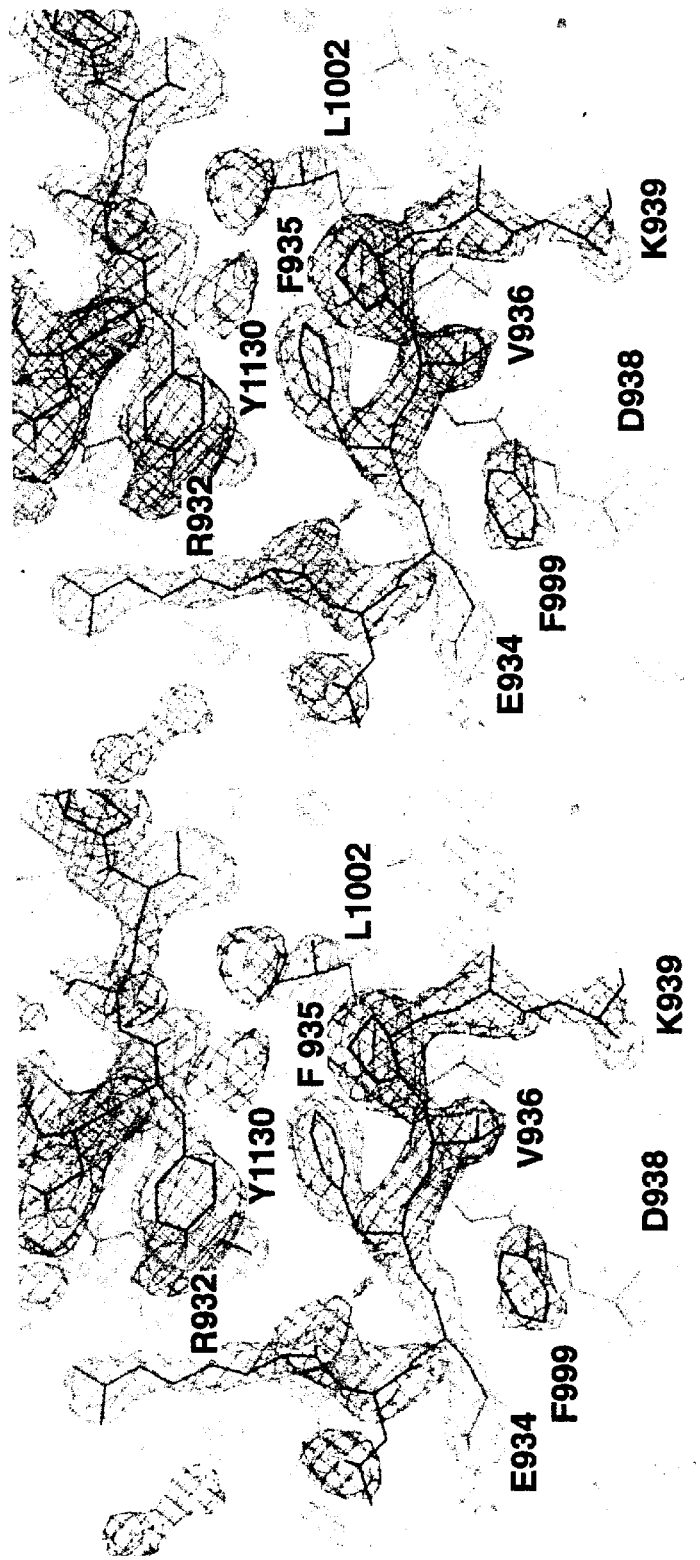
FIG. 5. Electron density map of the kinase insert domain area of VEGFR2Δ50P(SEQ ID No: 5). Stereo view of a $2F_o–F_c$ map computed at 2.4Å and contoured at 1.2 δ and superimposed with the refined model. Carbon atoms are yellow, oxygen atoms red, and nitrogen atoms are blue. Water molecules are depicted as red crosses. Figure created with Xfit (McRee et al., 1992).
Figure 6:
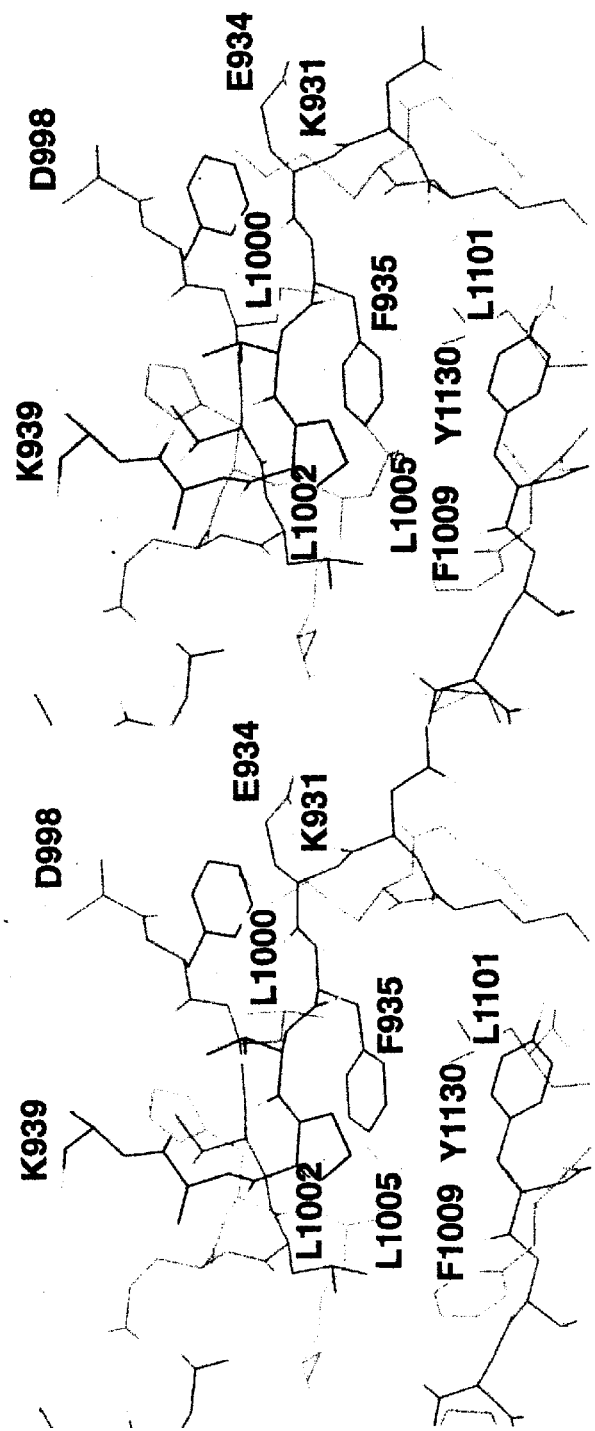
FIG. 6. Kinase insert domain of VEGFR2Δ50P(SEQ ID No: 5). Stereo cross section showing the ordered residues of the kinase insert domain of VEGFR2Δ50P(SEQ ID No: 5). Carbon atoms are yellow, oxygen atoms are red, nitrogen atoms are blue, and sulfur atoms are green. View is rotated roughly 180° from FIG. 5. Figure created with Xfit (McRee et al., 1992).

In the VEGFR2Δ50P (SEQ ID No: 5) structure following αD, residues N933–P937 form a loose turn and an extended strand whose ends are roughly perpendicular to the axes of αD and αI at the C-terminus. In different Fourier maps, the electron density is strong and clear for residues N933–P937 and becomes weak for Y938 and K939 (sidechains of Y938 and K939 are not modeled) (FIG. 5). The 50 residue deletion in VEGFR2Δ50 (SEQ ID No: 5) directly follows K939 so that the residue immediately C-terminal to K939 is V990, maintaining the residue numbering in full-length VEGFR-2. Residues V990–K997 are disordered and interpretable electron density begins again at D998. Residues D998–T1001 then form a short strand that joins αE at residue L1002 (FIGS. 5 and 6).

The two strands at the N-terminal and C-terminal ends of the KID form a pseudo two-stranded parallel β-sheet structure that is different from the conformations seen in this region of other kinase structures. The two ends of the KID thus make a variety of interactions which may help to stabilize the overall conformation and position of this domain in VEGFR-2. The sidechain of K931 makes an ionic interaction with the sidechain of E934 and also makes a hydrogen bond to the backbone carbonyl of D998. (FIG. 6). Hydrogen bonding interactions between the strands include: E934 backbone C=O to L1000 NH, V936 NH to L1000 C=O, and P937 C=O to L1002 NH. In addition to these polar interactions, the sidechains of F935, P937, and L1000 are involved in extensive hydrophobic contacts. The sidechain of F935 is nestled in a hydrophobic pocket formed by the sidechains of L928, P937, L1000, L1002, L1005, L1101, and Y1130 (FIGS. 5 and 6). The L1000 sidechain also packs against the sidechains of Y927, K931, H1004, and Y1008.

It has been found by the applicants that deletion of portions of the KID also impart other useful and desirable characteristics to the modified VEGFR-2 polyprotein. The modified polypeptide has exhibited greater stability when exposed to higher temperatures in solution than the wild-type protein. Additionally, the modified polypeptide has also exhibited improved solubility than the wild-type protein. It is apparent to those skilled in the art that these properties allow improvements in various commercial aspects of the present invention. Examples of potential uses for the modified proteins include high-throughput screening of potential ligands for the receptor by various methods including those based on gene-chip technology (Affymax, Inc,) phage-display peptide libraries (The Ph.D. Kit® by New England BioLabs, Inc.) as well as in-depth analysis via FT-NMR.

It is therefore contemplated that the entire KID can be deleted and retain some catalytic activity in other related RTKs such as but not limited to PDGFα and β and other previously mentioned proteins. Furthermore, in one embodiment of the invention the entire KID is deleted and replaced with a synthetic catalytic linker of at least one amino acids such that both the catalytic activity and the crystallizability of the protein is retained.

Cloning of the PDGFα Protein

In this example, the PDGFRα (SEQ ID No: 6) polyprotein is cloned using the methods outlined for VEGFR-2 above. The coding sequence for PDGFRα (SEQ ID No: 6) is derived from the sequence disclosed by Matsui,T., et al., (1989) *Science* 243: 800–804 (Accession No. 66814). PCR oligonucleotide primers are then made which code for residues located in the Kinase domain of the protein. The kinase domain of PDGFRα: is shown in FIG. 1, starting at residue 576 and ending at residue 961 (S). The kinase insert domain (KID) of PDGFRα (SEQ ID No: 6) is shown starting at residue 689 (N) and ending at residue 791 (T) in FIG. 1.

The remainder of the cloning and purification steps would be similar to those disclosed for the VEGFR2Δ50 protein (SEQ ID No: 5) and use technology well known to those skilled in the art.

It is contemplated that other members of the RTK family and other uses for the data disclosed herein and are not limited by the examples shown.

What is claimed is:

1. A modified receptor tyrosine kinase (RTK) polypeptide suitable for x-ray crystallography, wherein said modified RTK polypeptide comprises an RTK kinase domain α helix D linked to an RTK kinase domain α helix E by a truncated RTK kinase insert domain (KID).

2. The polypeptide of claim 1 wherein said truncated RTK kinase insert domain comprises a deletion of charged residues from the KID.

3. The polypeptide of claim 1 wherein said truncated RTK kinase insert domain comprises a deletion of 50 residues from the KID.

4. The polypeptide of claim 1 wherein said truncated RTK kinase insert domain comprises a deletion of 60 residues from the KID.

5. The polypeptide of claim 1 wherein said α helix D and said α helix E are linked by a truncated RTK kinase insert domain, said truncation being sufficient in length so as to allow said helices to maintain conformation associated with the kinase structure.

6. The polypeptide of claim 1 wherein said RTK polypeptide is a member of the protein derived growth factor receptor (PDGFR) family.

7. The polypeptide of claim 6 wherein said PDGFR member is selected from the group consisting of VEGFR-1, VEGFR-2, PDGFR-α, PDGFR-β, stem cell growth factor receptor (c-kit), and colony stimulating factor-1 receptor (CSF-1R/c-fms).

8. The polypeptide of claim 1 wherein said RTK polypeptide is selected from the group consisting of insulin receptor (IRK), fibroblast growth factor receptor-1 (FGFR-1), and vascular endothelial growth factor receptor-2 (VEGFR-2).

9. The polypeptide of claim 1 wherein said RTK polypeptide is VEGFR-2.

10. The polypeptide of claim 1 wherein said modified RTK polypeptide comprises the VEGFR2Δ50 polypeptide of SEQ ID NO: 5.

* * * * *